US011434233B2

(12) United States Patent
Di Francesco et al.

(10) Patent No.: US 11,434,233 B2
(45) Date of Patent: *Sep. 6, 2022

(54) HETEROCYCLIC INHIBITORS OF ATR KINASE

(71) Applicants: Board of Regents, The University of Texas System, Austin, TX (US); ChemPartner Corporation, South San Francisco, CA (US)

(72) Inventors: Maria Emilia Di Francesco, Houston, TX (US); Philip Jones, Houston, TX (US); Christopher Lawrence Carroll, Houston, TX (US); Jason Bryant Cross, Pearland, TX (US); Suyambu Kesava Vijayan Ramaswamy, Houston, TX (US); Michael Garrett Johnson, San Francisco, CA (US); Sarah Lively, San Carlos, CA (US); David Lapointe, Oakland, CA (US)

(73) Assignees: Board of Regents, The University of Texas System, Austin, TX (US); ChemPartner Corporation, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/009,428

(22) Filed: Sep. 1, 2020

(65) Prior Publication Data

US 2021/0047311 A1 Feb. 18, 2021

Related U.S. Application Data

(63) Continuation of application No. 16/507,851, filed on Jul. 10, 2019, now Pat. No. 10,800,769, which is a continuation of application No. 16/035,310, filed on Jul. 13, 2018, now Pat. No. 10,392,376.

(60) Provisional application No. 62/531,951, filed on Jul. 13, 2017.

(51) Int. Cl.
| | | |
|---|---|---|
| *C07D 413/14* | (2006.01) |
| *C07D 413/04* | (2006.01) |
| *C07D 411/14* | (2006.01) |
| *C07D 471/04* | (2006.01) |
| *C07D 417/14* | (2006.01) |
| *A61K 45/06* | (2006.01) |
| *A61P 35/00* | (2006.01) |

(52) U.S. Cl.
CPC ............ *C07D 413/14* (2013.01); *A61K 45/06* (2013.01); *A61P 35/00* (2018.01); *C07D 411/14* (2013.01); *C07D 413/04* (2013.01); *C07D 417/14* (2013.01); *C07D 471/04* (2013.01); *A61K 2300/00* (2013.01)

(58) Field of Classification Search
CPC .. C07D 413/14; C07D 413/04; C07D 411/14; C07D 417/14; C07D 471/04
See application file for complete search history.

(56) References Cited

U.S. PATENT DOCUMENTS

| 9,695,171 | B2 | 7/2017 | Galatsis |
| 10,392,376 | B2 | 8/2019 | Di Francesco |
| 10,421,765 | B2 | 9/2019 | Di Francesco |
| 10,745,420 | B2 | 8/2020 | Di Francesco |
| 10,800,769 | B2 | 10/2020 | Di Francesco |
| 10,800,774 | B2 | 10/2020 | Di Francesco |
| 10,894,052 | B2 | 1/2021 | Di Francesco |
| 2008/0292588 | A1 | 11/2008 | Zhou |
| 2009/0233926 | A1 | 9/2009 | Butterworth |
| 2010/0256143 | A1 | 10/2010 | Baker |
| 2011/0201599 | A1 | 8/2011 | Bahceci |
| 2012/0035407 | A1 | 2/2012 | Charrier |
| 2014/0315902 | A1 | 10/2014 | Sun |
| 2016/0287604 | A1 | 10/2016 | Wortmann |

FOREIGN PATENT DOCUMENTS

| WO | 2007080382 | 7/2007 |
| WO | 2008023159 | 2/2008 |
| WO | 2008125833 | 10/2008 |
| WO | 2009007748 | 1/2009 |
| WO | 2009007750 | 1/2009 |
| WO | 2009007751 | 1/2009 |
| WO | 2009110510 | 9/2009 |
| WO | 2010073034 | 7/2010 |
| WO | 2010120996 | 10/2010 |
| WO | 2011062253 | 5/2011 |
| WO | 2011103715 | 9/2011 |
| WO | 2011106276 | 9/2011 |
| WO | 2011107585 | 9/2011 |
| WO | 2011154737 | 12/2011 |
| WO | 2012004299 | 1/2012 |
| WO | 2012147890 | 11/2012 |
| WO | 2014089379 | 6/2014 |
| WO | 2015085132 | 6/2015 |
| WO | 2015187451 | 12/2015 |

(Continued)

OTHER PUBLICATIONS

Barsanti, P. et al., "Structure-Based Drug Design of Novel Potent and Selective Azabenzimidazoles (ABI) as ATR Inhibitors", ACS Med Chem Lett., 6:42-6, (2015).

(Continued)

*Primary Examiner* — Rebecca L Anderson
(74) *Attorney, Agent, or Firm* — Dennis A. Bennett; Lauren L. Stevens; Cynthia Hathaway

(57) ABSTRACT

The present disclosure relates to heterocyclic compounds and methods which may be useful as inhibitors of ATR kinase for the treatment or prevention of cancer.

21 Claims, No Drawings

(56) References Cited

FOREIGN PATENT DOCUMENTS

| | | |
|---|---|---|
| WO | 2016020320 | 2/2016 |
| WO | 2016061097 | 4/2016 |
| WO | 2017210545 | 12/2017 |
| WO | 2018218197 | 11/2018 |
| WO | 2019036641 | 2/2019 |
| WO | 2019178590 | 9/2019 |

OTHER PUBLICATIONS

Barsanti, P. et al., "Structure-Based Drug Design of Novel Potent and Selective Tetrahydropyrazolo[1,5-a] pyrazines as ATR Inhibitors", ACS Med Chem Lett., 6(1):37-41, (2015).

Bass, T. et al., "ETAA1 acts at stalled replication forks to maintain genome integrity", Nat Cell Biol, 18(11):1185-95, (25 page document), (2016).

Cancer [online], Retrieved from the Internet, URL: http://www.nlm.nih.gov/medlineplus/cancer.html on Jul. 6, 2007; (2007).

Charrier, J. et al., "Discovery of Potent and Selective Inhibitors of Ataxia Telangiectasia Mutated and Rad3 Related (ATR) Protein Kinase as Potential Anticancer Agents", J Med Chem., 54(7):2320-30, (2011).

Choi, M. et al., "ATM Mutations in Cancer: Therapeutic Implications", Mol Cancer Ther, 15(8):1781-91, (2016).

Coburn, C. et al., "Discovery of a pharmacologically active antagonist of the two-pore-domain potassium channel K2P9.1 (TASK-3)", Chem. Med. Chem., 7(1):123-33, (2012).

Foote, K.M. et al., "Discovery of 4-{4-[(3R)-3-Methylmorpholin-4-yl]-6-[1-(methylsulfonyl)cyclopropyl]pyrimidin-2-yl}-1H-indole (AZ20): A Potent and Selective Inhibitor of ATR Protein Kinase with Monotherapy in Vivo Antitumor Activity", J Med Chem., 56(5):2125-38, (2013).

Golub, T. et al., "Molecular Classification of Cancer: Class Discovery and Class Prediction by Gene Expression Monitoring", Science, 286(5439):531-7, (1999).

International Application No. PCT/US2018/034729; International Preliminary Report on Patentability, dated Nov. 26, 2019; 6 pages.

International Application No. PCT/US2018/034729; International Search Report and Written Opinion of the International Searching Authority, dated Nov. 9, 2018; 9 pages.

International Application No. PCT/US2018/042128 International Search Report and Written Opinion of the International Searching Authority, dated Oct. 30, 2018; 10 pages.

International Application No. PCT/US2018/046937; International Preliminary Report on Patentability, dated Feb. 27, 2020; 6 pages.

International Application No. PCT/US2018/046937; International Search Report and Written Opinion of the International Searching Authority, dated Jan. 9, 2019; 9 pages.

International Application No. PCT/US2019/022727; International Preliminary Report on Patentability, dated Oct. 1, 2020; 5 pages.

International Application No. PCT/US2019/022727; International Search Report and Written Opinion of the International Searching Authority, dated May 14, 2019; 8 pages.

Karnitz, L. et al., "Molecular Pathways: Targeting ATR in Cancer Therapy", Clin Cancer Res, 21(21):4780-5, (2015).

Kwok, M. et al., "ATR Inhibition Induces Synthetic Lathality and Overcomes Chemoresistance in TP53- or ATM-Defective Chronic Lymphocytic Leukemia Cells", Blood, 127(5):582-96, (2015).

Lala, P. et al., "Role of Nitric Oxide in Tumor Progression: Lessons From Experimental Tumors", Cancer Metastasis Rev., 17(1):91-106, (1998).

Menezes, D. et al., "A Synthetic Lethal Screen Reveals Enhanced Sensitivity to ATR Inhibitor Treatment in Mantle Cell Lymphoma with ATM Loss-of-Function", Mol Cancer Res., 13(1):120-9, (2015).

Mohni, K. et al., "ATR Pathway Inhibition Is Synthetically Lethal in Cancer Cells with ERCC1 Deficiency", Cancer Res., 74:2835-45, (2014).

Pubchem 53541968, 6-[4-(Morpholin-4-yl)-5H,6H,7H,8H-pyrido[4,3-d]pyrimidin-6-yl]pyridine-3-carbonitrile, Created on Dec. 3, 2011 (Dec. 3, 2011) pp. 1-11.

Pubchem 79023842, 4-Phenyl-5,6,7,8-tetrahydropyrido[4,3-d]pyrimidine, deposited on Oct. 19, 2014 (Oct. 19, 2014) pp. 1-10.

Toledo, L. et al., "A Cell-Based Screen Identifies ATR Inhibitors with Synthetic Lethal Properties for Cancer-Associated Mutations", Nat Struct Mol Biol, 18(6):121-7, (2011).

U.S. Appl. No. 16/104,561; Non-Final Office Action, dated Apr. 22, 2019; 26 pages.

U.S. Appl. No. 15/990,283; Non-Final Office Action, dated Dec. 26, 2018; 22 pages.

U.S. Appl. No. 15/990,283; Notice of Allowance, dated May 13, 2019; 13 pages.

U.S. Appl. No. 16/035,310; Corrected Notice of Allowability, dated Jun. 3, 2019; 10 pages.

U.S. Appl. No. 16/035,310; Examiner-Initiated Interview Summary, dated Apr. 11, 2019; 1 page.

U.S. Appl. No. 16/035,310; Notice of Allowance, dated Apr. 11, 2019; 10 pages.

U.S. Appl. No. 16/104,561; Examiner-Initiated Interview Summary, dated May 26, 2020; 1 page.

U.S. Appl. No. 16/104,561; Final Office Action, dated Feb. 24, 2020; 7 pages.

U.S. Appl. No. 16/104,561; Non-Final Office Action, dated Apr. 22, 2019; 33 pages.

U.S. Appl. No. 16/104,561; Notice of Allowance, dated May 26, 2020; 20 pages.

U.S. Appl. No. 16/356,450; Non-Final Office Action, dated Apr. 28, 2020; 22 pages.

U.S. Appl. No. 16/356,450; Notice of Allowance, dated Oct. 9, 2020; 16 pages.

U.S. Appl. No. 16/507,851; Examiner-Initiated Interview Summary, dated Feb. 20, 2020; 1 page.

U.S. Appl. No. 16/507,851; Non-Final Office Action, dated Feb. 20, 2020; 11 pages.

U.S. Appl. No. 16/507,851; Notice of Allowance, dated Jun. 2, 2020; 22 pages.

U.S. Appl. No. 16/539,693; Non-Final Office Action, dated Jan. 16, 2020; 7 pages.

U.S. Appl. No. 16/539,693; Notice of Allowance, dated Apr. 23, 2020; 23 pages.

U.S. Appl. No. 16/539,693; Supplemental Notice of Allowability, dated Jun. 11, 2020; 7 pages.

HETEROCYCLIC INHIBITORS OF ATR KINASE

This application is a continuation of U.S. application Ser. No. 16/507,851, filed Jul. 10, 2019, which is a continuation of U.S. application Ser. No. 16/035,310, filed Jul. 13, 2018, which claims the benefit of priority of U.S. Provisional Application No. 62/531,951, filed Jul. 13, 2017, the disclosures of which are hereby incorporated by reference as if written herein in their entireties.

Disclosed herein are new heterocyclic compounds and compositions and their application as pharmaceuticals for the treatment of disease. Methods of inhibition of ATR kinase activity in a human or animal subject are also provided for the treatment diseases such as cancer.

Ataxia-telangiectasia and Rad3-related kinase (ATR) is a member of the phosphatidylinositol 3-kinas-related protein kinase (PIKK) family, which also includes ataxia telangiectasia mutated (ATM) kinase, DNA-dependent protein kinase (DNA-PK), suppressor of morphogenesis in genitalia-1 (SMG-1), mammalian target of rapamycin (mTOR) and transformation/transcription associated protein (TRAPP). ATR and ATM are key regulators of the cellular DNA damage response (DDR) pathways, and are involved in maintaining the genome integrity in response to DNA-damage. Several distinct types of DNA lesions can occur as a consequence of diverse damaging events, including errors in normal replication processing, exposure to ionizing radiations (IR) and genotoxic agents, and different mechanisms of DNA repair have evolved to resolve specific kinds of DNA damage.

ATM is activated mainly by double-stranded DNA breaks (DSB), which may arise from collapsing of stalled replication forks or from exposure to IR. ATM has a key role in the activation of the G1/S checkpoint, which prevents cells with DNA damage to enter the S-phase, and allows DNA repair prior to the start of DNA replication. The effect is mediated primarily through the phosphorylation of two of the main downstream targets of ATM, CHK2 kinase and the tumor suppressor p53.

In turn, ATR is activated mainly in response to single stranded DNA breaks (SSB), that are found at stalled replication forks or are derived from DNA end-resection following processing of DNA DSBs. Replication protein A (RPA) binds to the DNA single strands, the ATR-interacting protein (ATRIP) binds then to the RPA-coated DNA strands and recruits ATR to the SSB damage site. Recruitment of additional protein components to the complex results in activation of ATR kinase, followed by phosphorylation and activation of its downstream effectors, including CHK1 kinase. Activation of ATR results in slow replication origin firing, stabilization of the stalled replication forks which prevents their collapse into DSBs, and restart of fork replication once the damage is repaired. The ATR/CHK1 pathway is a major regulator of the G2/M checkpoint, which prevents the premature entry of cells into mitosis in the presence of incomplete DNA replication and/or DNA damage (reviewed in M. J. O'Connor, Molecular Cell, 2015, 60, November 19, p. 547-560; A. M. Weber et al., Pharmacology and Therapeutics 2015, 149, 124-138).

Because of the critical role of ATR in DDR, pharmacological inhibition of ATR may be an effective cancer treatment in a number of specific settings. Indeed, several cancers (e.g. oncogene-driven tumors) are characterized by higher levels of replication stress compared to normal cells, and blockade of ATR can increase their genomic instability and induce substantial cell death (O. Gilad et al., Cancer Res. 70, 9693-9702, 2010). Moreover, most cancers are characterized by loss or deregulation of one or more DDR pathways, resulting in increased genomic instability and greater dependency on remaining DDR pathways for survival. For example, a cancer cell that has a defective G1 checkpoint as a consequence of mutations in p53, will rely more on the G2/M checkpoints to allow DNA repair and cell survival. Inhibition of ATR, a key regulator of the G2/M checkpoints, can result in complete loss of DNA damage checkpoints, ultimately leading to accumulation of DNA damage and mitotic catastrophe. Normal cells, with a functioning G1 checkpoint, would be less affected by pharmacological inhibition of ATR. Similarly, in cancer cells harboring ATM-deficiency, ATR inhibition results in a synthetic lethality dependency, leading to increased sensitivity and preferential killing. Therefore, ATR inhibition could be used for treatment of tumors with deficient ATM and/or p53 function (P. M. Reaper, M. R. Griffiths et al., Nature Chem. Bio. 7, 428-430, 2011)

Additional potential synthetic lethality interactions between ATR and other components of the DDR pathway have been reported, and might be exploited by treatment with ATR inhibitors, including treatment of cancers characterized by loss/deficiency of XRCC1, ERCC1, MRE11 and other components if the MRN complex (reviewed in A. M. Weber et al., Pharmacology and Therapeutics 2015, 149, 124-138). Recently, a synthetic lethality dependency has been reported for ATR inhibition in tumors deficient for ARID1-A, a member of the SWI/SNF chromatin-remodelling complex frequently mutated in human cancer (C. T. Williamson et al., Nature Communications, 2016, 7, 13837).

ATR inhibition can be exploited for treatment of cancer also in combination with DNA-damaging therapeutic agents, such as radiotherapy and chemotherapy. Widely used chemotherapies include antimetabolites (e.g. gemcitabine), DNA crosslinking agents such as platinum salts, alkylating agents (e.g. temozolomide) and inhibitors of topoisomerase (e.g. camptothecin, topotecan, irinotecan). Administration of these agents and/or ionizing radiation results in a variety of DNA lesions that ultimately bring the cancer cells towards mitotic catastrophe and cell death. In cancer cells treated with such agents, inhibition of ATR signalling can prevent DNA damage repair, thus further reducing the often already compromised abilities of cancer cells to respond to the induced replication stress, and hence potentiating the effectiveness of the above treatments.

An additional opportunity to leverage ATR inhibition in combination therapy is together with other DDR agents, for example in combination with inhibitors of Poly ADP ribose polymerase (PARP). PARP inhibitors prevent the repair of single strand DNA breaks, resulting into formation of DNA double strand breaks. In the context of cancers that are deficient in the homologous recombination (HR) DNA repair pathway, such as BRCA 1/2 mutant cancers, PARP inhibition has proven clinically efficacious. Recent reports highlight that targeting critical cell-cycle checkpoints at the same time—for example by combining a PARP inhibitor with an ATR inhibitor—results in increased sensitivity to PARP inhibition and in significant efficacy in several preclinical cancer models, including PARP inhibitor resistant patient derived models. These findings highlight the potential clinical applications of ATR inhibition in combination with other DDR inhibitors, and the field is likely to expand to several other combination opportunities beyond PARP inhibitors (H. Kim et al., Clinical Cancer Research, April 2017, DOI:10.1158/1078-0432.CCR-16-2273; A. Y. K. Lau et al., AACR National Meeting 2017, Abstract 2494/25, ATR inhibitor AZD6738 as monotherapy and in combination with olaparib or chemotherapy: defining pre-clinical dose-schedules and efficacy modelling).

Thus, disclosed herein are methods for treating cancers using ATR inhibitors, in particular cancers characterized by elevated levels of replication stress, defective in cell cycle checkpoints, or harboring defects in cellular DNA damage repair pathways, such as deficiency in the ATM/p53 pathway or additional synthetic lethality dependencies with other DDR components. Also disclosed herein are methods using ATR inhibitors to treat cancers that are mutated/defective in ARID1A, or are mutated/defective in cellular pathways that are in a synthetic lethal dependency with the ATR pathway. Disclosed herein are also methods for treatment of cancer using ATR inhibitors in combination with radiation, with DNA damaging chemotherapeutic agents, and with other DDR inhibitors, including PARP inhibitors.

Furthermore, inhibition of ATR offers an opportunity for treatment of certain cancers associated with the regulation of telomere length. Telomeres are nucleoprotein complexes comprising both hexanucleotide DNA repeat sequences and telomere-associated proteins, which act to stabilize the ends of chromosomes. In normal somatic cells, shortening of the telomeres over time leads to senescence or apoptosis, and this action can act as an upper limit on cellular life span. In most advanced cancers, the enzyme telomerase is activated, whose role is to add a repeat sequence to the 3' end of the DNA, thus reversing the telomere shortening process and increasing the cellular lifespan. Thus, activation of telomerase has been invoked in cancer cell immortalization. A second, telomerase-independent mechanism for maintaining telomeres, termed Alternate Lengthening of Telomers (ALT), has been implicated in approximately 5% of all human cancers, and it is prevalent in specific kinds of cancer, including osteosarcoma and glioblastoma. ALT is enriched in mesenchymal-originating tumors, and is usually associated with decreased survival rates. Studies revealed that ATR kinase is functionally required for ALT, and that ALT cells are more sensitive to ATR inhibition (R. L. Flynn, K. E. Cox, Science 2015, 347 (6219), 273-277).

There is a need for therapies having efficacy towards ALT-positive cancers. The ALT pathway is poorly understood, and cancers that feature ALT are resistant to the action of telomerase inhibitors. Thus, described herein are methods for treating cancers, particular ALT-positive types of cancers, using ATR inhibitors.

Disclosed herein are novel compounds and pharmaceutical compositions, certain of which have been found to inhibit ATR kinase, together with methods of synthesizing and using the compounds, including methods for the treatment of ATR kinase-mediated diseases in a patient by administering the compounds.

Provided herein is Embodiment 1: a compound having structural Formula (I):

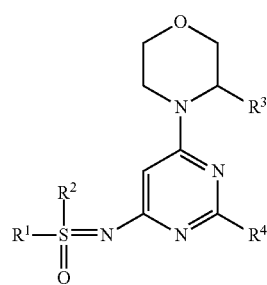

(I)

or a salt thereof, wherein:
$R^1$ and $R^2$ are independently chosen from $C_{1-4}$alkyl, $C_{1-4}$haloalkyl, $C_{3-6}$cycloalkyl, heterocycloalkyl, aryl, and heteroaryl, any of which is optionally substituted with one or more $R^5$ groups, or $R^1$ and $R^2$, together with the sulfur to which they are both attached, form a heterocycloalkyl ring which is optionally substituted with one or more $R^5$ groups;

$R^3$ is chosen from hydrogen, $C_{1-6}$alkyl, and $C_{1-6}$haloalkyl;

$R^4$ is chosen from $C_{5-10}$aryl and heteroaryl, either of which is optionally substituted with one or more $R^6$ groups;

each $R^5$ is independently chosen from $NR^8R^9$, halogen, cyano, hydroxy, oxo, alkyl, haloalkyl, cycloalkyl, heterocycloalkyl, hydroxyalkyl, $OR^8$, $NRC(O)R^8$, $NR^7C(O)OR^8$, $NR^7C(O)NR^8R^9$, $C(O)R^8$, $C(O)OR^8$, and $C(O)NR^8R^9$;

each $R^6$ is independently chosen from $NR^{11}R^{12}$, halogen, cyano, hydroxy, oxo, alkyl, haloalkyl, cycloalkyl, heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$;

each $R^7$, $R^8$ and $R^9$ is independently chosen from hydrogen, $C_{1-4}$alkyl, $C_{3-6}$cycloalkyl, and heterocycloalkyl, any of which is optionally substituted with halo, hydroxy, $C_{1-3}$alkyl, $C_{1-3}$haloalkyl, and $C_{1-3}$alkoxy; or any two of $R^7$, $R^8$ and $R^9$, together with the atom to which they are both attached can form a 3-7 membered cycloalkyl or heterocycloalkyl ring; and each $R^{10}$, $R^{11}$ and $R^{12}$ is independently chosen from hydrogen, $C_{1-4}$alkyl, $C_{3-6}$cycloalkyl, and heterocycloalkyl, any of which is optionally substituted with one or more groups chosen from halo, hydroxy, and alkoxy; or any two of $R^{10}$, $R^{11}$ and $R^{12}$, together with the atom to which they are both attached, can form a 3-7 membered cycloalkyl or heterocycloalkyl ring.

Certain compounds disclosed herein may possess useful ATR kinase inhibiting activity, and may be used in the treatment or prophylaxis of a disease or condition in which ATR kinase plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting ATR kinase. Other embodiments provide methods for treating an ATR kinase-mediated disorder in a patient in need of such treatment, comprising administering to the patient in need thereof a therapeutically effective amount of a compound or composition according to the present disclosure. Also provided is the use of certain compounds disclosed herein for use in the manufacture of a medicament for the treatment of a disease or condition ameliorated by the inhibition of ATR kinase.

In certain embodiments, $R^1$ and $R^2$ are independently chosen from $C_{1-4}$alkyl, $C_{1-4}$haloalkyl, $C_{3-6}$cycloalkyl, 3-6 membered heterocycloalkyl, $C_{5-10}$aryl, and 5-10 membered heteroaryl, any of which is optionally substituted with one or more $R^5$ groups, or $R^1$ and $R^2$, together with the sulfur to which they are both attached, form a heterocycloalkyl ring which is optionally substituted with one or more $R^5$ groups.

In certain embodiments, $R^1$ and $R^2$ are independently chosen from $C_{1-4}$alkyl, $C_{1-4}$haloalkyl, $C_{3-6}$cycloalkyl, 3-6 membered heterocycloalkyl, $C_{5-10}$aryl, and 5-10 membered heteroaryl, any of which is optionally substituted with one or more $R^5$ groups, or $R^1$ and $R^2$, together with the sulfur to which they are both attached, form a heterocycloalkyl ring which is optionally substituted with one or more $R^5$ groups.

In certain embodiments, $R^1$ and $R^2$ are independently chosen from $C_{1-4}$alkyl, $C_{1-4}$haloalkyl, $C_{3-6}$cycloalkyl, 3-6 membered heterocycloalkyl, $C_{5-10}$aryl, and 5-10 membered heteroaryl, any of which is optionally substituted with one or more $R^5$ groups, or $R^1$ and $R^2$, together with the sulfur to which they are both attached, form a 4, 5, 6, or 7-membered heterocycloalkyl ring which is optionally substituted with one or more $R^5$ groups.

In certain embodiments, $R^4$ is chosen from $C_{5-10}$ aryl and $C_{5-10}$heteroaryl, either of which is optionally substituted with one or more $R^6$ groups.

In certain embodiments, $R^4$ is chosen from $C_{5-10}$ aryl and 5-10 membered heteroaryl, either of which is optionally substituted with one or more $R^6$ groups.

In certain embodiments, $R^4$ is chosen from

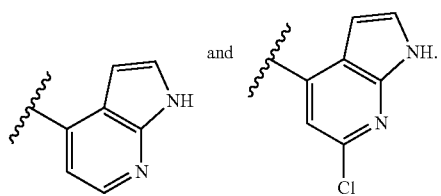 [SMILES: *c1ccnc2[nH]ccc12 ; *c1cc(Cl)nc2[nH]ccc12]

each $R^5$ is independently chosen from $NR^8R^9$, halogen, cyano, hydroxy, oxo, alkyl, haloalkyl, $C_{3-6}$cycloalkyl, 3-6 membered heterocycloalkyl, hydroxyalkyl, $OR^8$, $NRC(O)R^8$, $NR^7C(O)OR^8$, $NR^7C(O)NR^8R^9$, $C(O)R^8$, $C(O)OR^8$, and $C(O)NR^8R^9$ In certain embodiments, each $R^5$ is independently chosen from $NR^8R^9$, halogen, cyano, hydroxy, oxo, alkyl, haloalkyl, $C_{3-6}$cycloalkyl, 3-6 membered heterocycloalkyl, hydroxyalkyl, $OR^8$, $NR^7C(O)R^8$, $NR^7C(O)OR^8$, $NR^7C(O)NR^8R^9$, $C(O)R^8$, $C(O)OR^8$, and $C(O)NR^8R^9$.

In certain embodiments, each $R^5$ is independently chosen from $C(O)R^8$, $C(O)OR^8$, and $C(O)NR^8R^9$.

In certain embodiments, each $R^5$ is independently chosen from $C(O)R^8$ and $C(O)OR^8$.

In certain embodiments, each $R^6$ is independently chosen from $NR^{11}R^{12}$, halogen, cyano, hydroxy, oxo, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$.

In certain embodiments, each $R^6$ is independently chosen from $NR^{11}R^{12}$, halogen, cyano, hydroxy, and oxo.

In certain embodiments, each $R^6$ is independently chosen from halogen and cyano.

In certain embodiments, each $R^7$, $R^8$ and $R^9$ is independently chosen from hydrogen, $C_{1-4}$alkyl, $C_{3-6}$cycloalkyl, and 3-6 membered heterocycloalkyl, any of which is optionally substituted with halo, hydroxy, $C_{1-3}$alkyl, $C_{1-3}$haloalkyl, and $C_{1-3}$alkoxy; or any two of $R^7$, $R^8$ and $R^9$, together with the atom to which they are both attached can form a 3-7 membered cycloalkyl or heterocycloalkyl ring.

In certain embodiments, each $R^{10}$, $R^{11}$ and $R^{12}$ is independently chosen from hydrogen, $C_{1-4}$alkyl, $C_{3-6}$cycloalkyl, and 3-6 membered heterocycloalkyl, any of which is optionally substituted with halo, hydroxy, $C_{1-3}$alkyl, $C_{1-3}$haloalkyl, and $C_{1-3}$alkoxy; or any two of $R^7$, $R^8$ and $R^9$, together with the atom to which they are both attached can form a 3-7 membered cycloalkyl or heterocycloalkyl ring.

The disclosure provides the further embodiments:

Embodiment 2: The compound of Embodiment 1, or salt thereof, wherein $R^3$ is chosen from methyl, fluoromethyl, difluoromethyl, and trifluoromethyl.

Embodiment 3: The compound of Embodiment 1, or salt thereof, wherein $R^3$ is $C_{1-6}$alkyl.

Embodiment 4: The compound of Embodiment 3, or salt thereof, wherein $R^3$ is methyl.

Provided herein is Embodiment 5: a compound having structural Formula (II):

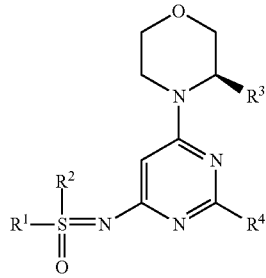

(II)

or a salt thereof, wherein:

$R^1$ and $R^2$ are independently chosen from $C_{1-4}$alkyl, $C_{1-4}$haloalkyl, $C_{3-6}$cycloalkyl, $C_{3-6}$ heterocycloalkyl, $C_{5-10}$aryl, and 5-10 membered heteroaryl, any of which is optionally substituted with one or more $R^5$ groups, or $R^1$ and $R^2$, together with the sulfur to which they are both attached, form a 4, 5, 6, or 7-membered heterocycloalkyl ring which is optionally substituted with one or more $R^5$ groups;

$R^3$ is chosen from hydrogen, $C_{1-6}$alkyl, and $C_{1-6}$haloalkyl;

$R^4$ is chosen from $C_{5-10}$aryl and 5-10 membered heteroaryl, either of which is optionally substituted with one or more $R^6$ groups;

each $R^5$ is independently chosen from $NR^8R^9$, halogen, cyano, hydroxy, oxo, alkyl, haloalkyl, $C_{3-6}$cycloalkyl, 3-6 membered heterocycloalkyl, hydroxyalkyl, $OR^8$, $NRC(O)R^8$, $NR^7C(O)OR^8$, $NR^7C(O)NR^8R^9$, $C(O)R^8$, $C(O)OR^8$, and $C(O)NR^8R^9$;

each $R^6$ is independently chosen from $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$;

each $R^7$, $R^8$ and $R^9$ is independently chosen from hydrogen, $C_{1-4}$alkyl, $C_{3-6}$cycloalkyl, and 3-6 membered heterocycloalkyl, any of which is optionally substituted with halo, hydroxy, $C_{1-3}$alkyl, $C_{1-3}$haloalkyl, and $C_{1-3}$alkoxy; or any two of $R^7$, $R^8$ and $R^9$, together with the atom to which they are both attached can form a 3-7 membered cycloalkyl or heterocycloalkyl ring; and each $R^{10}$, $R^{11}$ and $R^{12}$ is independently chosen from hydrogen, $C_{1-4}$alkyl, $C_{3-6}$cycloalkyl, and 3-6 membered heterocycloalkyl, any of which is optionally substituted with one or more groups chosen from halo, hydroxy, and alkoxy; or any two of $R^{10}$, $R^{11}$ and $R^{12}$, together with the atom to which they are both attached, can form a 3-7 membered cycloalkyl or heterocycloalkyl ring.

The disclosure provides the further embodiments:

Embodiment 6: The compound of Embodiment 5, or salt thereof, wherein $R^3$ is $C_{1-6}$alkyl.

Embodiment 7: The compound of Embodiment 6, or salt thereof, wherein $R^3$ is chosen from methyl, fluoromethyl, difluoromethyl, and trifluoromethyl.

Embodiment 8: The compound of Embodiment 6, or salt thereof, wherein $R^3$ is methyl.

Embodiment 9: The compound of any of Embodiments 5-7, or salt thereof, wherein $R^4$ is 5-10 membered heteroaryl and is optionally substituted with one or more $R^6$ groups.

Embodiment 10: The compound of Embodiment 9, or salt thereof, wherein $R^4$ is chosen from indole, pyrrolopyridine, pyrazolopyridine, imidazopyridine, pyrrolopyrazine, pyrazolopyrazine, pyrrolopyrimidine, pyrazolopyrimidine, imidazolopyrimidine, pyrrolopyridazine, pyrazolopyridazine, and imidazolopyridazine, any of which is optionally substituted with one or more $R^6$ groups.

Embodiment 11: The compound of Embodiment 9, wherein $R^4$ is pyridine and is optionally substituted with one or more $R^6$ groups.

Embodiment 12: The compound of Embodiment 11, wherein $R^4$ is unsubstituted pyridine.

Embodiment 13: The compound of Embodiment 11, wherein $R^4$ is pyridine and is substituted with one $R^6$ group.

Embodiment 14: The compound of Embodiment 11, wherein $R^4$ is pyridine and is substituted with two $R^6$ groups.

Embodiment 15: The compound of Embodiment 10, or salt thereof, wherein $R^4$ is selected from 1H-pyrrolo[2,3-b]pyridine, 7H-pyrrolo[2,3-c]pyridazine, 7H-pyrrolo[2,3-d]pyrimidine, and 5H-pyrrolo[2,3-b]pyrazine, any of which is optionally substituted with one, two, or three $R^6$ groups.

Embodiment 16: The compound of Embodiment 15, or salt thereof, wherein $R^4$ is 1H-pyrrolo[2,3-b]pyridine and is optionally substituted with one or two $R^6$ groups.

Embodiment 17: The compound of any of Embodiments 5-16, or salt thereof, wherein wherein each $R^6$ is independently selected from $NR^{11}R^{12}$, halogen, cyano, hydroxy, oxo, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$.

Embodiment 18: The compound of Embodiment 17, or salt thereof, wherein each $R^6$ is independently selected from $NR^{11}R^{12}$, halogen, cyano, hydroxy, and oxo.

Embodiment 19: The compound of Embodiment 5-18, or salt thereof, wherein $R^4$ is selected from

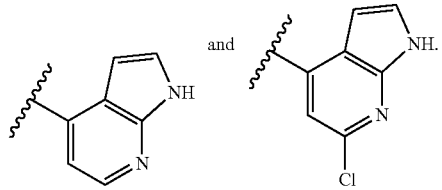 [SMILES: *c1ccnc2[nH]ccc12 ; *c1cc(Cl)nc2[nH]ccc12]

Embodiment 20: The compound of Embodiment 19, or salt thereof, wherein
$R^1$ and $R^2$ are independently chosen from $C_{1-4}$alkyl, $C_{1-4}$haloalkyl, $C_{3-6}$cycloalkyl, $C_{3-6}$heterocycloalkyl, $C_{5-10}$aryl and 5-10 membered heteroaryl, and are optionally substituted with one or two $R^5$ groups, or $R^1$ and $R^2$, together with the sulfur to which they are both attached, form a 4, 5, 6, or 7-membered heterocycloalkyl ring which is optionally substituted with one or two $R^5$ groups;
each $R^5$ is independently selected from $NR^8R^9$, halogen, cyano, hydroxy, oxo, alkyl, haloalkyl, $C_{3-6}$cycloalkyl, 3-6 membered heterocycloalkyl, hydroxyalkyl, $OR^8$, $NRC(O)R^8$, $NR^7C(O)OR^8$, $NR^7C(O)NR^8R^9$, $C(O)R^8$, $C(O)OR^8$, and $C(O)NR^8R^9$.

Embodiment 21: The compound of Embodiment 20, or salt thereof, wherein each $R^5$ is independently selected from alkyl, haloalkyl, $C_{3-6}$cycloalkyl, 3-6 membered heterocycloalkyl, hydroxyalkyl, $OR^8$, $NRC(O)R^8$, $NRC(O)OR^8$, $NR^7C(O)NR^8R^9$, $C(O)R^8$, $C(O)OR^8$, and $C(O)NR^8R^9$.

Embodiment 22: The compound of Embodiment 21, or salt thereof, wherein each $R^5$ is independently selected from $C(O)R^8$, $C(O)OR^8$, and $C(O)NR^8R^9$.

Embodiment 23: The compound of Embodiment 22, or salt thereof, wherein $R^1$ and $R^2$ are independently chosen from $C_{1-4}$alkyl, $C_{1-4}$haloalkyl, $C_{3-6}$cycloalkyl, 3-6 membered heterocycloalkyl, $C_{5-10}$aryl and 5-10 membered heteroaryl, and are optionally substituted with one or two $R^5$ groups.

Embodiment 24: The compound of Embodiment 23, or salt thereof, wherein $R^1$ and $R^2$ are independently chosen from $C_{1-4}$alkyl, $C_{1-4}$haloalkyl, $C_{3-6}$cycloalkyl, and 3-6 membered heterocycloalkyl, and are optionally substituted with one or two $R^5$ groups.

Embodiment 25: The compound of Embodiment 23, or salt thereof, wherein $R^1$ and $R^2$ are independently chosen from $C_{1-4}$alkyl and $C_{3-6}$cycloalkyl.

Embodiment 26: The compound of Embodiment 23, or salt thereof, wherein $R^1$ and $R^2$, together with the sulfur to which they are both attached, forms a heterocycloalkyl ring and is optionally substituted with one or two $R^5$ groups.

Embodiment 27: The compound of Embodiment 10, or salt thereof, wherein $R^4$ is chosen from 1H-pyrazol-1-yl, 1H-pyrazol-3-yl, 1H-pyrazol-4-yl, 1H-imidazol-1-yl, 1H-imidazol-2-yl, 1H-imidazol-4-yl, pyridin-3-yl, pyridin-4-yl, pyrimidin-4-yl, 1H-indol-1-yl, 1H-indol-4-yl, 1H-indazol-1-yl, 1H-indazol-4-yl, 1H-benzo[d]imidazol-1-yl, 1H-benzo[d]imidazol-4-yl, 1H-pyrrolo[2,3-b]pyridin-4-yl, 1H-pyrrolo[2,3-c]pyridin-4-yl, pyrazolo[1,5-a]pyridin-3-yl, imidazo[1,2-a]pyridin-3-yl, imidazo[1,2-a]pyridin-5-yl, 1H-imidazo[4,5-c]pyridin-1-yl, 7H-pyrrolo[2,3-d]pyrimidin-4-yl, 1H-pyrazolo[3,4-b]pyridin-4-yl, 3H-imidazo[4,5-b]pyridin-7-yl, and 1H-benzo[d][1,2,3]triazol-1-yl, any of which is optionally substituted with one or two $R^6$ groups.

Embodiment 28: The compound of Embodiment 27, wherein $R^4$ is chosen from 1H-benzo[d]imidazol-1-yl, 1H-pyrrolo[2,3-b]pyridin-4-yl)pyrimidin-4-yl)imino, 1H-indol-4-yl, pyridin-4-yl, any of which is optionally substituted with one or two $R^6$ groups chosen from amino, fluoro, methyl, methoxy, difluoromethyl, trifluoromethyl, hydroxymethyl, 1H-pyrrolo[2,3-c]pyridin-4-yl)pyrimidin-4-yl)imino.

Embodiment 29: The compound of Embodiment 27, or salt thereof, wherein each $R^6$ is independently chosen from $NR^{11}R^{12}$, halogen, cyano, hydroxy, oxo, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$.

Embodiment 30: The compound of Embodiment 29, or salt thereof, wherein each $R^5$ is independently chosen from $C(O)R^8$, $C(O)OR^8$, and $C(O)NR^8R^9$.

Embodiment 31: The compound of Embodiment 30, or salt thereof, wherein $R^1$ and $R^2$ are independently chosen from $C_{1-4}$alkyl, $C_{1-4}$haloalkyl, $C_{3-6}$cycloalkyl, 3-6 membered heterocycloalkyl, $C_{5-10}$aryl, and 5-10 membered heteroaryl, any of which is optionally substituted with one or two $R^5$ groups.

Embodiment 32: The compound of Embodiment 31, wherein $R^1$ and $R^2$ are independently chosen from $C_{1-4}$alkyl, C$_{1-4}$haloalkyl, C$_{3-6}$cycloalkyl, and 3-6 membered heterocycloalkyl, and are optionally substituted with one or two R$^5$ groups.

Embodiment 33: The compound of Embodiment 32, or salt thereof, wherein R$^1$ and R$^2$ are independently chosen from C$_{1-4}$alkyl, C$_{3-6}$cycloalkyl, and 3-6 membered heterocycloalkyl.

Embodiment 34: The compound of Embodiment 32, or salt thereof, wherein R$^1$ and R$^2$ are independently chosen from C$_{1-4}$alkyl, C$_{3-6}$cycloalkyl, and 3-6 membered heterocycloalkyl.

Embodiment 35: The compound of either of Embodiments 33 or 34, or salt thereof, wherein R$^4$ is chosen from pyrrolo[2,3-b]pyridin-4-yl, 1H-pyrrolo[2,3-b]pyridin-4-yl, pyrrolo[2,3-c]pyridin-4-yl, benzo[d]imidazol-1-yl.

Embodiment 36: The compound of Embodiment 36, or salt thereof, wherein R$^4$ is chosen from 1H-benzo[d]imidazol-1-yl and pyrrolo[2,3-b]pyridin-4-yl, either of which is optionally substituted with one or two R$^6$ groups.

Embodiment 37: The compound of Embodiment 36, or salt thereof, wherein R$^3$ is methyl.

Embodiment 38: The compound of Embodiment 37, or salt thereof, wherein R$^1$ and R$^2$ are independently chosen from methyl, cyclopropyl, and oxetan-3-yl.

Embodiment 39: The compound of Embodiment 30, or salt thereof, wherein R$^1$ and R$^2$, together with the sulfur to which they are both attached, form a thiomorpholine ring which is optionally substituted with one or two R$^5$ groups.

Embodiment 40: The compound of Embodiment 39, or salt thereof, wherein R$^1$ and R$^2$, together with the sulfur to which they are both attached, form a thiomorpholine ring which is substituted on the nitrogen eighth an R$^5$ group chosen from chosen from C(O)R$^8$ and C(O)OR$^8$.

Provided herein is Embodiment 41: a compound having structural Formula (III):

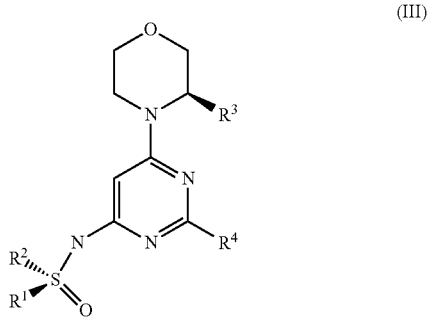

(III)

or a salt thereof, wherein:
R$^1$ and R$^2$ are independently chosen from C$_{1-4}$alkyl, C$_{1-4}$haloalkyl, C$_{3-6}$cycloalkyl, C$_{3-6}$ heterocycloalkyl, C$_{5-10}$aryl, and 5-10 membered heteroaryl, any of which is optionally substituted with one or more R$^5$ groups, or R$^1$ and R$^2$, together with the sulfur to which they are both attached, form a 4, 5, 6, or 7-membered heterocycloalkyl ring which is optionally substituted with one or more R$^5$ groups;
R$^3$ is chosen from hydrogen, C$_{1-6}$alkyl, and C$_{1-6}$haloalkyl;
R$^4$ is chosen from C$_{5-10}$aryl and 5-10 membered heteroaryl, either of which is optionally substituted with one or more R$^6$ groups;
each R$^5$ is independently chosen from NR$^8$R$^9$, halogen, cyano, hydroxy, oxo, alkyl, haloalkyl, C$_{3-6}$cycloalkyl, 3-6 membered heterocycloalkyl, hydroxyalkyl, OR$^8$, NRC(O)R$^8$, NR$^7$C(O)OR$^8$, NR$^7$C(O)NR$^8$R$^9$, C(O)R$^8$, C(O)OR$^8$, and C(O)NR$^8$R$^9$;
each R$^6$ is independently chosen from NR$^{11}$R$^{12}$, halogen, cyano, hydroxy, oxo, alkyl, haloalkyl, C$_{3-6}$cycloalkyl, 3-6 membered heterocycloalkyl, hydroxyalkyl, OR$^{11}$, NR$^{10}$C(O)R$^{11}$, NR$^{10}$C(O)OR$^{11}$, NR$^{10}$C(O)NR$^{11}$R$^{12}$, C(O)R$^{11}$, C(O)OR$^{11}$, and C(O)NR$^{11}$R$^{12}$;
each R$^7$, R$^8$ and R$^9$ is independently chosen from hydrogen, C$_{1-4}$alkyl, C$_{3-6}$cycloalkyl, and 3-6 membered heterocycloalkyl, any of which is optionally substituted with halo, hydroxy, C$_{1-3}$alkyl, C$_{1-3}$haloalkyl, and C$_{1-3}$alkoxy; or any two of R$^7$, R$^8$ and R$^9$, together with the atom to which they are both attached can form a 3-7 membered cycloalkyl or heterocycloalkyl ring; and
each R$^{10}$, R$^{11}$ and R$^{12}$ is independently chosen from hydrogen, C$_{1-4}$alkyl, C$_{3-6}$cycloalkyl, and 3-6 membered heterocycloalkyl, any of which is optionally substituted with one or more groups chosen from halo, hydroxy and alkoxy; or any two of R$^{10}$, R$^{11}$ and R$^{12}$, together with the atom to which they are both attached, can form a 3-7 membered cycloalkyl or heterocycloalkyl ring.

The disclosure provides the further embodiments:
Embodiment 42: The compound of Embodiment 1, or salt thereof, wherein R$^4$ is 5-10 membered heteroaryl and is optionally substituted with one or more R$^6$ groups.

Embodiment 43: The compound of Embodiment 42, or salt thereof, wherein R$^4$ is chosen from monocyclic 5-10 membered heteroaryl and bicyclic 5-10 membered heteroaryl, either of which is optionally substituted with one or more R$^6$ groups.

Embodiment 44: The compound of Embodiment 43, or salt thereof, wherein R$^4$ is chosen from pyrazolyl, imidazolyl, pyridinyl, pyrimidinyl, indolyl, indazolyl, benzimidazolyl, benzotriazolyl, pyrrolopyridinyl, pyrazolopyridinyl, imidazopyridinyl, pyrrolopyrazinyl, pyrazolopyrazinyl, pyrrolopyrimidinyl, pyrazolopyrimidinyl, imidazolopyrimidinyl, pyrrolopyridazinyl, pyrazolopyridazinyl, and imidazolopyridazinyl, any of which is optionally substituted with one or more R$^6$ groups.

Embodiment 45: The compound of Embodiment 44, or salt thereof, wherein R$^4$ is chosen from pyrazolyl, imidazolyl, pyridinyl, pyrimidinyl, indolyl, indazolyl, benzo[d]imidazolyl, imidazo[1,2-a]pyridinyl, pyrazolo[1,5-a]pyridinyl, pyrrolo[2,3-b]pyridinyl, pyrrolo[2,3-c]pyridinyl, benzo[d][1,2,3]triazolyl, pyrrolo[2,3-d]pyrimidinyl, pyrazolo[3,4-b]pyridinyl, imidazo[4,5-b]pyridinyl, and imidazo[4,5-c]pyridinyl, any of which is optionally substituted with one or more R$^6$ groups.

Embodiment 46: The compound of Embodiment 44, or salt thereof, wherein R$^4$ is chosen from 1H-pyrazol-1-yl, 1H-pyrazol-3-yl, 1H-pyrazol-4-yl, 1H-imidazol-1-yl, 1H-imidazol-2-yl, 1H-imidazol-4-yl, pyridin-3-yl, pyridin-4-yl, pyrimidin-4-yl, 1H-indol-1-yl, 1H-indol-4-yl, 1H-indazol-1-yl, 1H-indazol-4-yl, 1H-benzo[d]imidazol-1-yl, 1H-benzo[d]imidazol-4-yl, 1H-pyrrolo[2,3-b]pyridin-4-yl, 1H-pyrrolo[2,3-c]pyridin-4-yl, pyrazolo[1,5-a]pyridin-3-yl, imidazo[1,2-a]pyridin-3-yl, imidazo[1,2-a]pyridin-5-yl, 1H-imidazo[4,5-c]pyridin-1-yl, 7H-pyrrolo[2,3-d]pyrimidin-4-yl, 1H-pyrazolo[3,4-b]pyridin-4-yl, 3H-imidazo[4,5-b]pyridin-7-yl, and 1H-benzo[d][1,2,3]triazol-1-yl, any of which is optionally substituted with one or two R$^6$ groups.

Embodiment 47: The compound of Embodiment 45, or salt thereof, wherein R$^4$ is chosen from imidazo[4,5-b]pyridinyl, imidazo[4,5-c]pyridazinyl, and imidazo[4,5-b]pyrazinyl, any of which is optionally substituted with one, two, or three R$^6$ groups.

Embodiment 48: The compound of Embodiment 47, or salt thereof, wherein $R^4$ is chosen from pyrrolo[2,3-b]pyridinyl, pyrrolo[2,3-c]pyridazinyl, pyrrolo[2,3-d]pyrimidinyl, and pyrrolo[2,3-b]pyrazine, any of which is optionally substituted with one, two, or three $R^6$ groups.

Embodiment 49: The compound of Embodiment 48, or salt thereof, wherein $R^4$ is pyrrolo[2,3-b]pyridinyl and is optionally substituted with one or two $R^6$ groups.

Provided herein is Embodiment 50: a compound having structural Formula (IV):

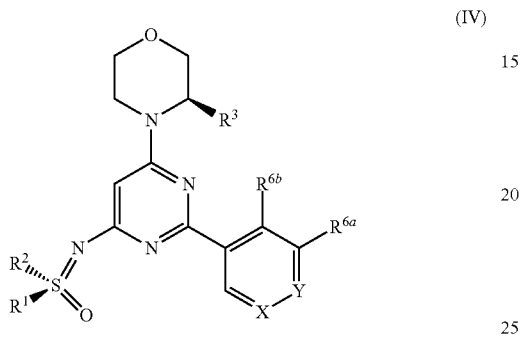

(IV)

or a salt thereof, wherein:

X is chosen from N and $CR^{6c}$;
Y is chosen from N and $CR^{6d}$;
$R^1$ and $R^2$ are independently chosen from $C_{1-4}$alkyl, $C_{1-4}$haloalkyl, $C_{3-6}$cycloalkyl, $C_{3-6}$ heterocycloalkyl, $C_{5-10}$aryl, and 5-10 membered heteroaryl, any of which is optionally substituted with one or more $R^5$ groups, or $R^1$ and $R^2$, together with the sulfur to which they are both attached, form a 4, 5, 6, or 7-membered heterocycloalkyl ring which is optionally substituted with one or more $R^5$ groups;
$R^3$ is chosen from hydrogen, $C_{1-6}$alkyl, and $C_{1-6}$haloalkyl;
each $R^5$ is independently chosen from $NR^8R^9$, halogen, cyano, hydroxy, oxo, alkyl, haloalkyl, $C_{3-6}$cycloalkyl, 3-6 membered heterocycloalkyl, hydroxyalkyl, $OR^8$, $NRC(O)R^8$, $NR^7C(O)OR^8$, $NR^7C(O)NR^8R^9$, $C(O)R^8$, $C(O)OR^8$, and $C(O)NR^8R^9$;
$R^{6a}$ and $R^{6b}$ are independently chosen from H, $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$,
or $R^{6a}$ and $R^{6b}$, together with the intervening atoms, combine to form a heteroaryl ring, which is optionally substituted with one or more $R^6$ groups;
each $R^{6c}$ and $R^{6d}$ is independently chosen from H, $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$;
$R^6$ is chosen from $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$;
each $R^7$, $R^8$ and $R^9$ is independently chosen from hydrogen, $C_{1-4}$alkyl, $C_{3-6}$cycloalkyl, and 3-6 membered heterocycloalkyl, any of which is optionally substituted with halo, hydroxy, $C_{1-3}$alkyl, $C_{1-3}$haloalkyl, and $C_{1-3}$alkoxy; or any two of $R^7$, $R^8$ and $R^9$, together with the atom to which they are both attached can form a 3-7 membered cycloalkyl or heterocycloalkyl ring; and
each $R^{10}$, $R^{11}$ and $R^{12}$ is independently chosen from hydrogen, $C_{1-4}$alkyl, $C_{3-6}$cycloalkyl, and 3-6 membered heterocycloalkyl, any of which is optionally substituted with one or more groups chosen from halo, hydroxy and alkoxy; or any two of $R^{10}$, $R^{11}$ and $R^{12}$, together with the atom to which they are both attached, can form a 3-7 membered cycloalkyl or heterocycloalkyl ring.

Provided herein is Embodiment 51: a compound having structural Formula (IVa):

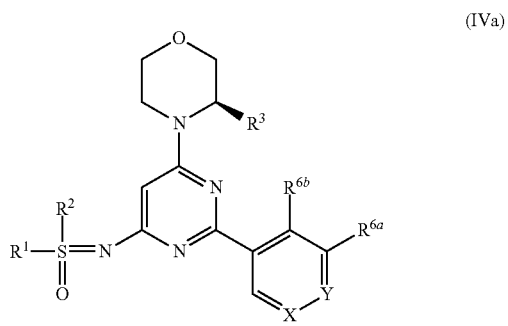

(IVa)

or a salt thereof, wherein:

X is chosen from N and $CR^6$;
Y is chosen from N and $CR^{6d}$;
$R^1$ and $R^2$ are independently chosen from $C_{1-4}$alkyl, $C_{1-4}$haloalkyl, $C_{3-6}$cycloalkyl, $C_{3-6}$ heterocycloalkyl, $C_{5-10}$aryl, and 5-10 membered heteroaryl, any of which is optionally substituted with one or more $R^5$ groups, or $R^1$ and $R^2$, together with the sulfur to which they are both attached, form a 4, 5, 6, or 7-membered heterocycloalkyl ring which is optionally substituted with one or more $R^5$ groups;
$R^3$ is chosen from hydrogen, $C_{1-6}$alkyl, and $C_{1-6}$haloalkyl;
each $R^5$ is independently chosen from $NR^8R^9$, halogen, cyano, hydroxy, oxo, alkyl, haloalkyl, $C_{3-6}$cycloalkyl, 3-6 membered heterocycloalkyl, hydroxyalkyl, $OR^8$, $NRC(O)R^8$, $NR^7C(O)OR^8$, $NR^7C(O)NR^8R^9$, $C(O)R^8$, $C(O)OR^8$, and $C(O)NR^8R^9$;
$R^{6a}$ and $R^{6b}$ are independently chosen from H, $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$ or $R^{6a}$ and $R^{6b}$, together with the intervening atoms, combine to form a heteroaryl ring, which is optionally substituted with one or more $R^6$ groups;
each $R^{6c}$ and $R^{6d}$ is independently chosen from H, $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$;
$R^6$ is chosen from $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$;
each $R^7$, $R^8$ and $R^9$ is independently chosen from hydrogen, $C_{1-4}$alkyl, $C_{3-6}$cycloalkyl, and 3-6 membered heterocycloalkyl, any of which is optionally substituted with halo, hydroxy, $C_{1-3}$alkyl, $C_{1-3}$haloalkyl, and $C_{1-3}$alkoxy; or any two of $R^7$, $R^8$ and $R^9$, together with the atom to which they are both attached can form a 3-7 membered cycloalkyl or heterocycloalkyl ring; and each $R^{10}$, $R^{11}$ and $R^{12}$ is independently chosen from hydrogen, $C_{1-4}$alkyl, $C_{3-6}$cycloalkyl, and 3-6 membered heterocycloalkyl, any of which is optionally substituted with one or more groups chosen from halo, hydroxy and alkoxy; or any two of $R^{10}$, $R^{11}$ and $R^{12}$, together with the atom to which they are both attached, can form a 3-7 membered cycloalkyl or heterocycloalkyl ring.

The disclosure provides the further embodiments:

Embodiment 52: The compound of either one of Embodiments 50 or 51, or salt thereof, wherein $R_3$ is $C_{1-6}$alkyl.

Embodiment 53: The compound of either one of Embodiments 50 or 51, or salt thereof, wherein wherein $R_3$ is chosen from methyl, fluoromethyl, difluoromethyl, and trifluoromethyl.

Embodiment 54: The compound of either one of Embodiments 50 or 51, or salt thereof, wherein $R_3$ is methyl.

Embodiment 55: The compound of any one of Embodiments 50-54, or salt thereof, wherein $R^{6a}$ and $R^{6b}$, together with the intervening atoms, combine to form a five-membered heteroaryl ring chosen from pyrrole, pyrazole, and imidazole, any of which is optionally substituted with one or more $R^6$ groups.

Embodiment 56: The compound of any one of Embodiments 50-55, or salt thereof, wherein $R^6$ is chosen from alkyl, haloalkyl, and cycloalkyl.

Embodiment 57: The compound of any one of Embodiments 50-56, or salt thereof, wherein:
X is $CR^{6c}$; and
Y is N.

Embodiment 58: The compound of any one of Embodiments 50-54 or salt thereof, wherein $R^{6a}$ and $R^{6b}$ are independently chosen from H, $NR^{11}R^{12}$, halogen, cyano, hydroxy, oxo, alkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$.

Embodiment 59: The compound of Embodiment 58, or salt thereof, wherein $R^{6b}$ is H.

Embodiment 60: The compound of either one of Embodiments 58 or 59, or salt thereof, wherein $R^{6a}$ is chosen from H, alkyl, haloalkyl, $C_{3-6}$cycloalkyl, 3-6 membered heterocycloalkyl, and $OR^{11}$.

Embodiment 61: The compound of any one of Embodiments 58-60, or salt thereof, wherein
X is $CR^{6c}$; and
Y is N.

Embodiment 62: The compound of any one of Embodiments 58-61, or salt thereof, wherein $R^6$, is $NH_2$.

Embodiment 63: The compound of any one of Embodiments 58-62, or salt thereof, wherein $R^{6a}$ is chosen from H and $OR^{11}$.

Embodiment 64: The compound of any one of Embodiments 58-63, or salt thereof, wherein $R^{11}$ is $C_{1-4}$alkyl.

Embodiment 65: The compound of any one of Embodiments 58-64, or salt thereof, wherein $R^1$ and $R^2$ are independently chosen from cyclopropyl, oxetan-3-yl, and methyl.

Embodiment 66: The compound of any one of Embodiments 58-65, or salt thereof, wherein at least one of $R^1$ and $R^2$ is methyl.

Embodiment 67: The compound of any one of Embodiments 58-66, or salt thereof, wherein one of $R^1$ and $R^2$ is methyl.

Embodiment 68: The compound of Embodiment 66, or salt thereof, wherein $R^1$ and $R^2$ are methyl.

Embodiment 69: The compound of Embodiment 66, or salt thereof, wherein $R^1$ is methyl and $R^2$ is cyclopropyl.

Embodiment 70: The compound Embodiment 66, or salt thereof, wherein $R^1$ is cyclopropyl and $R^2$ is methyl.

Provided herein is Embodiment 71: a compound having structural Formula (V):

(V)

or a salt thereof, wherein:

X is chosen from N and $CR^6$;

Y is chosen from N and $CR^{6d}$;

$R^1$ and $R^2$ are independently chosen from $C_{1-4}$alkyl, $C_{1-4}$haloalkyl, $C_{3-6}$cycloalkyl, $C_{3-6}$ heterocycloalkyl, $C_{5-10}$aryl, and heteroaryl, any of which is optionally substituted with one or more $R^5$ groups, or $R^1$ and $R^2$, together with the sulfur to which they are both attached, form a 4, 5, 6, or 7-membered heterocycloalkyl ring which is optionally substituted with one or more $R^5$ groups;

$R^3$ is chosen from hydrogen, $C_{1-6}$alkyl, and $C_{1-6}$haloalkyl;

each $R^5$ is independently chosen from $NR^8R^9$, halogen, cyano, hydroxy, oxo, alkyl, haloalkyl, $C_{3-6}$cycloalkyl, 3-6 membered heterocycloalkyl, hydroxyalkyl, $OR^8$, $NRC(O)R^8$, $NR^7C(O)OR^8$, $NR^7C(O)NR^8R^9$, $C(O)R^8$, $C(O)OR^8$, and $C(O)NR^8R^9$;

$R^{6a}$ and $R^{6b}$ are independently chosen from H, $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$ or $R^{6a}$ and $R^{6b}$, together with the intervening atoms, combine to form a heteroaryl ring, which is optionally substituted with one or more $R^6$ groups;

each $R^{6c}$ and $R^{6d}$ is independently chosen from H, $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$;

$R^6$ is chosen from $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$;

each $R^7$, $R^8$ and $R^9$ is independently chosen from hydrogen, $C_{1-4}$alkyl, $C_{3-6}$cycloalkyl, and 3-6 membered heterocycloalkyl, any of which is optionally substituted with halo, hydroxy, $C_{1-3}$alkyl, $C_{1-3}$haloalkyl, and $C_{1-3}$alkoxy; or any two of $R^7$, $R^8$ and $R^9$, together with the atom to which they are both attached can form a 3-7 membered cycloalkyl or heterocycloalkyl ring; and each $R^{10}$, $R^{11}$ and $R^{12}$ is independently chosen from hydrogen, $C_{1-4}$alkyl, $C_{3-6}$cycloalkyl, and 3-6 membered heterocycloalkyl, any of which is optionally substituted with one or more groups chosen from halo, hydroxy and alkoxy; or any two of $R^{10}$, $R^{11}$ and $R^{12}$, together with the atom to which they are both attached, can form a 3-7 membered cycloalkyl or heterocycloalkyl ring.

Provided herein is Embodiment 72: a compound having structural Formula (Va):

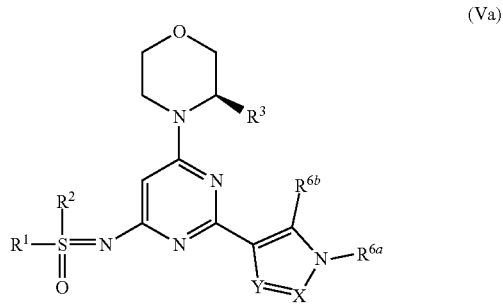

or a salt thereof, wherein:

X is chosen from N and $CR^6$;

Y is chosen from N and $CR^{6d}$;

$R^1$ and $R^2$ are independently chosen from $C_{1-4}$alkyl, $C_{1-4}$haloalkyl, $C_{3-6}$cycloalkyl, $C_{3-6}$ heterocycloalkyl, $C_{5-10}$aryl, and 5-10 membered heteroaryl, any of which is optionally substituted with one or more $R^5$ groups, or $R^1$ and $R^2$, together with the sulfur to which they are both attached, form a 4, 5, 6, or 7-membered heterocycloalkyl ring which is optionally substituted with one or more $R^5$ groups;

$R^3$ is chosen from hydrogen, $C_{1-6}$alkyl, and $C_{1-6}$haloalkyl;

each $R^5$ is independently chosen from $NR^8R^9$, halogen, cyano, hydroxy, oxo, alkyl, haloalkyl, $C_{3-6}$cycloalkyl, 3-6 membered heterocycloalkyl, hydroxyalkyl, $OR^8$, $NRC(O)R^8$, $NR^7C(O)OR^8$, $NR^7C(O)NR^8R^9$, $C(O)R^8$, $C(O)OR^8$, and $C(O)NR^8R^9$;

$R^{6a}$ and $R^{6b}$ are independently chosen from H, $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$ or $R^{6a}$ and $R^{6b}$, together with the intervening atoms, combine to form a heteroaryl ring, which is optionally substituted with one or more $R^6$ groups;

each $R^{6c}$ and $R^{6d}$ is independently chosen from H, $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$;

$R^6$ is chosen from $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$;

each $R^7$, $R^8$ and $R^9$ is independently chosen from hydrogen, $C_{1-4}$alkyl, $C_{3-6}$cycloalkyl, and 3-6 membered heterocycloalkyl, any of which is optionally substituted with halo, hydroxy, $C_{1-3}$alkyl, $C_{1-3}$haloalkyl, and $C_{1-3}$alkoxy; or any two of $R^7$, $R^8$ and $R^9$, together with the atom to which they are both attached can form a 3-7 membered cycloalkyl or heterocycloalkyl ring; and each $R^{10}$, $R^{11}$ and $R^{12}$ is independently chosen from hydrogen, $C_{1-4}$alkyl, $C_{3-6}$cycloalkyl, and 3-6 membered heterocycloalkyl, any of which is optionally substituted with one or more groups chosen from halo, hydroxy and alkoxy; or any two of $R^{10}$, $R^{11}$ and $R^{12}$, together with the atom to which they are both attached, can form a 3-7 membered cycloalkyl or heterocycloalkyl ring.

The disclosure provides the further embodiments:

Embodiment 73: The compound either one of Embodiments 71 or 72, or salt thereof, wherein $R^{6a}$ and $R^{6b}$, together with the intervening atoms, combine to form a pyridyl ring.

Embodiment 74: The compound of any one of Embodiments 71-73, or salt thereof, wherein:

$R^{6a}$ and $R^{6b}$ are independently chosen from H, alkyl, haloalkyl, $C_{3-6}$cycloalkyl, 3-6 membered heterocycloalkyl, and hydroxyalkyl; and each $R^{6c}$ and $R^{6d}$ is independently chosen from H, alkyl, haloalkyl, $C_{3-6}$cycloalkyl, 3-6 membered heterocycloalkyl, and hydroxyalkyl.

Embodiment 75: The compound of Embodiment 71, wherein the compound is

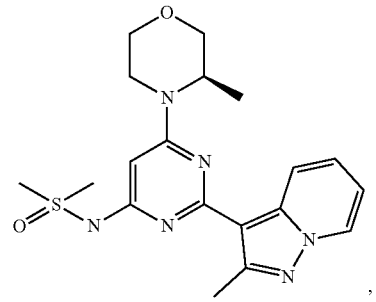

or a salt thereof.

Provided herein is Embodiment 76: a compound having structural Formula (VI):

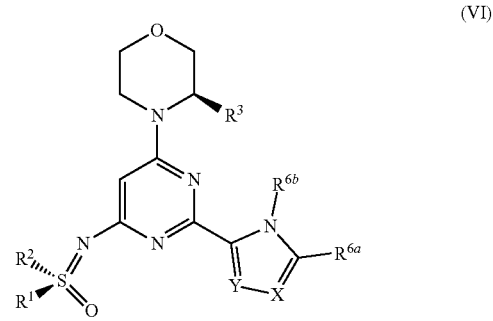

or a salt thereof, wherein:

X is chosen from N and $CR^6$;

Y is chosen from N and $CR^{6d}$;

$R^1$ and $R^2$ are independently chosen from $C_{1-4}$alkyl, $C_{1-4}$haloalkyl, $C_{3-6}$cycloalkyl, $C_{3-6}$ heterocycloalkyl, $C_{5-10}$aryl, and 5-10 membered heteroaryl, any of which is optionally substituted with one or more $R^5$ groups, or $R^1$ and $R^2$, together with the sulfur to which they are both attached, form a 4, 5, 6, or 7-membered heterocycloalkyl ring which is optionally substituted with one or more $R^5$ groups;

$R^3$ is chosen from hydrogen, $C_{1-6}$alkyl, and $C_{1-6}$haloalkyl;

each $R^5$ is independently chosen from $NR^8R^9$, halogen, cyano, hydroxy, oxo, alkyl, haloalkyl, $C_{3-6}$cycloalkyl, 3-6 membered heterocycloalkyl, hydroxyalkyl, $OR^8$, $NRC(O)R^8$, $NR^7C(O)OR^8$, $NR^7C(O)NR^8R^9$, $C(O)R^8$, $C(O)OR^8$, and $C(O)NR^8R^9$;

$R^{6a}$ and $R^{6b}$ are independently chosen from H, $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$, or $R^{6a}$ and $R^{6b}$, together with the intervening atoms, combine to form a heteroaryl ring, which is optionally substituted with one or more $R^6$ groups;

each $R^{6c}$ and $R^{6d}$ is independently chosen from H, $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$;

$R^6$ is chosen from $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$;

each $R^7$, $R^8$ and $R^9$ is independently chosen from hydrogen, $C_{1-4}$alkyl, $C_{3-6}$cycloalkyl, and 3-6 membered heterocycloalkyl, any of which is optionally substituted with halo, hydroxy, $C_{1-3}$alkyl, $C_{1-3}$haloalkyl, and $C_{1-3}$alkoxy; or any two of $R^7$, $R^8$ and $R^9$, together with the atom to which they are both attached can form a 3-7 membered cycloalkyl or heterocycloalkyl ring; and each $R^{10}$, $R^{11}$ and $R^{12}$ is independently chosen from hydrogen, $C_{1-4}$alkyl, $C_{3-6}$cycloalkyl, and 3-6 membered heterocycloalkyl, any of which is optionally substituted with one or more groups chosen from halo, hydroxy and alkoxy; or any two of $R^{10}$, $R^{11}$ and $R^{12}$, together with the atom to which they are both attached, can form a 3-7 membered cycloalkyl or heterocycloalkyl ring.

Provided herein is Embodiment 77: a compound having structural Formula (VIa):

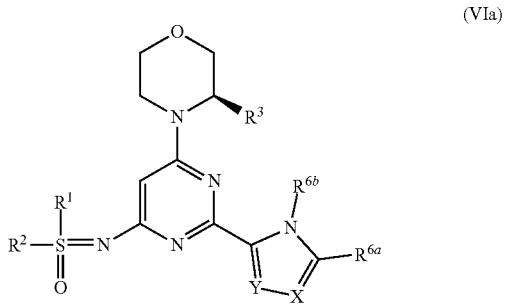

(VIa)

or a salt thereof, wherein:

X is chosen from N and $CR^6$;

Y is chosen from N and $CR^{6d}$;

$R^1$ and $R^2$ are independently chosen from $C_{1-4}$alkyl, $C_{1-4}$haloalkyl, $C_{3-6}$cycloalkyl, $C_{3-6}$ heterocycloalkyl, $C_{5-10}$aryl, and 5-10 membered heteroaryl, any of which is optionally substituted with one or more $R^5$ groups, or $R^1$ and $R^2$, together with the sulfur to which they are both attached, form a 4, 5, 6, or 7-membered heterocycloalkyl ring which is optionally substituted with one or more $R^5$ groups;

$R^3$ is chosen from hydrogen, $C_{1-6}$alkyl, and $C_{1-6}$haloalkyl;

each $R^5$ is independently chosen from $NR^8R^9$, halogen, cyano, hydroxy, oxo, alkyl, haloalkyl, $C_{3-6}$cycloalkyl, 3-6 membered heterocycloalkyl, hydroxyalkyl, $OR^8$, $NRC(O)R^8$, $NR^7C(O)OR^8$, $NR^7C(O)NR^8R^9$, $C(O)R^8$, $C(O)OR^8$, and $C(O)NR^8R^9$;

$R^{6a}$ and $R^{6b}$ are independently chosen from H, $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$, or $R^{6a}$ and $R^{6b}$, together with the intervening atoms, combine to form a heteroaryl ring, which is optionally substituted with one or more $R^6$ groups;

each $R^{6c}$ and $R^{6d}$ is independently chosen from H, $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$;

$R^6$ is chosen from $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$;

each $R^7$, $R^8$ and $R^9$ is independently chosen from hydrogen, $C_{1-4}$alkyl, $C_{3-6}$cycloalkyl, and 3-6 membered heterocycloalkyl, any of which is optionally substituted with halo, hydroxy, $C_{1-3}$alkyl, $C_{1-3}$haloalkyl, and $C_{1-3}$alkoxy; or any two of $R^7$, $R^8$ and $R^9$, together with the atom to which they are both attached can form a 3-7 membered cycloalkyl or heterocycloalkyl ring; and each $R^{10}$, $R^{11}$ and $R^{12}$ is independently chosen from hydrogen, $C_{1-4}$alkyl, $C_{3-6}$cycloalkyl, and 3-6 membered heterocycloalkyl, any of which is optionally substituted with one or more groups chosen from halo, hydroxy and alkoxy; or any two of $R^{10}$, $R^{11}$ and $R^{12}$, together with the atom to which they are both attached, can form a 3-7 membered cycloalkyl or heterocycloalkyl ring.

The disclosure provides the further embodiments:

Embodiment 78: The compound of either one Embodiment 76 or 77, or salt thereof, wherein $R^{6a}$ and $R^{6b}$, together with the intervening atoms, combine to form a pyridyl ring.

Embodiment 79: The compound of any one of Embodiments 76-78, or salt thereof, wherein each $R^{6c}$ and $R^{6d}$ is independently chosen from H, alkyl, haloalkyl, $C_{3-6}$cycloalkyl, 3-6 membered heterocycloalkyl, and hydroxyalkyl.

Embodiment 80: The compound of Embodiment 76, wherein the compound is chosen from

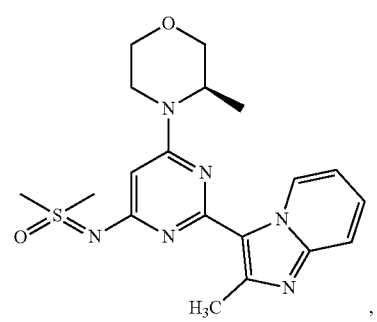

-continued

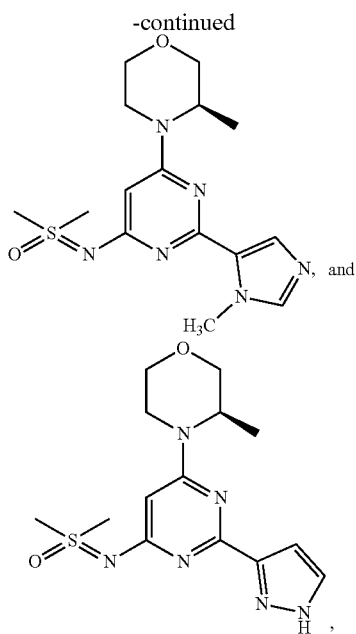

or a salt thereof.

Provided herein is Embodiment 81: a compound having structural Formula (VII):

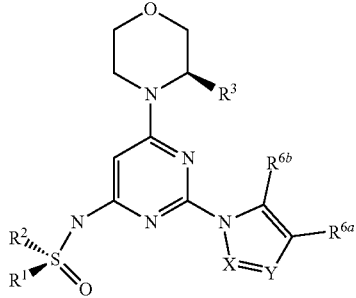

or a salt thereof, wherein:
X is chosen from N and $CR^{6c}$;
Y is chosen from N and $CR^{6d}$;
$R^1$ and $R^2$ are independently chosen from $C_{1-4}$alkyl, $C_{1-4}$haloalkyl, $C_{3-6}$cycloalkyl, $C_{3-6}$ heterocycloalkyl, $C_{5-10}$aryl, and 5-10 membered heteroaryl, any of which is optionally substituted with one or more $R^5$ groups, or $R^1$ and $R^2$, together with the sulfur to which they are both attached, form a 4, 5, 6, or 7-membered heterocycloalkyl ring which is optionally substituted with one or more $R^5$ groups;
$R^3$ is chosen from hydrogen, $C_{1-6}$alkyl, and $C_{1-6}$haloalkyl;
each $R^5$ is independently chosen from $NR^8R^9$, halogen, cyano, hydroxy, oxo, alkyl, haloalkyl, $C_{3-6}$cycloalkyl, 3-6 membered heterocycloalkyl, hydroxyalkyl, $OR^8$, $NRC(O)R^8$, $NR^7C(O)OR^8$, $NR^7C(O)NR^8R^9$, $C(O)R^8$, $C(O)OR^8$, and $C(O)NR^8R^9$;
$R^{6a}$ and $R^{6b}$ are independently chosen from H, $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$, or $R^{6a}$ and $R^{6b}$, together with the intervening atoms, combine to form an aryl or heteroaryl ring, which is optionally substituted with one or more $R^6$ groups;
each $R^{6c}$ and $R^{6d}$ is independently chosen from H, $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$;
$R^6$ is chosen from $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$;
each $R^7$, $R^8$ and $R^9$ is independently chosen from hydrogen, $C_{1-4}$alkyl, $C_{3-6}$cycloalkyl, and 3-6 membered heterocycloalkyl, any of which is optionally substituted with halo, hydroxy, $C_{1-3}$alkyl, $C_{1-3}$haloalkyl, and $C_{1-3}$alkoxy; or any two of $R^7$, $R^8$ and $R^9$, together with the atom to which they are both attached can form a 3-7 membered cycloalkyl or heterocycloalkyl ring; and
each $R^{10}$, $R^{11}$ and $R^{12}$ is independently chosen from hydrogen, $C_{1-4}$alkyl, $C_{3-6}$cycloalkyl, and 3-6 membered heterocycloalkyl, any of which is optionally substituted with one or more groups chosen from halo, hydroxy and alkoxy; or any two of $R^{10}$, $R^{11}$ and $R^{12}$, together with the atom to which they are both attached, can form a 3-7 membered cycloalkyl or heterocycloalkyl ring.

Provided herein is Embodiment 82: a compound having structural Formula (VIIa):

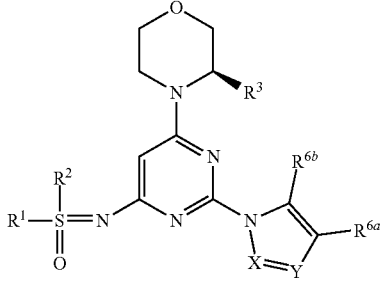

or a salt thereof, wherein:
X is chosen from N and $CR^6$;
Y is chosen from N and $CR^{6d}$;
$R^1$ and $R^2$ are independently chosen from $C_{1-4}$alkyl, $C_{1-4}$haloalkyl, $C_{3-6}$cycloalkyl, $C_{3-6}$ heterocycloalkyl, $C_{5-10}$aryl, and 5-10 membered heteroaryl, any of which is optionally substituted with one or more $R^5$ groups, or $R^1$ and $R^2$, together with the sulfur to which they are both attached, form a 4, 5, 6, or 7-membered heterocycloalkyl ring which is optionally substituted with one or more $R^5$ groups;
$R^3$ is chosen from hydrogen, $C_{1-6}$alkyl, and $C_{1-6}$haloalkyl;
each $R^5$ is independently chosen from $NR^8R^9$, halogen, cyano, hydroxy, oxo, alkyl, haloalkyl, $C_{3-6}$cycloalkyl, 3-6 membered heterocycloalkyl, hydroxyalkyl, $OR^8$, $NRC(O)R^8$, $NR^7C(O)OR^8$, $NR^7C(O)NR^8R^9$, $C(O)R^8$, $C(O)OR^8$, and $C(O)NR^8R^9$;
$R^{6a}$ and $R^{6b}$ are independently chosen from H, $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$, or $R^{6a}$ and $R^{6b}$, together with the intervening atoms, combine to form an aryl or heteroaryl ring, which is optionally substituted with one or more $R^6$ groups;

each $R^{6c}$ and $R^{6d}$ is independently chosen from H, $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$;

$R^6$ is chosen from $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$;

each $R^7$, $R^8$ and $R^9$ is independently chosen from hydrogen, $C_{1-4}$alkyl, $C_{3-6}$cycloalkyl, and 3-6 membered heterocycloalkyl, any of which is optionally substituted with halo, hydroxy, $C_{1-3}$alkyl, $C_{1-3}$haloalkyl, and $C_{1-3}$alkoxy; or any two of $R^7$, $R^8$ and $R^9$, together with the atom to which they are both attached can form a 3-7 membered cycloalkyl or heterocycloalkyl ring; and each $R^{10}$, $R^{11}$ and $R^{12}$ is independently chosen from hydrogen, $C_{1-4}$alkyl, $C_{3-6}$cycloalkyl, and 3-6 membered heterocycloalkyl, any of which is optionally substituted with one or more groups chosen from halo, hydroxy and alkoxy; or any two of $R^{10}$, $R^{11}$ and $R^{12}$, together with the atom to which they are both attached, can form a 3-7 membered cycloalkyl or heterocycloalkyl ring.

The disclosure provides the further embodiments:

Embodiment 83: The compound of either one of Embodiments 81 or 82, or salt thereof, wherein $R^{6a}$ and $R^{6b}$, together with the intervening atoms, combine to form a phenyl ring, which is optionally substituted with one or two $R^6$ groups.

Embodiment 84: The compound of any one of Embodiments 81-83, or salt thereof, wherein X is $CR^{6'}$ and Y is N.

Embodiment 85: The compound of any one of Embodiments 81-84, or salt thereof, wherein $R^{6c}$ is chosen from H, alkyl, haloalkyl, $C_{3-6}$cycloalkyl, 3-6 membered heterocycloalkyl, and hydroxyalkyl.

Embodiment 86: The compound of Embodiment 85, or salt thereof, wherein $R^{6c}$ is chosen from H and alkyl.

Embodiment 87: The compound of Embodiment 86, or salt thereof, wherein $R^{6c}$ is chosen from H and methyl.

Embodiment 88: The compound of Embodiment 86, or salt thereof, wherein $R^{6c}$ is methyl.

Embodiment 89: The compound of any one of Embodiments 81-88, or salt thereof, wherein $R^1$ and $R^2$ are independently chosen from $C_{1-4}$alkyl, $C_{3-6}$cycloalkyl, 3-6 membered heterocycloalkyl.

Embodiment 90: The compound of any one of Embodiments 81-88, or salt thereof, wherein $R^1$ and $R^2$ are independently chosen from $C_{1-4}$alkyl, $C_{3-6}$cycloalkyl, and 3-6 membered heterocycloalkyl.

Embodiment 91: The compound of Embodiment 89, or salt thereof, wherein at least one of $R^1$ and $R^2$ is methyl.

Embodiment 92: The compound of Embodiment 89, or salt thereof, wherein exactly one of $R^1$ and $R^2$ is chosen from cyclopropyl and oxetan-3-yl.

Embodiment 93: The compound of Embodiment 91, or salt thereof, wherein exactly one of $R^1$ and $R^2$ is cyclopropyl.

Embodiment 94: The compound of Embodiment 91, or salt thereof, wherein $R^1$ and $R^2$ are methyl.

Embodiment 95: The compound of any one of Embodiments 81-93, or salt thereof, wherein $R^1$ and $R^2$ are are independently chosen from $C_{1-4}$alkyl and $C_{3-6}$cycloalkyl.

Embodiment 96: The compound of Embodiment 81, or salt thereof, wherein the compound is chosen from:

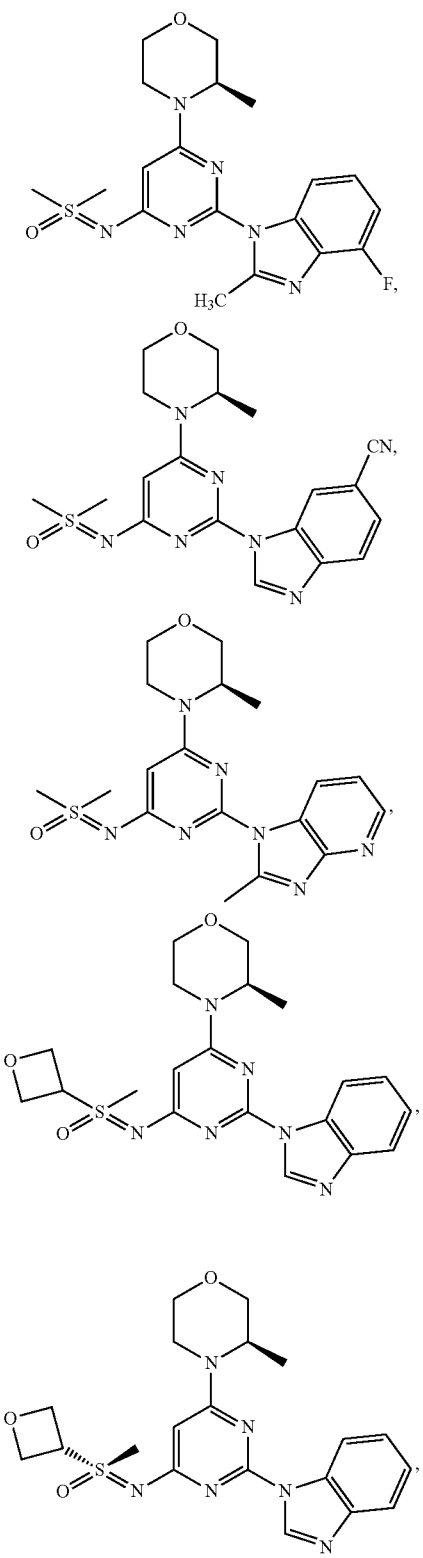

23
-continued
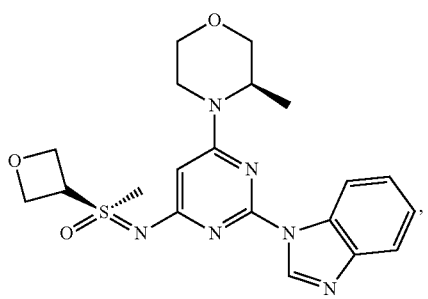
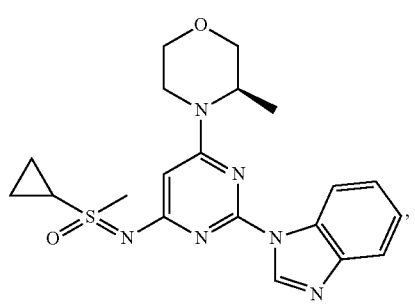
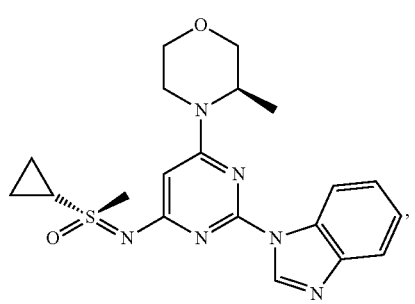
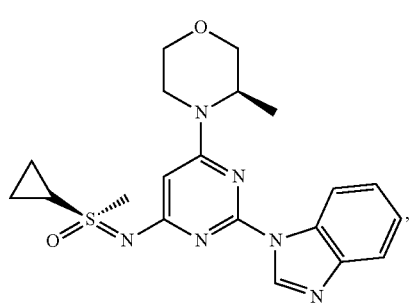
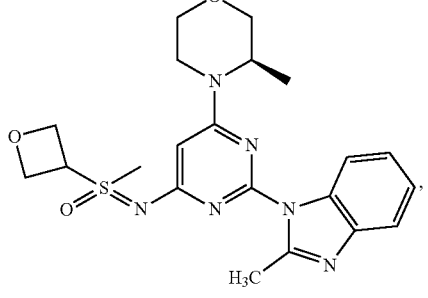
24
-continued
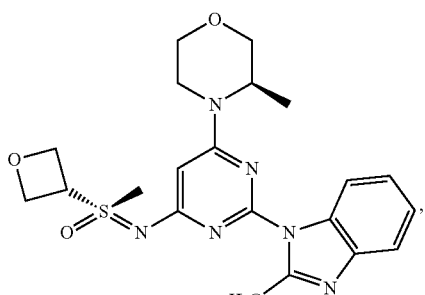
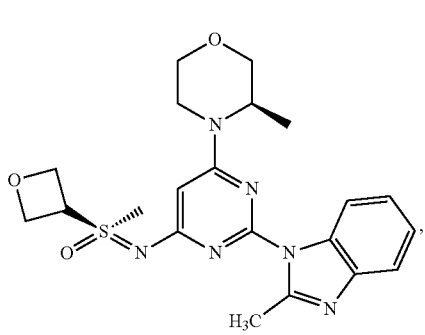
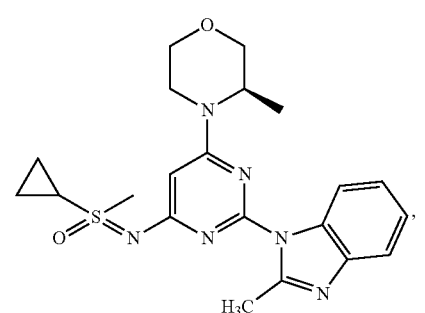
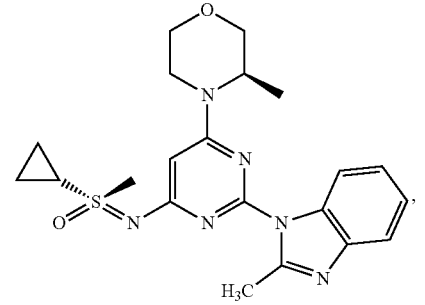
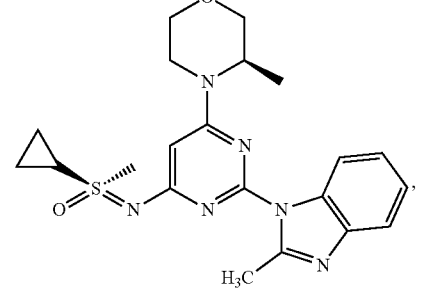

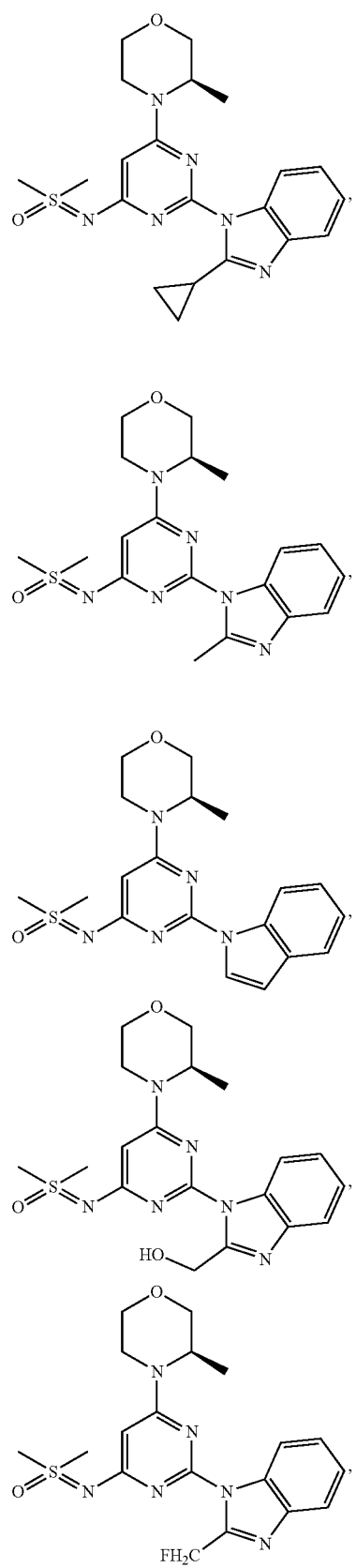
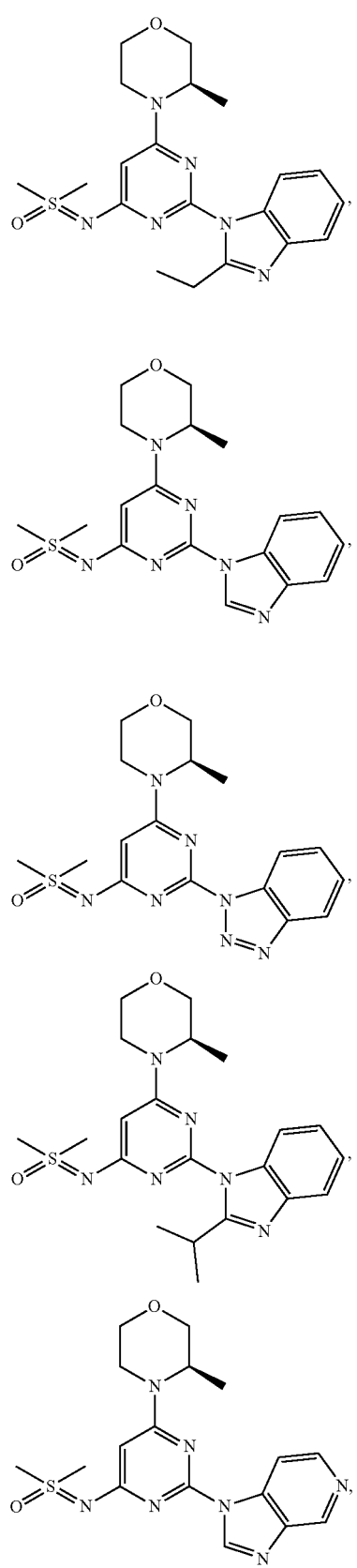

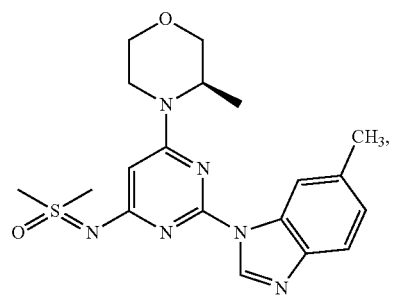
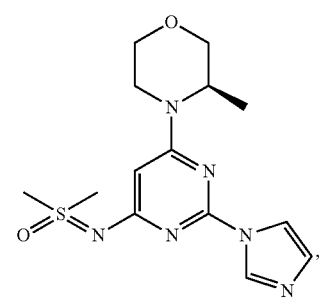
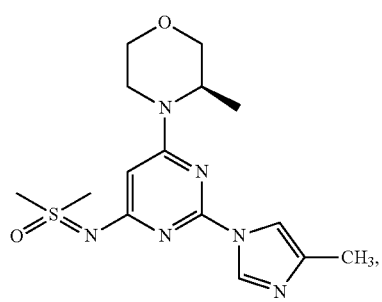
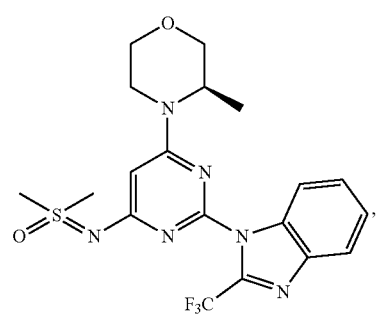
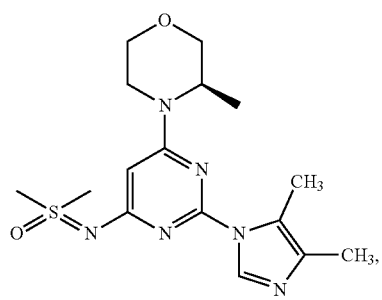
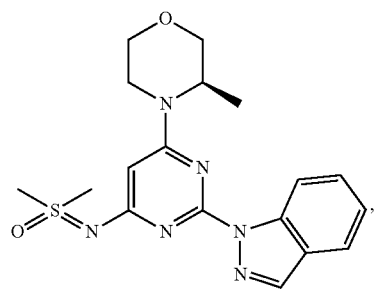
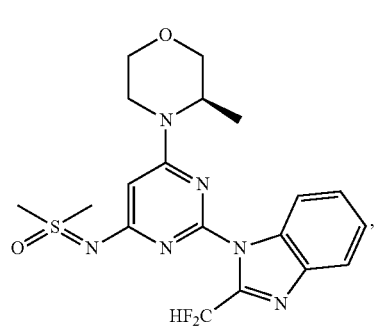
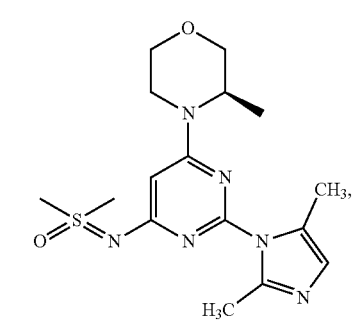
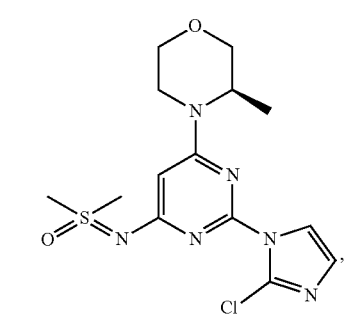
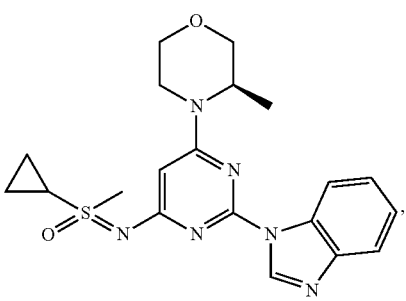

-continued
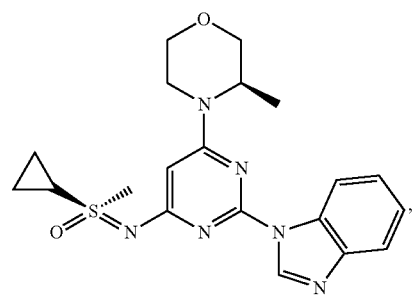
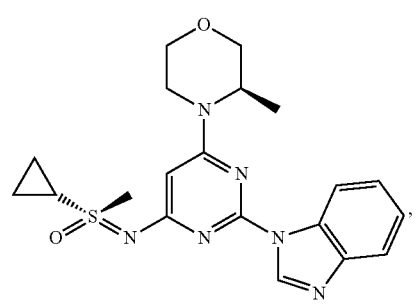
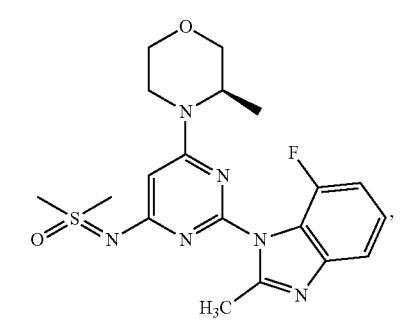
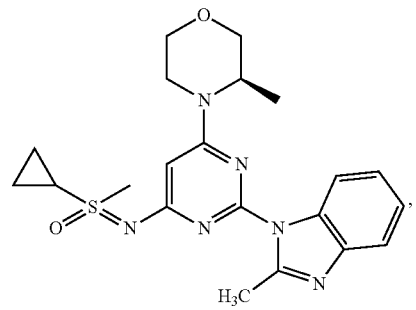
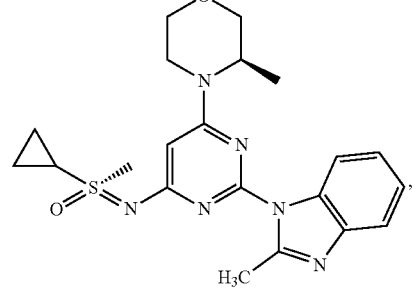
-continued
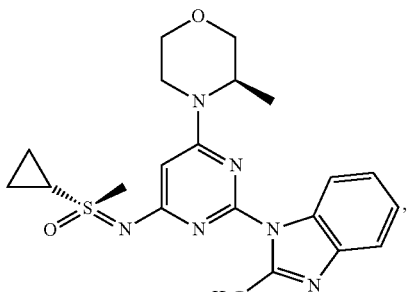
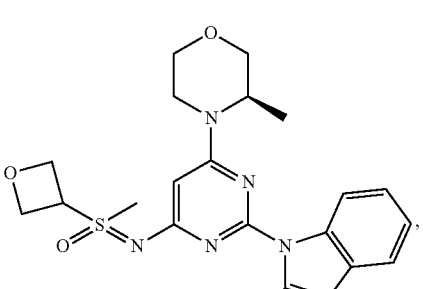
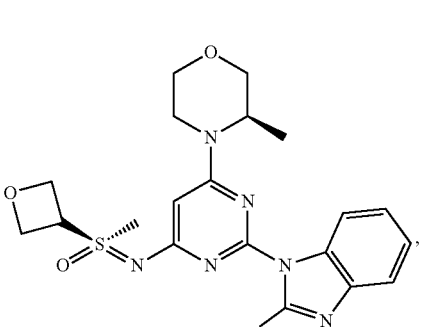
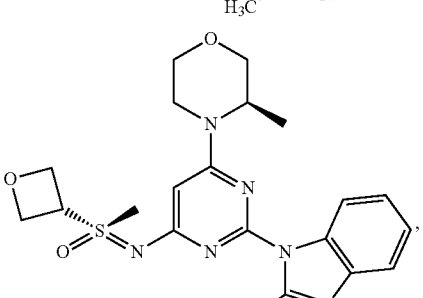
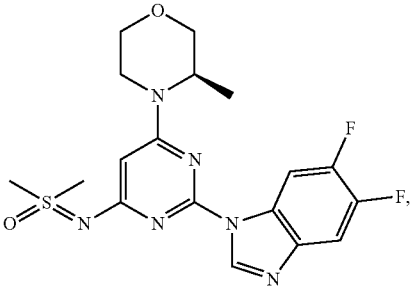

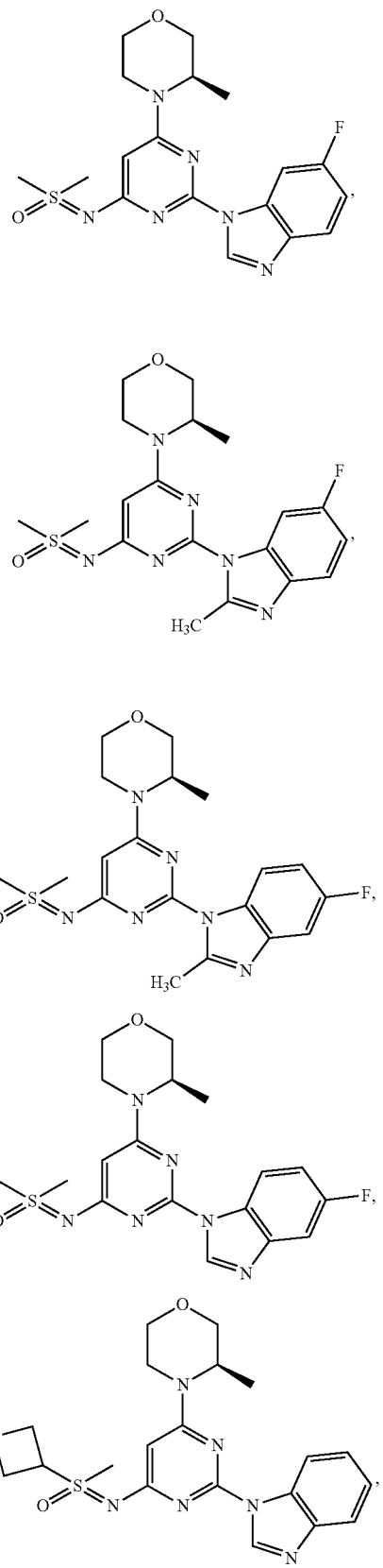

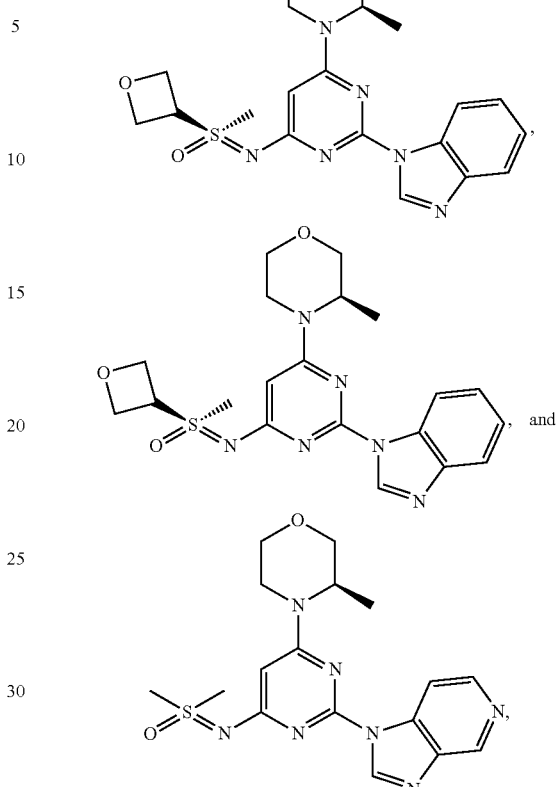

or a salt thereof.

In certain embodiments of compounds having formula chosen from (IV), (IVa), (V), (Va), (VI), (VIa), (VII), (VIIa), $R^{6a}$ and $R^{6b}$, together with the intervening atoms, combine to form a heteroaryl ring, which is optionally substituted with one or more $R^6$ groups.

In certain embodiments of compounds having formula chosen from (IV), (IVa), (V), (Va), (VI), (VIa), (VII), (VIIa), $R^{6a}$ and $R^{6b}$, together with the intervening atoms, combine to form a five-membered heteroaryl ring, which is optionally substituted with one or two $R^6$ groups.

In certain embodiments of compounds having formula chosen from (IV), (IVa), (V), (Va), (VI), (VIa), (VII), (VIIa), $R^{6a}$ and $R^{6b}$, together with the intervening atoms, combine to form a five-membered heteroaryl ring chosen from pyrrole, pyrazole, and imidazole, any of which is optionally substituted with one or two $R^6$ groups.

In certain embodiments of compounds having formula chosen from (IV), (IVa), (V), (Va), (VI), (VIa), (VII), (VIIa), $R^{6a}$ and $R^{6b}$, together with the intervening atoms, combine to form a six-membered heteroaryl ring, which is optionally substituted with one or two $R^6$ groups.

In certain embodiments of compounds having formula chosen from (IV), (IVa), (V), (Va), (VI), (VIa), (VII), (VIIa), $R^{6a}$ and $R^{6b}$, together with the intervening atoms, combine to form a pyridine ring, which is optionally substituted with one or two $R^6$ groups.

In certain embodiments of compounds having formula chosen from (IV) and (IVa), $R^{6a}$ and $R^{6b}$, together with the intervening atoms, combine to form an aryl ring, which is optionally substituted with one or more $R^6$ groups.

In certain embodiments of compounds having formula chosen from (IV) and (IVa), $R^{6a}$ and $R^{6b}$, together with the intervening atoms, combine to form a phenyl ring, which is optionally substituted with one or two $R^6$ groups.

In certain embodiments of compounds having formula chosen from (IV), (IVa), (V), (Va), (VI), (VIa), (VII), (VIIa), $R^6$ is chosen from halogen, cyano, alkyl, haloalkyl, and cycloalkyl.

In certain embodiments of compounds having formula chosen from (IV), (IVa), (V), (Va), (VI), (VIa), (VII), (VIIa), X is N and Y is $CR^6$.

In certain embodiments of compounds having formula chosen from (IV), (IVa), (V), (Va), (VI), (VIa), (VII), (VIIa), X is $CR^{6'}$ and Y is N.

In certain embodiments of compounds having formula chosen from (IV), (IVa), (V), (Va), (VI), (VIa), (VII), (VIIa), X and Y are both $CR^6$.

In certain embodiments of compounds having formula chosen from (IV), (IVa), (V), (Va), (VI), (VIa), (VII), (VIIa), $R^{6a}$ and $R^{6b}$ are independently chosen from H, $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^1$, $C(O)OR^{11}$, and $C(O)NR^{11}R^{12}$;

In certain embodiments of compounds having formula chosen from (IV), (IVa), (V), (Va), (VI), (VIa), (VII), (VIIa), $R^{6a}$ and $R^{6b}$ are independently chosen from H, $NR^{11}R^{12}$, halogen, alkyl, haloalkyl, $C_{3-6}$cycloalkyl, and 3-6 membered heterocycloalkyl.

In certain embodiments of compounds having formula chosen from (IV), (IVa), (V), (Va), (VI), (VIa), (VII), (VIIa), $R^{6b}$ is H.

In certain embodiments of compounds having formula chosen from (IV), (IVa), (V), (Va), (VI), (VIa), (VII), (VIIa), $R^{6a}$ is H.

In certain embodiments of compounds having formula chosen from (IV), (IVa), (V), (Va), (VI), (VIa), (VII), (VIIa), each $R^{6c}$ and $R^{6d}$ is independently chosen from H, $NH_2$, halogen, cyano, alkyl, $OR^{11}$, and $C(O)NR^{11}R^{12}$.

In certain embodiments of compounds having formula chosen from (IV), (IVa), (V), (Va), (VI), (VIa), (VII), (VIIa), at most one $R^6$, is not H In certain embodiments of compounds having formula chosen from (IV), (IVa), (V), (Va), (VI), (VIa), (VII), (VIIa), $R^{6c}$ is H.

In certain embodiments of compounds having formula chosen from (IV), (IVa), (V), (Va), (VI), (VIa), (VII), (VIIa), $R^1$ and $R^2$ are independently chosen from $C_{1-4}$alkyl, $C_{1-4}$haloalkyl, $C_{3-6}$cycloalkyl, 3-6 membered heterocycloalkyl, $C_{5-10}$aryl, and 5-10 membered heteroaryl, any of which is optionally substituted with one or more $R^5$ groups.

In certain embodiments of compounds having formula chosen from (IV), (IVa), (V), (Va), (VI), (VIa), (VII), (VIIa), $R^1$ and $R^2$ are independently chosen from $C_{1-4}$alkyl, $C_{1-4}$haloalkyl, $C_{3-6}$cycloalkyl, and 3-6 membered heterocycloalkyl, any of which is optionally substituted with one or more $R^5$ groups.

In certain embodiments of compounds having formula chosen from (IV), (IVa), (V), (Va), (VI), (VIa), (VII), (VIIa), $R^1$ and $R^2$ are independently chosen from $C_{1-4}$alkyl, $C_{3-6}$cycloalkyl, and 3-6 membered heterocycloalkyl, any of which is optionally substituted with one or two $R^5$ groups.

In certain embodiments of compounds having formula chosen from (IV), (IVa), (V), (Va), (VI), (VIa), (VII), (VIIa), at least one of $R^1$ and $R^2$ is $C_{1-4}$alkyl.

In certain embodiments of compounds having formula chosen from (IV), (IVa), (V), (Va), (VI), (VIa), (VII), (VIIa), least one of $R^1$ and $R^2$ is methyl.

In certain embodiments of compounds having formula chosen from (IV), (IVa), (V), (Va), (VI), (VIa), (VII), (VIIa), $R^1$ and $R^2$ are independently chosen from $C_{1-4}$alkyl, $C_{1-4}$haloalkyl, $C_{3-6}$cycloalkyl, and 3-6 membered heterocycloalkyl.

In certain embodiments of compounds having formula chosen from (IV), (IVa), (V), (Va), (VI), (VIa), (VII), (VIIa), at least one of $R^1$ and $R^2$ is $C_{1-4}$alkyl.

In certain embodiments of compounds having formula chosen from (IV), (IVa), (V), (Va), (VI), (VIa), (VII), (VIIa), at least one of $R^1$ and $R^2$ is methyl.

In certain embodiments of compounds having formula chosen from (IV), (IVa), (V), (Va), (VI), (VIa), (VII), (VIIa), one of $R^1$ and $R^2$ is chosen from $C_{3-6}$cycloalkyl, and 3-6 membered heterocycloalkyl.

In certain embodiments of compounds having formula chosen from (IV), (IVa), (V), (Va), (VI), (VIa), (VII), (VIIa), one of $R^1$ and $R^2$ is chosen from cyclopropyl and oxetan-3-yl.

In certain embodiments of compounds having formula chosen from (IV), (IVa), (V), (Va), (VI), (VIa), (VII), (VIIa), $R^1$ and $R^2$ are methyl.

In certain embodiments of compounds having formula chosen from (IV), (IVa), (V), (Va), (VI), (VIa), (VII), (VIIa), $R^1$ and $R^2$, together with the sulfur to which they are both attached, form a 4, 5, 6, or 7-membered heterocycloalkyl ring which is optionally substituted with one or more $R^5$ groups.

In certain embodiments of compounds having formula chosen from (IV), (IVa), (V), (Va), (VI), (VIa), (VII), (VIIa), $R^1$ and $R^2$, together with the sulfur to which they are both attached, form a 5-7 membered heterocycloalkyl ring which is optionally substituted with one or two $R^5$ groups.

In certain embodiments of compounds having formula chosen from (IV), (IVa), (V), (Va), (VI), (VIa), (VII), (VIIa), $R^1$ and $R^2$, together with the sulfur to which they are both attached, form a 5-7 membered heterocycloalkyl ring chosen from thiane and thiomorpholine, either of which is optionally substituted with one or two $R^5$ groups.

In certain embodiments of compounds having formula chosen from (IV), (IVa), (V), (Va), (VI), (VIa), (VII), (VIIa), $R^1$ and $R^2$, together with the sulfur to which they are both attached, form a 4, 5, 6, or 7-membered heterocycloalkyl ring.

In certain embodiments of compounds having formula chosen from (IV), (IVa), (V), (Va), (VI), (VIa), (VII), (VIIa), each $R^5$ is independently chosen from halogen, cyano, hydroxy, $OR^8$, $C(O)R^8$, $C(O)OR^8$, and $C(O)NR^8R^9$.

In certain embodiments of compounds having formula chosen from (IV), (IVa), (V), (Va), (VI), (VIa), (VII), (VIIa), each $R^5$ is independently chosen from $C(O)R^8$ and $C(O)OR^8$.

In certain embodiments of compounds having formula chosen from (IV), (IVa), (V), (Va), (VI), (VIa), (VII), (VIIa), each $R^8$ is independently chosen from hydrogen, $C_{1-4}$alkyl, $C_{3-6}$cycloalkyl, and 3-6 membered heterocycloalkyl, any of which is optionally substituted with halo, hydroxy, and $C_{1-3}$alkoxy.

In certain embodiments of compounds having formula chosen from (IV), (IVa), (V), (Va), (VI), (VIa), (VII), (VIIa), $R^3$ is H.

In certain embodiments of compounds having formula chosen from (IV), (IVa), (V), (Va), (VI), (VIa), (VII), (VIIa), $R^3$ is chosen from $C_{1-6}$alkyl and $C_{1-6}$haloalkyl.

In certain embodiments of compounds having formula chosen from (IV), (IVa), (V), (Va), (VI), (VIa), (VII), (VIIa), $R^3$ is chosen from $C_{1-6}$alkyl and $C_{1-6}$fluoroalkyl.

In certain embodiments of compounds having formula chosen from (IV), (IVa), (V), (Va), (VI), (VIa), (VII), (VIIa), $R^3$ is chosen from methyl, fluoromethyl, difluoromethyl, and trifluoromethyl.

In certain embodiments of compounds having formula chosen from (IV), (IVa), (V), (Va), (VI), (VIa), (VII), (VIIa), $R^3$ is $C_{1-6}$alkyl.

In certain embodiments of compounds having formula chosen from (IV), (IVa), (V), (Va), (VI), (VIa), (VII), (VIIa), $R^3$ is methyl.

In certain embodiments of compounds having formula chosen from (I), (II), (III), (IIIa), (IV), (IVa), (V), (Va), (VI), (VIa), (VII), (VIIa), any alkoxy recited is a $C_{1-3}$alkoxy.

In certain embodiments, the compound is chosen from:

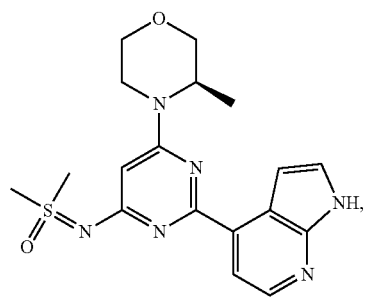

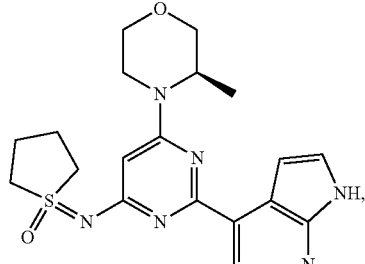

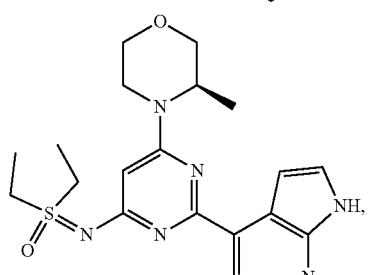

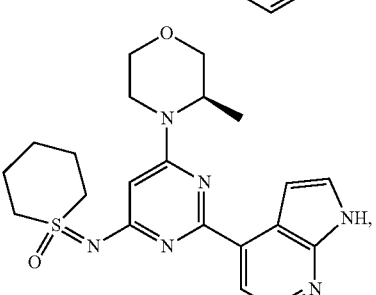

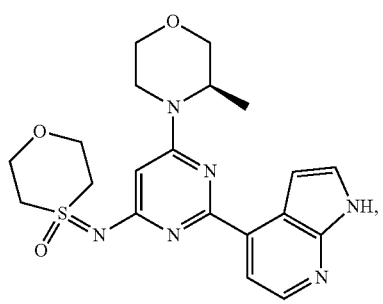

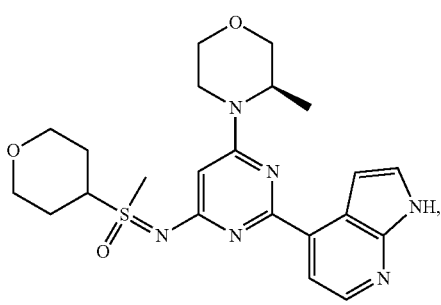

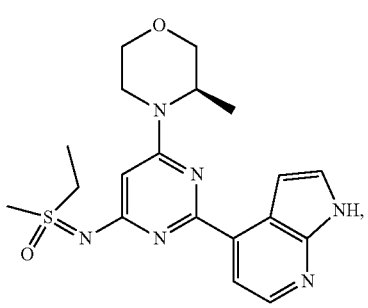

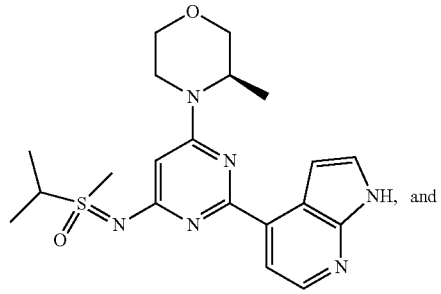

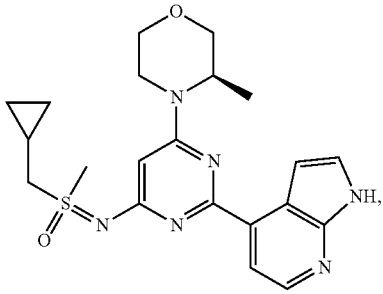

or a salt of any of the foregoing.

In certain embodiments, the compound is chosen from:
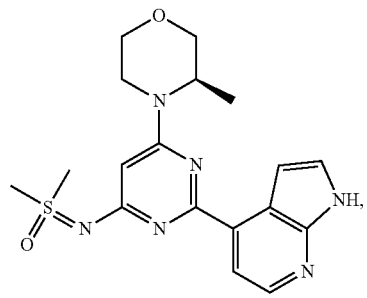
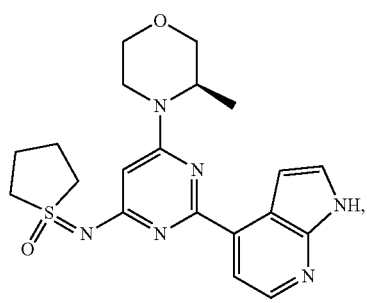
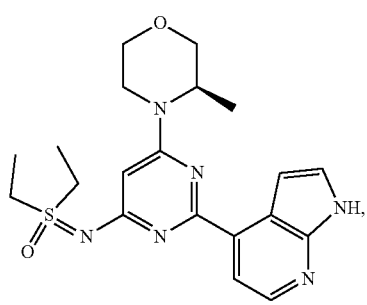
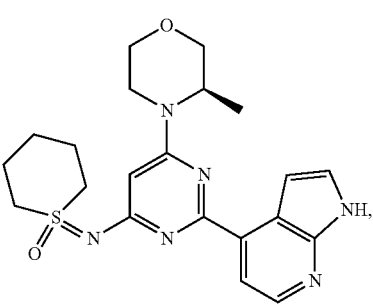
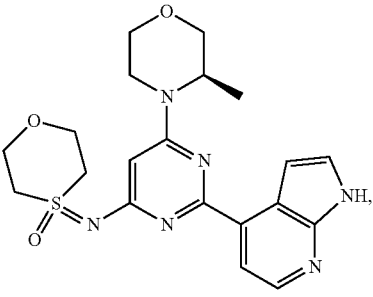
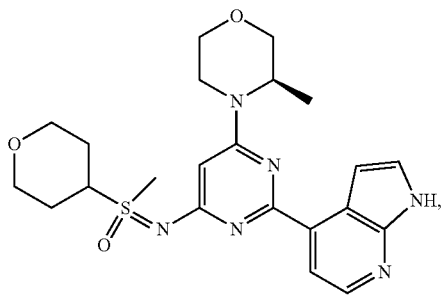
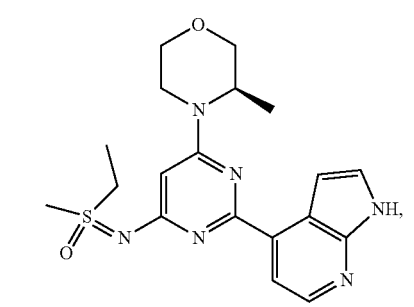
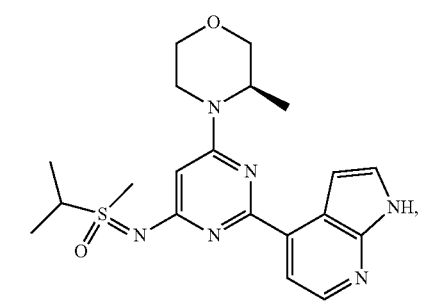
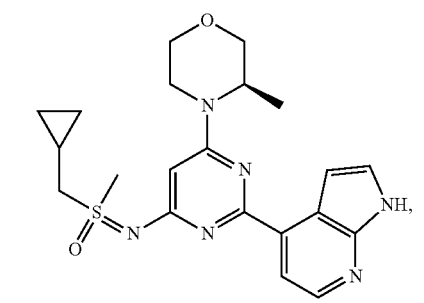
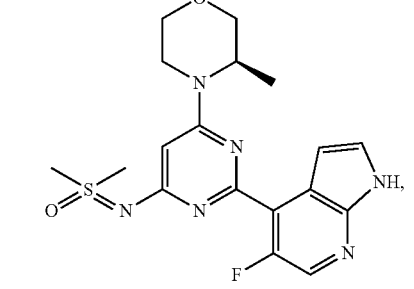

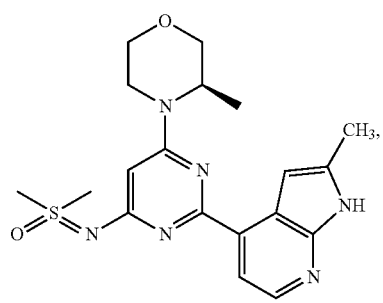
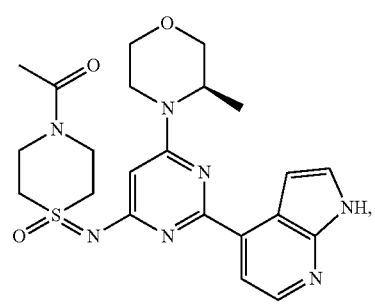
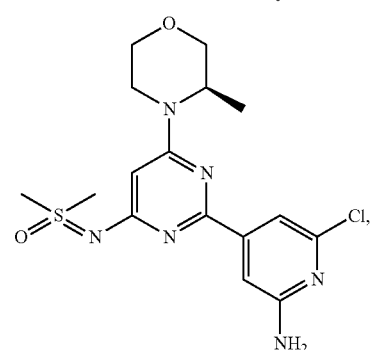
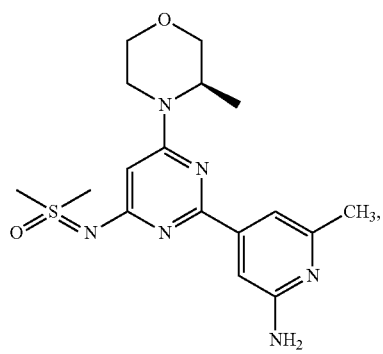
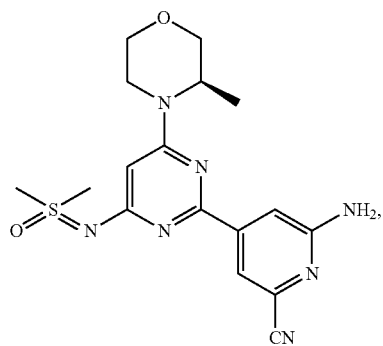
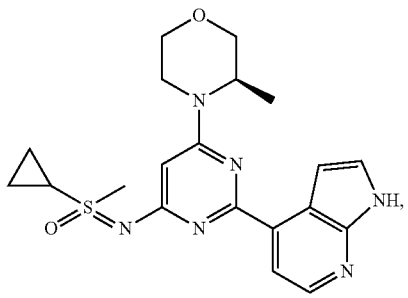
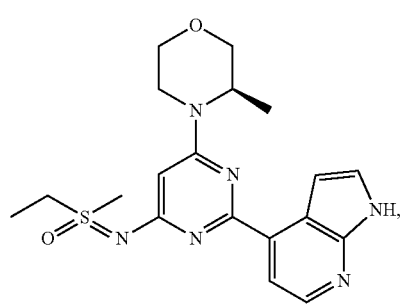
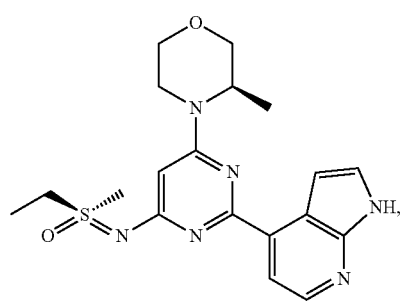
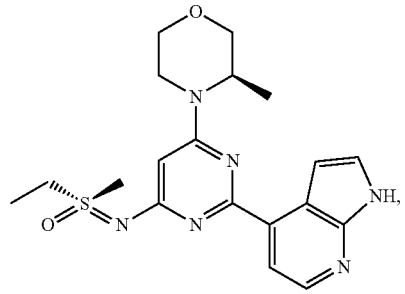
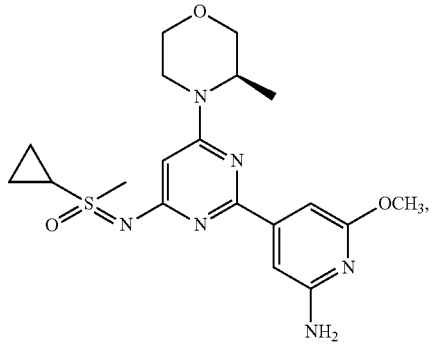

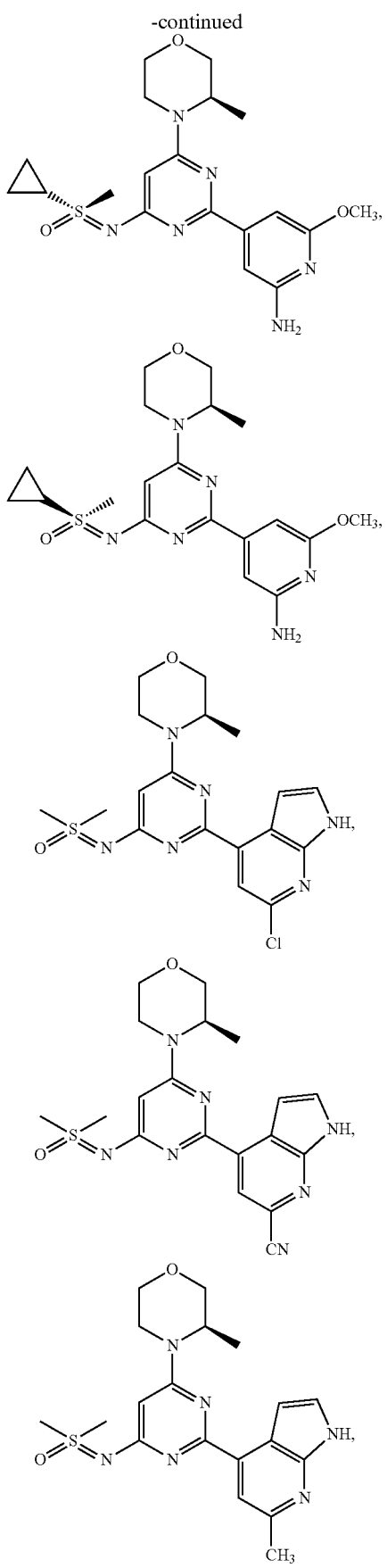
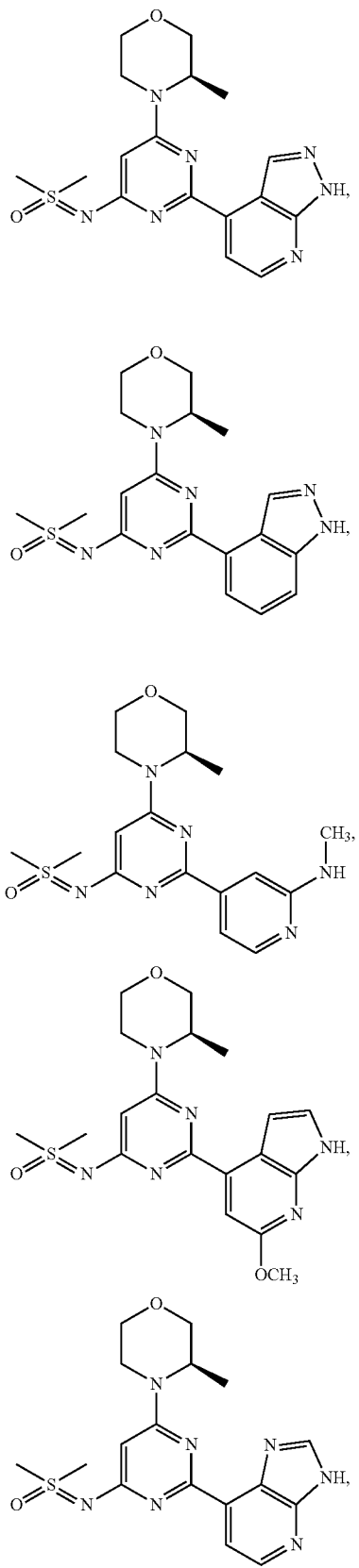

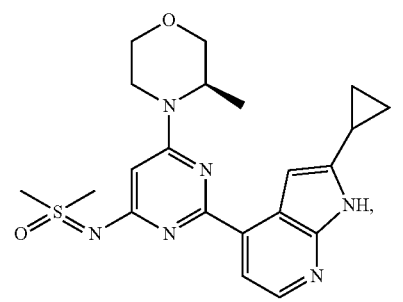
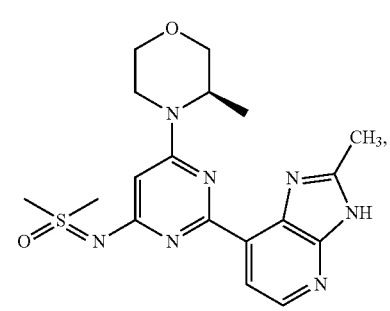
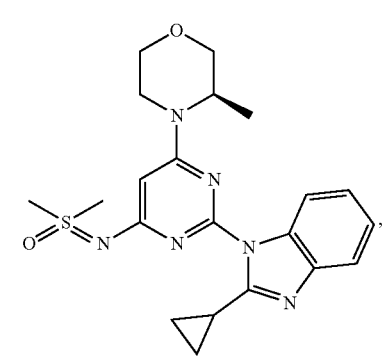
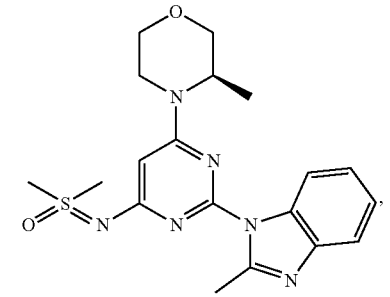
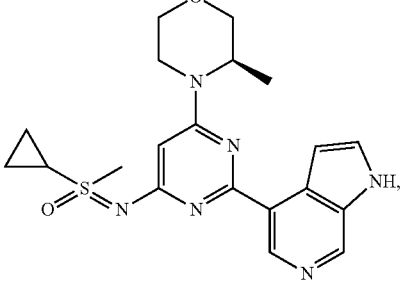
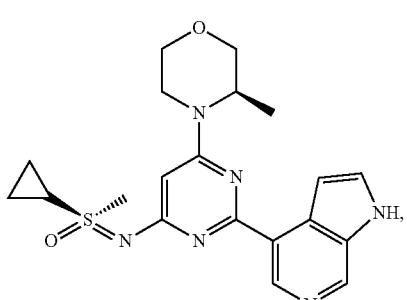
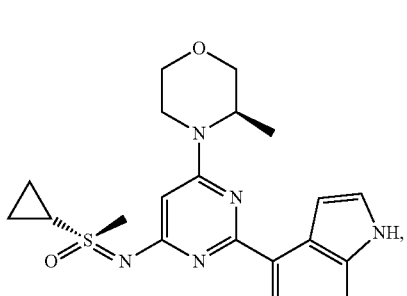
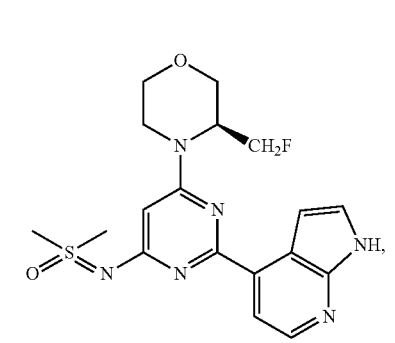
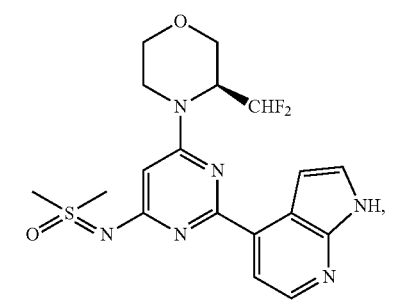
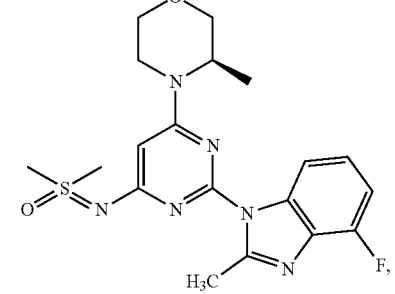

45
-continued
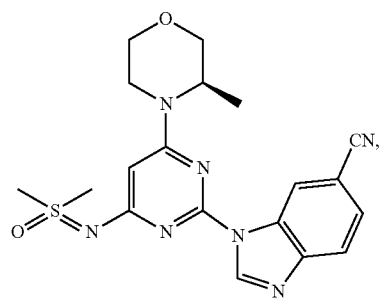
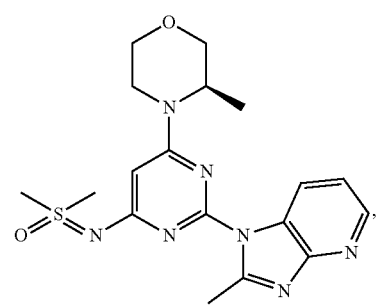
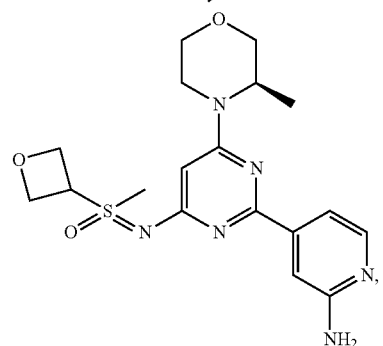
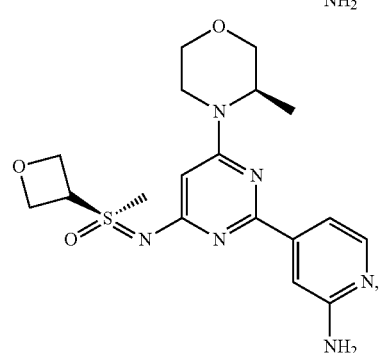
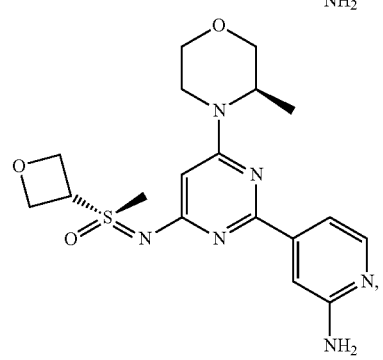
46
-continued
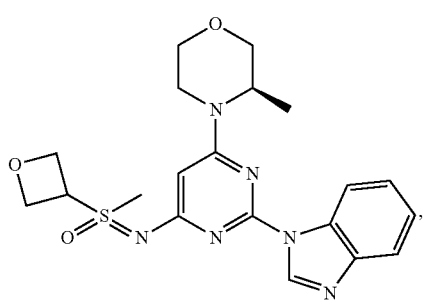
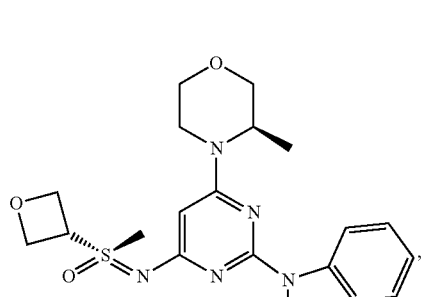
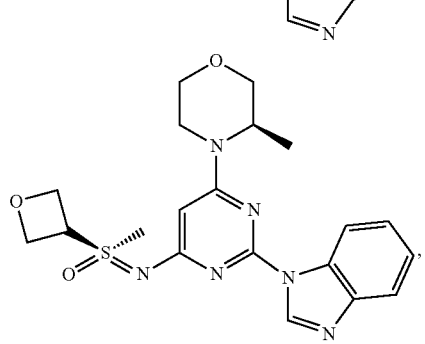
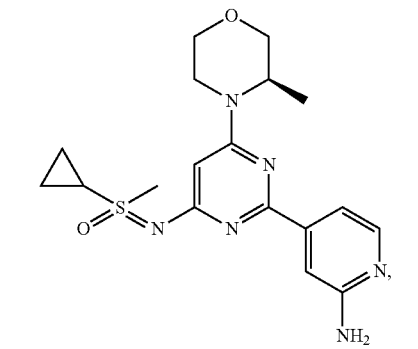
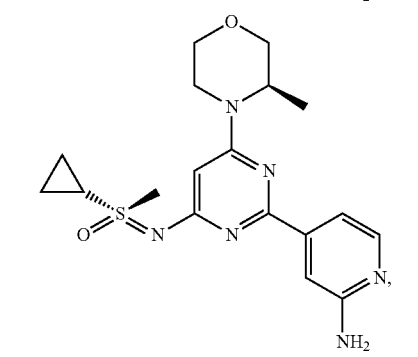

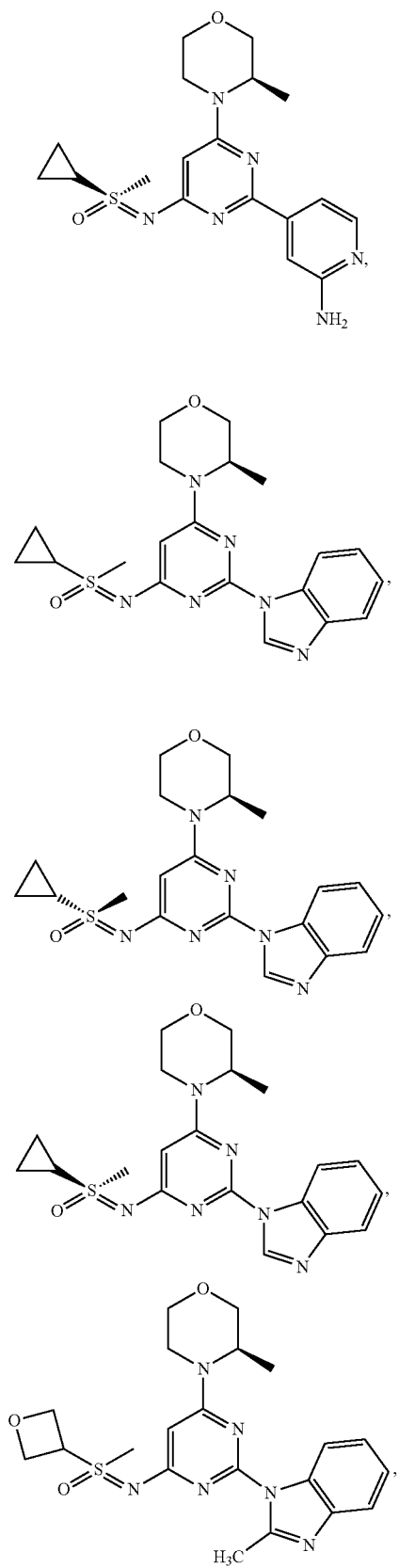
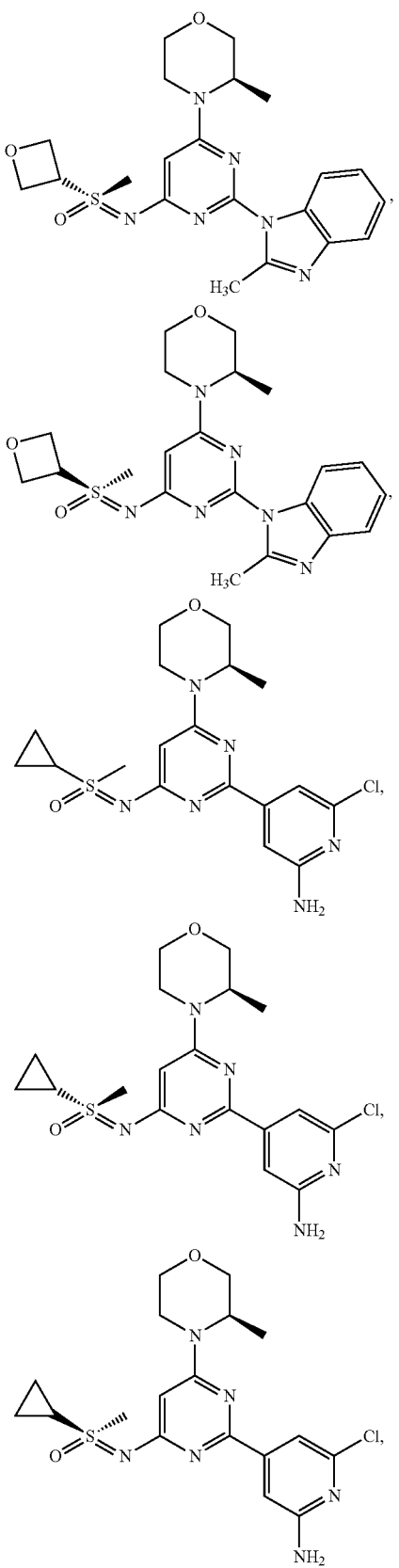

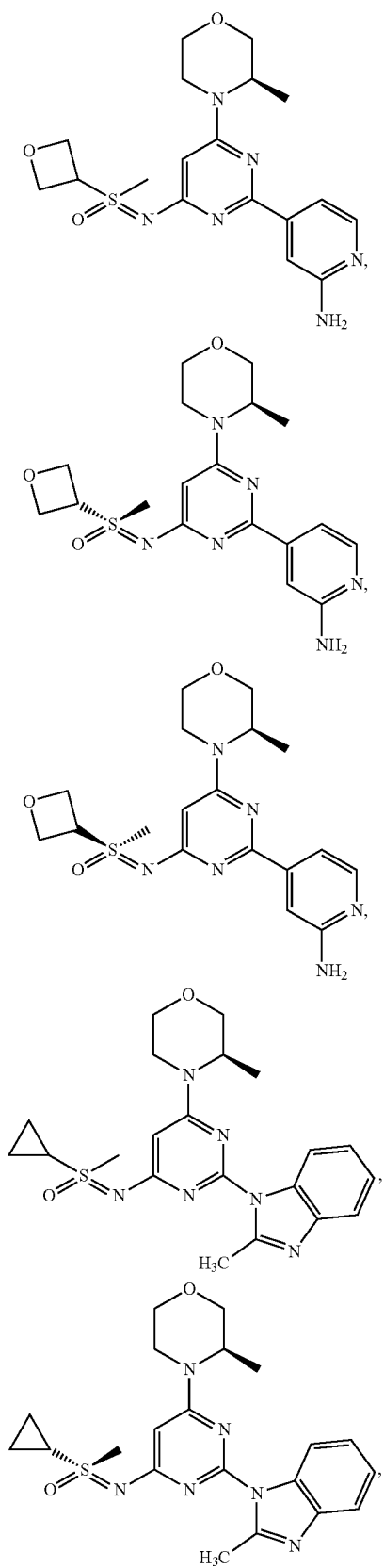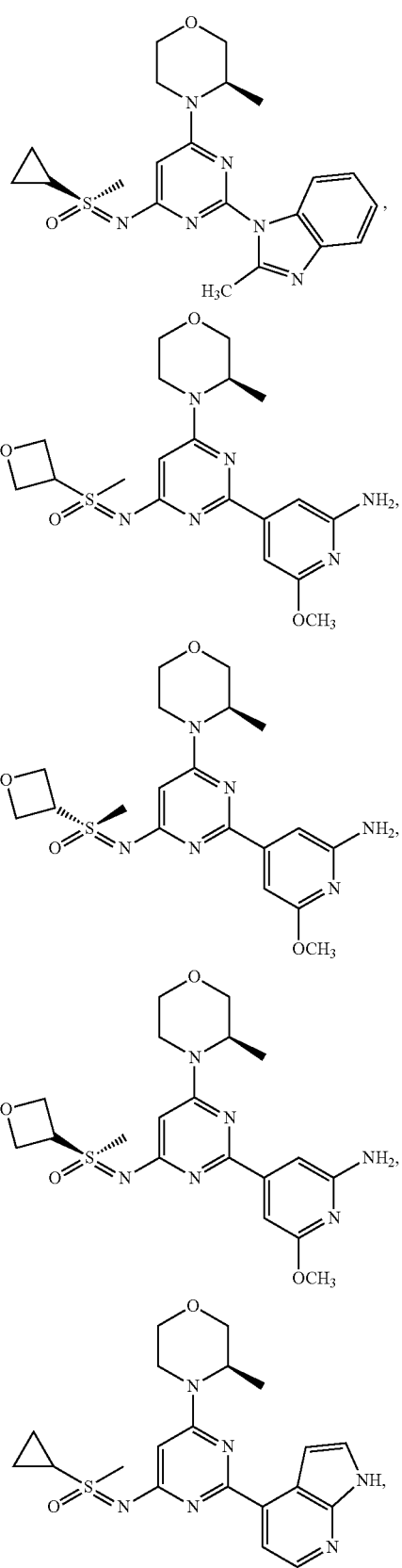

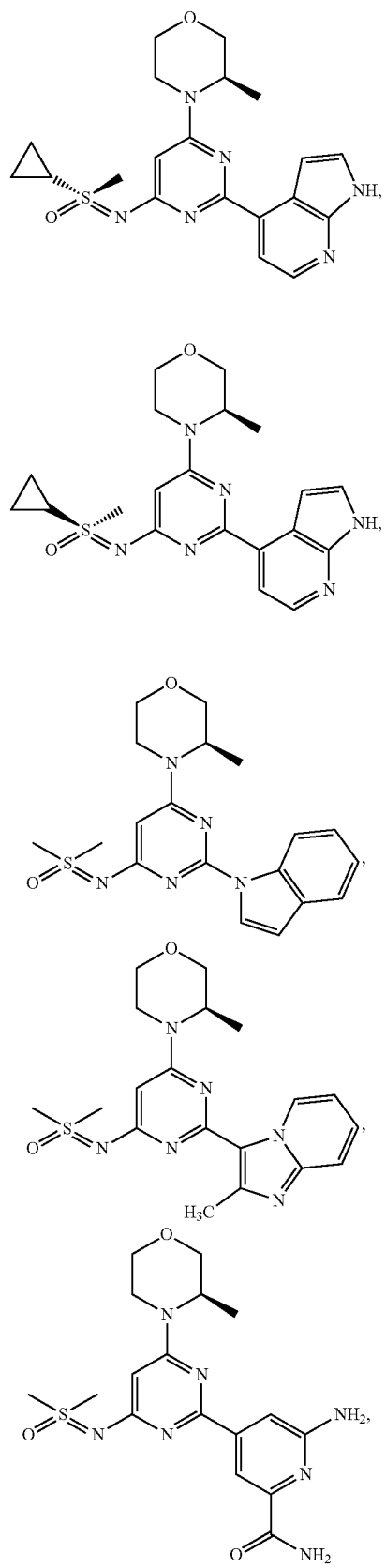
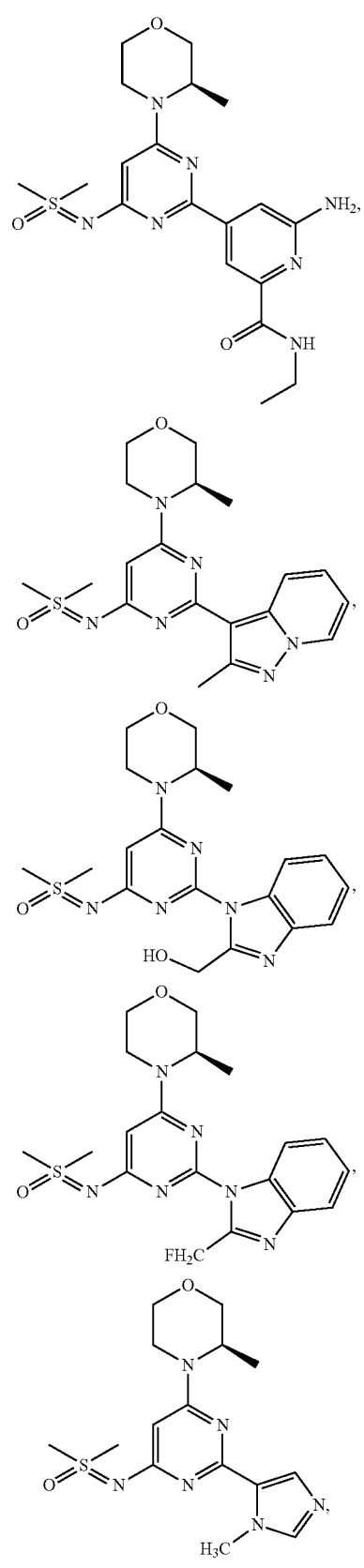

53
-continued
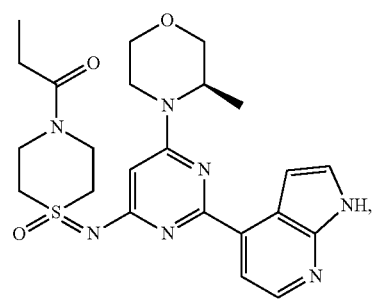
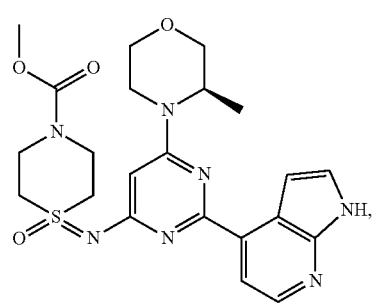
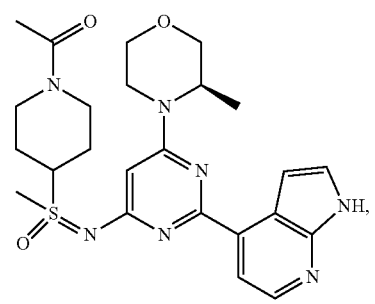
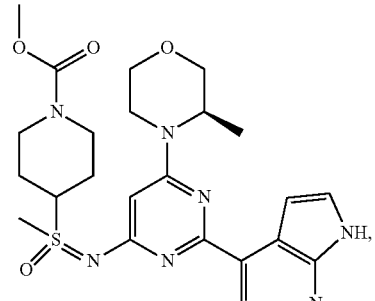
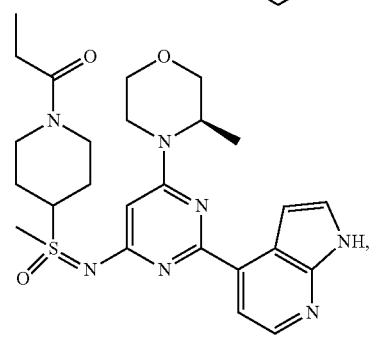
54
-continued
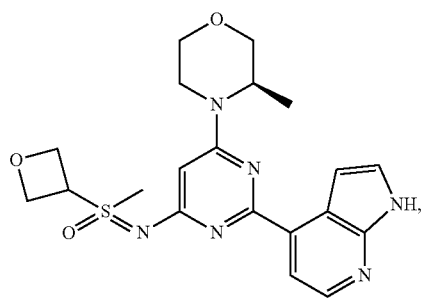
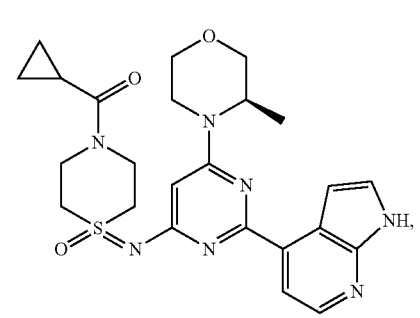
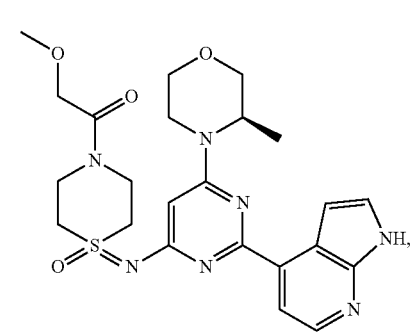
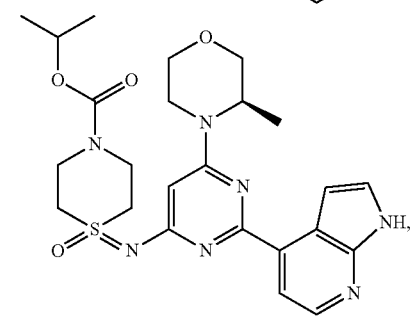
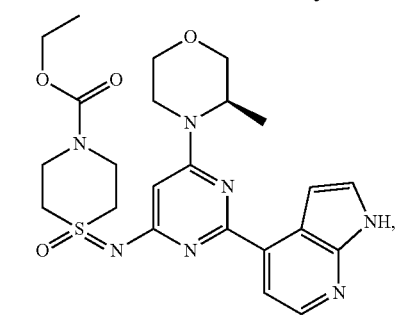

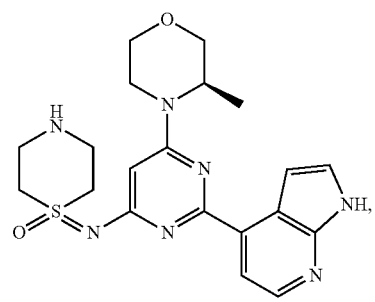
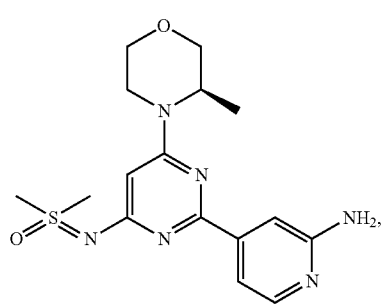
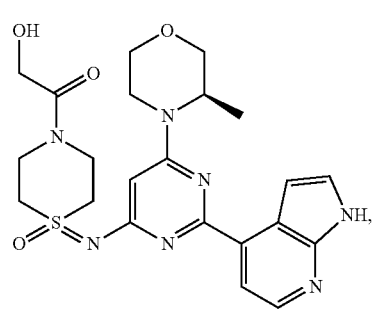
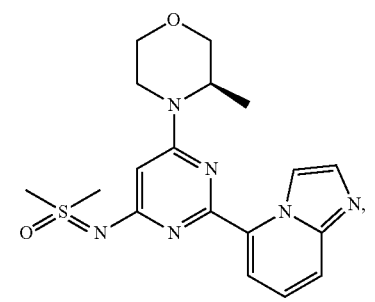
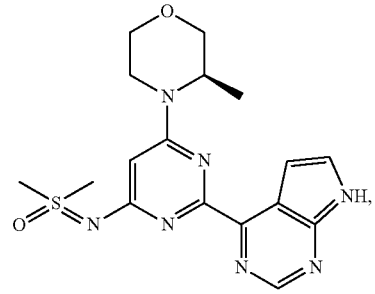
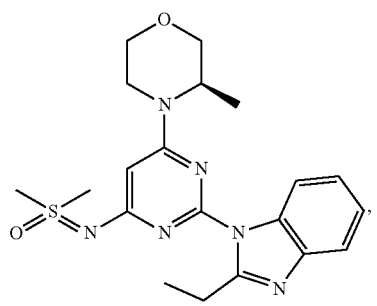
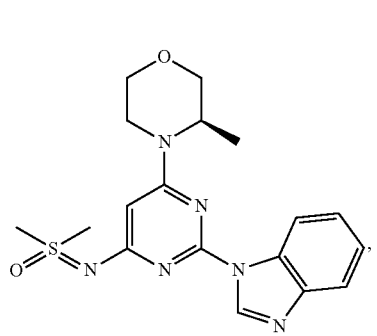
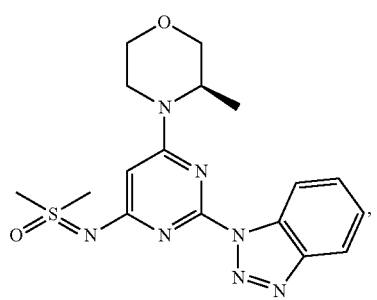
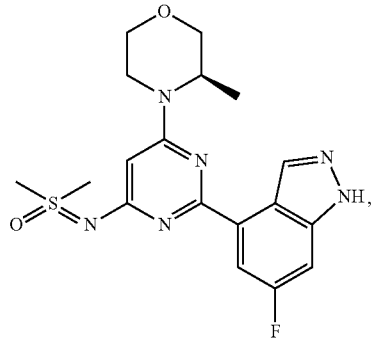
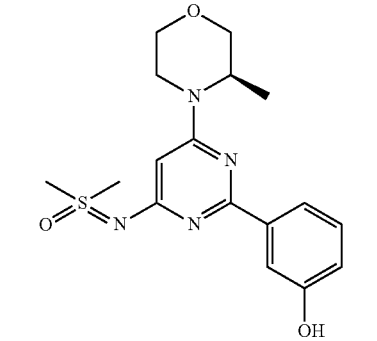

-continued
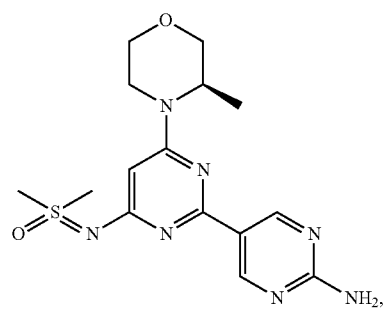
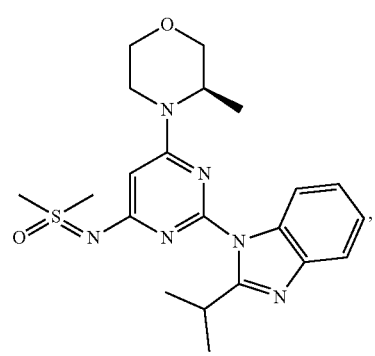
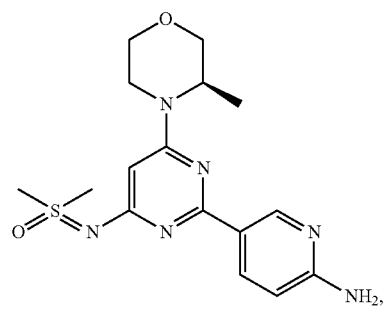
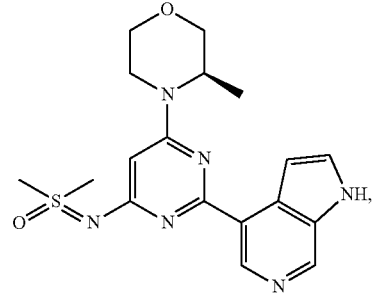
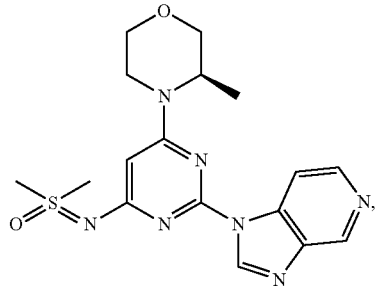
-continued
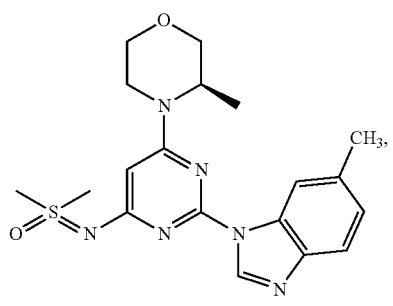
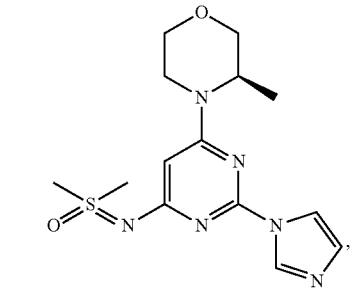
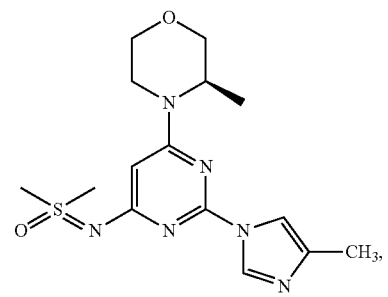
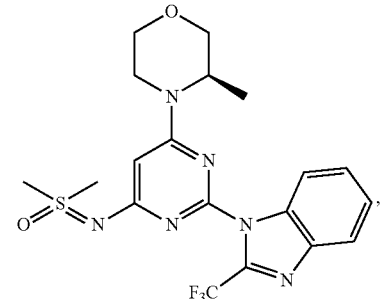
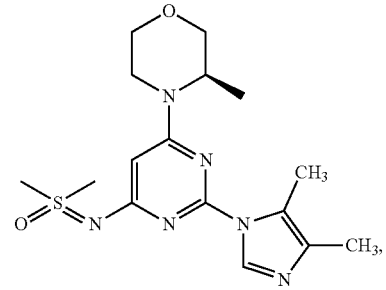

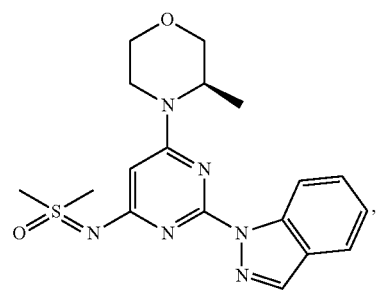
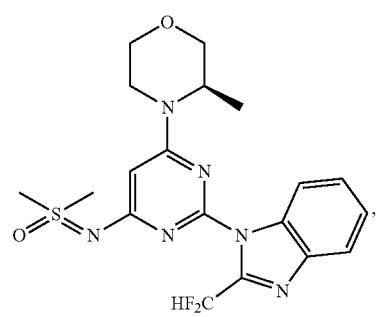
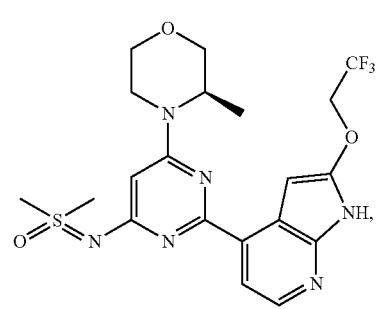
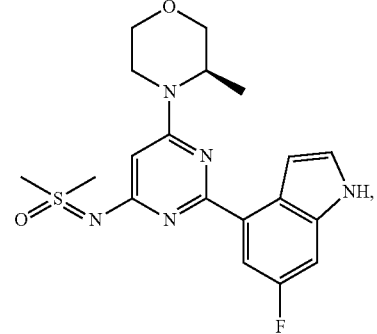
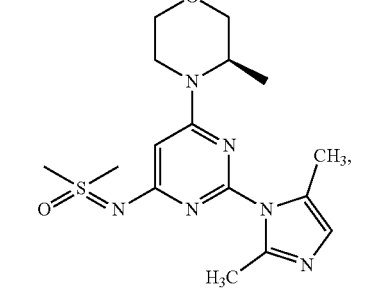
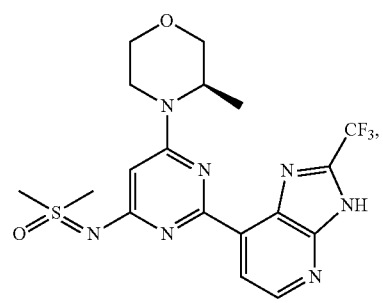
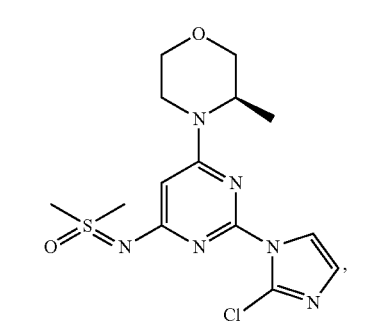
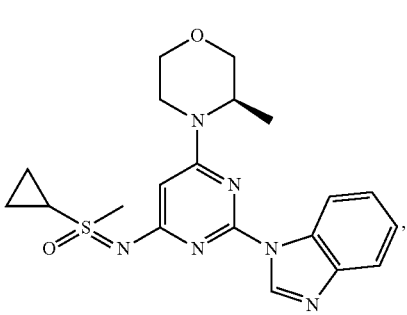
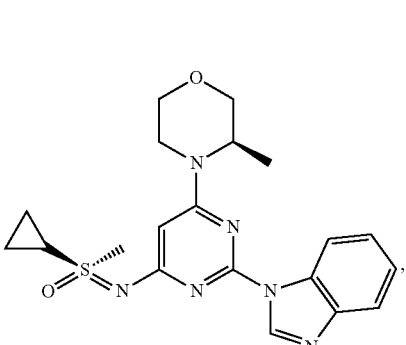
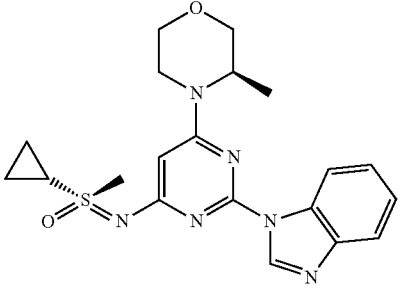

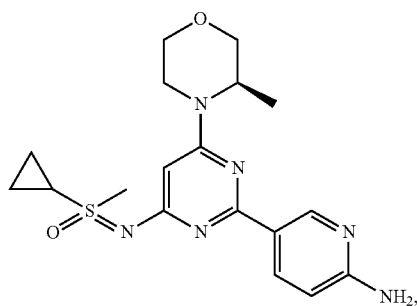
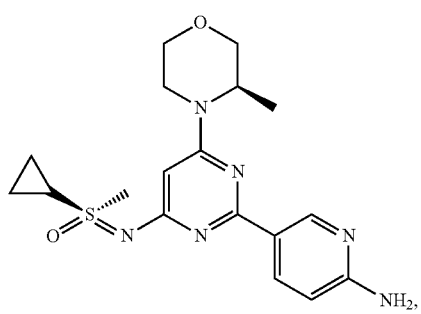
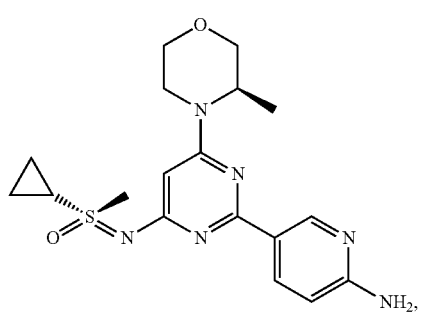
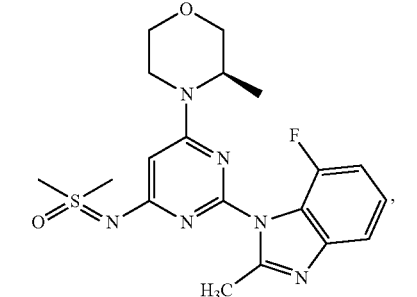
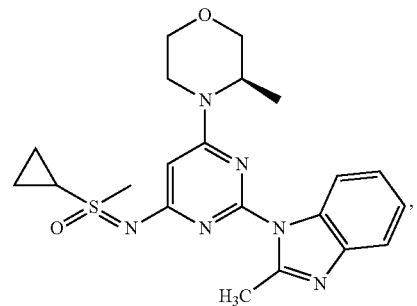
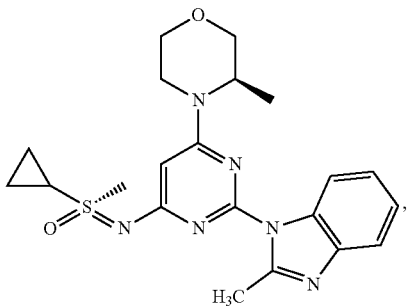
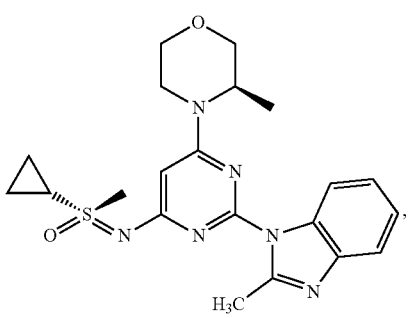
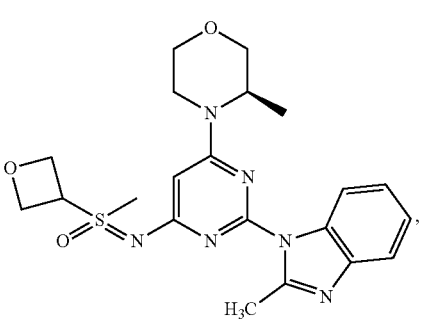
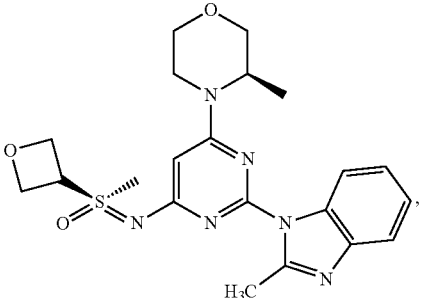
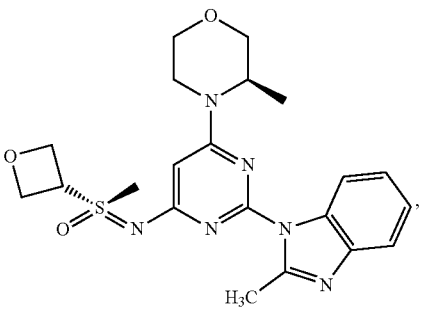

63
-continued
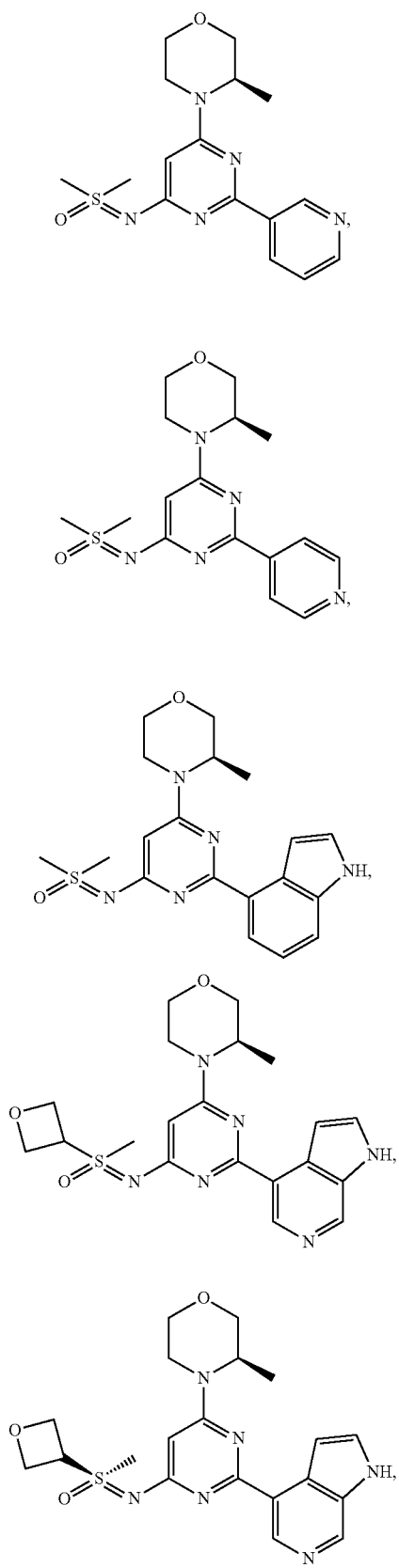
64
-continued
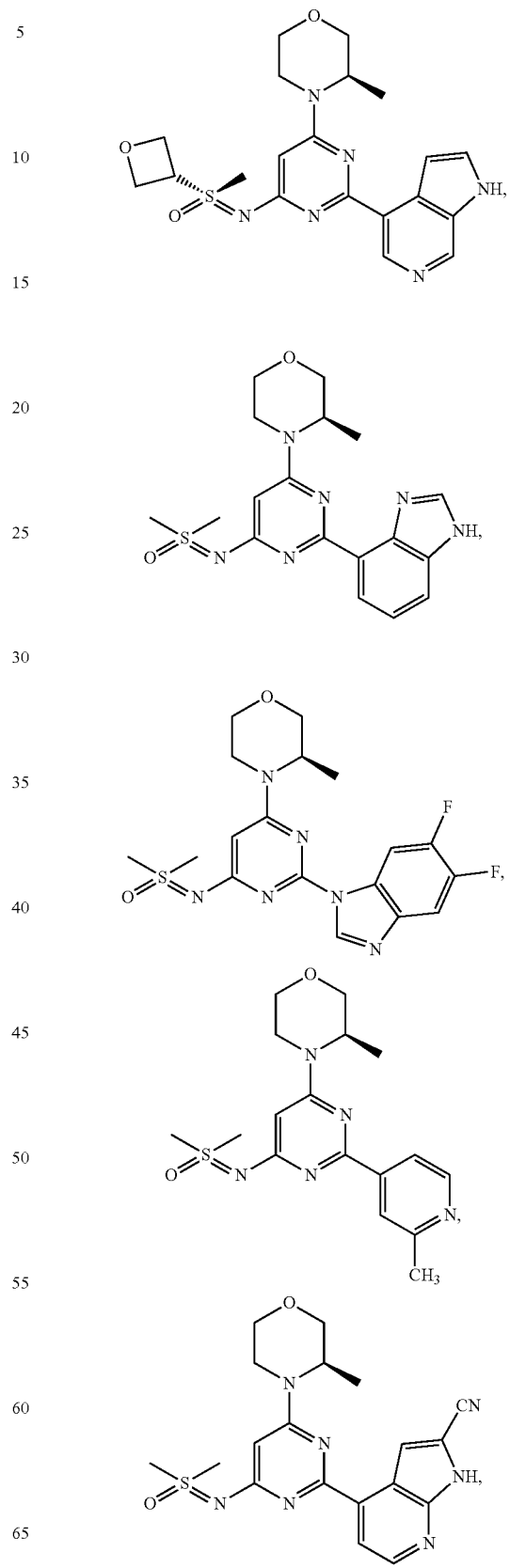

-continued
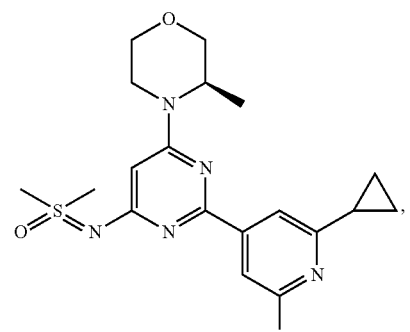
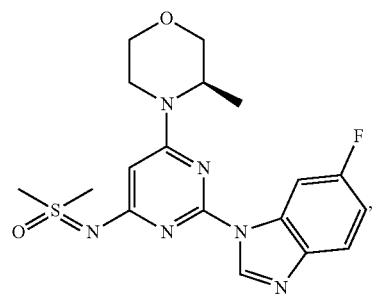
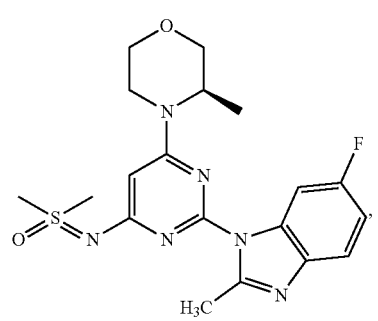
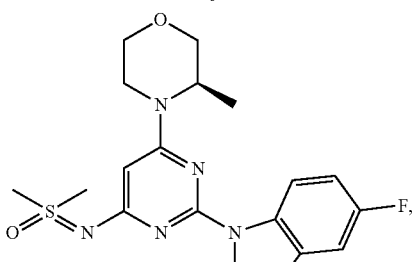
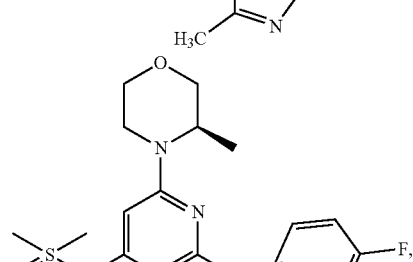
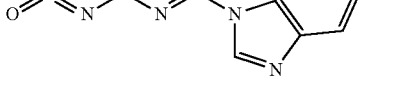
-continued
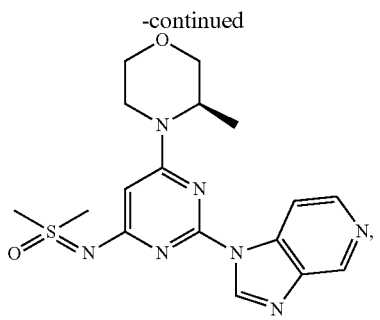
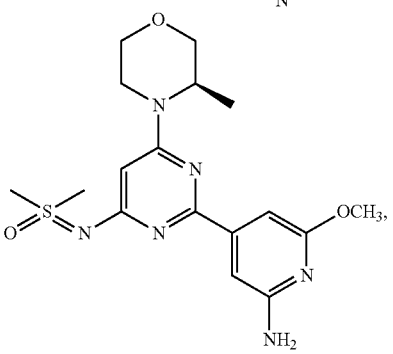
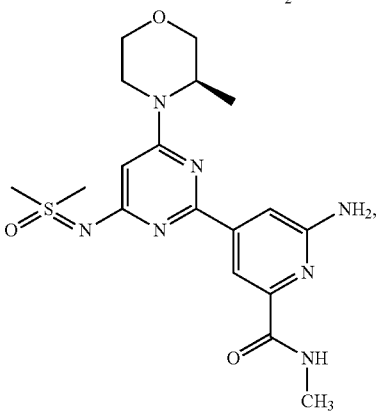
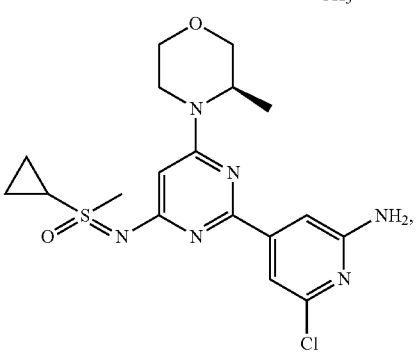
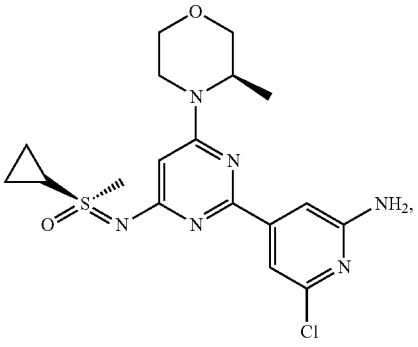

67
-continued
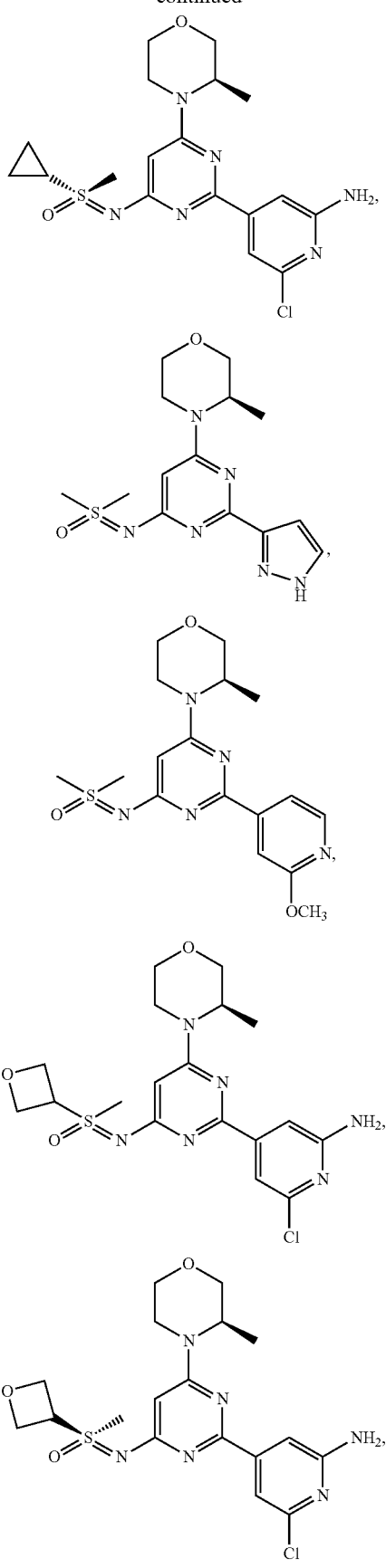
68
-continued
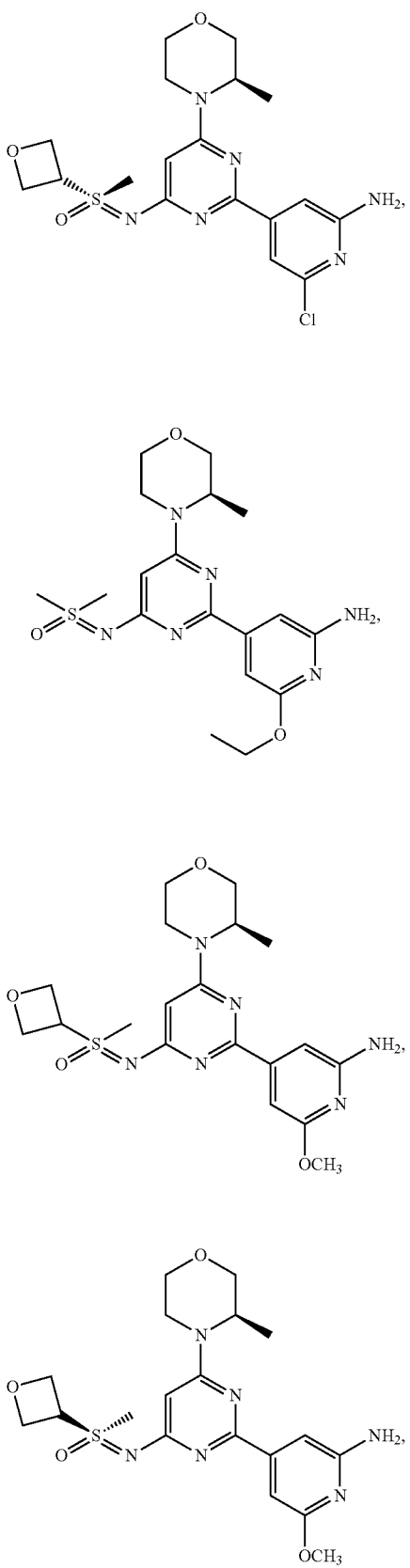

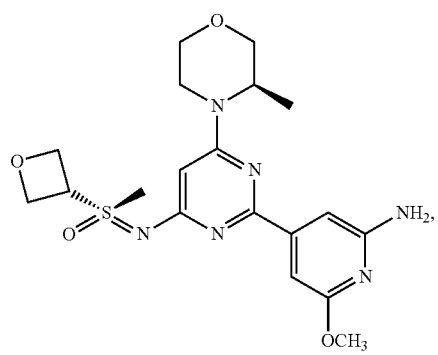
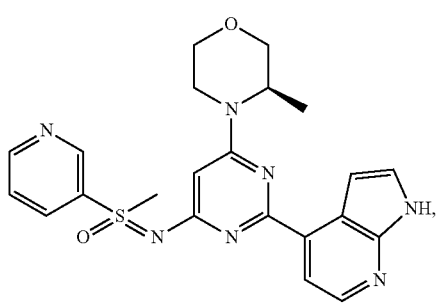
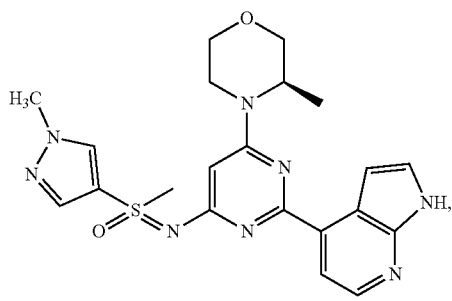
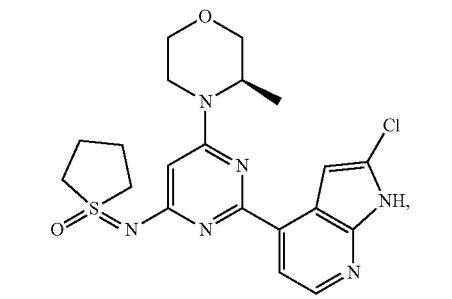
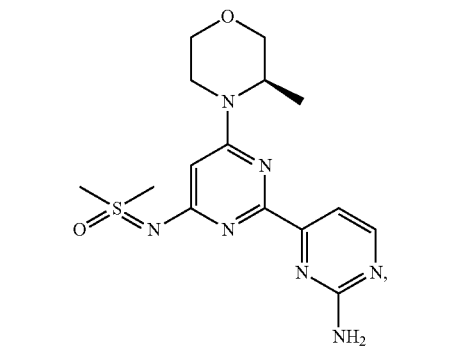
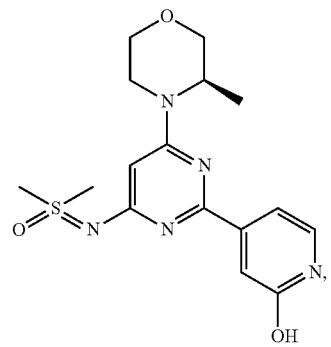
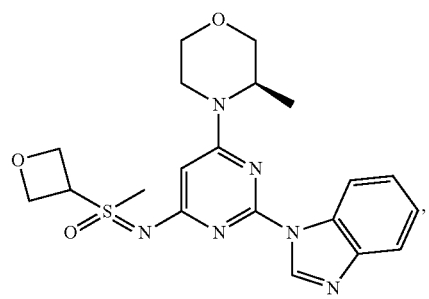
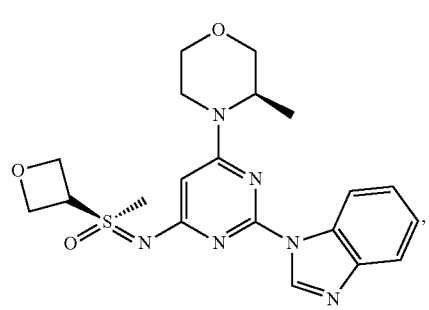
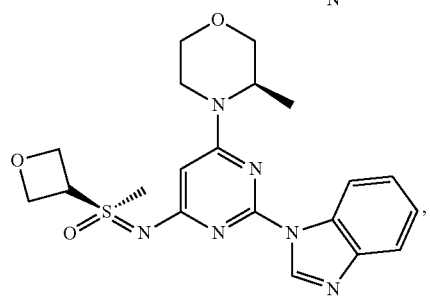
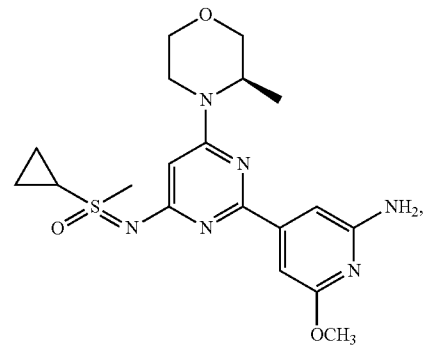

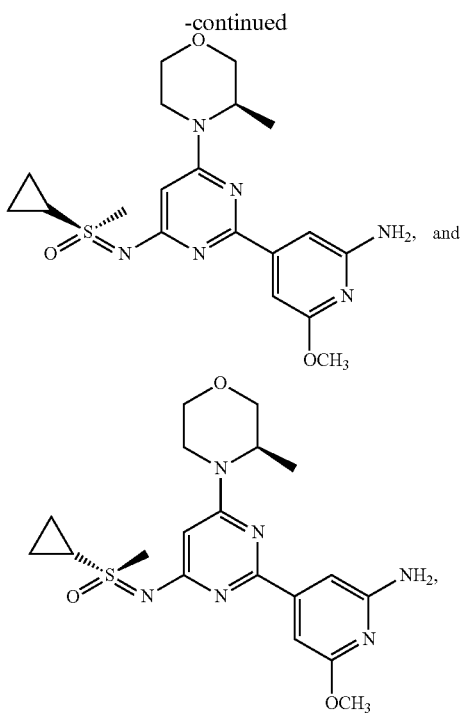

or a salt of any of the foregoing.

The disclosure provides the further embodiments:

Embodiment 97: The compound of any one of Embodiments 50, 51, 71, 72, 76, 77, 81, or 82, or salt thereof, wherein $R^{6a}$ and $R^{6b}$, together with the intervening atoms, combine to form a heteroaryl ring, which is optionally substituted with one or more $R^6$ groups.

Embodiment 98: The compound of Embodiment 97, or salt thereof, wherein $R^{6a}$ and $R^{6b}$, together with the intervening atoms, combine to form a five-membered heteroaryl ring, which is optionally substituted with one or two $R^6$ groups.

Embodiment 99: The compound of Embodiment 98, or salt thereof, wherein $R^{6a}$ and $R^{6b}$, together with the intervening atoms, combine to form a five-membered heteroaryl ring chosen from pyrrole, pyrazole, and imidazole, any of which is optionally substituted with one or two $R^6$ groups.

Embodiment 100: The compound of Embodiment 97, or salt thereof, wherein $R^{6a}$ and $R^{6b}$, together with the intervening atoms, combine to form a six-membered heteroaryl ring, which is optionally substituted with one or two $R^6$ groups.

Embodiment 101: The compound of Embodiment 100, or salt thereof, wherein $R^{6a}$ and $R^{6b}$, together with the intervening atoms, combine to form a pyridine ring, which is optionally substituted with one or two $R^6$ groups.

Embodiment 102: The compound of Embodiment 81, or salt thereof, wherein $R^{6a}$ and $R^{6b}$, together with the intervening atoms, combine to form an aryl ring, which is optionally substituted with one or more $R^6$ groups.

Embodiment 103: The compound of Embodiment 102, or salt thereof, wherein $R^{6a}$ and $R^{6b}$, together with the intervening atoms, combine to form a phenyl ring, which is optionally substituted with one or two $R^6$ groups.

Embodiment 104: The compound of any one of Embodiments 97-103, or salt thereof, wherein $R^6$ is chosen from halogen, cyano, alkyl, haloalkyl, and cycloalkyl.

Embodiment 105: The compound of any one of Embodiments 50-104, or salt thereof, wherein X is N and Y is $CR^6$.

Embodiment 106: The compound of any one of Embodiments 50-104, or salt thereof, wherein X is $CR^{6c}$ and Y is N.

Embodiment 107: The compound of any one of Embodiments 50-104, or salt thereof, wherein X and Y are both $CR^6$.

Embodiment 108: The compound of any one of Embodiments 50-81, or salt thereof, wherein $R^{6a}$ and $R^{6b}$ are independently chosen from H, $NR^{11}R^{12}$, halogen, cyano, hydroxy, oxo, alkyl, haloalkyl, $C_{3-6}$cycloalkyl, 3-6 membered heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$.

Embodiment 109: The compound of Embodiment 108, wherein $R^{6a}$ and $R^{6b}$ are independently chosen from H, $NR^{11}R^{12}$, halogen, alkyl, haloalkyl, $C_{3-6}$cycloalkyl, and 3-6 membered heterocycloalkyl.

Embodiment 110: The compound of either one of Embodiments 108 or 109, or salt thereof, wherein $R^{6b}$ is H.

Embodiment 111: The compound of any one of Embodiments 108, 109, or 110, or salt thereof, wherein $R^{6a}$ is H.

Embodiment 112: The compound of any one of Embodiments 50-111, or salt thereof, wherein each $R^{6c}$ and $R^{6d}$ is independently chosen from H, $NH_2$, halogen, cyano, alkyl, $OR^{11}$, and $C(O)NR^{11}R^{12}$.

Embodiment 113: The compound of Embodiment 112, or salt thereof, wherein at most one $R^6$, is not H.

Embodiment 114: The compound of Embodiment 112, or salt thereof, wherein $R^6$, is H.

Embodiment 115: The compound of any one of Embodiments 1-114, or salt thereof, wherein $R^1$ and $R^2$ are independently chosen from $C_{1-4}$alkyl, $C_{1-4}$haloalkyl, $C_{3-6}$cycloalkyl, 3-6 membered heterocycloalkyl, $C_{5-10}$aryl, and 5-10 membered heteroaryl, any of which is optionally substituted with one or more $R^5$ groups.

Embodiment 116: The compound of Embodiment 115, or salt thereof, wherein $R^1$ and $R^2$ are independently chosen from $C_{1-4}$alkyl, $C_{1-4}$haloalkyl, $C_{3-6}$cycloalkyl, and 3-6 membered heterocycloalkyl, any of which is optionally substituted with one or more $R^5$ groups.

Embodiment 117: The compound of Embodiment 116, or salt thereof, wherein $R^1$ and $R^2$ are independently chosen from $C_{1-4}$alkyl, $C_{3-6}$cycloalkyl, and 3-6 membered heterocycloalkyl, any of which is optionally substituted with one or two $R^5$ groups.

Embodiment 118: The compound of any one of Embodiment 115-117, or salt thereof, wherein at least one of $R^1$ and $R^2$ is $C_{1-4}$alkyl.

Embodiment 119: The compound of Embodiment 118, or salt thereof, wherein at least one of $R^1$ and $R^2$ is methyl.

Embodiment 120: The compound of Embodiment 116, or salt thereof, wherein $R^1$ and $R^2$ are independently chosen from $C_{1-4}$alkyl, $C_{1-4}$haloalkyl, $C_{3-6}$cycloalkyl, and 3-6 membered heterocycloalkyl.

Embodiment 121: The compound of Embodiment 120, or salt thereof, wherein at least one of $R^1$ and $R^2$ is $C_{1-4}$alkyl.

Embodiment 122: The compound of Embodiment 121, or salt thereof, wherein at least one of $R^1$ and $R^2$ is methyl.

Embodiment 123: The compound of either one of Embodiments 121 or 122, or salt thereof, wherein one of $R^1$ and $R^2$ is chosen from $C_{3-6}$cycloalkyl, and 3-6 membered heterocycloalkyl.

Embodiment 124: The compound of Embodiment 123, or salt thereof, wherein one of $R^1$ and $R^2$ is chosen from cyclopropyl and oxetan-3-yl.

Embodiment 125: The compound of Embodiment 122, or salt thereof, wherein $R^1$ and $R^2$ are methyl.

Embodiment 126: The compound of any one of Embodiments 1-111, or salt thereof, wherein $R^1$ and $R^2$, together with the sulfur to which they are both attached, form a 4, 5, 6, or 7-membered heterocycloalkyl ring which is optionally substituted with one or more $R^5$ groups.

Embodiment 127: The compound of Embodiment 126, or salt thereof, wherein $R^1$ and $R^2$, together with the sulfur to which they are both attached, form a 5-7 membered heterocycloalkyl ring which is optionally substituted with one or two $R^5$ groups.

Embodiment 128: The compound of Embodiment 127, or salt thereof, wherein $R^1$ and $R^2$, together with the sulfur to which they are both attached, form a 5-7 membered heterocycloalkyl ring chosen from thiane and thiomorpholine, either of which is optionally substituted with one or two $R^5$ groups.

Embodiment 129: The compound of Embodiment 126, or salt thereof, wherein $R^1$ and $R^2$, together with the sulfur to which they are both attached, form a 4, 5, 6, or 7-membered heterocycloalkyl ring.

Embodiment 130: The compound of any one of Embodiments 115, 116, 117, 118, 119, 126, 127, or 128, or salt thereof, wherein each $R^5$ is independently chosen from halogen, cyano, hydroxy, $OR^8$, $C(O)R^8$, $C(O)OR^8$, and $C(O)NR^8R^9$.

Embodiment 131: The compound of Embodiment 130, or salt thereof, wherein each $R^5$ is independently chosen from $C(O)R^8$ and $C(O)OR^8$.

Embodiment 132: The compound of either one of Embodiment 130 or 131, or salt thereof, wherein each $R^8$ is independently chosen from hydrogen, $C_{1-4}$alkyl, $C_{3-6}$cycloalkyl, and 3-6 membered heterocycloalkyl, any of which is optionally substituted with halo, hydroxy, and $C_{1-3}$alkoxy.

Embodiment 133: The compound of any one of Embodiments 1-132, or salt thereof, wherein $R^3$ is H.

Embodiment 134: The compound of any one of Embodiments 1-132, or salt thereof, wherein $R^3$ is chosen from $C_{1-6}$alkyl and $C_{1-6}$haloalkyl.

Embodiment 135: The compound of Embodiment 134, or salt thereof, wherein $R^3$ is chosen from $C_{1-6}$alkyl and $C_{1-6}$fluoroalkyl.

Embodiment 136: The compound of Embodiment 135, or salt thereof, wherein $R^3$ is chosen from methyl, fluoromethyl, difluoromethyl, and trifluoromethyl.

Embodiment 137: The compound of Embodiment 134, or salt thereof, wherein $R^3$ is $C_{1-6}$alkyl.

Embodiment 138: The compound of Embodiment 137, or salt thereof, wherein $R^3$ is methyl.

Also provided is a pharmaceutical composition comprising a compound as disclosed herein, or salt thereof, together with a pharmaceutically acceptable carrier. In certain embodiments, the compound is one disclosed in any of the embodiments above, including in any of Embodiments 1-138.

In certain embodiments, the pharmaceutical composition is formulated for oral administration.

In certain embodiments, the oral pharmaceutical composition is chosen from a tablet and a capsule.

In certain embodiments, the pharmaceutical composition is formulated for parenteral administration.

The present disclosure also relates to a method of inhibiting at least one ATR kinase function comprising the step of contacting ATR kinase with a compound as described herein, or salt thereof. The cell phenotype, cell proliferation, activity of ATR kinase, change in biochemical output produced by active ATR kinase, expression of ATR kinase, or binding of ATR kinase with a natural binding partner may be monitored. Such methods may be modes of treatment of disease, biological assays, cellular assays, biochemical assays, or the like.

Also provided herein is a method of treatment of an ATR kinase-mediated disease comprising the administration of a therapeutically effective amount of a compound as disclosed herein, or a salt thereof, to a patient in need thereof. In certain embodiments, the compound is one disclosed in any of the embodiments above, including in any of Embodiments 1-138.

In certain embodiments, the ATR kinase-mediated disease is a proliferative disease.

In certain embodiments, the proliferative disease is a myeloproliferative disorder.

In certain embodiments, the proliferative disease is cancer.

In certain embodiments, the cancer is lymphoma.

In certain embodiments, the cancer is B cell lymphoma.

In certain embodiments, the cancer is pancreatic cancer.

Also provided herein is a compound as disclosed herein, or salt thereof, for use as a medicament; or a pharmaceutical composition as disclosed herein for use as a medicament. In either case, in certain embodiments, the compound is one disclosed in any of the embodiments above, including in any of Embodiments 1-138.

Also provided herein is a compound as disclosed herein, or salt thereof, for use as a medicament for the treatment of an ATR kinase-mediated disease. In either case, in certain embodiments, the compound is one disclosed in any of the embodiments above, including in any of Embodiments 1-138. In certain embodiments, the ATR kinase-mediated disease is a proliferative disease. In certain embodiments, the proliferative disease is a myeloproliferative disorder. In certain embodiments, the proliferative disease is cancer. In certain embodiments, the cancer is lymphoma. In certain embodiments, the cancer is B cell lymphoma. In certain embodiments, the cancer is pancreatic cancer.

Also provided is the use of a compound as disclosed herein, or salt thereof, as a medicament; or the use of a pharmaceutical composition as disclosed herein as a medicament. In certain embodiments, the compound is one disclosed in any of the embodiments above, including in any of Embodiments 1-138.

Also provided is the use of a compound as disclosed herein, or salt thereof, as a medicament for the treatment of an ATR kinase-mediated disease; or the use of a pharmaceutical composition as disclosed herein as a medicament for the treatment of an ATR kinase-mediated disease; a compound as disclosed herein, or salt thereof, for use in the manufacture of a medicament for the treatment of an ATR kinase-mediated disease; or a pharmaceutical composition as disclosed herein for use in the manufacture of a medicament for the treatment of an ATR kinase-mediated disease; or the use of a compound as disclosed herein, or salt thereof, for the treatment of an ATR kinase-mediated disease; or the use of a pharmaceutical composition as disclosed herein for the treatment of an ATR kinase-mediated disease. In certain embodiments, the compound is one disclosed in any of the embodiments above, including in any of Embodiments 1-138. In and of these cases, in certain embodiments, the compound is one disclosed in any of the embodiments above, including in any of Embodiments 1-138. In certain embodiments, the ATR kinase-mediated disease is a proliferative disease. In certain embodiments, the proliferative disease is a myeloproliferative disorder. In certain embodiments, the proliferative disease is cancer. In certain embodiments, the cancer is lymphoma. In certain embodiments, the cancer is B cell lymphoma. In certain embodiments, the cancer is pancreatic cancer.

Also provided herein is a method of inhibition of ATR kinase comprising contacting ATR kinase with a compound as disclosed herein, or a salt thereof. In certain embodiments, the compound is one disclosed in any of the embodiments above, including in any of Embodiments 1-138.

Also provided herein is a method for achieving an effect in a patient comprising the administration of a therapeutically effective amount of a compound as disclosed herein, or a salt thereof, to a patient, wherein the effect is chosen from cognition enhancement. In certain embodiments, the compound is one disclosed in any of the embodiments above, including in any of Embodiments 1-138.

Also provided is a method of modulation of an ATR kinase-mediated function in a subject comprising the administration of a therapeutically effective amount of a compound as disclosed herein, or salt thereof. In certain embodiments, the compound is one disclosed in any of the embodiments above, including in any of Embodiments 1-138.

Terms

As used herein, the terms below have the meanings indicated.

When ranges of values are disclosed, and the notation "from $n_1$ ... to n2" or "between $n_1$ ... and n2" is used, where $n_1$ and n2 are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, the alkenyl will comprise from 2 to 6 carbon atoms. The term "alkenylene" refers to a carbon-carbon double bond system attached at two or more positions such as ethenylene [(—CH=CH—), (—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, the alkyl will comprise from 1 to 10 carbon atoms. In further embodiments, the alkyl will comprise from 1 to 8 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, the alkynyl comprises from 2 to 6 carbon atoms. In further embodiments, the alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH₃C(O)NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C₆H4=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, the cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1.1.1]pentane, camphor, adamantane, and bicyclo[3.2.1]octane. "Cycloalkyl", as used herein, alone or in combination, encompasses "bicycloalkyl", "bridged cycloalkyl", and "spirocycloalkyl", as defined below.

The term "bicycloalkyl", as used herein, alone or in combination, refers to a cyclic alkyl system that is characterized by the presence of two atoms, termed "bridgehead atoms" that are connected to each other via three bond pathways. "Bicycloalkyl" thus encompasses, by way of example, bicyclo[2.2.1]heptane, also known as norbornane, bicyclo[2.2.2]octane, bicyclo[2.2.0]hexane and bicyclo[3.3.0]octane.

The term "bridged cycloalkyl", as used herein, alone or in combination, refers to a bicycloalkyl system in which all three of the bond pathways between bridgehead atoms contain at least one atom. "Bridged cycloalkyl" thus encompasses, by way of example, bicyclo[2.2.1]heptane, also known as norbornane, and bicyclo[2.2.2]octane. "Bridged cycloalkyl" thus does not encompass bicyclo[2.2.0]hexane or bicyclo[3.3.0]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF₂—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH₂—NH—OCH₃.

The term "heteroaryl", as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, the heteroaryl will contain from 1 to 4 heteroatoms as ring members. In certain embodiments, the heteroaryl will contain from 1 to 3 heteroatoms as ring members. In further embodiments, the heteroaryl will contain from 1 to 2 heteroatoms as ring members. In certain embodiments, the heteroaryl will contain from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridinyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

Certain heteroaryl groups are depicted below:

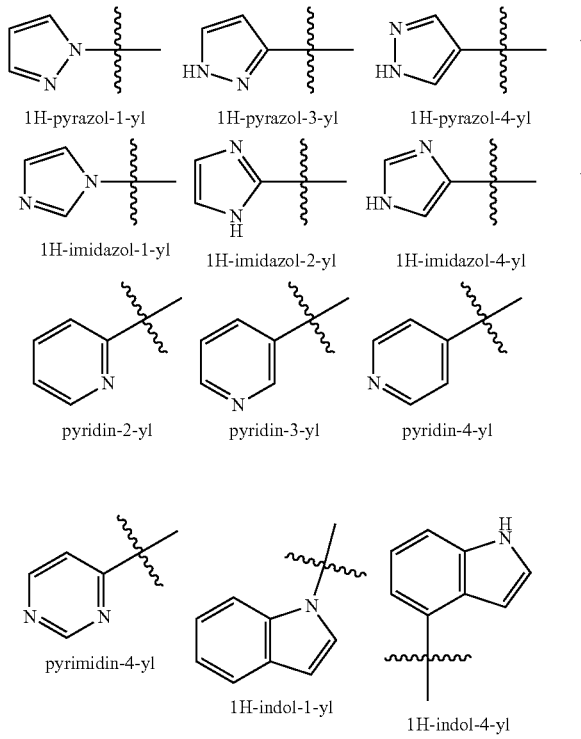
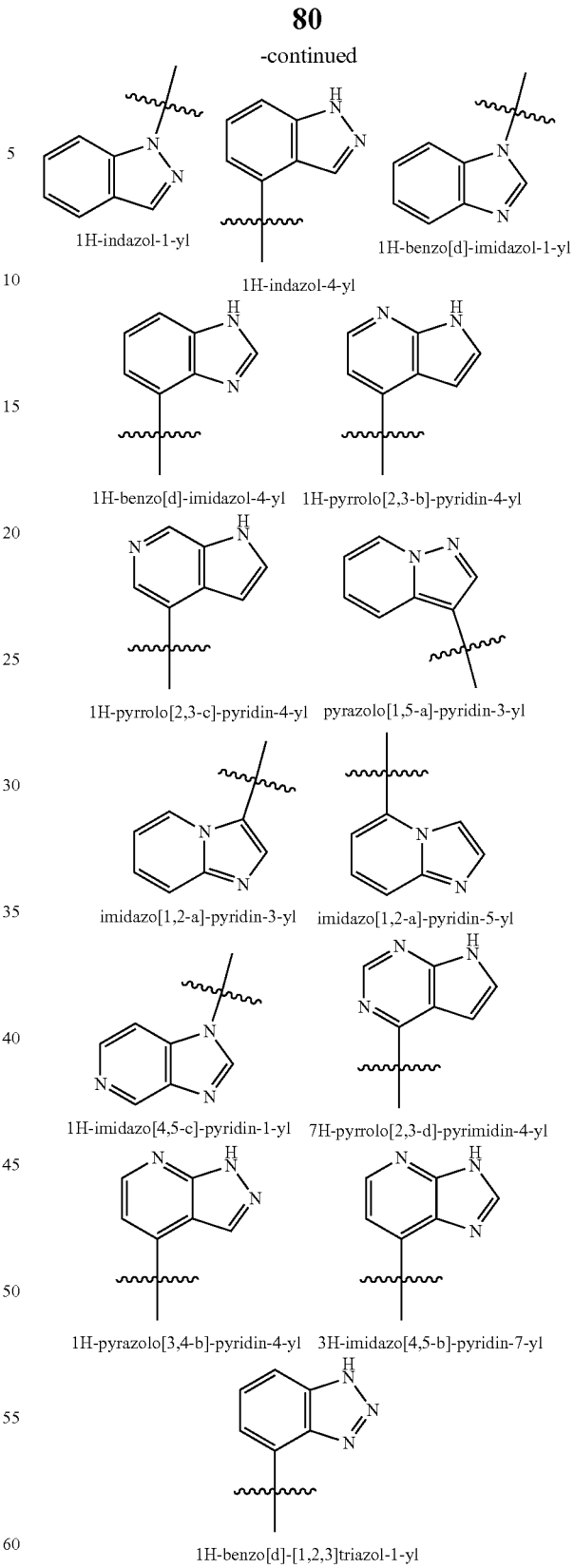

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each the heteroatom may be independently chosen from nitrogen, oxygen, and sulfur. In certain embodiments, the hetercycloalkyl will contain 1, 2, 3, or 4 heteroatoms as ring members. In certain embodiments, the hetercycloalkyl will contain 1, 2, or 3 heteroatoms as ring members. In further embodiments, the hetercycloalkyl will contain 1 or 2 heteroatoms as ring members. In certain embodiments, the hetercycloalkyl will contain from 3 to 6 ring members in each ring. In certain embodiments, the hetercycloalkyl will contain from 3 to 8 ring members in each ring. In further embodiments, the hetercycloalkyl will contain from 3 to 7 ring members in each ring. In yet further embodiments, the hetercycloalkyl will contain from 5 to 6 ring members in each ring. "Heterocycloalkyl" and "heterocycle" are intended to include sulfones, sulfoxides, sulfoximines, sulfimides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited. The term "heterocycloalkyl", as used herein, alone or in combination, is understood to encompass "heterobicycloalkyl" and "bridged heterocycloalkyl", as defined below.

The term "heterobicycloalkyl", as used herein, alone or in combination, refers to a heterocyclic alkyl system that is characterized by the presence of two atoms, termed "bridgehead atoms" that are connected to each other via three bond pathways. "Bicycloalkyl" thus encompasses, by way of example, bicyclo[2.2.1]heptane, also known as norbornane, bicyclo[2.2.2]octane, bicyclo[2.2.0]hexane and bicyclo [3.3.0]octane.

The term "bridged heterocycloalkyl", as used herein, alone or in combination, refers to a heterobicycloalkyl system in which all three of the bond pathways between bridgehead atoms contain at least one atom. "Bridged heterocycloalkyl" thus encompasses, by way of example, 1,4-diazabicyclo[2.2.2]octane, also known as DABCO, and 7-azabicyclo[2.2.1]heptane.

Bicyclic ring systems can be described using terminology that will be recognized by the person in the art. A bicyclic compound can be named as the fusion of two ring systems. For example, "benzobenzene" is understood to refer to naphthalene. Unless specifically restricted, any ring fusion isomer will be embraced by this terminology. For example, "benzonaphthalene" is understood to embrace both anthracene and phenanthrene. As a further example, pyrrolopyridine is understood to embrace any compound having pyrrole fused to pyridine, and thus embraces 4-azaindole, 5-azaindole, 6-azaindole, and 7-azaindole.

The term "heterobicycloalkyl", as used herein, alone or in combination, refers to a saturated, partially unsaturated, or fully unsaturated (but nonaromatic) cyclic alkyl system, containing at least one heteroatom as a ring member, that is characterized by the presence of two atoms, termed "bridgehead atoms" that are connected to each other via three bond pathways. "Heterobicycloalkyl" thus encompasses, by way of example, 7-azabicyclo[2.2.1]heptane, 1,4-diazabicyclo [2.2.2]octane, also referred to as "DABCO", 1-azabicyclo [2.2.0]hexane, and 3-azabicyclo [3.3.0]octane.

The term "bridged heterocycloalkyl", as used herein, alone or in combination, refers to a heterobicycloalkyl system in which all three of the bond pathways between bridgehead atoms contain at least one atom. "Bridged heterocycloalkyl" thus encompasses, by way of example, 7-azabicyclo[2.2.1]heptane, 1,4-diazabicyclo[2.2.2]octane, also referred to as "DABCO", but not 1-azabicyclo[2.2.0] hexane, or 3-azabicyclo[3.3.0]octane.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group. Examples of hydroxyalkyl groups include hydroxymethyl, 1-hydroxyethyl, 2-hydroxyethyl, and 2-hydroxy-2-propyl.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently chosen from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four the members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen and lower alkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "spirocycloalkyl", as used herein, alone or in combination, refers to an alkyl group having two rings that has a single atom common to both rings. Examples of spirocycloalkyl systems include spiro[3.3]heptane and spiro[4.4]nonane.

The term "spiroheterocycloalkyl", as used herein, alone or in combination, refers to a heteroalkyl group having two rings that has a single atom common to both rings. Examples of spirocycloalkyl systems include 2-azaspiro[3.3]heptane and 3-azaspiro[4.4]nonane.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The term "sulfimide" refers to a RS(=NR')R" group with R, R', and R" as defined herein.

The term "sulfoximine" refers to a RS(=O)(=NR')R" group with R, R', and R" as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that the group is absent.

The term "optionally substituted" means the anteceding group may be substituted or unsubstituted. When substituted, the substituents of an "optionally substituted" group may include, without limitation, one or more substituents independently chosen from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', or the term R", appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R, R' and R" groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

The term "enantiomer", as used herein, alone or in combination, refers to one of a pair of compounds that differ in absolute stereochemistry at every stereocenter. Each enantiomer in a pair of compounds is thus the mirror image of the other enantiomer.

The term "epimer", as used herein, alone or in combination, refers to one of a pair of compounds that differ in absolute stereochemistry at a single stereocenter.

The term "diastereomer", as used herein, alone or in combination, refers to one of a pair of compounds that neither have identical stereochemistry nor are enantiomers of each other.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as D-isomers and L-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

Certain of the compounds disclosed herein can exist as a mixture of two diastereomers. In some embodiments, the two diastereomers are present in equal amounts. In some embodiments, the compound contains 60% or more of the major diastereomer. In some embodiments, the compound contains 70% or more of the major diastereomer. In some embodiments, the compound contains 80% or more of the major diastereomer. In some embodiments, the compound contains 90% or more of the major diastereomer. In some embodiments, the compound contains 95% or more of the major diastereomer. In some embodiments, the compound contains 98% or more of the major diastereomer.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"ATR inhibitor" is used herein to refer to a compound that exhibits an $IC_{50}$ with respect to ATR kinase activity of no more than about 10 µM and more typically not more than about 5 µM, as measured in the ATR/ATRIP biochemical assay or in the ATR kinase pCHK1 cellular assay described generally herein. "$IC_{50}$" is that concentration of inhibitor which reduces to half-maximal level the activity of an enzyme (e.g., ATR kinase), or the ATR-induced phosphorylation of CHK1 at Serine 345 in cells. Certain compounds disclosed herein have been discovered to exhibit inhibition against ATR kinase. In certain embodiments, compounds will exhibit an $IC_{50}$ with respect to ATR kinase of no more than about 1 µM; in further embodiments, compounds will exhibit an $IC_{50}$ with respect to ATR kinase of no more than about 2 µM; in yet further embodiments, compounds will exhibit an IC50 with respect to ATR kinase of not more than about 1 µM; in yet further embodiments, compounds will exhibit an $IC_{50}$ with respect to ATR kinase of not more than about 500 nM; in yet further embodiments, compounds will exhibit an $IC_{50}$ with respect to ATR kinase of not more than about 200 nM; in yet further embodiments, compounds will exhibit an $IC_{50}$ with respect to ATR kinase of not more than about 100 nM, as measured in the ATR kinase assay described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease. In certain embodiments, the treatment is not prophylactic. For example, treatment is undertake after a diagnosis of disease or the appearance of symptoms of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

Salts

The compounds disclosed herein can exist as salts, including pharmaceutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable.

The term "pharmaceutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, paratoluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides.

Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

Formulations

While it may be possible for the compounds of the subject disclosure, or salts thereof, to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds (including in the form of compositions described herein) disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds (including in the form of compositions described herein) may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds (including in the form of compositions described herein) may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds (including in the form of compositions described herein) can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

Combinations and Combination Therapies

In certain instances, it may be appropriate to administer at least one of the compounds described herein (or a pharmaceutically acceptable salt, ester, or prodrug thereof or composition thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

The compounds of the present disclosure can be used, alone or in combination with other pharmaceutically active compounds, to treat conditions such as those previously described hereinabove. The compound(s) of the present disclosure and other pharmaceutically active compound(s) can be administered simultaneously (either in the same dosage form or in separate dosage forms) or sequentially.

Accordingly, in one embodiment, the present disclosure comprises methods for treating a condition by administering to the subject a therapeutically-effective amount of one or more compounds of the present disclosure and one or more additional pharmaceutically active compounds.

In another embodiment, there is provided a pharmaceutical composition comprising one or more compounds of the present disclosure, one or more additional pharmaceutically active compounds, and a pharmaceutically acceptable carrier.

In another embodiment, the one or more additional pharmaceutically active compounds is chosen from anti-cancer drugs, anti-proliferative drugs, and anti-inflammatory drugs.

ATR inhibitor compositions described herein are also optionally used in combination with other therapeutic reagents that are chosen for their therapeutic value for the condition to be treated. In general, the compounds described herein and, in embodiments where combination therapy is employed, other agents do not have to be administered in the same pharmaceutical composition and, because of different physical and chemical characteristics, are optionally administered by different routes. The initial administration is generally made according to established protocols and then, based upon the observed effects, the dosage, modes of administration and times of administration subsequently modified. In certain instances, it is appropriate to administer an ATR inhibitor compound, as described herein, in combination with another therapeutic agent. By way of example only, the therapeutic effectiveness of an ATR inhibitor is enhanced by administration of another therapeutic agent (which also includes a therapeutic regimen) that also has therapeutic benefit. Regardless of the disease, disorder or condition being treated, the overall benefit experienced by the patient is either simply additive of the two therapeutic agents or the patient experiences an enhanced (i.e., synergistic) benefit. Alternatively, if a compound disclosed herein has a side effect, it may be appropriate to administer an agent to reduce the side effect; or the therapeutic effectiveness of a compound described herein may be enhanced by administration of an adjuvant.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is an ATR inhibitor as described herein) may be administered in any order, or simultaneously. If simultaneously, the multiple therapeutic agents are optionally provided in a single, unified form, or in multiple forms (by way of example only, either as a single pill or as two separate pills).

In another embodiment, an ATR inhibitor is optionally used in combination with procedures that provide additional benefit to the patient. An ATR inhibitor and any additional therapies are optionally administered before, during or after the occurrence of a disease or condition, and the timing of administering the composition containing an ATR inhibitor varies in some embodiments. Thus, for example, an ATR inhibitor is used as a prophylactic and is administered continuously to subjects with a propensity to develop conditions or diseases in order to prevent the occurrence of the disease or condition. An ATR inhibitor and compositions are optionally administered to a subject during or as soon as possible after the onset of the symptoms. While embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that in some embodiments of the disclosure various alternatives to the embodiments described herein are employed in practicing the disclosure.

An ATR inhibitor can be used in combination with anti-cancer drugs, including but not limited to the following classes: alkylating agsents, anti-metabolites, plant alkaloids and terpenoids, topoisomerase inhibitors, cytotoxic antibiotics, angiogenesis inhibitors and tyrosine kinase inhibitors.

For use in cancer and neoplastic diseases an ATR inhibitor may be optimally used together with one or more of the following non-limiting examples of anti-cancer agents:

1) inhibitors or modulators of a protein involved in one or more of the DNA damage repair (DDR) pathways such as:
   a. PARP1/2, including, but not limited to: olaparib, niraparib, rucaparib;
   b. checkpoint kinase 1 (CHK1), including, but not limited to: UCN-01, AZD7762, PF477736, SCH900776, MK-8776, LY2603618, V158411, and EXEL-9844;
   c. checkpoint kinase 2 (CHK2), including, but not limited to: PV1019, NSC 109555, and VRX0466617;
   d. dual CHK1/CHK2, including, but not limited to: XL-844, AZD7762, and PF-473336;
   e. WEE1, including, but not limited to: MK-1775 and PD0166285;
   f. ATM, including, but not limited to KU-55933,
   g. DNA-dependent protein kinase, including, but not limited to NU7441 and M3814; and
   h. Additional proteins involved in DDR;
2) Inhibitors or modulators of one or more immune checkpoints, including, but not limited to:
   a. PD-1 inhibitors such as nivolumab (OPDIVO), pembrolizumab (KEYTRUDA), pidilizumab (CT-011), and AMP-224 (AMPLIMMUNE);
   b. PD-L1 inhibitors such as Atezolizumab (TECENTRIQ), Avelumab (Bavencio), Durvalumab (Imfinzi), MPDL3280A (Tecentriq), BMS-936559, and MEDI4736;
   c. anti-CTLA-4 antibodies such as ipilimumab (YERVOY) and CP-675,206 (TREMELIMUMAB);
   d. inhibitors of T-cell immunoglobulin and mucin domain 3 (Tim-3);
   e. inhibitors of V-domain Ig suppressor of T cell activation (Vista);
   f. inhibitors of band T lymphocyte attenuator (BTLA);
   g. inhibitors of lymphocyte activation gene 3 (LAG3); and
   h. inhibitors of T cell immunoglobulin and immunoreceptor tyrosine-based inhibitory motif domain (TIGIT);
3) telomerase inhibitors or telomeric DNA binding compounds;
4) alkylating agents, including, but not limited to: chlorambucil (LEUKERAN), oxaliplatin (ELOXATIN), streptozocin (ZANOSAR), dacarbazine, ifosfamide, lomustine (CCNU), procarbazine (MATULAN), temozolomide (TEMODAR), and thiotepa;
5) DNA crosslinking agents, including, but not limited to: carmustine, chlorambucil (LEUKERAN), carboplatin (PARAPLATIN), cisplatin (PLATIN), busulfan (MYLERAN), melphalan (ALKERAN), mitomycin (MITOSOL), and cyclophosphamide (ENDOXAN);
6) anti-metabolites, including, but not limited to: cladribine (LEUSTATIN), cytarbine, (ARA-C), mercaptopurine (PURINETHOL), thioguanine, pentostatin (NIPENT), cytosine arabinoside (cytarabine, ARA-C), gemcitabine (GEMZAR), fluorouracil (5-FU, CARAC), capecitabine (XELODA), leucovorin (FUSILEV), methotrexate (RHEUMATREX), and raltitrexed;
7) antimitotics, which are often plant alkaloids and terpenoids, or derivateves thereof including but limited to: taxanes such as docetaxel (TAXITERE), paclitaxel (ABRAXANE, TAXOL), vinca alkaloids such as vincristine (ONCOVIN), vinblastine, vindesine, and vinorelbine (NAVELBINE);
8) topoisomerase inhibitors, including, but not limited to: amsacrine, camptothecin (CTP), genisten, irinotecan (CAMPTOSAR), topotecan (HYCAMTIN), doxorubicin (ADRIAMYCIN), daunorubicin (CERUBIDINE), epirubicin (ELLENCE), ICRF-193, teniposide (VUMON), mitoxantrone (NOVANTRONE), and etoposide (EPOSIN);
9) DNA replication inhibitors, including, but not limited to: fludarabine (FLUDARA), aphidicolin, ganciclovir, and cidofovir;
10) ribonucleoside diphosphate reductase inhibitors, including, but not limited to: hydroxyurea;
11) transcription inhibitors, including, but not limited to: actinomycin D (dactinomycin, COSMEGEN) and plicamycin (mithramycin);
12) DNA cleaving agents, including, but not limited to: bleomycin (BLENOXANE), idarubicin,
13) cytotoxic antibiotics, including, but not limited to: actinomycin D (dactinomycin, COSMEGEN),
14) aromatase inhibitors, including, but not limited to: aminoglutethimide, anastrozole (ARIMIDEX), letrozole (FEMARA), vorozole (RIVIZOR), and exemestane (AROMASIN);
15) angiogenesis inhibitors, including, but not limited to: genistein, sunitinib (SUTENT), and bevacizumab (AVASTIN);
16) anti-steroids and anti-androgens, including, but not limited to: aminoglutethimide (CYTADREN), bicalutamide (CASODEX), cyproterone, flutamide (EULEXIN), nilutamide (NILANDRON);
17) tyrosine kinase inhibitors, including, but not limited to: imatinib (GLEEVEC), erlotinib (TARCEVA), lapatininb (TYKERB), sorafenib (NEXAVAR), and axitinib (INLYTA);
18) mTOR inhibitors, including, but not limited to: everolimus, temsirolimus (TORISEL), and sirolimus;
19) monoclonal antibodies, including, but not limited to: trastuzumab (HERCEPTIN) and rituximab (RITUXAN);
20) apoptosis inducers such as cordycepin;
21) protein synthesis inhibitors, including, but not limited to: clindamycin, chloramphenicol, streptomycin, anisomycin, and cycloheximide;
22) antidiabetics, including, but not limited to: metformin and phenformin;
23) antibiotics, including, but not limited to:
   a. tetracyclines, including, but not limited to: doxycycline;
   b. erythromycins, including, but not limited to: azithromycin;

c. glycylglycines, including, but not limited to: tigecyline;

d. antiparasitics, including, but not limited to: pyrvinium pamoate;

e. beta-lactams, including, but not limited to the penicillins and cephalosporins;

f. anthracycline antibiotics, including, but not limited to: daunorubicin and doxorubicin;

g. other antibiotics, including, but not limited to: chloramphenicol, mitomycin C, and actinomycin;

24) antibody therapeutical agents, including, but not limited to: muromonab-CD3, infliximab (REMICADE), adalimumab (HUMIRA), omalizumab (XOLAIR), daclizumab (ZENAPAX), rituximab (RITUXAN), ibritumomab (ZEVALIN), tositumomab (BEXXAR), cetuximab (ERBITUX), trastuzumab (HERCEPTIN), ADCETRIS, alemtuzumab (CAMPATH-1H), Lym-1 (ONCOLYM), ipilimumab (YERVOY), vitaxin, bevacizumab (AVASTIN), and abciximab (REOPRO); and 25) other agents, such as *Bacillus* Calmette-Gudrin (B-C-G) vaccine; buserelin (ETILAMIDE); chloroquine (ARALEN); clodronate, pamidronate, and other bisphosphonates; colchicine; demethoxyviridin; dichloroacetate; estramustine; filgrastim (NEUPOGEN); fludrocortisone (FLORINEF); goserelin (ZOLADEX); interferon; leucovorin; leuprolide (LUPRON); levamisole; lonidamine; mesna; metformin; mitotane (o,p'-DDD, LYSODREN); nocodazole; octreotide (SANDOSTATIN); perifosine; porfimer (particularly in combination with photo- and radiotherapy); suramin; tamoxifen; titanocene dichloride; tretinoin; anabolic steroids such as fluoxymesterone (HALOTESTIN); estrogens such as estradiol, diethylstilbestrol (DES), and dienestrol; progestins such as medroxyprogesterone acetate (MPA) and megestrol; and testosterone.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneously, the timing between the multiple doses may be any duration of time ranging from a few minutes to four weeks.

Thus, in another aspect, certain embodiments provide methods for treating ATR kinase-mediated disorders in a human or animal subject in need of such treatment comprising administering to the subject an amount of a compound disclosed herein, or a salt thereof effective to reduce or prevent the disorder in the subject, in combination with at least one additional agent for the treatment of the disorder that is known in the art. In a related aspect, certain embodiments provide therapeutic compositions comprising at least one compound disclosed herein in combination with one or more additional agents for the treatment of ATR kinase-mediated disorders.

Specific diseases to be treated by the compounds, compositions, and methods disclosed herein include proliferative and hyperproliferative diseases, including cancer.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Provided below are exemplary embodiments of the disclosure.

Embodiment I-1: A compound of structural Formula (I):

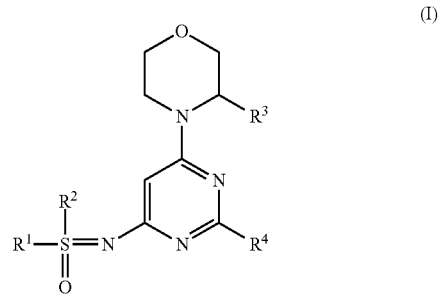

(I)

or a salt thereof, wherein:

$R^1$ and $R^2$ are independently selected from $C_{1-4}$alkyl, $C_{1-4}$haloalkyl, $C_{3-6}$cycloalkyl, $C_{3-6}$ heterocycloalkyl, aryl, and heteroaryl, each of which is optionally substituted with one or more RS groups, or $R^1$ and $R^2$, together with the sulfur to which they are both attached, form a heterocycloalkyl ring which is optionally substituted with one or more $R^5$ groups;

$R^3$ is selected from hydrogen, $C_{1-6}$alkyl, and $C_{1-6}$haloalkyl;

$R^4$ is selected from $C_{5-10}$aryl and $C_{5-10}$heteroaryl, each of which is optionally substituted with one or more $R^6$ groups;

each $R^5$ is independently selected from $NR^8R^9$, halogen, cyano, hydroxy, oxo, alkyl, haloalkyl, cycloalkyl, heterocycloalkyl, hydroxyalkyl, $OR^8$, $NRC(O)R^8$, $NR^7C(O)OR^8$, $NR^7C(O)NR^8R^9$, $C(O)R^8$, $C(O)OR^8$, and $C(O)NR^8R^9$;

each $R^6$ is independently selected from $NR^{11}R^{12}$, halogen, cyano, hydroxy, oxo, alkyl, haloalkyl, cycloalkyl, heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$;

each $R^7$, $R^8$ and $R^9$ is independently selected from hydrogen, $C_{1-4}$alkyl, $C_{3-6}$cycloalkyl, and heterocycloalkyl and is optionally substituted with halo, hydroxy, $C_{1-3}$alkyl, $C_{1-3}$ haloalkyl, and $C_{1-3}$alkoxy; or any two of $R^7$, $R^8$ and $R^9$, together with the atom to which they are both attached can form a 3-7 membered cycloalkyl or heterocycloalkyl ring; and each $R^{10}$, $R^{11}$ and $R^{12}$ is independently selected from hydrogen, $C_{1-4}$alkyl, $C_{3-6}$cycloalkyl, and heterocycloalkyl and is optionally substituted with one or more groups selected from halo, hydroxy and alkoxy; or any two of $R^{10}$, $R^{11}$ and $R^{12}$, together with the atom to which they are both attached, can form a 3-7 membered cycloalkyl or heterocycloalkyl ring.

Embodiment I-2: The compound as recited in Embodiment I-1, wherein $R^3$ is $C_{1-6}$alkyl.

Embodiment I-3: The compound as recited in Embodiment I-2, wherein $R^3$ is methyl.

Embodiment II-4: A compound of structural Formula (II):

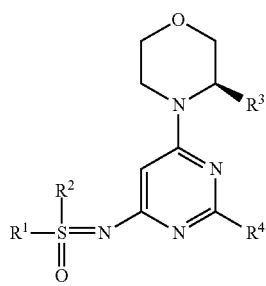

or a salt thereof, wherein:
$R^1$ and $R^2$ are independently selected from $C_{1-4}$alkyl, $C_{1-4}$haloalkyl, $C_{3-6}$cycloalkyl, $C_{3-6}$ heterocycloalkyl, aryl, and heteroaryl, each of which is optionally substituted with one or more RS groups, or $R^1$ and $R^2$, together with the sulfur to which they are both attached, form a heterocycloalkyl ring which is optionally substituted with one or more $R^5$ groups;
$R^3$ is selected from hydrogen, $C_{1-6}$alkyl, and $C_{1-6}$haloalkyl;
$R^4$ is selected from $C_{5-10}$aryl or $C_{5-10}$ heteroaryl and is optionally substituted with one or more $R^6$ groups;
each $R^5$ is independently selected from $NR^8R^9$, halogen, cyano, hydroxy, oxo, alkyl, haloalkyl, cycloalkyl, heterocycloalkyl, hydroxyalkyl, $OR^8$, $NRC(O)R^8$, $NR^7C(O)OR^8$, $NR^7C(O)NR^8R^9$, $C(O)R^8$, $C(O)OR^8$, and $C(O)NR^8R^9$;
each $R^6$ is independently selected from $NR^{11}R^{12}$, halogen, cyano, hydroxy, oxo, alkyl, haloalkyl, cycloalkyl, heterocycloalkyl, hydroxyalkyl, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$;
each $R^7$, $R^8$ and $R^9$ is independently selected from hydrogen, $C_{1-4}$alkyl, $C_{3-6}$cycloalkyl and heterocycloalkyl and is optionally substituted with halo, hydroxy, $C_{1-3}$alkyl, $C_{1-3}$ haloalkyl and $C_{1-3}$alkoxy; or any two of $R^7$, $R^8$ and $R^9$, together with the atom to which they are both attached can form a 3-7 membered cycloalkyl or heterocycloalkyl ring; and
each $R^{10}$, $R^{11}$ and $R^{12}$ is independently selected from hydrogen, $C_{1-4}$alkyl, $C_{3-6}$cycloalkyl and heterocycloalkyl and is optionally substituted with one or more groups selected from halo, hydroxy and alkoxy; or any two of $R^{10}$, $R^{11}$ and $R^{12}$, together with the atom to which they are both attached, can form a 3-7 membered cycloalkyl or heterocycloalkyl ring.

Embodiment II-5: The compound as recited in Embodiment II-4, wherein $R^3$ is $C_{1-6}$alkyl.

Embodiment II-6: The compound as recited in Embodiment II-5, wherein $R^3$ is methyl.

Embodiment II-7: The compound as recited in Embodiment II-6, wherein $R^4$ is $C_{5-10}$heteroaryl and is optionally substituted with one or more $R^6$ groups.

Embodiment II-8: The compound as recited in Embodiment II-7, wherein $R^4$ is selected from indole, pyrrolopyridine, pyrazolopyridine, imidazolopyridine, pyrrolopyrazine, pyrazolopyrazine, pyrrolopyrimidine, pyrazolopyrimidine, imidazolopyrimidine, pyrrolopyridazine, pyrazolopyridazine, and imidazolopyridazine, and is optionally substituted with one or more $R^6$ groups.

Embodiment II-9: The compound as recited in Embodiment II-8, wherein $R^4$ is selected from 1H-pyrrolo[2,3-b]pyridine, 7H-pyrrolo[2,3-c]pyridazine, 7H-pyrrolo[2,3-d]pyrimidine, and 5H-pyrrolo[2,3-b]pyrazine and is optionally substituted with one, two, or three $R^6$ groups.

Embodiment II-10: The compound as recited in Embodiment II-9, wherein $R^4$ is 1H-pyrrolo[2,3-b]pyridine and is optionally substituted with one or two $R^6$ groups.

Embodiment II-11: The compound as recited in Embodiment II-10, wherein each $R^6$ is independently selected from $NR^{11}R^{12}$, halogen, cyano, hydroxy, oxo, $OR^{11}$, $NR^{10}C(O)R^{11}$, $NR^{10}C(O)OR^{11}$, $NR^{10}C(O)NR^{11}R^{12}$, $C(O)R^{11}$, $C(O)OR^{11}$, and $C(O)NR^{11}R^{12}$.

Embodiment II-12: The compound as recited in Embodiment II-11, wherein each $R^6$ is independently selected from $NR^{11}R^{12}$, halogen, cyano, hydroxy, and oxo.

Embodiment II-13: The compound as recited in Embodiment II-12, wherein $R^4$ is selected from

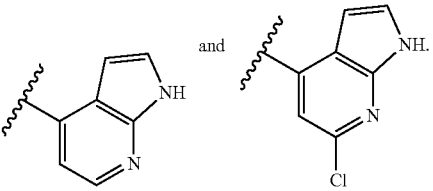 [SMILES: *c1ccnc2[nH]ccc12 ; *c1cc(Cl)nc2[nH]ccc12]

Embodiment II-14: The compound as recited in Embodiment II-13, wherein
$R^1$ and $R^2$ are independently selected from $C_{1-4}$alkyl, $C_{1-4}$haloalkyl, $C_{3-6}$cycloalkyl, $C_{3-6}$ heterocycloalkyl, aryl, and heteroaryl and are optionally substituted with one or two $R^5$ groups, or $R^1$ and $R^2$, together with the sulfur to which they are both attached, form a heterocycloalkyl ring which is optionally substituted with one or two $R^5$ groups;
each $R^5$ is independently selected from $NR^8R^9$, halogen, cyano, hydroxy, oxo, alkyl, haloalkyl, cycloalkyl, heterocycloalkyl, hydroxyalkyl, $OR^8$, $NRC(O)R^8$, $NR^7C(O)OR^8$, $NR^7C(O)NR^8R^9$, $C(O)R^8$, $C(O)OR^8$, and $C(O)NR^8R^9$.

Embodiment II-15: The compound as recited in Embodiment II-14, wherein each $R^5$ is independently selected from alkyl, haloalkyl, cycloalkyl, heterocycloalkyl, hydroxyalkyl, $OR^8$, $NR^7C(O)R^8$, $NR^7C(O)OR^8$, $NR^7C(O)NR^8R^9$, $C(O)R^8$, $C(O)OR^8$, and $C(O)NR^8R^9$.

Embodiment II-16: The compound as recited in Embodiment II-15, wherein each $R^5$ is independently selected from $C(O)R^8$, $C(O)OR^8$, and $C(O)NR^8R^9$.

Embodiment II-17: The compound as recited in Embodiment II-16, wherein $R^1$ and $R^2$ are independently selected from $C_{1-4}$alkyl, $C_{1-4}$haloalkyl, $C_{3-6}$cycloalkyl, $C_{3-6}$heterocycloalkyl, aryl, and heteroaryl and are optionally substituted with one or two $R^5$ groups.

Embodiment II-18: The compound as recited in Embodiment II-17, wherein $R^1$ and $R^2$ are independently selected from $C_{1-4}$alkyl, $C_{1-4}$haloalkyl, $C_{3-6}$cycloalkyl, and $C_{3-6}$heterocycloalkyl and are optionally substituted with one or two $R^5$ groups.

Embodiment II-19: The compound as recited in Embodiment II-17, wherein $R^1$ and $R^2$ are independently selected from $C_{1-4}$alkyl and $C_{3-6}$cycloalkyl.

Embodiment II-20: The compound as recited in Embodiment II-17, wherein $R^1$ and $R^2$, together with the sulfur to which they are both attached, forms a heterocycloalkyl ring and is optionally substituted with one or two $R^5$ groups.

Embodiment C-21: The compound as recited in Embodiment I-1, wherein the structure is selected from

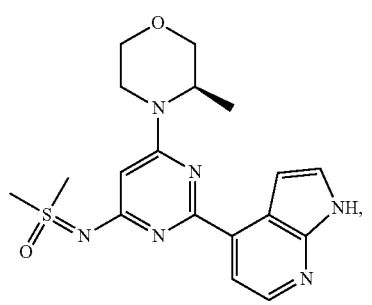
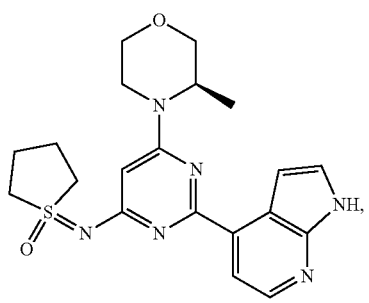
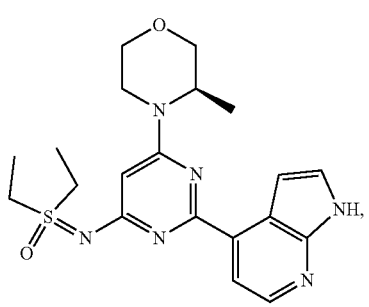
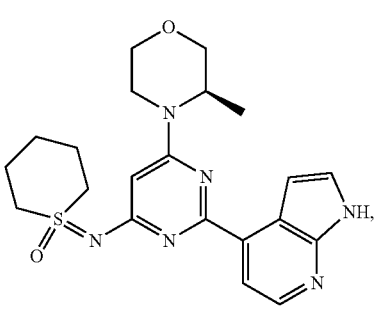
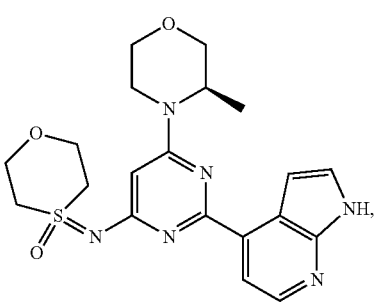

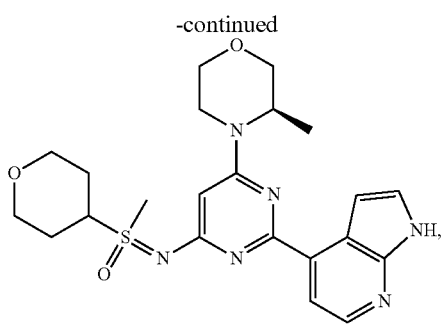
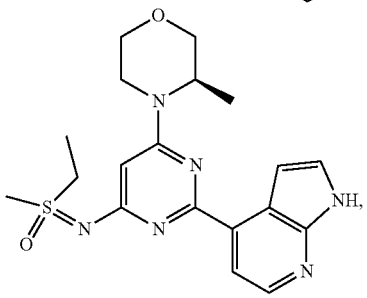
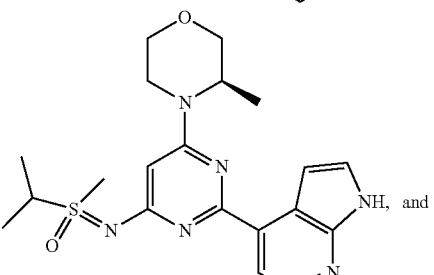
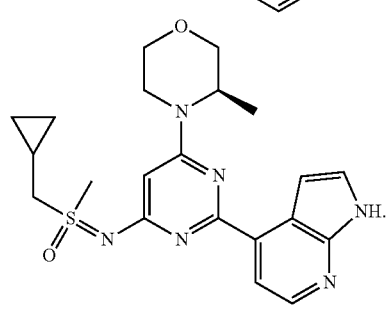

Embodiment C-22: The compound as recited in Embodiment I-1 for use as a medicament.

Embodiment C-23: The compound as recited in Embodiment I-1 for use in the manufacture of a medicament for the prevention or treatment of a disease or condition ameliorated by the inhibition of ATR kinase.

Embodiment C-24: The compound as recited in Embodiment C-23, wherein the disease is cancer.

Embodiment C-25: The compound as recited in Embodiment C-24, wherein the cancer is a chemotherapy-resistant cancer.

Embodiment C-26: The compound as recited in Embodiment C-24, wherein the cancer is a radiotherapy-resistant cancer.

Embodiment C-27: The compound as recited in Embodiment C-24, wherein the cancer is an ALT-positive cancer.

Embodiment C-28: The compound as recited in Embodiment C-24, wherein the cancer is a sarcoma.

Embodiment C-29: The compound as recited in Embodiment C-24, wherein the cancer is selected from osteosarcoma and glioblastoma.

Embodiment C-30: The compound as recited in Embodiment C-24, wherein the cancer is selected from lung cancer, head and neck cancer, pancreatic cancer, gastric cancer, and brain cancer.

Embodiment C-31: The compound as recited in Embodiment C-24, wherein the cancer is selected from non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, and ovarian cancer.

Embodiment C-32: The compound as recited in Embodiment C-24, wherein the cancer has a defect in a base excision repair protein.

Embodiment C-33: A pharmaceutical composition comprising a compound as recited in Embodiment I-1 together with a pharmaceutically acceptable carrier.

Embodiment M-34: A method of sensitizing cells to DNA-damaging agents comprising administering to a patient a compound as recited in Embodiment I-1.

Embodiment M-35: A method of preventing cell repair from DNA damage comprising administering to a patient a compound as recited in Embodiment I-1.

Embodiment M-36: A method of inhibition of ATR kinase comprising contacting ATR kinase with a compound as recited in Embodiment I-1.

Embodiment M-37: A method of treatment of an ATR kinase-mediated disease comprising the administration of a therapeutically effective amount of a compound as recited in Embodiment I-1 to a patient in need thereof.

Embodiment M-38: The method as recited in Embodiment M-37, wherein the disease is cancer.

Embodiment M-39: The method as recited in Embodiment M-38, wherein the cancer is a chemotherapy-resistant cancer.

Embodiment M-40: The method as recited in Embodiment M-38, wherein the cancer is a radiotherapy-resistant cancer.

Embodiment M-41: The method as recited in Embodiment M-38, wherein the cancer is an ALT-positive cancer.

Embodiment M-42: The method as recited in Embodiment M-38, wherein the cancer is a sarcoma.

Embodiment M-43: The method as recited in Embodiment M-38, wherein the cancer is selected from osteosarcoma and glioblastoma.

Embodiment M-44: The method as recited in Embodiment M-38, wherein the cancer is selected from lung cancer, head and neck cancer, pancreatic cancer, gastric cancer, and brain cancer.

Embodiment M-45: The method as recited in Embodiment M-38, wherein the cancer is selected from non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, and ovarian cancer.

Embodiment M-46: The method as recited in Embodiment M-38, wherein the cancer has a defect in a base excision repair protein.

Embodiment M-47: The method as recited in Embodiment M-38, wherein the cancer has defects in the ATM signaling cascade.

Embodiment M-48: The method as recited in Embodiment M-47, wherein the defect is altered expression or activity of one or more of the following: TM, p53, CHK2, MRE11, RAD50, NBS 1, 53BP1, MDC1, H2AX, MCPH1/BRIT1, CTIP, or SMC1.

Embodiment M-49: The method as recited in Embodiment M-38, further comprising administering to the patient another therapeutic agent, wherein the other therapeutic agent inhibits or modulates a base excision repair protein.

Embodiment M-50: A method of treatment of an ATR kinase-mediated disease comprising the administration of:
a. a therapeutically effective amount of a compound as recited in Embodiment I-1; and
b. another therapeutic agent.

Embodiment M-51: The method as recited in Embodiment M-50, wherein the other therapeutic agent is a CHK1 inhibitor.

Embodiment M-52: The method as recited in Embodiment M-50, wherein the CHK1 inhibitor is selected from MK-8776, LY2603618, V158411, PF-477736, UCN-01, and AZD7762.

Embodiment M-53: The method as recited in Embodiment M-50, wherein the other therapeutic agent is a DNA-damaging agent.

Embodiment M-54: The method as recited in Embodiment M-53, wherein the DNA-damaging agent is selected from ionizing radiation, radiomimetic neocarzinostatin, a platinating agent, a Topo I inhibitor, a Topo II inhibitor, an antimetabolite, an alkylating agent, an alkyl sulphonate, and an antibiotic.

Embodiment M-55: The method as recited in Embodiment M-54, wherein the platinating agent is selected from cisplatin, oxaliplatin, carboplatin, nedaplatin, lobaplatin, triplatin tetranitrate, picoplatin, satraplatin, ProLindac, and aroplatin.

Embodiment M-56: The method as recited in Embodiment M-54, wherein the Topo I inhibitor is selected from camptothecin, topotecan, irinotecan/SN38, rubitecan and belotecan.

Embodiment M-57: The method as recited in Embodiment M-54, wherein the Topo II inhibitor is selected from etoposide, daunorubicin, doxorubicin, clarubicin, epirubicin, idarubicin, amrubicin, pirarubicin, valrubicin, zorubicin and teniposide.

Embodiment M-58: The method as recited in Embodiment M-54, wherein the antimetabolite is selected from aminopterin, methotrexate, pemetrexed, raltitrexed, pentostatin, cladribine, clofarabine, fludarabine, thioguanine, mercaptopurine, fluorouracil, capecitabine, tegafur, carmofur, floxuridine, cytarabine, gemcitabine, azacitidine, and hydroxyurea.

Embodiment M-59: The method as recited in Embodiment M-54, wherein the alkylating agent is selected from mechlorethamine, cyclophosphamide, ifosfamide, trofosfamide, chlorambucil, melphalan, prednimustine, bendamustine, uramustine, estramustine, carmustine, lomustine, semustine, fotemustine, nimustine, ranimustine, streptozocin, busulfan, mannosulfan, treosulfan, carboquone, thioTEPA, triaziquone, triethylenemelamine, procarbazine, dacarbazine, temozolomide, altretamine, mitobronitol, actinomycin, bleomycin, mitomycin, and plicamycin.

Embodiment M-60: The method as recited in Embodiment M-38, wherein the method further comprises administering non-chemical methods of cancer treatment.

Embodiment M-61: The method as recited in Embodiment M-60, wherein the method further comprises administering radiation therapy.

Embodiment M-62: The method as recited in Embodiment M-60, wherein the method further comprises administering surgery, thermoablation, focused ultrasound therapy, cryotherapy, or any combination thereof.

Embodiment M-63: A method of increasing the sensitivity of cancer cells to a cancer therapy selected from chemotherapy or radiation therapy by administering to a patient a compound as recited in Embodiment I-1.

Embodiment M-64: The method as recited in Embodiment M-63, wherein the cancer cells are pancreatic cancer cells.

Embodiment M-65: A method for achieving an effect in a patient comprising the administration of a therapeutically effective amount of a compound as recited in claim 1 to a patient, wherein the effect is increased sensitivity to chemotherapic agents.

List of Abbreviations

Boc=tert-butyloxycarbonyl; BPin=4,4,5,5-tetramethyl-1,3,2-dioxaborolan-2-yl; $Br_2$=bromine; Bu=n-butyl; t-Bu=tert-butyl=2,2-dimethylethyl; °C.=Celsius; CBz=carboxybenzyl; $CDCl_3$=deuterated chloroform; $CD_3CN$=deuterated acetonitrile; DBN=1,5-Diazabicyclo(4.3.0)non-5-ene; DBU=1,8-diazabicyclo(5.4.0)undec-7-ene; DCM=$CH_2Cl_2$=dichloromethane; DDTT=3-((dimethylaminomethylidene)amino)-3H-1,2,4-dithiazole-5-thione; DIPEA=$iPr_2NEt$=diisopropylethylamine; DMAP=4-Dimethylaminopyridine; DMF=dimethylformamide; DMF-$d_7$=dimethylformamide-$d_7$; DMSO=dimethyl sulfoxide; DMSO-$d_6$=dimethyl sulfoxide-$d_6$; DMTr=dimethoxytrityl=(4-methoxyphenyl)$_2$(phenyl)methyl; $D_2O$=deuterated water; dppf=1,1'-bis(diphenylphosphino)ferrocene; EA=EtOAc=ethyl acetate; ES+=electrospray positive ionization; ES−=electrospray negative ionization; Et=ethyl; EtOH=ethanol; h=hour; H=hydrogen; HCl=hydrogen chloride; $HCO_2NH_4$=ammonium formate; $H_2O$=water; HPLC=high pressure liquid chromatography, also known as preparative high performance liquid chromatography; int.=intermediate; iPr=isopropyl=2-propyl; M=molar; mCPBA=m-chloroperbenzoic acid; MeCN=$CH_3CN$=acetonitrile; MeOH=methanol; MHz=megahertz; mL=milliliter; min=minute; MS=mass spectrometry; MsCl=methanesulfonyl chloride; μW=microwave; $N_2$=nitrogen; $NH_3$=ammonia; $NH_4OH$=ammonium hydroxide; NMP=N-Methyl-2-pyrrolidone; $^1$H-NMR=proton nuclear magnetic resonance; $^{31}$P-NMR=phosphorous nuclear magnetic resonance; PBS=phosphate buffered saline; PE=petroleum ether; Pin=pinacol=2,3-dimethylbutane-2,3-diol; $Pin_2B2$=4,4,4',4',5,5,5',5'-octamethyl-2,2'-bi(1,3,2-dioxaborolane); Piv=pivaloyl=$(CH_3)_3C$—$C(=O)$—; PPA=polyphosphoric acid; prep-HPLC=preparative high pressure liquid chromatography, also known as preparative high performance liquid chromatography; RT=room temperature; NaOH=sodium hydroxide; $Pd(dppf)Cl_2$=[1,1'-bis(diphenylphosphino)ferrocene]palladium(II) dichloride; RuPhos=dicyclohexyl(2',6'-diisopropoxy-[1,1'-biphenyl]-2-yl)phosphine; THF=tetrahydrofuran; Py=pyridine; SFC=supercritical fluid chromatography; TBSCl=tert-butyldimethylsilyl chloride; TEA=triethylamine; TEAB=tetraethyl ammonium bicarbonate; TMSCl=trimethylsilyl chloride; TFA=trifluoroacetic acid; $K_2CO_3$=potassium carbonate; μL=ul=microliter.

General Synthetic Methods for Preparing Compounds

The following schemes can be used to practice the present disclosure.

SCHEME I

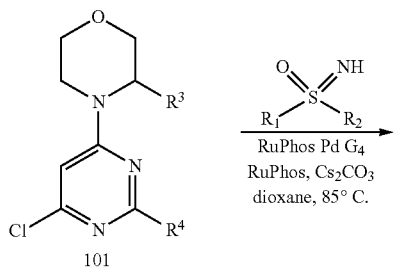

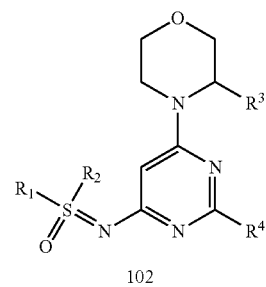

A Buchwald coupling reaction with chloro-pyrimidine 101 and a sulfoximine gives the substituted pyrimidine compound 102.

SCHEME II

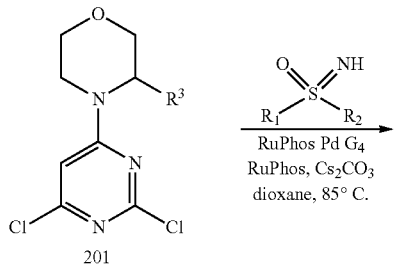

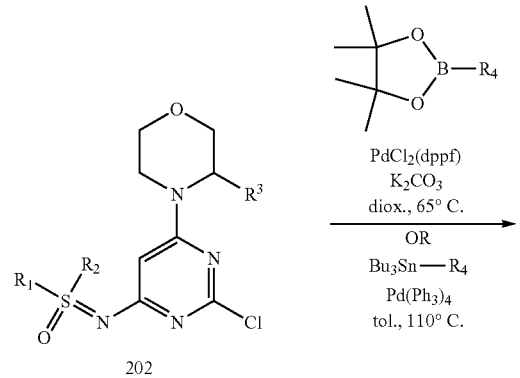

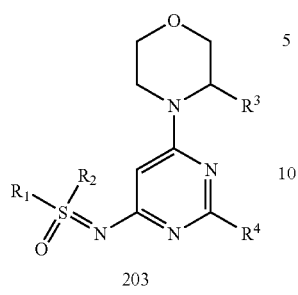

203

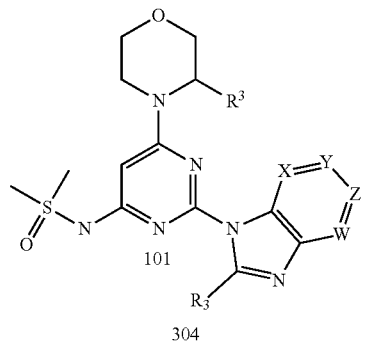

304

One route for preparation of compounds of the present disclosure is depicted in Scheme II. A Buchwald coupling with intermediate 201 and a sulfoximine provides chloropyrimidine 202. A subsequent Suzuki coupling with a boronic ester or a Stille coupling with a stannane affords the pyrimidine compound 203.

One route for preparation of compounds of the present disclosure is depicted in Scheme III. A Buchwald coupling with chloropyrimidine 301 and an aryl amine, followed by iron mediated reduction or palladium catalyzed hydrogenation, provides the amino intermediate 303. Subsequent cyclization with either an orthoester or a carboxylic acid affords the pyrimidine compound 304.

SCHEME III

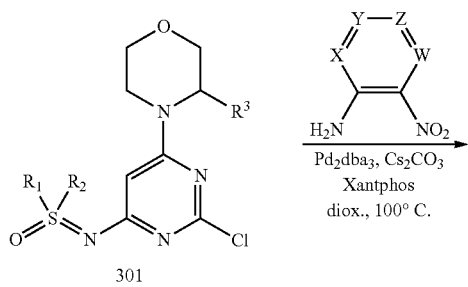

301

SCHEME IV

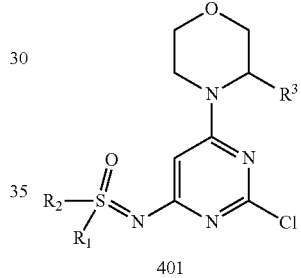

401 i) n-BuLi, iPr$_2$NH, THF, -10° C.
ii) Bu$_3$SnH, -10° C. to 0° C.
iii) Int. 401, -78° C.

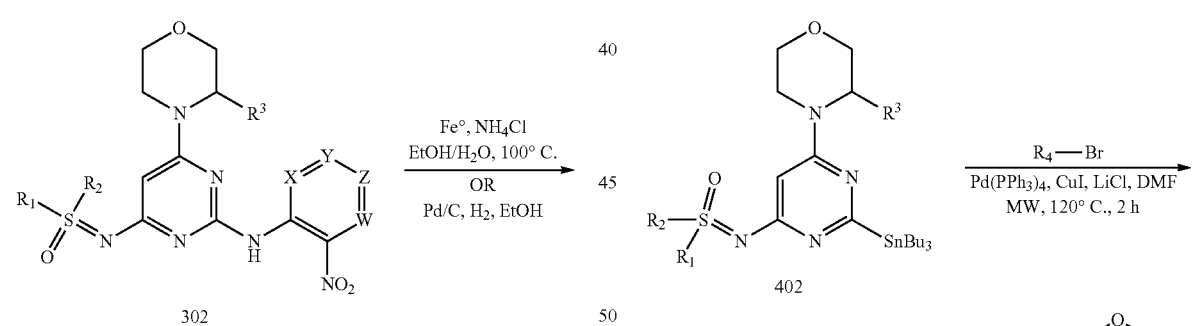

302

Fe°, NH$_4$Cl
EtOH/H$_2$O, 100° C.
OR
Pd/C, H$_2$, EtOH

402

R$_4$—Br
Pd(PPh$_3$)$_4$, CuI, LiCl, DMF
MW, 120° C., 2 h

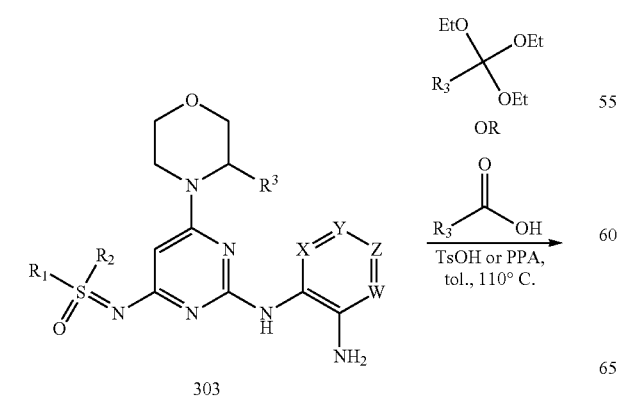

303

EtO, OEt
R$_3$ OEt
OR
R$_3$—C(=O)—OH
TsOH or PPA, tol., 110° C.

403

One route for preparation of compounds of the present disclosure is depicted in Scheme IV. Conversion of chloropyrimidine 401 to stannane 402 and subsequent Stille coupling with an aryl bromide affords the pyrimidine compound 403.

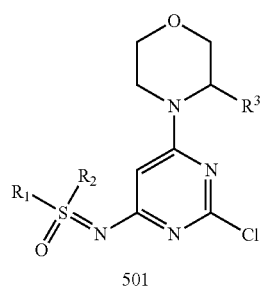
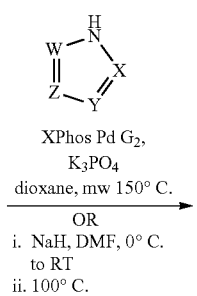

501

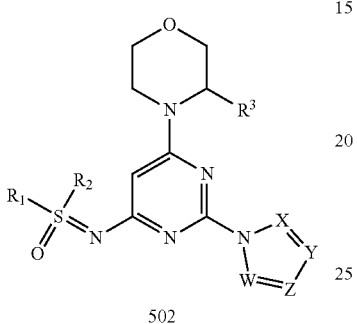

502

One route for preparation of compounds of the present disclosure is depicted in Scheme V. A Buchwald coupling or a S$_N$Ar addition with chloropyrimidine 501 and an aminoheterocycle affords the pyrimidine compound 402.

Intermediate A

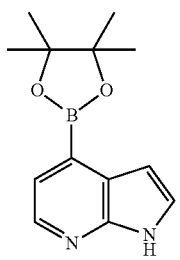 [SMILES: CC1(C)OB(c2ccnc3[nH]ccc23)OC1(C)C]

4-(4,4,5,5-Tetramethyl-1,3,2-dioxaborolan-2-yl)-1H-pyrrolo[2,3-b]pyridine

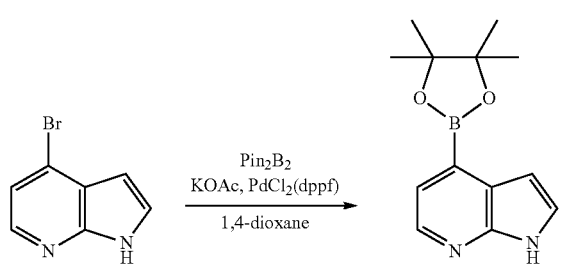 [SMILES: Brc1ccnc2[nH]ccc12 ; CC1(C)OB(c2ccnc3[nH]ccc23)OC1(C)C]

4-(4,4,5,5-Tetramethyl-1,3,2-dioxaborolan-2-yl)-1H-pyrrolo[2,3-b]pyridine

A mixture of 4-bromo-1H-pyrrolo[2,3-b]pyridine (10.0 g, 51.0 mmol), Pin$_2$B$_2$ (15.5 g, 61.0 mmol), PdCl$_2$(dppf) (2.0 g, 2.5 mmol) and KOAc (10.0 g, 102 mmol) in 1,4-dioxane (200 mL) was degassed with Ar for 5 minutes. The reaction mixture was heated to 80° C. and stirred for 16 h. The mixture was cooled to RT, filtered through CELITE® and concentrated under reduced pressure. The residue was purified via silica gel chromatography (0-25% EtOAc in hexanes) to afford the title compound (3.8 g, 31% yield) as a white solid.

MS (ES$^+$) C$_{13}$H$_{17}$BN$_2$O$_2$ requires: 244, found: 245 [M+H]$^+$.

Intermediate B

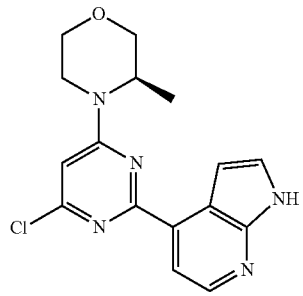 [SMILES: C[C@@H]1COCCN1c1cc(Cl)nc(-c2ccnc3[nH]ccc23)n1]

(R)-4-(6-chloro-2-(1H-pyrrolo[2,3-b]pyridin-4-yl)pyrimidin-4-yl)-3-methylmorpholine

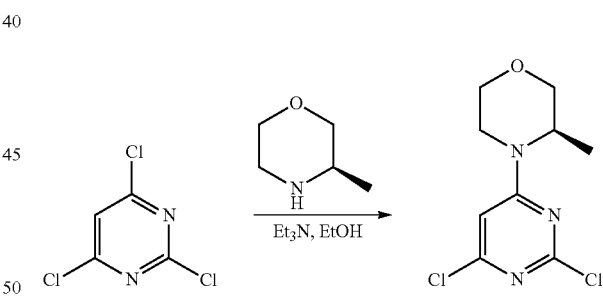

6(R)-4-(2,6-Dichloropyrimidin-4-yl)-3-methylmorpholine To a solution of 2,4,6-trichloropyrimidine (12.3 g, 67.3 mmol) and Et$_3$N (14.2 mL, 101 mmol) in EtOH (80 mL) was added (R)-3-methylmorpholine (6.8 g, 67 mmol). The reaction mixture was stirred at RT for 16 h. The mixture was concentrated under reduced pressure. The residue was diluted with CH$_2$Cl$_2$ (200 mL), partitioned with H$_2$O (150 mL) and the layers were separated. The aqueous layer was extracted with CH$_2$Cl$_2$ (3×150 mL). The combined organic layers were dried over Na$_2$SO$_4$, filtered and concentrated under reduced pressure. The residue was purified via silica gel chromatography (0-5% EtOAc in hexanes) to afford the title compound (11.8 g, 71% yield) as a white solid.

MS (ES+) C$_9$H$_{11}$Cl$_2$N$_3$O requires: 241, found: 248 [M+H]$^+$.

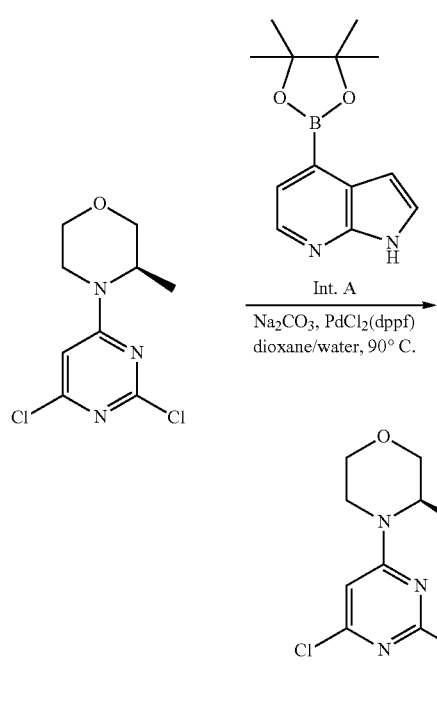

MgO (1.6 g, 40 mmol) in CH$_2$Cl$_2$ (100 mL) was added PhI(OAc)$_2$ (4.8 g, 15 mmol). The resulting mixture was stirred at RT for 16 h. The reaction mixture was filtered and concentrated under reduced pressure. The residue was purified via flash chromatography (0-90% EtOAc in petroleum ether) to afford the title compound (900 mg, 40% yield) as a white solid.

MS (ES$^+$) C$_{10}$H$_{13}$NO$_3$S requires: 227, found: 228 [M+H]$^+$.

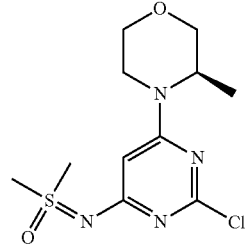

Iminodimethyl-$\lambda^6$-sulfanone The product from the previous step (600 mg, 2.6 mmol) and Pd/C (243 mg, 2.6 mmol) were suspended in MeOH (20 mL). The mixture was stirred under an atmosphere of H$_2$ at 1 atm for 16 h. The reaction mixture was purged with N$_2$, filtered through CELITE® and the filter pad was washed with MeOH (10 mL). The mixture was concentrated under reduced pressure to afford the title compound (205 mg, 85% yield) as a colorless oil.

MS (ES$^+$) C$_2$H$_7$NOS requires: 93, found 94 [M+H]$^+$.

Intermediate D (R)-4-(6-Chloro-2-(1H-pyrrolo[2,3-b]pyridin-4-yl)pyrimidin-4-yl)-3-methylmorpholine A mixture of the product from the previous step (3.0 g, 12 mmol), Int. A (2.8 g, 12 mmol), PdCl$_2$(dppf) (0.44 g, 0.60 mmol) and Na$_2$CO$_3$ (2.6 g, 24 mmol) in 1,4-dioxane (60 mL) and water (15 mL) was degassed with Ar for 5 minutes. The reaction mixture was heated to 90° C. and stirred for 16 h. The reaction mixture was cooled to RT and concentrated under reduced pressure. The residue was purified via silica gel chromatography (0-50% EtOAc in hexanes) to afford the title compound (1.84 g, 46% yield) as a yellow solid.

MS (ES+) C$_{16}$H$_{16}$ClN$_5$O requires: 329, found: 330 [M+H]$^+$.

Intermediate C

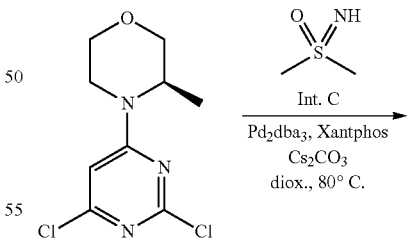

(R)-((2-Chloro-6-(3-methylmorpholino)pyrimidin-4-yl)imino)dimethyl-$\lambda^6$-sulfanone

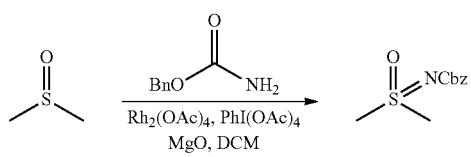

Iminodimethyl-$\lambda^6$-sulfanone

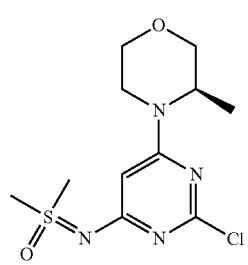

Benzyl (dimethyl(oxo)-$\lambda^6$-sulfaneylidene)carbamate To a suspension of DMSO (780 mg, 10.0 mmol), benzyl carbamate (2.3 g, 15 mmol), Rh$_2$(OAc)$_4$ (110 mg, 0.25 mmol) and (R)-((2-Chloro-6-(3-methylmorpholino)pyrimidin-4-yl)imino)dimethyl-λ⁶-sulfanone: A reaction vial was charged with (R)-4-(2,6-dichloropyrimidin-4-yl)-3-methylmorpholine (synthesized as described for Int. B, step 1) (500 mg, 2.02 mmol), Int. C (225 mg, 2.42 mmol) and dioxane (10 mL) and the mixture was degassed with N₂ for 30 seconds. Cs₂CO₃ (1.97 g, 6.05 mmol), Pd₂dba₃ (185 mg, 0.202 mmol) and xantphos (233 mg, 0.403 mmol) were added and the mixture was degassed with N₂ for 30 seconds. The vial was sealed and heated at 85° C. for 16 h. The mixture was cooled to RT, filtered through CELITE® and concentrated under reduced pressure. The residue was purified via silica gel chromatography (0-10% MeOH in EtOAc) to afford (R)-((2-Chloro-6-(3-methylmorpholino)pyrimidin-4-yl)imino)dimethyl-λ⁶-sulfanone (362 mg, 59% yield) as a pale yellow solid and (R)-((4-chloro-6-(3-methylmorpholino)pyrimidin-2-yl)imino)dimethyl-λ⁶-sulfanone (222 mg, 36% yield) as a pale yellow solid.

¹H NMR (600 MHz, CDCl₃) δ 5.73 (s, 1H), 4.21-4.15 (m, 1H), 3.96 (dd, J=11.5, 3.7 Hz, 1H), 3.91 (d, J=13.0 Hz, 1H), 3.74 (d, J=11.5 Hz, 1H), 3.67 (dd, J=11.5, 3.2 Hz, 1H), 3.52 (td, J=11.9, 3.1 Hz, 1H), 3.37 (d, J=3.1 Hz, 6H), 3.19 (td, J=12.8, 3.9 Hz, 1H), 1.26 (d, J=6.8 Hz, 3H); MS (ES⁺) C₁₁H₁₇ClN₄O₂S requires: 304, found: 305 [M+H]⁺.

Intermediate E

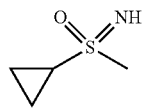

Cyclopropyl(imino)(methyl)-λ⁶-sulfanone

Step 1

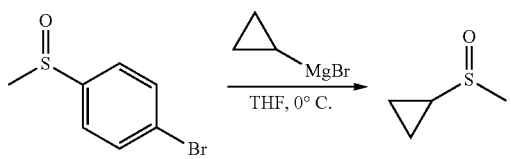

(Methylsulfinyl)cyclopropane: To a solution of 1-bromo-4-(methylsulfinyl)benzene (10.5 g, 48.0 mmol) in THF (100 mL) was added cyclopropylmagnesium bromide (1M, 72 mL, 72 mmol) at 0° C. slowly. The mixture was stirred at 0° C. for 1.5 h. Saturated aqueous NH₄Cl was added (200 mL), the layers were separated and the aqueous layer was extracted with CH₂Cl₂ (5×150 mL). The combined organic layers were dried over Na₂SO₄, filtered and concentrated under reduced pressure. The residue was purified via flash chromatography (50-100% EtOAc in petroleum ether) to afford the title compound (3.2 g, 64% yield) as a yellow oil.

MS (ES⁺) C₄H₈OS requires: 104, found 105 [M+H]⁺.

Step 2

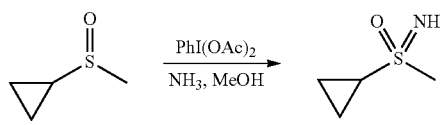

Cyclopropyl(imino)(methyl)-λ⁶-sulfanone: To the solution of the product from the previous step (22 g, 0.21 mol) and PhI(OAc)₂ (204 g, 0.64 mol) in MeOH (100 mL) at 0° C. was added NH₃ (120 mL, 0.84 mol, 7 N in MeOH) dropwise. The resulting mixture was allowed to warm to RT and stirred for 2 hours. The reaction mixture was concentrated under reduced pressure. The residue was purified via flash chromatography (15% EtOAc in petroleum ether, then with 2% MeOH in CH₂Cl₂) to afford the title compound (20 g, 79%) as a yellow oil: ¹H NMR (400 MHz, CDCl3) δ 3.06 (s, 3H), 2.58 (tt, J=7.9, 4.8 Hz, 1H), 1.26-1.19 (m, 1H), 1.19-1.12 (m, 1H), 1.05 (dt, J=11.1, 4.5 Hz, 2H).

Intermediate F

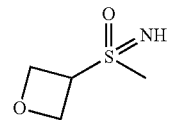

Imino(methyl)(oxetan-3-yl)-λ⁶-sulfanone

Step 1

3-(methylsulfinyl)oxetane: To a solution of 3-iodooxetane (6.0 g, 32.6 mmol) in DMF (60 mL) was added CH₃SNa (2.28 g, 32.6 mmol) under N₂. The reaction mixture was stirred at RT for 1 h. EtOAc (120 mL) and water (80 mL) were added, the layers were separated and the organic layer was washed with brine (80 mL), dried over MgSO₄ and filtered. The solution of EtOAc was added MeOH (60 mL), water (60 mL) and NaIO₄ (6.2 g, 29.3 mmol) and the reaction mixture was stirred at RT for 16 h. The mixture was filtered and concentrated under reduced pressure. The residue was purified via flash chromatography (50% EtOAc in petroleum ether to 10% MeOH in CH₂Cl₂) to afford the title compound (3.5 g, 90% yield) as pale yellow oil.

MS (ES⁺) C₄H₈O₂S requires: 120, found 121 [M+H]⁺.

Step 2

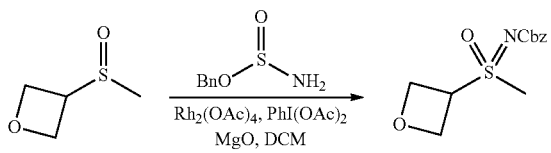

Benzyl (methyl(oxetan-3-yl)(oxo)-λ⁶-sulfaneylidene)carbamate: To a solution of the product from the previous step (3.5 g, 29 mmol) in CH$_2$Cl$_2$ (260 mL) were added benzyl carbamate (6.58 g, 43.6 mmol), Rh$_2$(OAc)$_4$ (383 mg, 0.873 mmol), PhI(OAc)$_2$ (14.0 g, 43.6 mmol) and MgO (4.7 g, 116 mmol) and the mixture was stirred at RT under an atmosphere of N$_2$ for 16 h. The reaction mixture was filtered through CELITE® and concentrated under reduced pressure. The residue was purified via flash chromatography (20-50% EtOAc in petroleum ether) to afford the title compound (4.1 g, 52% yield) as pale yellow oil.

MS (ES$^+$) C$_{12}$H$_{15}$NO$_4$S requires: 269, found 270 [M+H]$^+$.

Step 3

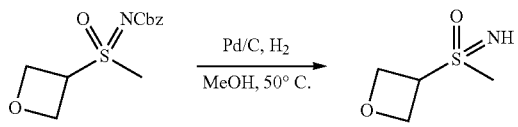

Imino(methyl)(oxetan-3-yl)-λ⁶-sulfanone: To a solution of the product from the previous step (4.1 g, 15 mmol) in MeOH (60 mL) was added Pd/C (4.1 g) under N$_2$. The atmosphere was removed and purged with H$_2$ (3×). The mixture was heated to 50° C. and stirred for 3 h under a H$_2$ atmosphere. The mixture was cooled to RT, filtered through CELITE® and concentrated under reduced pressure to afford the title compound (1.7 g, 83% yield) as pale yellow oil.

MS (ES$^+$) C$_4$H$_9$NO$_2$S requires: 135, found 136 [M+H]$^+$.

Intermediate G

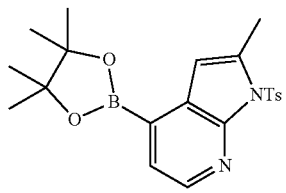

2-Methyl-4-(4,4,5,5-tetramethyl-1,3,2-dioxaborolan-2-yl)-1-tosyl-1H-pyrrolo[2,3-b]pyridine

Step 1

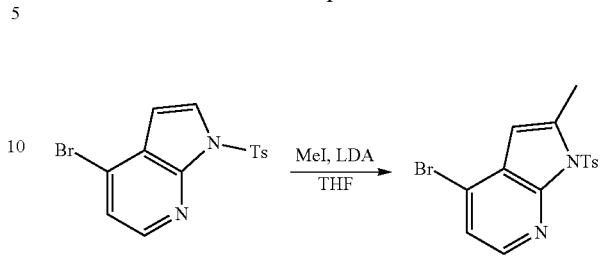

4-Bromo-2-methyl-1-tosyl-1H-pyrrolo[2,3-b]pyridine:
To a solution of 4-bromo-1-tosyl-1H-pyrrolo[2,3-b]pyridine (1.0 g, 2.9 mmol) in THF (30 mL) at −78° C. was added LDA (2.9 mL, 2 M, in THF) and the mixture was stirred for 1 h at −78° C. under an atmosphere of Ar. MeI (4.0 g, 29 mmol) was added and the mixture was allowed to warm to RT and stirred for 3 h. Saturated aqueous NH$_4$Cl (50 mL) was added and the aqueous layer was extracted with EtOAc (3×50 mL). The combined organic layers were dried over Na$_2$SO$_4$, filtered and concentrated under reduced pressure. The residue was purified by reverse phase preparative HPLC (Mobile phase: A=10 mM NH$_4$HCO$_3$/H$_2$O, B=MeCN; Gradient: B=65-95%; 18 min; Column: Welch XB-C18, 10 μm, 21.2×250 mm) to afford the title compound (420 mg, 40% yield) as a white solid.

MS (ES$^+$) C$_{15}$H$_{13}$BrN$_2$O$_2$S requires: 364, found 365 [M+H]$^+$.

Step 2

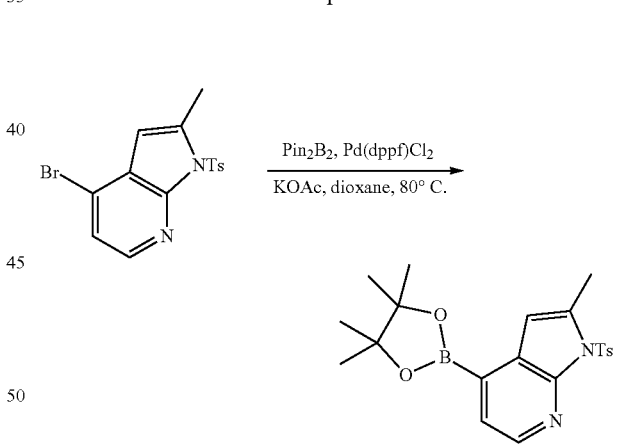

2-Methyl-4-(4,4,5,5-tetramethyl-1,3,2-dioxaborolan-2-yl)-1-tosyl-1H-pyrrolo[2,3-b]pyridine: A reaction vial was charged with the product from the previous reaction (410 mg, 1.13 mmol), Pin$_2$B$_2$ (345 mg, 1.3 mmol), KOAc (277 mg, 2.8 mmol) and Pd(dppf)Cl$_2$ (82 mg, 0.11 mmol) in dioxane (5 mL). The mixture was degassed by bubbling Ar for 1 min. The mixture was heated at 80° C. and stirred for 5 h. The mixture was cooled to RT, filtered through CELITE® and concentrated under reduced pressure. the residue was purified via flash chromatography (20% EtOAc in petroleum ether) to afford the title compound (350 mg, 75% yield) as a white solid.

MS (ES$^+$) C$_{21}$H$_{25}$BN$_2$O$_4$S requires 412, found 331 [M-81]$^+$.

Intermediate H

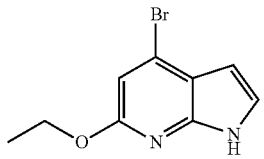

4-Bromo-6-ethoxy-1H-pyrrolo[2,3-b]pyridine

Step 1

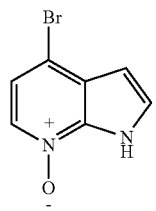

i. (MeO)₂SO₂, CH₃CN reflux ii. sodium ethanolate EtOH, reflux

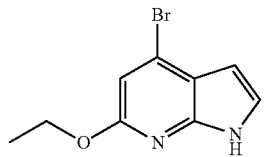

4-Bromo-6-ethoxy-1H-pyrrolo[2,3-b]pyridine: A mixture of 4-bromo-1H-pyrrolo[2,3-b]pyridine 7-oxide (426 mg, 2.0 mmol) and dimethyl sulfate (303 mg, 2.4 mmol) in CH₃CN (10 mL) was heated to 70° C. for 24 h. The reaction mixture was cooled to RT, sodium ethanolate (40 mg, 6.0 mmol) was added and the mixture was heated to 70° C. for 24 h. The reaction mixture was cooled to RT, neutralized with AcOH to pH=7 and then concentrated under reduced pressure. The residue was dissolved in CH₂Cl₂ (50 mL), washed with aq. sat. NaHCO₃(20 mL) and brine (15 mL), dried over Na₂SO₄, filtered and concentrated under reduced pressure. The residue was purified via silica gel chromatography (0-20% EtOAc in petroleum ether) to afford the title compound (151 mg, 31% yield) as a white solid.

MS (ES⁺) $C_9H_9BrN_2O$ requires: 240, found: 241 [M+H]⁺.

Intermediate I

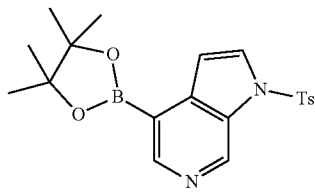 [SMILES: Cc1ccc(S(=O)(=O)n2ccc3c(B4OC(C)(C)C(C)(C)O4)cncc32)cc1]

4-(4,4,5,5-Tetramethyl-1,3,2-dioxaborolan-2-yl)-1-tosyl-1H-pyrrolo[2,3-c]pyridine

Step 1

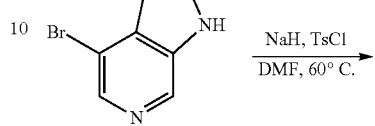

4-Bromo-1-tosyl-1H-pyrrolo[2,3-c]pyridine: To a solution of 4-bromo-1H-pyrrolo[2,3-c]pyridine (300 mg, 1.5 mmol) in DMF (10 mL) at 0° C. was added NaH (92 mg, 2.25 mmol, 60%) and the reaction mixture was stirred at 0° C. for 2 h. The reaction mixture was allowed to warm to RT, TsCl (429 mg, 2.25 mmol) was added and the mixture was heated to 60° C. and stirred for an additional 2 h. H₂O (10 mL) was added, the layers were separated and the aqueous layer was extracted with EtOAc (3×15 mL). The combined organic layers were dried over Na₂SO₄, filtered and concentrated under reduced pressure. The residue was purified by flash chromatography (0-20% EtOAc in petroleum ether) to afford the title compound (300 mg, 57% yield) as a white solid.

MS (ES⁺) $C_{14}H_{11}BrN_2O_2S$ requires 350, found 351 [M-81]⁺.

Step 2

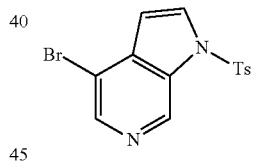

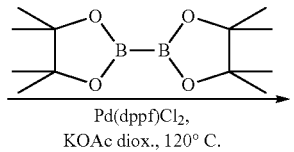

Pd(dppf)Cl₂, KOAc diox., 120° C.

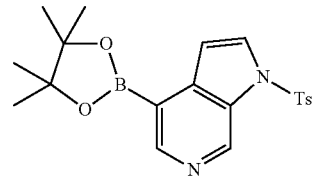

4-(4,4,5,5-Tetramethyl-1,3,2-dioxaborolan-2-yl)-1-tosyl-1H-pyrrolo[2,3-c]pyridine: A mixture of the product from the previous step (300 mg, 0.86 mmol), 4,4,4',4',5,5,5',5'-octamethyl-2,2'-bi(1,3,2-dioxaborolane) (254 mg, 1.0 mmol), Pd(dppf)Cl₂ (63 mg, 0.086 mmol) and KOAc (169 mg, 1.72 mmol) in dioxane (10 mL) was degassed with Ar and the reaction mixture was heated at 120° C. for 4 h. The reaction mixture was cooled to RT, filtered through CELITE® and concentrated under reduced pressure. The residue was purified by flash chromatography (10-60% EtOAc in petroleum ether) to afford the title compound (100 mg, 29% yield) as a white solid.

MS (ES⁺) $C_{20}H_{23}BN_2O_4S$ requires 398, found 399 [M+H]⁺.

117

Intermediate J

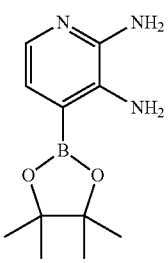 [SMILES: CC1(C)OB(c2ccnc(N)c2N)OC1(C)C]

4-(4,4,5,5-Tetramethyl-1,3,2-dioxaborolan-2-yl)pyridine-2,3-diamine

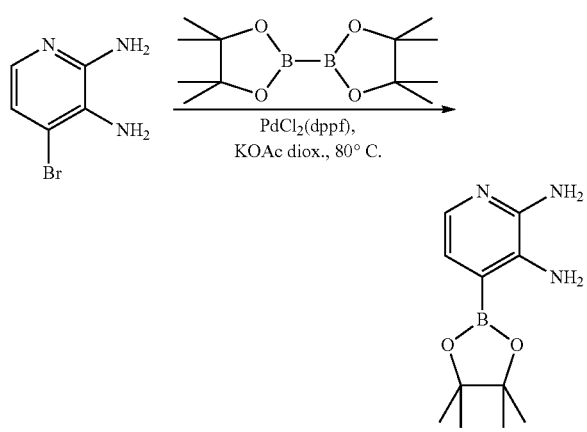

4-(4,4,5,5-Tetramethyl-1,3,2-dioxaborolan-2-yl)pyridine-2,3-diamine: To a solution of 4-bromopyridine-2,3-diamine (200 mg, 1.07 mmol), KOAc (262 mg, 2.67 mmol) and Pin$_2$B$_2$ (544 mg, 2.14 mmol) in dioxane (10 mL) was added Pd(dppf)Cl$_2$ (63 mg, 0.086 mmol) and the mixture was stirred at 80° C. for 16 h under an atmosphere of Ar. The reaction mixture was cooled to RT, filtered through CELITE® and concentrated under reduced pressure. The residue was taken up in petroleum ether (20 mL) and stirred for 10 minutes, filtered and concentrated to afford the title compound (>250 mg, assumed quantitative) as a brown solid.

MS (ES$^+$) C$_{11}$H$_{18}$BN$_3$O$_2$ requires: 235, found 154 [M-81]$^+$.

Intermediate K

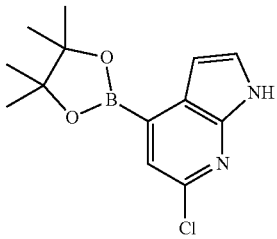 [SMILES: CC1(C)OB(c2cc(Cl)nc3[nH]ccc23)OC1(C)C]

118

6-Chloro-4-(4,4,5,5-tetramethyl-1,3,2-dioxaborolan-2-yl)-1H-pyrrolo[2,3-b]pyridine

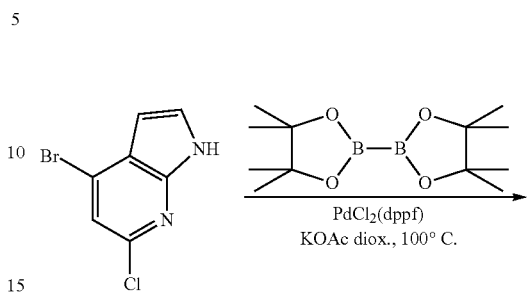

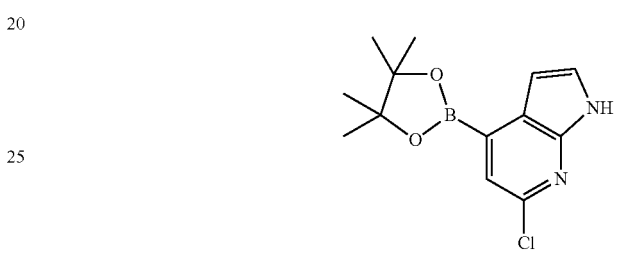

6-Chloro-4-(4,4,5,5-tetramethyl-1,3,2-dioxaborolan-2-yl)-1H-pyrrolo[2,3-b]pyridine: A suspension of 4-bromo-6-chloro-1H-pyrrolo[2,3-b]pyridine (100 mg, 0.432 mmol), Pin$_2$B$_2$ (121 mg, 0.475 mmol) and KOAc (127 mg, 1.30 mmol) in dioxane (2160 µL) was degassed with N$_2$ for 1 minute. PdCl$_2$(dppf)-CH$_2$Cl$_2$ (17 mg, 0.022 mmol) was added and the mixture was degassed with N$_2$ for an additional 1 minute. The reaction mixture was heated to 100° C. and stirred for 12 h. The mixture was cooled to RT, filtered through CELITE® and concentrated under reduced pressure to afford the title compound (assumed quantitative) as a brown solid.

MS (ES$^+$) C$_{13}$H$_{16}$BCN$_2$O$_2$ requires: 278, found: 279 [M+H]$^+$.

Intermediate L

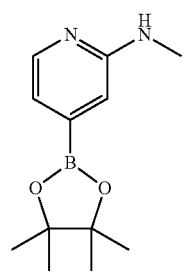

N-methyl-4-(4,4,5,5-tetramethyl-1,3,2-dioxaborolan-2-yl)pyridin-2-amine

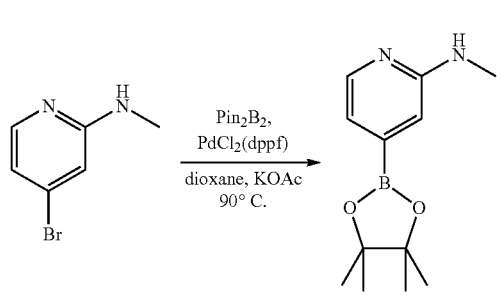

N-methyl-4-(4,4,5,5-tetramethyl-1,3,2-dioxaborolan-2-yl)pyridin-2-amine: To a solution of 4-bromo-N-methylpyridin-2-amine (85 mg, 0.45 mmol), KOAc (132 mg, 1.35 mmol) and Pin$_2$B$_2$ (220 mg, 0.9 mmol) in dioxane (15 mL) was added Pd(dppf)Cl$_2$ (15 mg, 0.02 mmol) and the mixture was heated at 90° C. and stirred for 16 h under an atmosphere of N$_2$. The reaction mixture was cooled to RT, EtOAc (50 mL) was added and the mixture was stirred for 5 min. The mixture was filtered through CELITE® and concentrated under reduced pressure to give the title compound (100 mg) as a brown solid, which was used without further purification.

MS (ES$^+$) C$_{12}$H$_{19}$BN$_2$O$_2$ requires: 234, found: 153 [M-81]$^+$.

Intermediate M

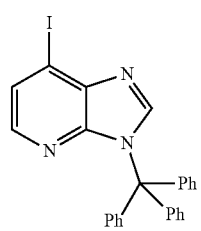 [SMILES: Ic1ccnc2c1ncn2C(c1ccccc1)(c1ccccc1)c1ccccc1]

7-Iodo-3-trityl-3H-imidazo[4,5-b]pyridine

Step 1

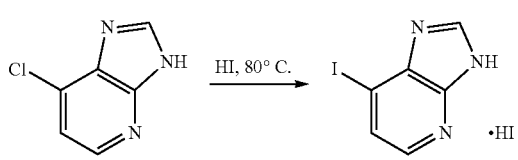

7-Iodo-3H-imidazo[4,5-b]pyridine hydroiodide: A mixture of 7-chloro-3H-imidazo[4,5-b]pyridine (735 mg, 4.80 mmol) in aq. HI (12 mL) was heated at 80° C. and stirred for 16 h. The mixture was cooled to RT, the solid was collected by vacuum filtration and dried under vacuum to afford the title compound (1.5 g, 84% yield) as a yellow solid.

MS (ES$^+$) C$_6$H$_4$IN$_3$ requires: 245, found: 246 [M+H]$^+$.

Step 2

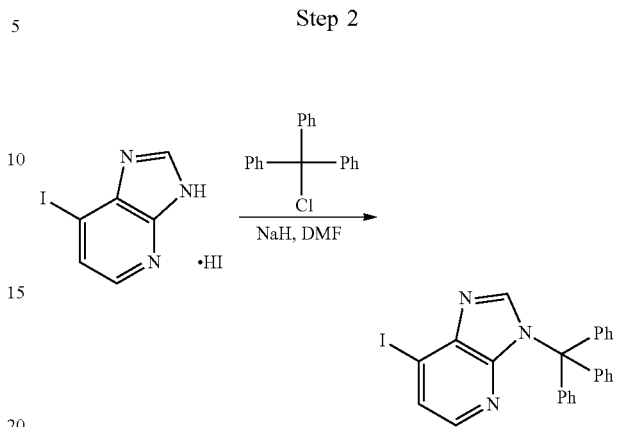

7-Iodo-3-trityl-3H-imidazo[4,5-b]pyridine: To a solution of the product from the previous step (735 mg, 1.97 mmol) in DMF (8 mL) at 5° C. was added NaH (158 mg, 3.94 mmol, 60% in mineral oil) and the resulting mixture was stirred at this temperature for 2 h. The the reaction mixture was added a solution of trityl chloride (822 mg, 2.96 mmol) in DMF (2 mL) dropwise and the resulting mixture was stirred an additional 2 h. The reaction mixture was concentrated under reduced pressure. The residue was purified via silica gel chromatography (10-25% EtOAc in hexanes) to afford the title compound (620 mg, 65% yield) as a white solid.

$^1$H NMR (500 MHz, DMSO-d$_6$) δ 8.23 (s, 1H), 7.71 (d, J=5.0 Hz, 1H), 7.64 (d, J=5.0 Hz, 1H), 7.39-7.25 (m, 9H), 7.20 (d, J=7.2 Hz, 6H).

Intermediate N

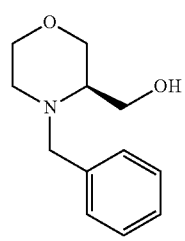 [SMILES: OC[C@@H]1COCCN1Cc1ccccc1]

(R)-(4-benzylmorpholin-3-yl)methanol

Step 1

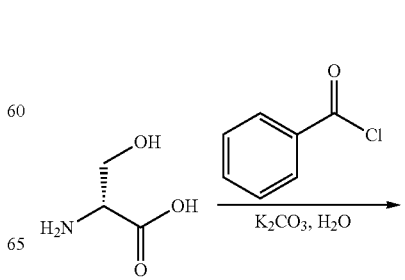

-continued

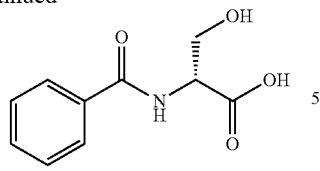

Benzoyl-D-serine: To a stirred solution of (R)-2-amino-3-hydroxypropanoic acid (50 g, 476 mmol), benzoyl chloride (66.64 g, 476 mmol) and K$_2$CO$_3$ (131.6 g, 952 mmol) in H$_2$O (500 mL) at 25° C. for 16 h. The reaction mixture was adjusted to pH=3-4 with 1 N HCl and the aqueous layer was extracted with EtOAc (800 mL). The organic layer was washed with brine (2×500 mL), dried over Na$_2$SO$_4$, filtered and concentrated under reduced pressure to afford the title compound (35.8 g, 40% yield) as a white solid.

MS (ES$^+$) C$_{10}$H$_{11}$NO$_4$ requires: 209, found: 210 [M+H]$^+$.

Step 2

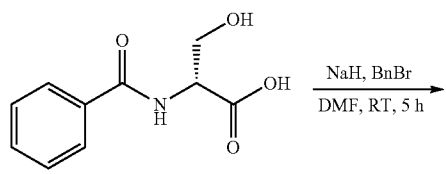

N-benzoyl-O-benzyl-D-serine: To suspension of NaH (33.06 g, 1378 mmol) in DMF (300 mL) at 0° C. under an atmosphere of N$_2$ was added the product from the previous step (96 g, 459 mmol) in DMF (300 mL) and the resulting mixture was stirred for 1 h at 0° C. Benzyl bromide (54.54 mL, 459.2 mmol) was added and the mixture was allowed to warm to RT and stirred for 5 h. The reaction mixture was poured into ice water, the layers were separated and the aqueous phase was extracted with Et$_2$O (1200 mL). The aqueous phase was acidified with 4 N HCl and extracted with CH$_2$Cl$_2$ (1200 mL). The organic layer was dried over Na$_2$SO$_4$, filtered and concentrated under reduced pressure to afford the title compound (126 g, 69% yield), which was used without further purification.

MS (ES$^+$) C$_{17}$H$_{17}$NO$_4$ requires: 299, found: 300 [M+H]$^+$.

Step 3

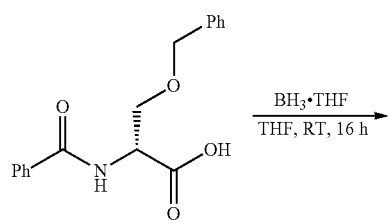

-continued

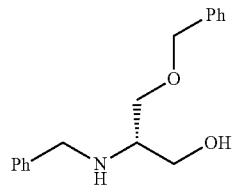

(S)-2-(benzylamino)-3-(benzyloxy)propan-1-ol: To a solution of the product from the previous step (50 g, 167 mmol) in THF (500 mL) was added BH$_3$-THF (1 M in THF, 1.8 L, 1672 mmol) at 0° C. under an atmosphere of N$_2$ and the resulting mixture was warmed to RT and stirred for 16 h. MeOH (1 L) was added dropwise and the mixture was concentrated under reduced pressure. MeOH (1.5 L) and 1 N aq. NaOH (2.225 L) was added to the residue, and the mixture was heated at reflux for 3 h. The mixture was cooled to RT and concentrated under reduced pressure. The residue was partitioned between H$_2$O (2 L) and EtOAc (2 L) and the layers were separated. The organic layer was dried over Na$_2$SO$_4$, filtered and concentrated under reduced pressure to afford the title compound (40 g, 88% yield) as colorless oil, which was used without further purification.

MS (ES$^+$) C$_{17}$H$_{21}$NO$_2$ requires: 271, found: 272 [M+H]$^+$.

Step 4

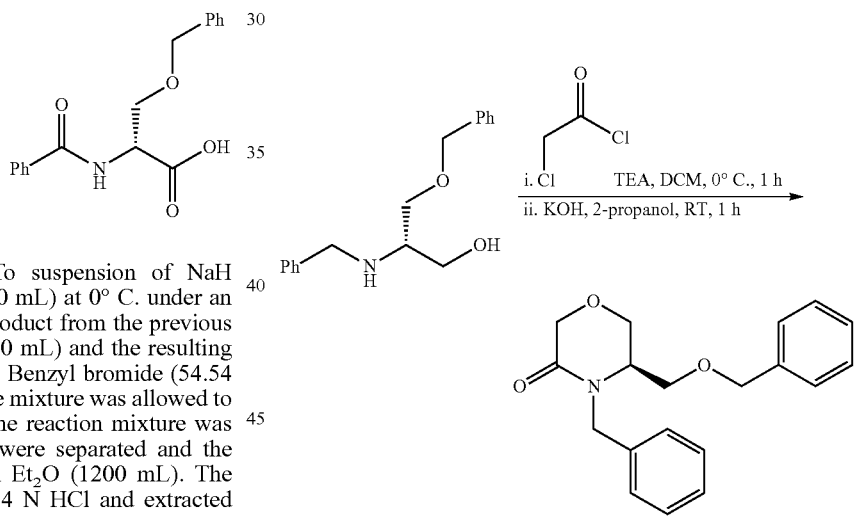

(R)-4-benzyl-5-((benzyloxy)methyl)morpholin-3-one: To a solution of the product from the previous step (10 g, 37 mmol) in CH$_2$Cl$_2$ (100 mL) at 0° C. was added triethylamine (5.91 mL, 42.4 mmol) and chloroacetyl chloride (3.35 ml, 42.4 mmol) and the resulting mixture was stirred for 1 h at 0° C. The reaction mixture was partitioned between 1N HCl (100 mL) and CH$_2$Cl$_2$ (100 mL) and the layers were separated. The organic layer was washed with brine (150 mL), dried over Na$_2$SO$_4$, filtered and concentrated under reduced pressure. The residue was dissolved into 2-propanol (150 mL), KOH (4.14 g, 73.8 mmol) was added and the mixture was stirred for 15 hours at RT. The mixture was concentrated under reduced pressure, the residue was partitioned between water (100 mL) and EtOAc (100 mL) and the layers were separated. The organic layer was washed with brine (100 mL), dried over Na$_2$SO$_4$, filtered and concentrated under reduced pressure. The residue was purified by silica gel column chromatography (50% EtOAc in hexanes) to afford the title compound (7.46 g, 65% yield) as a yellowish oil.

MS (ES⁺) $C_{19}H_{21}NO_3$ requires: 311, found: 312 [M+H]⁺.

Step 5

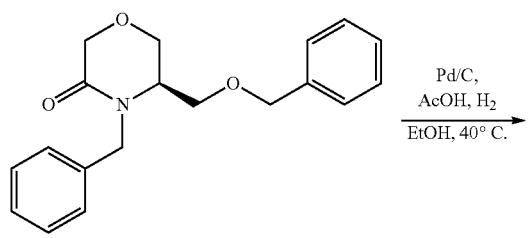

(R)-4-benzyl-5-(hydroxymethyl)morpholin-3-one: To a suspension of the product from the previous step (25 g, 80 mmol) and 10% palladium on activated carbon (13 g, 8 mmol) in EtOH (150 mL) and acetic acid (50 mL) was stirred at 40° C. under an atmosphere of H₂ at 1 atm for 16 h. The mixture was cooled to RT, purged with N₂, filtered through CELITE® and concentrated under reduced pressure. The residue was concentrated from toluene (2×100 mL) to afford the title compound (32 g, assumed quantitative), which was used without further purification.

MS (ES⁺) $C_{12}H_{15}NO_3$ requires: 221, found: 222 [M+H]⁺.

Step 6

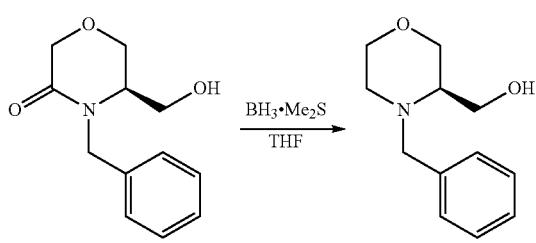 [SMILES: O=C1COC[C@@H](CO)N1Cc1ccccc1 ; OC[C@@H]1COCCN1Cc1ccccc1 ; "THF"]

(R)-(4-benzylmorpholin-3-yl)methanol: To a solution of the product from the previous step (24 g, 108.55 mmol) in THF (50 mL) under an atmosphere of N₂ was added borane-methyl sulfide complex (1.0 M in THF, 40 mL) and the resulting was heated at 80° C. for 16 h. The mixture was cooled to RT, MeOH (60 mL) was added dropwise and concentrated under reduced pressure. The residue was partitioned between MeOH (40 mL) and 1 N aq. NaOH (40 mL) and the layers were separated. The organic layer was dried over Na₂SO₄, filtered and concentrated under reduced pressure. The residue was purified by silica gel chromatography (5-10% EtOAc in hexanes) to afford the title compound (21.8 g, 97% yield) as a white solid.

¹H NMR (400 MHz, DMSO-d₆) δ 7.37-7.18 (m, 5H), 4.59 (t, J=5.3 Hz, 1H), 4.04 (d, J=13.6 Hz, 1H), 3.79-3.64 (m, 2H), 3.58 (dt, J=11.0, 3.4 Hz, 1H), 3.45-3.35 (m, 3H), 3.27 (d, J=13.6 Hz, 1H), 2.56-2.44 (m, 2H), 2.11 (ddd, J=12.1, 9.1, 3.2 Hz, 1H); MS (ES⁺) $C_{12}H_{17}NO_2$ requires: 207, found: 208 [M+H]⁺.

Intermediate O

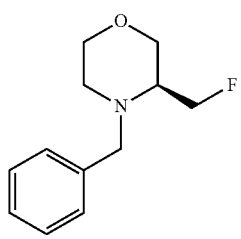

(S)-3-(Fluoromethyl)morpholine

Step 1

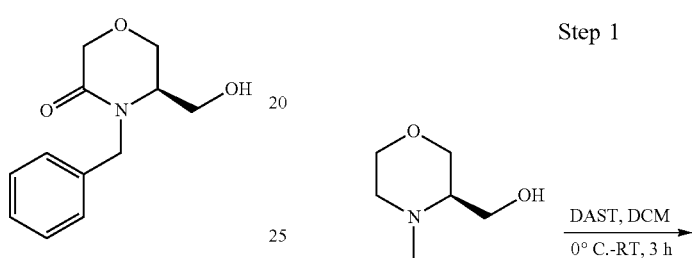

(S)-4-benzyl-3-(fluoromethyl)morpholine: To a solution of Int. N (6.81 g, 3.28 mmol) in CH₂Cl₂ (50 mL) at 0° C. was added diethylaminosulfur trifluoride (6.26 mL, 4.9 mmol) dropwise and the resulting mixture was stirred at RT for 3 h. The reaction mixture was added dropwise to ice-water, aq. sat. NaHCO₃ was added to adjust to pH=8, and the aqueous layer was extracted with CH₂Cl₂ (3×50 mL). The combined organic layers were dried over Na₂SO₄, filtered and concentrated under reduced pressure. The residue was purified by silica gel chromatography (90% EtOAc in hexanes) to afford the title compound (5.18 g, 70% yield) as a yellow liquid.

MS (ES⁺) $C_{12}H_{16}FNO$ requires: 209, found: 210 [M+H]⁺.

Step 2

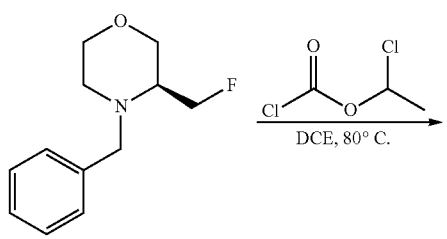

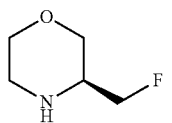

(S)-3-(Fluoromethyl)morpholine: A solution of the product from the previous step (5.18 g, 24.7 mmol) in DCE (50 mL) was added 1-chloroethyl chloroformate (26.7 mL, 247 mmol) and the resulting mixture was heated at 80° C. and stirred for 16 h. The resulting mixture was cooled to RT, MeOH was added until no bubbles were observed, DCE was removed under reduced pressure and the residue was heated at reflux for 1 h. The mixture was cooled to RT, concentrated under pressure and n-heptane was added and the mixture was concentrated under reduced pressure (2×50 mL). The residue was triturated with EtOAc to afford the title compound (25 g, 60% yield) as a white solid.

MS (ES$^+$) C$_5$H$_{10}$FNO requires: 119, found: 120 [M+H]$^+$.

Intermediate P

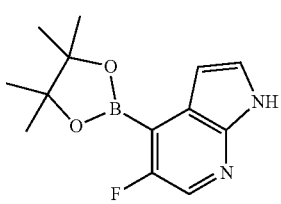 [SMILES: CC1(C)OB(c2c(F)cnc3[nH]ccc23)OC1(C)C]

5-Fluoro-4-(4,4,5,5-tetramethyl-1,3,2-dioxaborolan-2-yl)-1H-pyrrolo[2,3-b]pyridine Step 1

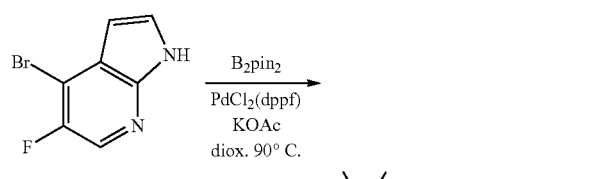

5-Fluoro-4-(4,4,5,5-tetramethyl-1,3,2-dioxaborolan-2-yl)-1H-pyrrolo[2,3-b]pyridine: A sealed tube charged with 4-bromo-5-fluoro-1H-pyrrolo[2,3-b]pyridine (100 mg, 0.465 mmol), KOAc (137 mg, 1.40 mmol), Pin$_2$B$_2$ (142 mg, 0.558 mmol), PdCl$_2$(dppf)·CH$_2$Cl$_2$ (19 mg, 0.023 mmol) followed by dioxane (3.1 mL). The mixture was degassed by bubbling with stream of N$_2$ for 1 minute. The tube was sealed and the reaction mixture was heated for at 90° C. for 18 h. The reaction mixture was cooled to RT, filtered through CELITE®, washed with EtOAc (5 mL), and concentrated under reduced pressure. The residue was purified via silica gel chromatography (0-10% MeOH in CH$_2$Cl$_2$) to afford the title compound (112 mg, 46% yield) as a pale yellow solid.

MS (ES$^+$) C$_{13}$H$_{16}$BFN$_2$O$_2$ requires: 262, found: 181 [M-81]$^+$.

Intermediate Q

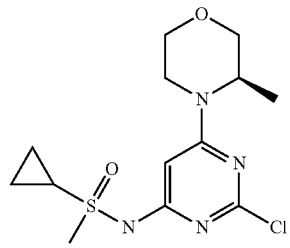

((2-Chloro-6-((R)-3-methylmorpholino)pyrimidin-4-yl)imino)(cyclopropyl)(methyl)-λ$^6$-sulfanone

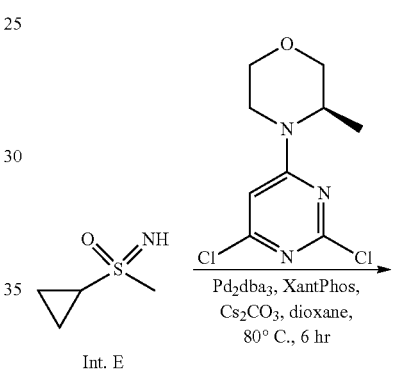

((2-Chloro-6-((R)-3-methylmorpholino)pyrimidin-4-yl)imino)(cyclopropyl)(methyl)-λ$^6$-sulfanone: To the mixture of Int. E (47 g, 0.19 mol), (R)-4-(2,6-dichloropyrimidin-4-yl)-3-methylmorpholine (synthesized as described for Int. B, step 1) (22 g, 0.19 mol) in dioxane (750 mL) were added Pd$_2$(dba)$_3$ (8.6 g, 9.4 mmol), XantPhos (5.5 g, 9.4 mmol) and Cs$_2$CO$_3$ (184 g, 0.57 mol). The reaction mixture was degassed with N$_2$ for 1 minute and heated to 80° C. and stirred under an atmosphere of N$_2$ for 6 h. The mixture was cooled to RT, filtered through CELITE® and concentrated under reduced pressure. The residue was purified via silica gel chromatography (0-100% EtOAc in hexanes) to afford the title compound (26 g, 41% yield) as an off-white solid.

$^1$H NMR (400 MHz, DMSO-d$_6$) δ 5.86 (s, 1H), 4.22 (d, J=5.3 Hz, 1H), 3.92-3.80 (m, 2H), 3.66 (d, J=11.4 Hz, 1H), 3.54 (dd, J=11.5, 2.9 Hz, 1H), 3.45 (s, 3H), 3.39 (td, J=11.9, 3.0 Hz, 1H), 3.12-2.93 (m, 2H), 1.26-1.19 (m, 1H), 1.17-1.04 (m, 6H). MS (ES$^+$) C$_{13}$H$_9$CN$_4$O$_2$S requires: 330, found: 331 [M+H]$^+$.

127

Intermediate R

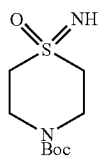

Tert-butyl 1-imino-1λ⁶-thiomorpholine-4-carboxylate 1-oxide

Step 1

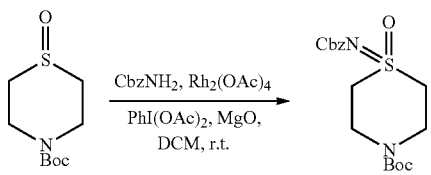

tert-Butyl 1-(((benzyloxy)carbonyl)imino)-1λ⁶-thiomorpholine-4-carboxylate 1-oxide: To a suspension of tert-butyl thiomorpholine-4-carboxylate 1-oxide (2.0 g, 9.1 mmol), benzyl carbamate (2.10 g, 13.7 mmol), MgO (1.5 g, 36 mmol) and Rh₂(OAc)₄ (0.1 g, 0.23 mmol) in CH₂Cl₂ (20 mL) was added PhI(OAc)₂ (4.40 g, 13.7 mmol) and the resulting mixture was stirred at RT for 18 h. The reaction mixture was filtered through CELITE® and concentrated under reduced pressure. The residue was purified via silica gel chromatography (0-40% EtOAc in petroleum ether) to afford the title compound (2.4 g, 36% yield) as a white solid.

MS (ES⁺) $C_{17}H_{24}N_2O_5S$ requires: 368, found: 369 [M+H]⁺.

Step 2

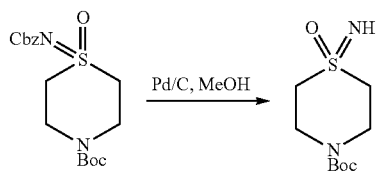

tert-Butyl 1-imino-1)⁶-thiomorpholine-4-carboxylate 1-oxide: A suspension of the product from the previous step (1.0 g, 2.7 mmol) and 10% Pd/C (250 mg, 0.235 mmol) in MeOH (20 mL) was stirred under H₂ for 16 h. The reaction mixture was filtered through CELITE® and concentrated under reduced pressure to afford the title compound (500 mg, 79% yield) as colorless oil. The crude product was used for subsequent step without further purification.

MS (ES⁺) $C_9H_{18}N_2O_3S$ requires: 234, found: 235 [M+H]⁺.

128

Intermediate S

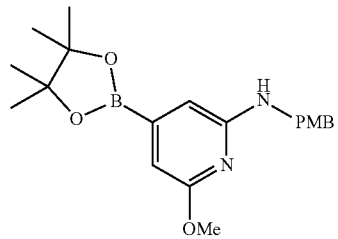

6-Methoxy-N-(4-methoxybenzyl)-4-(4,4,5,5-tetramethyl-1,3,2-dioxaborolan-2-yl)-pyridin-2-amine Step 1

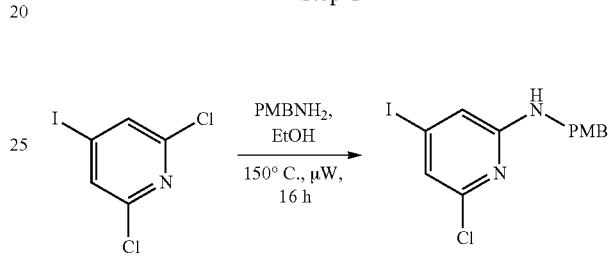

6-Chloro-4-iodo-N-(4-methoxybenzyl)pyridin-2-amine: A microwave vial was charged with 2,6-dichloro-4-iodopyridine (10 g, 36 mmol), 4-methoxybenzylamine (23.4 mL, 179 mmol) and ethanol (20 mL). The vial was sealed and the reaction mixture was heated to 150° C. in a microwave reactor for 4 h. The mixture was cooled to RT, poured into water (20 mL) and the aqueous layer was extracted with EtOAc (3×20 mL). The combined organic fractions were dried over Na₂SO₄, filtered and concentrated under reduced pressure. The residue was purified via silica gel chromatography (0-20% EtOAc in hexanes) to afford the title compound (9.24 g, 69% yield) as a white solid.

MS (ES⁺) $C_{13}H_{12}C_1IN_2O$ requires: 374, found: 375 [M+H]⁺.

Step 2

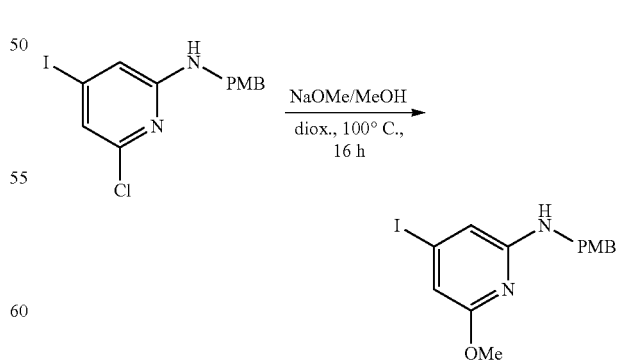

4-Iodo-6-methoxy-N-(4-methoxybenzyl)pyridin-2-amine: To a suspension of the product from the previous step (1.0 g, 2.67 mmol) in dioxane (5.3 mL) at 0° C. was added sodium methoxide (1.8 mL, 8.0 mmol, 25% in MeOH) and the resulting mixture was stirred at 100° C. for 16 h. 1 N HCl (5 mL) was added, the layers were separated and the aqueous layer was extracted with EtOAc (3×30 mL). The combined organic layers were washed with brine (10 mL), dried over MgSO$_4$, filtered through CELITE® and concentrated under reduced pressure. The residue was purified via silica gel chromatography (0-20% EtOAc in hexanes) to afford the title compound (844 mg, 85% yield) as a colorless liquid.

MS (ES$^+$) C$_{14}$H$_{15}$IN$_2$O$_2$ requires: 370, found: 371 [M+H]$^+$.

Step 3

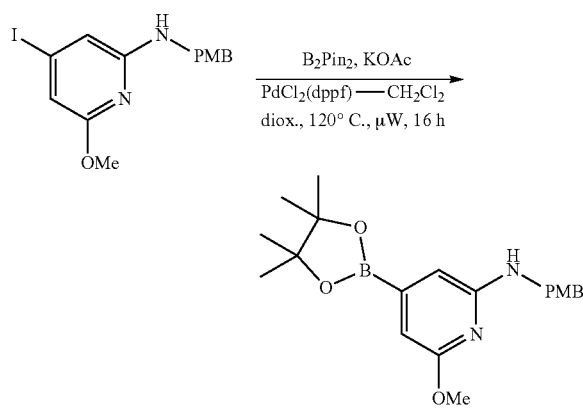

6-Methoxy-N-(4-methoxybenzyl)-4-(4,4,5,5-tetramethyl-1,3,2-dioxaborolan-2-yl)pyridin-2-amine: A suspension of the product from the previous step (900 mg, 2.43 mmol), Pin$_2$B$_2$ (741 mg, 2.92 mmol) and KOAc (716 mg, 7.29 mmol) in dioxane (12.2 mL) was degassed with N$_2$ for 1 minute. PdCl$_2$(dppf)-CH$_2$Cl2 (99 mg, 0.12 mmol) was added and the mixture was degassed with N$_2$ for an additional 1 minute. The reaction mixture was heated at 120° C. in a microwave reactor for 10 h. The mixture was cooled to RT, filtered through CELITE® and concentrated under reduced pressure. The residue was purified via silica gel chromatography (0-60% EtOAc in hexanes) to afford the title compound (860 mg, 72% yield) as a pale yellow liquid.

MS (ES$^+$) C$_{20}$H$_{27}$BN$_2$O$_4$ requires: 370, found: 289 [M-81]$^+$.

Intermediate T

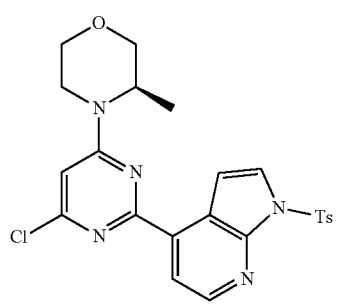 [SMILES: Cc1ccc(S(=O)(=O)n2ccc3c(-c4nc(Cl)cc(N5CCOC[C@H]5C)n4)ccnc32)cc1]

(R)-4-(6-chloro-2-(1-tosyl-1H-pyrrolo[2,3-b]pyridin-4-yl)pyrimidin-4-yl)-3-methylmorpholine

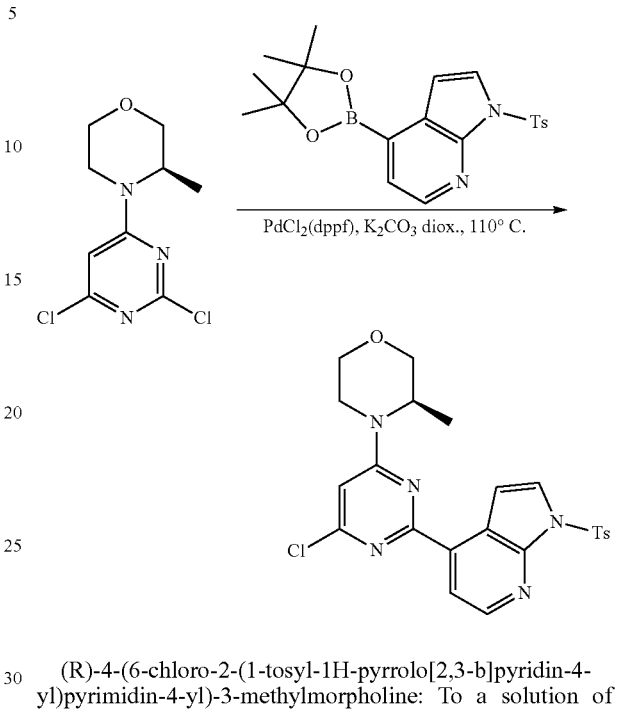

(R)-4-(6-chloro-2-(1-tosyl-1H-pyrrolo[2,3-b]pyridin-4-yl)pyrimidin-4-yl)-3-methylmorpholine: To a solution of (R)-4-(2,6-dichloropyrimidin-4-yl)-3-methylmorpholine (synthesized as described for Int. B, step 1) (467 mg, 1.88 mmol) and 4-(4,4,5,5-tetramethyl-1,3,2-dioxaborolan-2-yl)-1-tosyl-1H-pyrrolo[2,3-b]pyridine (900 mg, 2.26 mmol) in dioxane (7.1 mL) and water (2.4 µL) were added Na$_2$CO$_3$ (439 mg, 4.14 mmol) and PdCl$_2$(dppf)-CH$_2$Cl$_2$ (77 mg, 0.094 mmol) and the resulting mixture was degassed with N$_2$ for 1 minute and stirred at 110° C. for 4 h. The reaction mixture was cooled to RT, partitioned between EtOAc (5 mL) and H$_2$O (2 mL), the layers were separated and the aqueous layer was extracted with EtOAc (3×5 mL). The combined organic layers were washed with brine (2 mL), dried over Na$_2$SO$_4$, filtered and concentrated under reduced pressure. The residue was purified via silica gel chromatography (0-60% EtOAc in hexanes) to afford the title compound (300 mg, 33% yield) as an off-white solid.

$^1$H NMR (600 MHz, CDCl$_3$) δ 8.52 (d, J=5.3 Hz, 1H), 8.06 (t, J=7.1 Hz, 3H), 7.83 (d, J=4.0 Hz, 1H), 7.48 (d, J=3.9 Hz, 1H), 7.26 (d, J=1.5 Hz, 2H), 6.46 (s, 1H), 4.40 (s, 1H), 4.07 (dd, J=11.4, 3.5 Hz, 2H), 3.85 (d, J=11.6 Hz, 1H), 3.75 (dd, J=11.7, 3.1 Hz, 1H), 3.60 (td, J=11.9, 2.8 Hz, 1H), 3.37 (td, J=12.8, 4.0 Hz, 1H), 2.36 (s, 3H), 1.37 (d, J=6.9 Hz, 3H); MS (ES$^+$) C$_{23}$H$_{22}$ClN$_5$O$_3$S: 483, found: 484 [M+H]$^+$.

Intermediate U

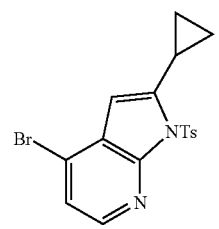 [SMILES: Cc1ccc(S(=O)(=O)n2c(C3CC3)cc3c(Br)ccnc32)cc1]

131

4-Bromo-2-cyclopropyl-1-tosyl-1H-pyrrolo[2,3-b]pyridine

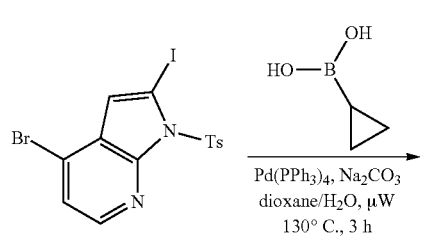

132

(R)-dimethyl((6-(3-methylmorpholino)-2-(tributyl-stannyl)pyrimidin-4-yl)imino)-$\lambda^6$-sulfanone

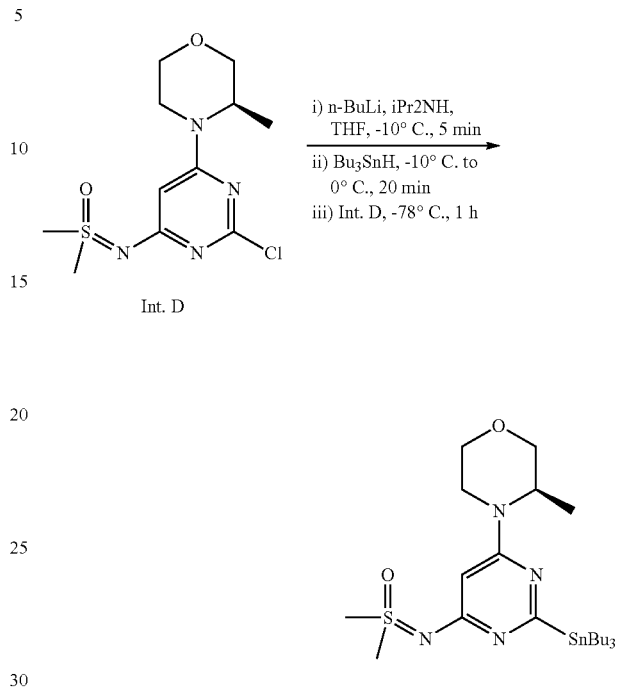

Int. D

4-Bromo-2-cyclopropyl-1-tosyl-1H-pyrrolo[2,3-b]pyridine: A mixture of 4-bromo-2-iodo-1-tosyl-1H-pyrrolo[2,3-b]pyridine (0.3 g, 0.63 mmol), cyclopropylboronic acid (0.054 g, 0.63 mmol), Pd(PPh$_3$)$_4$ (73 mg, 0.063 mmol), Na$_2$CO$_3$ (134 mg, 1.26 mmol), dioxane (10 mL) and H$_2$O (2 mL) was purged with Ar$_2$, sealed and heated at 130° C. for 3 h in a microwave reactor. The reaction mixture was cooled to RT, filtered through CELITE® and concentrated under reduced pressure. The residue was purified via silica gel chromatography (0-10% EtOAc in hexanes) to afford the title compound (30 mg, 12% yield) as a white solid.

MS (ES$^+$) C$_{17}$H$_{15}$BrN$_2$O$_2$S requires: 390 found: 391 [M+H]$^+$.

Intermediate V

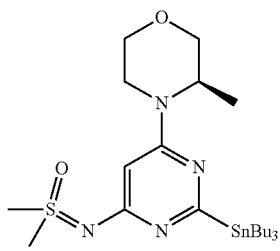

(R)-dimethyl((6-(3-methylmorpholino)-2-(tributylstannyl)pyrimidin-4-yl)imino)-$\lambda^6$-sulfanone, intermediate 5: To a flame dried round bottom flask, under an atmosphere of Ar, was added anhydrous THF (2 mL) and di-isopropylamine (310 µL, 2.2 mmol). The solution was cooled to −10° C. and n-BuLi (2.5 M in hexanes, 0.84 mL, 2.1 mmol) was added dropwise and the resulting mixture was warmed to 0° C. over 5 minutes. A solution of Bu$_3$SnH (538 µL, 2.0 mmol) in THF (2.0 mL) was added dropwise and the resulting mixture was stirred at 0° C. for 20 minutes, and then cooled to −78° C. A solution of Int. D (610 mg, 2.0 mmol) in THF (2.0 mL) was added to the mixture at −78° C. and the resulting mixture was stirred at −78° C. for 1 h. Water (10 ml) was added to the mixture, the layers were separated and the aqueous layer was extracted with EtOAc (3×5 mL). The combined organic layers were dried over Na$_2$SO$_4$, filtered and concentrated under reduced pressure. The residue was purified via silica gel chromatography (20 to 100% EtOAc in hexanes) to afford the title compound (350 mg, 31% yield) as a colorless oil.

MS (ES$^+$) C$_{23}$H$_{44}$N$_4$O$_2$SSn requires: 560, found: 561 [M+H]$^+$.

Intermediate W

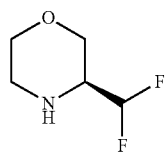

(S)-3-(difluoromethyl)morpholine hydrochloride

Step 1

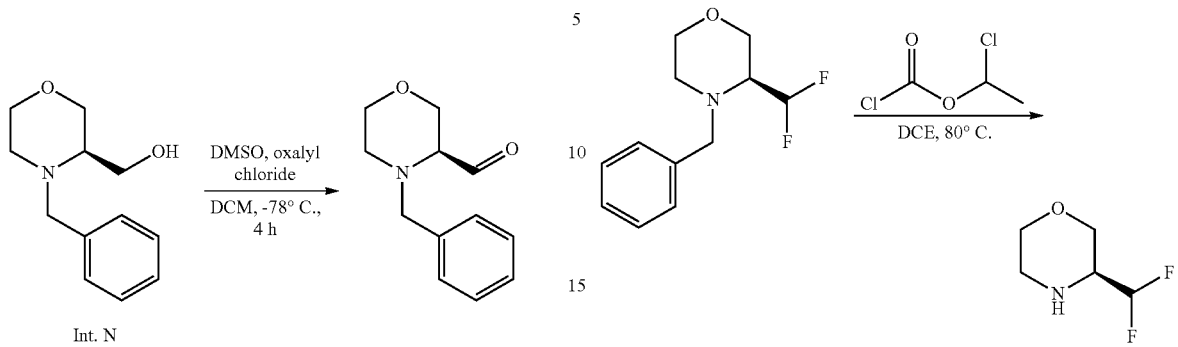

Int. N (S)-4-benzylmorpholine-3-carbaldehyde: To a solution of DMSO (20.6 mL, 290 mmol) in $CH_2Cl_2$ (100 mL) at −78° C. was added a solution of oxalyl chloride (12.2 mL, 145 mmol) in $CH_2Cl_2$ (50 mL) dropwise and the resulting mixture was stirred was at −78° C. for 15 minutes. A solution of Int. N (10 g, 48 mmol) in $CH_2Cl_2$ (50 mL) was added over 30 min. and the resulting mixture was warmed to RT and stirred for 30 min. To the reaction mixture was added sat. aq. $NaHCO_3$ (200 mL) and the layers were separated. The organic layer was dried over $Na_2SO_4$, filtered and concentrated under reduced pressure to afford the title compound (9.9 g, 99% yield), which was used immediately without further purification.

MS (ES+) $C_{12}H_{15}NO_2$ requires: 205 found: 206 $[M+H]^+$.

Step 2

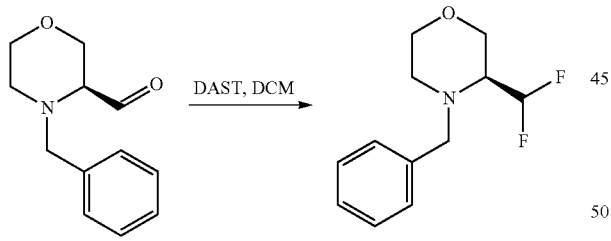

(S)-4-benzyl-3-(difluoromethyl)morpholine: To a solution of the product from the previous step (9.9 g, 48.267 mmol) in $CH_2Cl_2$ (100 mL) at 0° C. was added DAST (19.14 mL, 44.8 mmol) was added dropwise while maintaining a temperature of 0-5° C. and the resulting reaction mixture was warmed to RT and stirred for 16 hours. To the reaction mixture was added sat. aq. $NaHCO_3$ (50 mL) and the layers were separated. The organic layer was washed with water (20 mL), dried over $Na_2SO_4$, filtered and concentrated under reduced pressure. The residue was purified by silica gel chromatography (hexanes) to afford the title compound (5 g, 45.45% yield) as a yellowish oil.

MS (ES+) $C_{12}H_{15}F_2NO$ requires: 227 found: 228 $[M+H]^+$.

Step 3

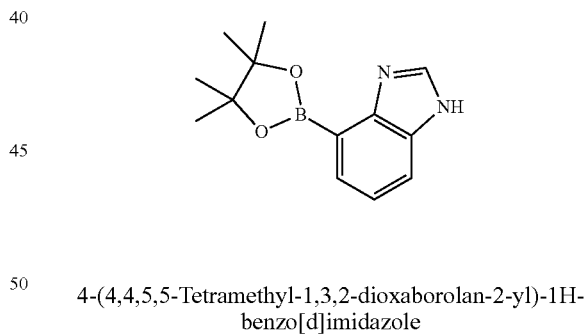

(S)-3-(difluoromethyl)morpholine hydrochloride: To a solution of the product from the previous step (2.0 g, 8.806 mmol) in DCE (10 mL) was added 1-chloroethyl chloroformate (9.44 mL, 88.1 mmol) and the resulting mixture was heated at 80° C. and stirred for 16 h. The resulting mixture was cooled to RT, MeOH was added until no bubbles were observed, DCE was removed under reduced pressure and the residue was heated at reflux for 1 h. The mixture was cooled to RT, concentrated under pressure and 2-propanol was added and the mixture was concentrated under reduced pressure (2×10 mL). The residue was triturated with EtOAc to afford the title compound (1.9 g, quantitative yield) as a white solid.

$^1H$ NMR (400 MHz, DMSO-$d_6$) δ 6.42 (td, J=53.7, 3.9 Hz, 1H), 4.04 (dd, J=12.3, 3.5 Hz, 1H), 4.00-3.83 (m, 2H), 3.82-3.60 (m, 2H), 3.25 (dt, J=12.9, 2.7 Hz, 1H), 3.20-3.06 (m, 1H); MS (ES+) $CH_9F_2NO$ requires: 137 found: 138 $[M+H]^+$.

Intermediate X 4-(4,4,5,5-Tetramethyl-1,3,2-dioxaborolan-2-yl)-1H-benzo[d]imidazole

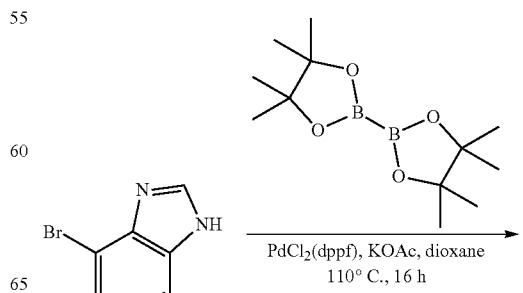

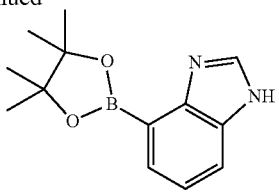

4-(4,4,5,5-Tetramethyl-1,3,2-dioxaborolan-2-yl)-1H-benzo[d]imidazole: A mixture of 4-bromo-1H-benzo[d]imidazole (0.5 g, 2.5 mmol), Pin₂B₂ (0.77 g, 3.1 mmol), PdCl₂(dppf) (93 mg, 0.13 mmol) and KOAc (0.5 g, 5.1 mmol) in dioxane (20 mL) was degassed with $N_2$ for 1 min. and the resulting mixture was heated at 90° C. and stirred for 16 h. The reaction mixture was cooled to RT, filtered through CELITE® and concentrated under reduced pressure to afford the title compound (0.6 g, assumed quantitative) as a black solid, which was directly used for the next step without further purification.

MS (ES⁺) $C_{13}H_{17}BN_2O_2$ requires: 244 found: 163 [M-81]⁺.

Intermediate Y

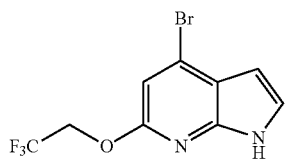

6-Chloro-N-(4-methoxybenzyl)-4-(4,4,5,5-tetramethyl-1,3,2-dioxaborolan-2-yl)-pyridin-2-amine

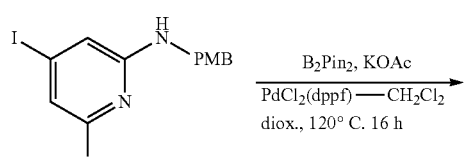

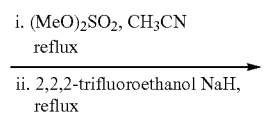

6-Chloro-N-(4-methoxybenzyl)-4-(4,4,5,5-tetramethyl-1,3,2-dioxaborolan-2-yl)pyridin-2-amine: A sealed tube was charged with 6-chloro-4-iodo-N-(4-methoxybenzyl)pyridin-2-amine (synthesized as described for Int. S, step 1) (500 mg, 1.24 mmol), KOAc (365 mg, 3.72 mmol), Pin₂B₂ (378 mg, 1.49 mmol), PdCl₂(dppf)-CH₂Cl₂ (0.051 g, 0.062 mmol) and dioxane (8.28 mL) and the resulting mixture was degassed with $N_2$ for 1 minute. The reaction tube was sealed and the reaction mixture was heated at 90° C. for 18 h. The reaction mixture was cooled to RT, filtered through CELITE®, washed with EtOAc and concentrated under reduced pressure. The residue was purified via silica gel chromatography (0-50% EtOAc in hexanes) to afford the title compound (525 mg, 56% yield) as an orange liquid.

MS (ES⁺) $C_{19}H_{24}BCN_2O_3$ requires: 374, found: 293 [M-81]⁺.

Intermediate Z

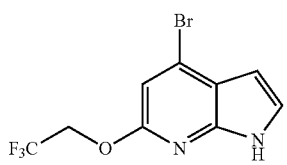 [SMILES: FC(F)(F)COc1cc(Br)c2cc[nH]c2n1]

4-Bromo-6-(2,2,2-trifluoroethoxy)-1H-pyrrolo[2,3-b]pyridine

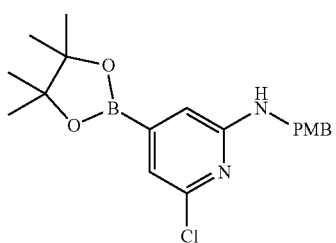

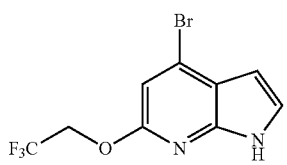 [SMILES: FC(F)(F)COc1cc(Br)c2cc[nH]c2n1]

4-Bromo-6-(2,2,2-trifluoroethoxy)-1H-pyrrolo[2,3-b]pyridine: A solution of 4-bromo-1H-pyrrolo[2,3-b]pyridine 7-oxide (1.73 g, 8.13 mmol) and dimethyl sulfate (1.23 g, 9.75 mmol) in CH₃CN (50 mL) was heated to 70° C. for 24 h. The reaction mixture was cooled to RT. To a suspension of mixture of NaH (6.24 g, 156 mmol, 60% in mineral oil) in CH₃CN (50 mL) at 0° C. was added 2,2,2-trifluoroethanol (5.2 g, 52 mmol) and the resulting mixture was stirred at 0° C. for 30 minutes. The reaction mixture was then added to the mixture prepared above and the resulting mixture was stirred at 70° C. for 16 h. The mixture was cooled to RT and concentrated under reduced pressure. The residue was purified via silica gel chromatography (0-67% EtOAc in petroleum ether; then 0-40% acetone in petroleum ether) to afford the title compound (450 mg, 19% yield) as a white solid.

MS (ES⁺) $C_9H_6BrF_3N_2O$ requires: 294, 296, found: 295, 297[M+H]⁺.

Intermediate AA

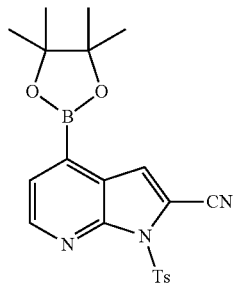 [SMILES: Cc1ccc(S(=O)(=O)n2c(C#N)cc3c(B4OC(C)(C)C(C)(C)O4)ccnc32)cc1]

4-(4,4,5,5-Tetramethyl-1,3,2-dioxaborolan-2-yl)-1-tosyl-1H-pyrrolo[2,3-b]-pyridine-2-carbonitrile Step 1

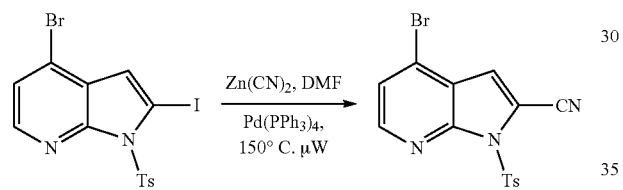

4-Bromo-1-tosyl-1H-pyrrolo[2,3-b]pyridine-2-carbonitrile: A microwave vial was charged with 4-bromo-2-iodo-1-tosyl-1H-pyrrolo[2,3-b]pyridine (200 mg, 0.42 mmol), Zn(CN)$_2$ (24 mg, 0.21 mmol), Pd(PPh$_3$)$_4$ (24 mg, 0.021 mmol) and DMF (5 mL). The vial was sealed and the reaction mixture was heated at 150° C. in a microwave reactor for 30 minutes. The reaction mixture was cooled to RT, filtered through CELITE® and concentrated under reduced pressure. The residue was purified by reverse phase preparative HPLC (Mobile phase: A=10 mM NH$_4$HCO$_3$/H$_2$O, B=MeCN; Gradient: B=50-80%; 18 min; Column: Welch XB-C18, 10 μm, 21.2×250 mm) to afford the title compound (20 mg, 12% yield) as a white solid.

MS (ES$^+$) C$_{15}$H$_{10}$BrN$_3$O$_2$S requires: 375, found: 376 [M+H]$^+$.

Step 2

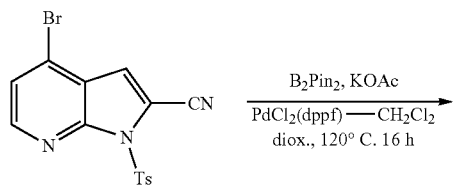

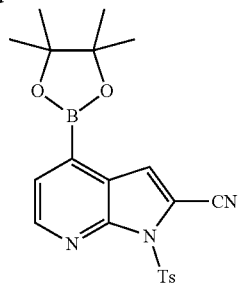

4-(4,4,5,5-Tetramethyl-1,3,2-dioxaborolan-2-yl)-1-tosyl-1H-pyrrolo[2,3-b]pyridine-2-carbonitrile: A sealed tube was charged with 4-bromo-1-tosyl-H-pyrrolo[2,3-b]pyridine-2-carbonitrile (25 mg, 0.066 mmol), KOAc (19.6 mg, 0.199 mmol), bis(pinacolato)diboron (20.3 mg, 0.0800 mmol), PdCl$_2$(dppf)-CH$_2$Cl$_2$ (2.7 mg, 3.3 μmol) and dioxane (443 μL). The reaction mixture was degassed with N$_2$ for 30 seconds, sealed and heated at 90° C. for 18 h. The reaction mixture was cooled to RT, filtered through CELITE®, washed with EtOAc and concentrated under reduced pressure. The residue was purified via silica gel chromatography (0-80% EtOAc in hexanes) to afford the title compound (11 mg, 20% yield) as a pale yellow liquid.

MS (ES$^+$) C$_{21}$H$_{22}$BN$_3$O$_4$S requires: 423, found: 342 [M-81]$^+$.

Intermediate BB

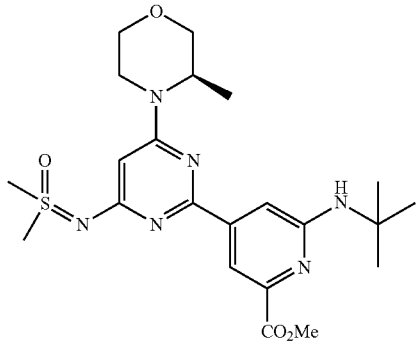 [SMILES: COC(=O)c1cc(-c2nc(N=S(C)(C)=O)cc(N3CCOC[C@H]3C)n2)cc(NC(C)(C)C)n1]

Methyl (R)-6-(tert-butylamino)-4-(4-((dimethyl(oxo)-λ$^6$-sulfaneylidene)amino)-6-(3-methylmorpholino)pyrimidin-2-yl)picolinate Step 1

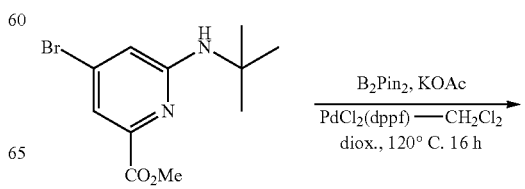

-continued

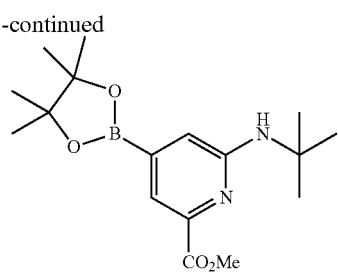

Methyl 6-(tert-butylamino)-4-(4,4,5,5-tetramethyl-1,3,2-dioxaborolan-2-yl)-picolinate: A suspension of methyl 4-bromo-6-(tert-butylamino)picolinate (222 mg, 0.773 mmol), Pin$_2$B$_2$ (216 mg, 0.850 mmol) and KOAc (228 mg, 2.32 mmol) in dioxane (3.87 mL) was degassed with N$_2$ for 1 minute. PdCl$_2$(dppf)-CH$_2$Cl$_2$ (31.6 mg, 0.039 mmol) was added and the mixture was degassed with N$_2$ for an additional 1 minute. The reaction mixture was heated to 100° C. and stirred for 12 h. The mixture was cooled to RT, filtered through CELITE® and concentrated under reduced pressure. The residue was purified via silica gel chromatography (0-20% MeOH in CH$_2$Cl$_2$) to afford the title compound (226 mg, 87% yield) as a brown liquid.

MS (ES$^+$) C$_{17}$H$_{27}$BN$_2$O$_4$ requires: 334, found: 253 [M-81]$^+$.

Step 2

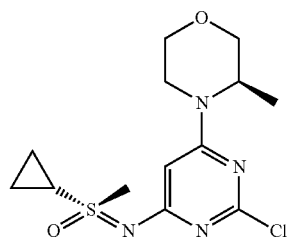 [SMILES: C[C@@H]1COCCN1c1cc(N=[S@](C)(=O)C2CC2)nc(Cl)n1]

Methyl (R)-6-(tert-butylamino)-4-(4-((dimethyl(oxo)-λ$^6$-sulfaneylidene)amino)-6-(3-methylmorpholino)pyrimidin-2-yl)picolinate: A suspension of Int. D (81 mg, 0.264 mmol), the product from the previous step (200 mg, 0.599 mmol) and K$_2$CO$_3$ (73 mg, 0.53 mmol) in THF (1.2 mL) and water (120 µL) was degassed with N$_2$ for 1 minute. PdCl$_2$(dppf)-CH$_2$Cl$_2$ (11 mg, 0.013 mmol) was added and the mixture was degassed with N$_2$ for an additional 1 minute. The reaction mixture was heated to 60° C. and stirred for 2 h. The mixture was cooled to RT and the layers were separated. The aqueous layer was extracted with EtOAc (3×1 mL). The combined organic layers were washed with brine (1 mL), dried over Na$_2$SO$_4$, filtered and concentrated under reduced pressure. The residue was purified via silica gel chromatography (0-60% EtOAc in hexanes) to afford the title compound (150 mg, quantitative yield) as a pale yellow liquid.

MS (ES$^+$) C$_{22}$H$_{32}$N$_6$O$_4$S requires: 476, found: 477 [M+H]$^+$.

Intermediate CC

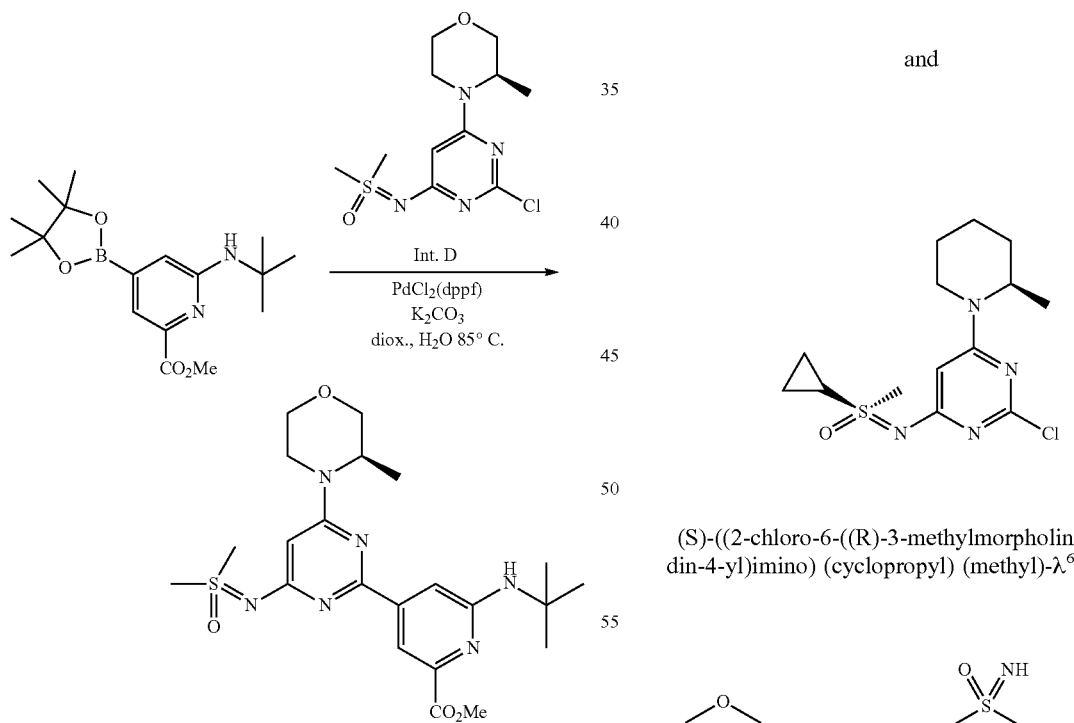

(R)-((2-chloro-6-((R)-3-methylmorpholino)pyrimidin-4-yl)imino)(cyclopropyl)(methyl)-λ$^6$-sulfanone and (S)-((2-chloro-6-((R)-3-methylmorpholino)pyrimidin-4-yl)imino) (cyclopropyl) (methyl)-λ$^6$-sulfanone -continued

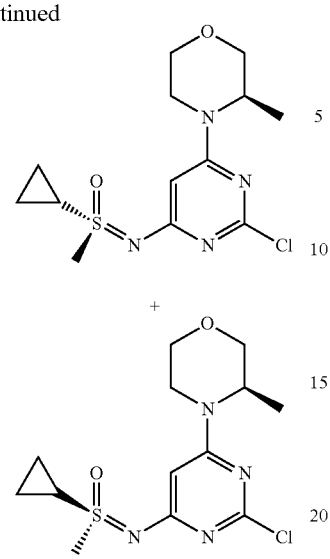

(R)-((2-chloro-6-((R)-3-methylmorpholino)pyrimidin-4-yl)imino)(cyclopropyl)-(methyl)-λ⁶-sulfanone and (S)-((2-chloro-6-((R)-3-methylmorpholino)pyrimidin-4-yl)imino)(cyclopropyl)(methyl)-λ⁶-sulfanone: To solution of Int. E (47 g, 0.19 mol) and (R)-4-(2,6-dichloropyrimidin-4-yl)-3-methylmorpholine (synthesized as described for Int. B, step 1) (22 g, 0.19 mol) in dioxane (750 mL) were added Pd$_2$(dba)$_3$ (8.6 g, 9.4 mmol), XantPhos (5.5 g, 9.4 mmol) and Cs$_2$CO$_3$ (184 g, 0.57 mol) and the resulting mixture was purged with N$_2$ (3×), heated to 80° C. and stirred under an atmosphere of N$_2$ for 6 h. The reaction mixture was cooled to RT, filtered through CELITE® and concentrated under reduced pressure. The residue was purified via silica gel chromatography (0-100% EtOAc in hexanes) to afford the title compounds as a mixture of two diastereomers of unknown absolute stereochemistry at the sulfur atom (26 g, 41% yield) as an off-white solid.

A solution of the mixture of diastereomers (35 g, 0.11 mol) in CH$_2$Cl$_2$ (300 mL) was separated by Chiral SFC (Mobile phase: CO$_2$/EtOH=75/25; Flow rate: 70 g/min; 4 min; Column temperature: 35° C.; Back pressure: 100 bar; Column: Daicel CHIRALPAK® AD, 10 μm, 20 mm×250 mm) to afford the two diastereomers of unknown absolute stereochemistry at the sulfur atom Isomer 1a (15.0 g, 86%) as a light yellow solid and Isomer 1b (14.2 g, 81%) as a light yellow solid.

Isomer 1a ((R)-cyclopropyl(methyl)-λ⁶-sulfanone or (S)-cyclopropyl(methyl)-λ⁶-sulfanone): ¹H NMR (400 MHz, CDCl$_3$) δ 5.69 (s, 1H), 4.15-4.05 (m, 1H), 3.93-3.79 (m, 2H), 3.67 (d, J=11.5 Hz, 1H), 3.59 (app. d, J=11.5 Hz, 1H), 3.51-3.39 (m, 1H), 3.36 (s, 3H), 3.12 (td, J=12.8, 3.4 Hz, 1H), 2.87-2.76 (m, 1H), 1.51-1.40 (m, 1H), 1.28-1.21 (m, 1H), 1.19 (d, J=6.7 Hz, 3H), 1.14-0.99 (m, 2H); MS (ES⁺) C$_{13}$H$_{19}$CN$_4$O$_2$S requires: 330, found: 331 [M+H]⁺; R$_t$=3.19 min.

Isomer 1b ((R)-cyclopropyl(methyl)-λ⁶-sulfanone or (S)-cyclopropyl(methyl)-λ⁶-sulfanone): ¹H NMR (400 MHz, CDCl$_3$) δ 5.68 (s, 1H), 4.14-4.05 (m, 1H), 3.88 (dd, J=11.5, 3.9 Hz, 1H), 3.83 (d, J=13.6 Hz, 1H), 3.67 (d, J=11.5 Hz, 1H), 3.59 (dd, J=11.5, 3.2 Hz, 1H), 3.45 (td, J=11.9, 3.1 Hz, 1H), 3.37 (s, 3H), 3.12 (td, J=12.8, 3.9 Hz, 1H), 2.81 (ddd, J=12.8, 8.0, 4.8 Hz, 1H), 1.49-1.41 (m, 1H), 1.27-1.20 (m, 1H), 1.18 (d, J=6.8 Hz, 3H), 1.14-1.01 (m, 2H); MS (ES⁺) C$_{13}$H$_{19}$CN$_4$O$_2$S requires: 330, found: 331 [M+H]⁺; R$_t$=5.62 min.

Intermediate DD

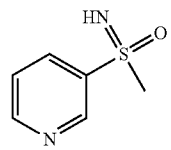

Imino(methyl)(pyridin-3-yl)-λ⁶-sulfanone

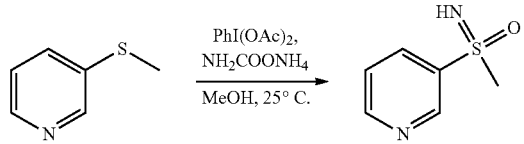

Imino(methyl)(pyridin-3-yl)-λ⁶-sulfanone: To a solution of 3-(methylthio)pyridine (1.09 g, 8.72 mmol) in MeOH (10 mL) were added NH$_2$COONH$_4$ (1.7 g, 21.8 mmol) and PhI(OAc)$_2$ (7.02 g, 21.8 mmol) and the resulting mixture was stirred for 3 h. The reaction mixture was concentrated under reduced pressure. The residue was purified by reverse phase preparative HPLC (Mobile Phase: A=10 mM NH$_4$HCO$_3$ in H$_2$O, B=MeCN; Gradient: B=95%; 13 min; 30 mL/min; column: Xtimate Prep C18 OBD 21.2×250 mm, 10 μm) to afford the title compound (760 mg, 55%) as an off-white solid.

(ES⁺) C$_6$H$_8$N$_2$OS requires: 156, found: 157 [M+H]⁺.

Intermediate EE

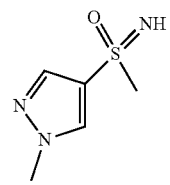

Imino(methyl)(1-methyl-1H-pyrazol-4-yl)-λ⁶-sulfanone

Step 1

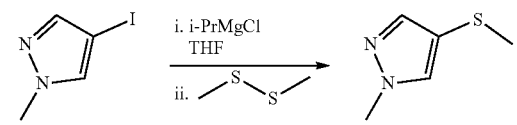

1-Methyl-4-(methylthio)-1H-pyrazole: To a solution of 4-iodo-1-methyl-1H-pyrazole (0.5 mL, 5.2 mmol) in THF (2 mL) at −78° C. under an atmosphere of N₂ was added isopropylmagnesium chloride (5.2 mL, 10.4 mmol) and the resulting mixture was stirred for 30 minutes. To the reaction mixture was added dimethyl disulfide (1 mL, 11 mmol). The reaction was poured into aq. sat. NH₄Cl (25 mL), the layers were separated and the aqueous layer was extracted with Et₂O (100 mL). The combined organic layers were dried over Na₂SO₄, filtered, and concentrated under reduced pressure. The residue was purified by reverse phase preparative HPLC (Mobile Phase: A=10 mM NH₄HCO₃ in H₂O, B=MeCN; Gradient: B=95%; 13 min; 30 mL/min; column: Xtimate Prep C18 OBD 21.2×250 mm, 10 μm) to afford the title compound (740 mg, 29%) as an off-white solid.

(ES⁺) C₅H₈N₂S requires: 128, found: 129 [M+H]⁺.

Step 2

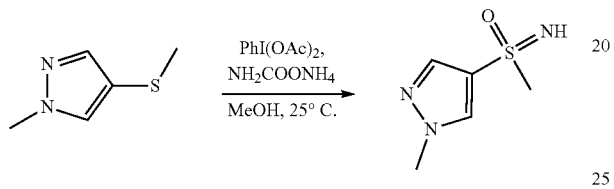

Imino(methyl)(1-methyl-1H-pyrazol-4-yl)-λ⁶-sulfanone: To solution of the product from the previous step (1.09 g, 8.72 mmol) in MeOH (10 mL) were added NH₂COONH₄ (1.7 g, 21.8 mmol) and PhI(OAc)₂ (7.02 g, 21.8 mmol) and the resulting mixture was stirred for 3 h. The reaction mixture was concentrated under reduced pressure. The residue was purified by reverse phase preparative HPLC (Mobile Phase: A=10 mM NH₄HCO₃ in H₂O, B=MeCN; Gradient: B=95%; 13 min; 30 mL/min; column: Xtimate Prep C18 OBD 21.2×250 mm, 10 μm) to afford the title compound (730 mg, 53%) as an off-white solid.

(ES⁺) C₅H₉N₃OS requires: 159, found: 160 [M+H]⁺.

Intermediate FF

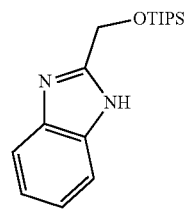

2-(((Triisopropylsilyl)oxy)methyl)-1H-benzo[d]imidazole

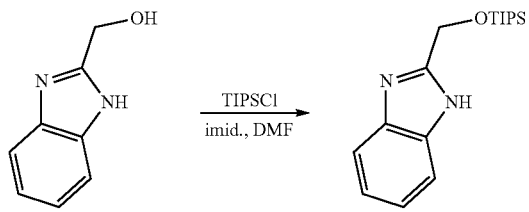

2-(((Triisopropylsilyl)oxy)methyl)-1H-benzo[d]imidazole: To a solution of (1H-benzo[d]imidazol-2-yl)methanol (1.66 g, 11.2 mmol), imidazole (0.92 g, 13 mmol) and DMAP (0.068 g, 0.56 mmol) in DMF (10 mL) was added neat TIPSCl (2.87 mL, 13.4 mmol) and the resulting mixture was stirred at RT for 48 h. The reaction mixture was poured into water (100 mL), the layers were separated and the aqueous layer was extracted with Et₂O (2×100 mL). The combined organic layers were washed with water (2×100 mL) followed by brine (100 mL), stirred over MgSO₄, filtered and concentrated under reduced pressure to afford the title compound (3.40 g, 99% yield) as a white solid.

MS (ES⁺) C₁₇H₂₈N₂OSi requires: 304 found: 305 [M+H]⁺.

EXAMPLE 1

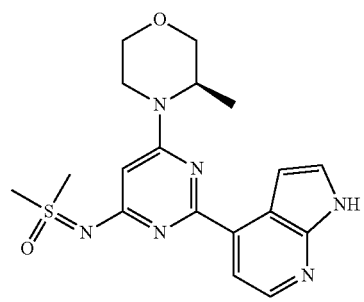 [SMILES: C[C@@H]1COCCN1c1cc(N=S(C)(C)=O)nc(-c2ccnc3[nH]ccc23)n1]

(R)-dimethyl ((6-(3-methylmorpholino)-2-(1H-pyrrolo[2,3-b]pyridin-4-yl)-pyrimidin-4-yl)imino)-λ⁶-sulfanone

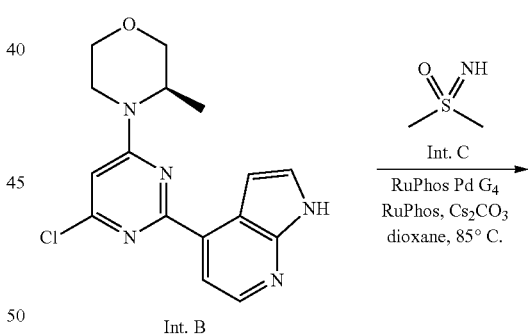

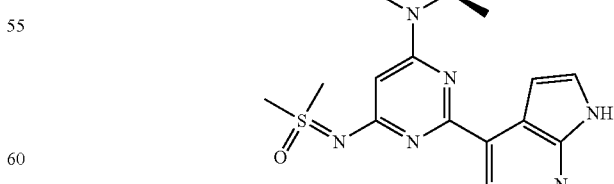

(R)-dimethyl((6-(3-methylmorpholino)-2-(1H-pyrrolo[2,3-b]pyridin-4-yl)pyrimidin-4-yl)imino)-λ⁶-sulfanone A reaction vial was charged with Int. B (100 mg, 0.30 mmol), Int. C (34 mg, 0.36 mmol), RuPhos Pd G4 (26 mg, 0.030 mmol), RuPhos (14 mg, 0.030 mmol), Cs₂CO₃ (293 mg, 0.90 mmol) and 1,4-dioxane (2 mL). The vial was purged with N₂ and sealed. The reaction mixture was stirred at 85° C. for 16 h. The reaction mixture was cooled to RT, filtered through CELITE®, and concentrated under reduced pressure. The residue was purified by reverse phase preparative HPLC (Mobile phase: A=10 M NH₄HCO₃/H₂O, B=MeCN; Gradient: B=20-50%; 10 min; Column: Venusil ASB C18, 10 μm, 150A, 21.2 mm×250 mm) to afford the title compound (33.0 mg, 28% yield) as a white solid.

$^1$H NMR (500 MHz, DMSO) δ 11.72 (s, 1H), 8.31 (d, J=5.0 Hz, 1H), 7.89 (d, J=5.0 Hz, 1H), 7.59-7.49 (m, 1H), 7.41 (dd, J=3.3, 1.9 Hz, 1H), 5.92 (s, 1H), 4.45 (s, 1H), 4.06 (d, J=12.8 Hz, 1H), 3.96 (dd, J=11.3, 3.4 Hz, 1H), 3.75 (d, J=11.3 Hz, 1H), 3.64 (dd, J=11.3, 2.9 Hz, 1H), 3.53-3.47 (m, 1H), 3.45 (s, 6H), 3.15 (td, J=12.8, 3.8 Hz, 1H), 1.20 (d, J=6.7 Hz, 3H); MS (ES⁺) C₁₈H₂₂N₆O₂S requires: 386, found: 387 [M+H]⁺.

The compounds reported in Table 2 were synthesized using the method described for the previously disclosed Examples. The appropriate sulfoximines were prepared as described for Intermediates C.

TABLE 1

Example compounds 2-9

| Ex | Structure | IUPAC Name | MWt | [M + H] | Ex. Method |
|---|---|---|---|---|---|
| 2 | 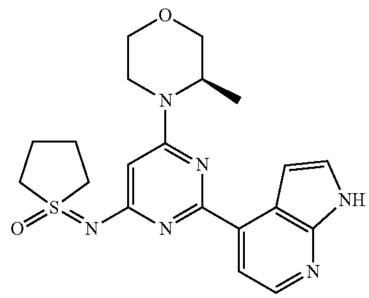 [SMILES: C[C@@H]1COCCN1c1cc(N=S2(=O)CCCC2)nc(-c2ccnc3[nH]ccc23)n1] | 1-({6-[(3R)-3-methyl-morpholin-4-yl]-2-{1H-pyrrolo[2,3-b]pyridin-4-yl}pyrimidin-4-yl}-imino)-1λ⁶-thiolan-1-one | 412 | 413 | 1 |
| 3 | 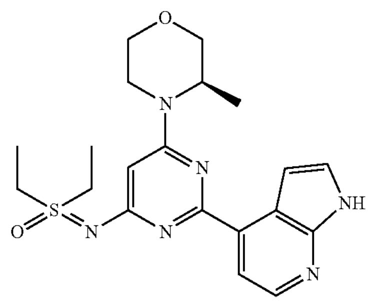 [SMILES: CCS(=O)(CC)=Nc1cc(N2CCOC[C@H]2C)nc(-c2ccnc3[nH]ccc23)n1] | diethyl ({6[(3R)-3-methylmorpholin-4-yl]-2-{1H-pyrrolo[2,3-b]-pyridin-4-yl}pyrimidin-4-yl}imino)-λ⁶-sulfanone | 414 | 415 | 1 |
| 4 | 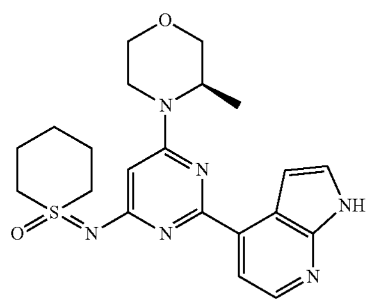 [SMILES: C[C@@H]1COCCN1c1cc(N=S2(=O)CCCCC2)nc(-c2ccnc3[nH]ccc23)n1] | 1-({6-[(3R)-3-methyl-morpholin-4-yl]-2-{1H-pyrrolo[2,3-b]pyridin-4-yl}pyrimidin-4-yl}-imino)-1λ⁶-thian-1-one | 426 | 427 | 1 |
| 5 | 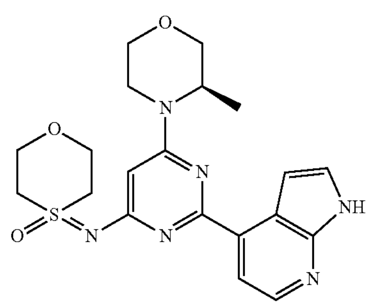 [SMILES: C[C@@H]1COCCN1c1cc(N=S2(=O)CCOCC2)nc(-c2ccnc3[nH]ccc23)n1] | 4-({6-[(3R)-3-methyl-morpholin-4-yl]-2-{1H-pyrrolo[2,3-b]pyridin-4-yl}pyrimidin-4-yl}-imino)-4λ⁶-1,4-oxathian-4-one | 428 | 429 | 1 |

TABLE 1-continued

Example compounds 2-9

| Ex | Structure | IUPAC Name | MWt | [M + H] | Ex. Method |
|---|---|---|---|---|---|
| 6 | 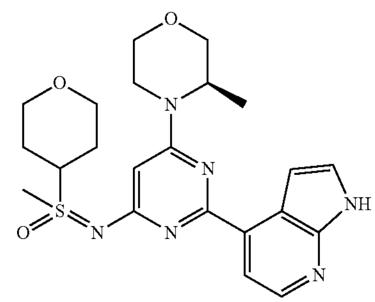 [SMILES: C[C@@H]1COCCN1c1cc(N=S(C)(=O)C2CCOCC2)nc(-c2ccnc3[nH]ccc23)n1] | methyl tetrahydropyran-4-yl ({6-[(3R)-3-methyl-morpholin-4-yl]-2-{1H-pyrrolo[2,3-b]pyridin-4-yl}pyrimidin-4-yl}-imino)-$\lambda^6$-sulfanone | 456 | 457 | 1 |
| 7 | 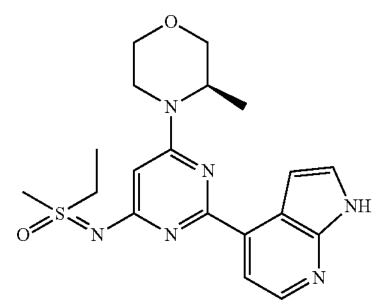 [SMILES: CCS(C)(=O)=Nc1cc(N2CCOC[C@H]2C)nc(-c2ccnc3[nH]ccc23)n1] | methyl ethyl ({6-[(3R)-3-methylmorpholin-4-yl]-2-{1H-pyrrolo[2,3-b]-pyridin-4-yl}pyrimidin-4-yl}imino)-$\lambda^6$-sulfanone | 400 | 401 | 1 |
| 8 | 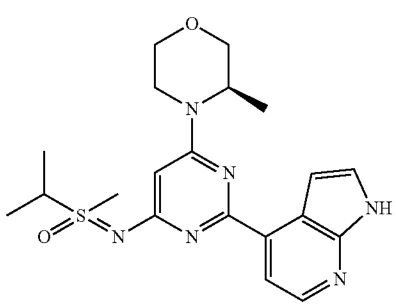 [SMILES: CC(C)S(C)(=O)=Nc1cc(N2CCOC[C@H]2C)nc(-c2ccnc3[nH]ccc23)n1] | methyl 2-propyl ({6-[(3R)-3-methyl-morpholin-4-yl]-2-{1H-pyrrolo[2,3-b]pyridin-4-yl}pyrimidin-4-yl}-imino)-$\lambda_6$-sulfanone | 414 | 415 | 1 |
| 9 | 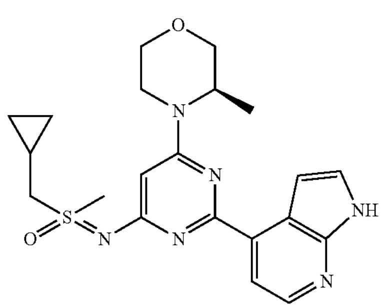 [SMILES: C[C@@H]1COCCN1c1cc(N=S(C)(=O)CC2CC2)nc(-c2ccnc3[nH]ccc23)n1] | methyl (cyclopropyl)-methyl ({6-[(3R)-3-methylmorpholin-4-yl]-2-{1H-pyrrolo[2,3-b]-pyridin-4-yl}pyrimidin-4-yl}imino)-$\lambda^6$-sulfanone | 426 | 427 | 1 |

EXAMPLE 10

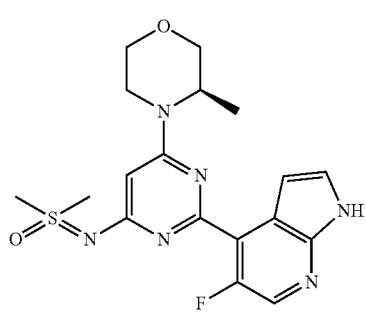 [SMILES: C[C@@H]1COCCN1c1cc(N=S(C)(C)=O)nc(-c2c(F)cnc3[nH]ccc23)n1]

(R)-((2-(5-fluoro-1H-pyrrolo[2,3-b]pyridin-4-yl)-6-(3-methylmorpholino)pyrimidin-4-yl)imino)dimethyl-$\lambda^6$-sulfanone Step 1

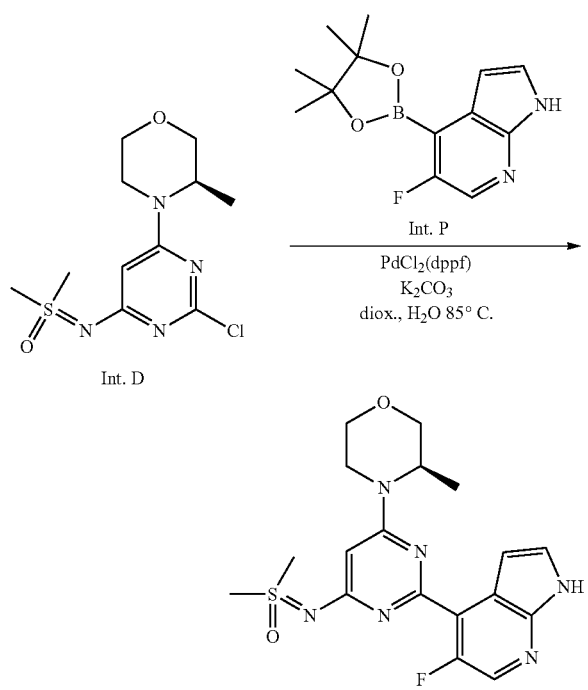

(R)-((2-(5-fluoro-1H-pyrrolo[2,3-b]pyridin-4-yl)-6-(3-methylmorpholino)-pyrimidin-4-yl)imino)dimethyl-$\lambda^6$-sulfanone: A solution of Int. D (45 mg, 0.148 mmol), Int. P (101 mg, 0.192 mmol) and K$_2$CO$_3$ (51 mg, 0.37 mmol) in dioxane (671 μL) and water (67 μL) was degassed with a stream of N$_2$ for 1 minute. PdCl$_2$(dppf)-CH$_2$Cl$_2$ (6.0 mg, 7.9 μmol) was added, the mixture was degassed with a stream of N$_2$ for an additional 1 minute, and the reaction mixture was heated at 85° C. for 3 h. The reaction mixture was cooled to RT, filtered through CELITE®, washed with CH$_2$Cl$_2$ (2 mL) and concentrated under reduced pressure. The residue was purified by mass-triggered preparative HPLC (Mobile phase: A=0.1% TFA/H$_2$O, B=0.1% TFA/MeCN; Gradient: B=10-40%; 20 min; Column: XBridge C18, 5 μm, 19 mm×150 mm) to afford the title compound (32 mg, 34% yield) as a pale yellow solid.

$^1$H NMR (600 MHz, Methanol-d4) δ 8.31 (d, J=3.0 Hz, 1H), 7.66 (d, J=3.4 Hz, 1H), 6.71 (d, J=3.5 Hz, 1H), 6.31 (s, 1H), 4.63 (s, 1H), 4.19 (s, 1H), 4.04 (dd, J=11.9, 3.8 Hz, 1H), 3.83 (d, J=11.8 Hz, 1H), 3.75 (dd, J=11.9, 3.2 Hz, 1H), 3.61 (td, J=11.9, 2.9 Hz, 1H), 3.57 (d, J=5.4 Hz, 6H), 3.51 (t, J=13.5 Hz, 1H), 1.42 (d, J=6.8 Hz, 3H); MS (ES$^+$) C$_{18}$H$_{21}$FN$_6$O$_2$S requires: 404, found: 405 [M+H]$^+$.

EXAMPLE 11

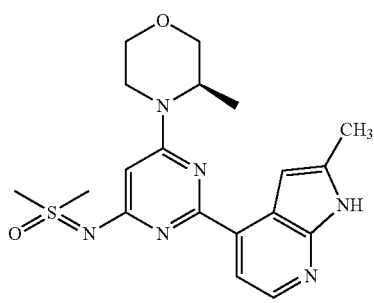

(R)-Dimethyl((2-(2-methyl-1H-pyrrolo[2,3-b]pyridin-4-yl)-6-(3-methylmorpholino)pyrimidin-4-yl)imino)-$\lambda^6$-sulfanone Step 1

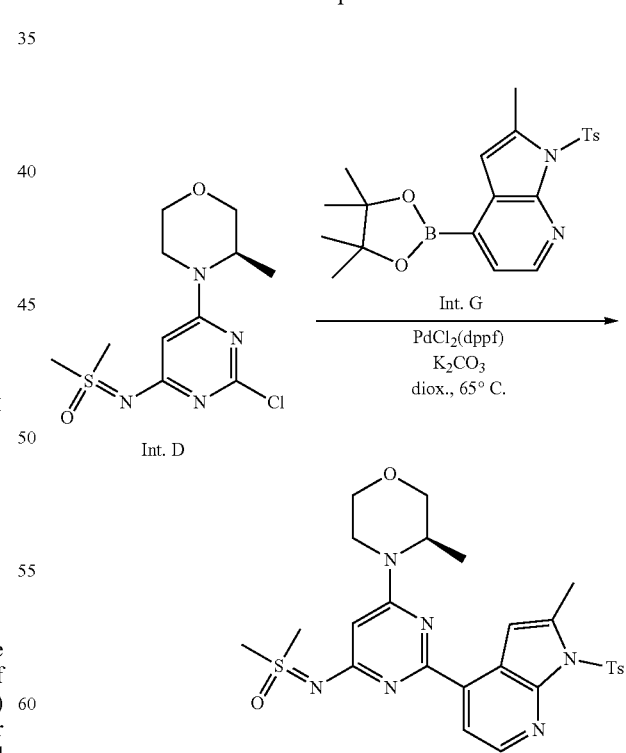

(R)-dimethyl((2-(2-methyl-1-tosyl-1H-pyrrolo[2,3-b]pyridin-4-yl)-6-(3-methylmorpholino)pyrimidin-4-yl)imino)-$\lambda^6$-sulfanone: A reaction vial was charged with Int. D (103 mg, 0.5 mmol), Int. G (280 mg, 0.68 mmol), Na$_2$CO$_3$ (216 mg, 2.04 mmol), PdCl$_2$(dppf) (25 mg, 0.034 mmol), dioxane (3 mL) and H$_2$O (1 mL). The vial was purged with N$_2$ and sealed. The reaction mixture was stirred at 80° C. for 3 h. The reaction mixture was cooled to RT, filtered through CELITE® and concentrated under reduced pressure. The residue was purified by prep-TLC (50% EtOAc in hexanes) to afford the title compound (50 mg, 26% yield) as a white solid.

MS (ES$^+$) C$_{26}$H$_{30}$N$_6$O$_4$S$_2$ requires: 554, found: 555 [M+H]$^+$.

Step 2

(R)-Dimethyl((2-(2-methyl-1H-pyrrolo[2,3-b]pyridin-4-yl)-6-(3-methylmorpholino)pyrimidin-4-yl)imino)-λ$^6$-sulfanone: A mixture of the product from the previous step (50 mg, 0.09 mmol), NaOH (72 mg, 1.8 mmol), H$_2$O (1 mL) and MeOH (2 mL) was stirred at 70° C. for 2 h. The reaction mixture was cooled to RT and concentrated under reduced pressure. MeOH (30 mL) was added, the mixture was stirred for 5 min, filtered and concentrated under reduced pressure. The residue was purified by reverse phase preparative HPLC (Mobile phase: A=10 mM NH$_4$HCO$_3$/H$_2$O, B=MeCN; Gradient: B=30-60%; 18 min; Column: Welch XB-C18, 10 μm, 150 Å, 21.2 mm×250 mm) to afford the title compound (15 mg, 41% yield) as a white solid.

$^1$H NMR (500 MHz, DMSO-d$_6$) δ 11.53 (s, 1H), 8.16 (d, J=5.2 Hz, 1H), 7.81 (d, J=4.8 Hz 1H), 7.11 (s, 1H), 5.89 (s, 1H), 4.44 (s, 1H), 4.04 (s, 1H), 3.95 (s, 1H), 3.75 (d, J=12.6 Hz, 1H), 3.65 (s, 1H), 3.47 (d, J=19.4 Hz, 7H), 3.14 (s, 1H), 2.42 (s, 3H), 1.20 (d, J=6.7 Hz, 3H); MS (ES$^+$) C$_{19}$H$_{24}$N$_6$O$_2$S requires: 400, found: 401 [M+H]$^+$.

EXAMPLE 12

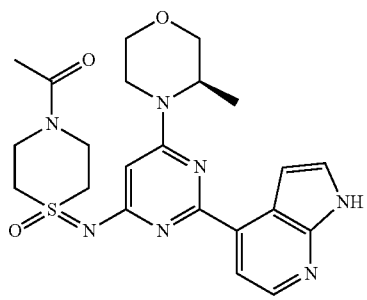 [SMILES: CC(=O)N1CCS(=O)(=Nc2cc(N3CCOC[C@H]3C)nc(-c3ccnc4[nH]ccc34)n2)CC1]

(R)-1-(1-((6-(3-Methylmorpholino)-2-(1H-pyrrolo[2,3-b]pyridin-4-yl)pyrimidin-4-yl)imino)-1-oxido-1λ$^6$-thiomorpholino)ethan-1-one Step 1

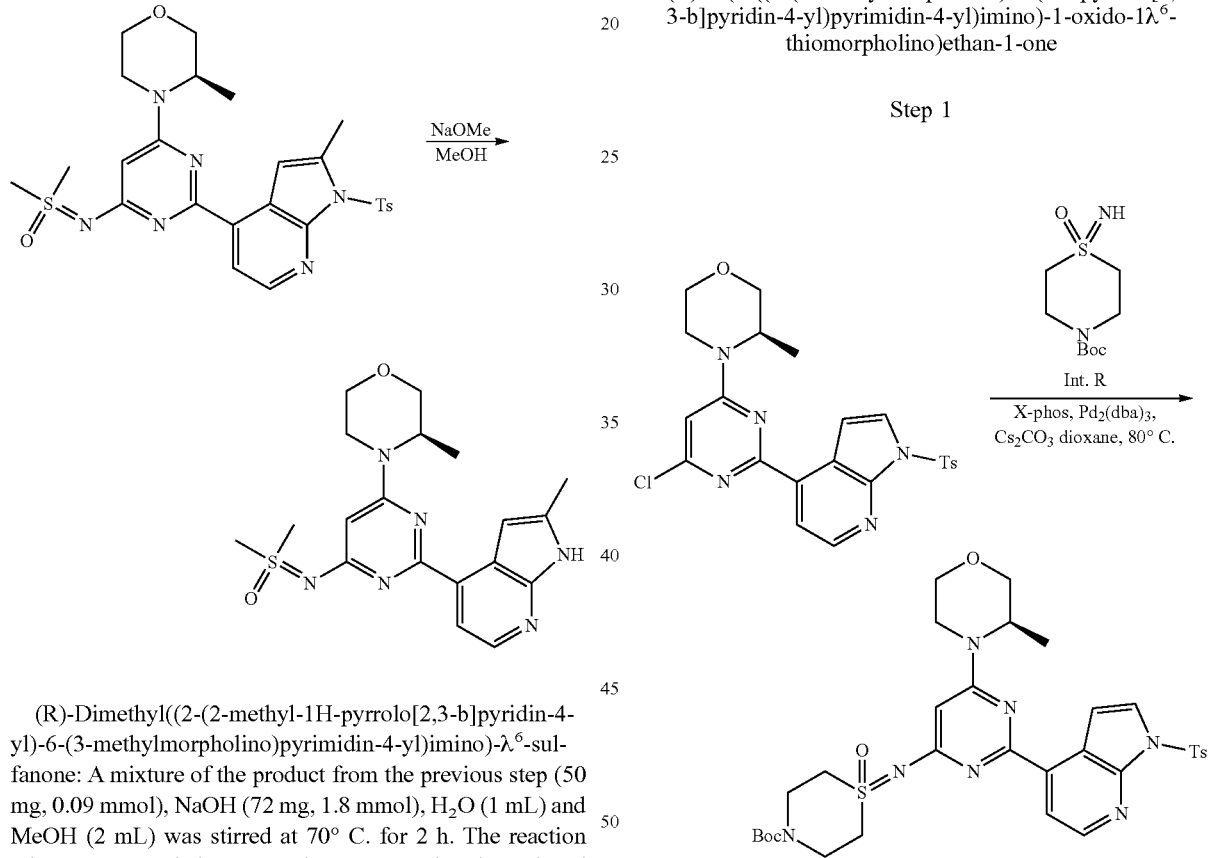

Tert-butyl (R)-1-((6-(3-methylmorpholino)-2-(1-tosyl-1H-pyrrolo[2,3-b]pyridin-4-yl)pyrimidin-4-yl)imino)-1λ$^6$-thiomorpholine-4-carboxylate 1-oxide A mixture Int. R (145 mg, 0.62 mmol), Int. T (300 mg, 0.62 mmol), Pd$_2$(dba)$_3$ (57 mg, 0.062 mmol), X-phos (30 mg, 0.062 mmol) and Cs$_2$CO$_3$ (407 mg, 1.24 mmol) in dioxane (10 mL) was degassed with Ar for 5 minutes. The reaction mixture was heated to 100° C. and stirred for 3 h. The mixture was cooled to RT, filtered through CELITE® and concentrated under reduced pressure. The residue was purified via silica gel chromatography (0-50% EtOAc in hexanes) to afford the title compound (310 mg, 73% yield) as a yellow solid.

MS (ES$^+$) C$_{32}$H$_{39}$N$_7$O$_6$S$_2$ requires: 681, found: 682 [M+H]$^+$.

Step 2

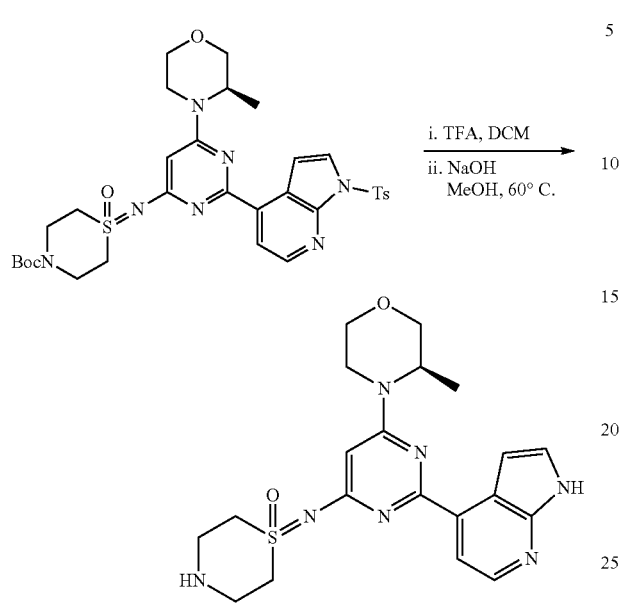

(R)-1-((6-(3-methylmorpholino)-2-(1H-pyrrolo[2,3-b]pyridin-4-yl)pyrimidin-4-yl)imino)-1$\lambda^6$-thiomorpholine 1-oxide A mixture of the product from the previous step (300 mg, 0.44 mmol), TFA (1 mL) and CH$_2$Cl$_2$ (5 mL) was stirred at RT for 1 h. The reaction mixture was concentrated under reduced pressure to give a yellow oil. MeOH (5 mL) and NaOH (18 mg, 0.88 mmol) were added and the mixture was stirred at 60° C. for 1 h. The mixture was cooled to RT, H$_2$O (10 mL) was added and the aqueous layer was extracted with CH$_2$Cl$_2$ (3×15 mL). The combined organic layers were dried over Na$_2$SO$_4$, filtered and concentrated under reduced pressure to afford the title compound (150 mg, 80% yield) as a white solid.

$^1$H NMR (500 MHz, DMSO-d$_6$) δ 11.78 (s, 1H), 9.03 (s, 1H), 8.31 (d, J=5.1 Hz, 1H), 7.86 (d, J=5.0 Hz, 1H), 7.57 (s, 1H), 7.33 (s, 1H), 6.07 (s, 1H), 4.50 (s, 1H), 3.98 (d, J=11.4 Hz, 6H), 3.87-3.82 (m, 3H), 3.52 (s, 4H), 3.19 (s, 1H), 1.23 (d, J=6.7 Hz, 3H); MS (ES$^+$) C$_{20}$H$_{25}$N$_7$O$_2$S requires: 427, found: 428 [M+H]$^+$.

Step 3

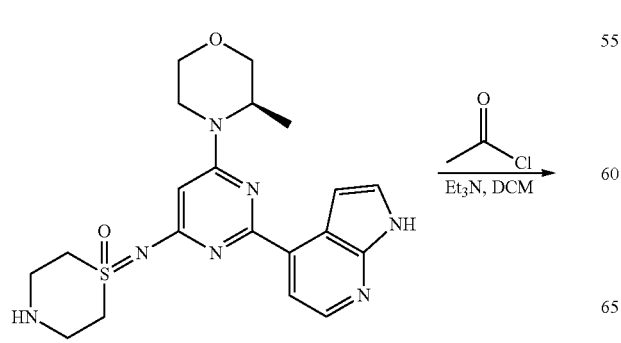

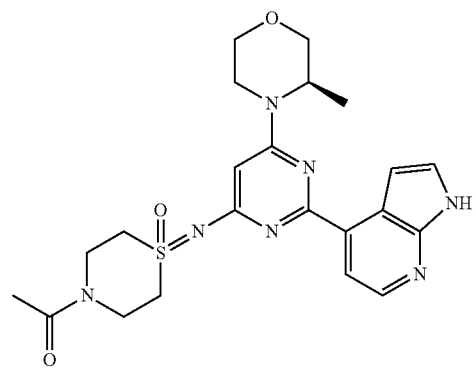

(R)-1-(1-(((6-(3-methylmorpholino)-2-(1H-pyrrolo[2,3-b]pyridin-4-yl)pyrimidin-4-yl)imino)-1-oxido-1$\lambda^6$-thiomorpholino)ethan-1-one: To a solution of the product from the previous step (100 mg, 0.23 mmol) and Et$_3$N (0.5 mL, 0.5 mmol) in CH$_2$Cl$_2$ (5 mL) at 0° C. was added acetyl chloride (18 mg, 0.23 mmol) and the resulting mixture was warmed to RT and stirred for 30 minutes. The reaction mixture was filtered and concentrated under reduced pressure. The residue was purified by reverse phase preparative HPLC (Mobile phase: A=10 mM NH$_4$HCO$_3$/H$_2$O, B=MeCN; Gradient: B=25-55%; 15 min; Column: Welch XB-C18, 10 μm, 21.2× 250 mm) to afford the title compound (36 mg, 33% yield) as a white solid.

$^1$H NMR (500 MHz, DMSO-d$_6$) δ 11.72 (s, 1H), 8.30 (d, J=5.0 Hz, 1H), 7.86 (d, J=5.0 Hz, 1H), 7.59-7.50 (m, 1H), 7.37 (dd, J=3.2, 2.0 Hz, 1H), 6.02 (s, 1H), 4.49 (s, 1H), 4.18 (s, 1H), 4.11-3.82 (m, 4H), 3.79-3.56 (m, 6H), 3.53-3.39 (m, 2H), 3.17 (s, 1H), 2.07 (d, J=2.0 Hz, 3H), 1.22 (d, J=6.6 Hz, 3H); MS (ES$^+$) C$_{22}$H$_{27}$N$_7$O$_3$S requires: 469, found: 470 [M+H]$^+$.

EXAMPLE 13

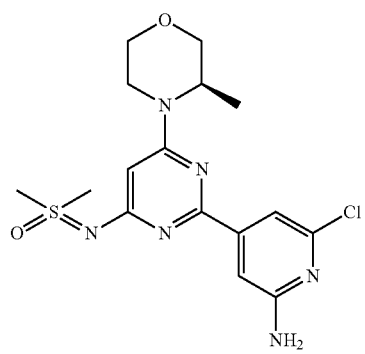 [SMILES: C[C@@H]1COCCN1c1cc(N=S(C)(C)=O)nc(-c2cc(N)nc(Cl)c2)n1]

155

(R)-((2-(2-amino-6-chloropyridin-4-yl)-6-(3-methyl-morpholino)pyrimidin-4-yl)imino)dimethyl-λ⁶-sulfanone Step 1

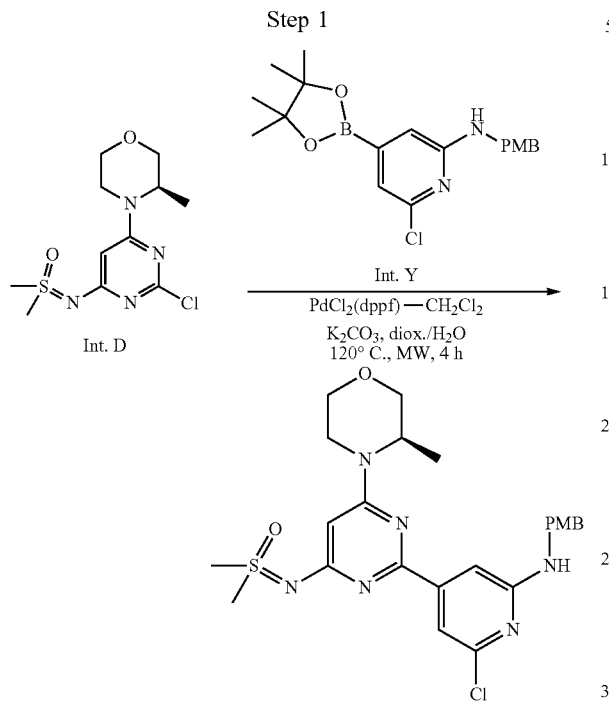

(R)-((2-(2-chloro-6-((4-methoxybenzyl)amino)pyridin-4-yl)-6-(3-methylmorpholino)pyrimidin-4-yl)imino)dimethyl-λ⁶-sulfanone: A solution of Int. D (150 mg, 0.492 mmol), Int. Y (516 mg, 0.689 mmol) and K₂CO₃ (170 mg, 1.23 mmol) in dioxane (2.2 mL) and water (224 μL) was degassed with N₂ for 1 minute. PdCl₂(dppf)-CH₂Cl₂A (20.1 mg, 0.025 mmol) was added and the mixture was degassed with N₂ for an additional 1 minute. The reaction mixture was heated at 85° C. for 3 h. The reaction mixture was cooled to RT, filtered through CELITE®, washed with CH₂Cl₂ and concentrated under reduced pressure. The residue was purified by mass-triggered preparative HPLC (Mobile phase: A=0.1% TFA/H₂O, B=0.1% TFA/MeCN; Gradient: B=40-80%; 16 min; Column: XBridge C18, 5 μm, 19 mm×150 mm) to afford the title compound (166 mg, 23% yield) as a pale yellow solid.

MS (ES⁺) C₂₄H₂₉ClN₆O₃S requires: 516, found: 517 [M+H]⁺.

Step 2

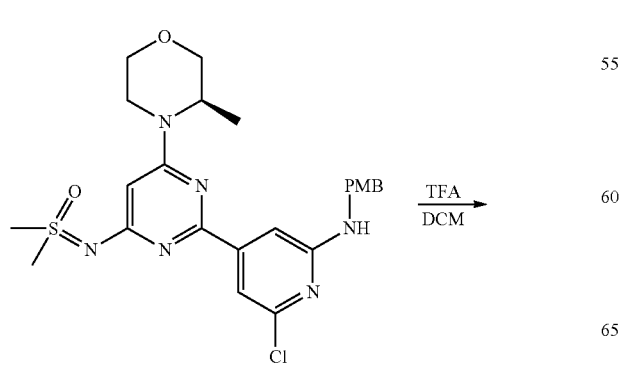

156

-continued

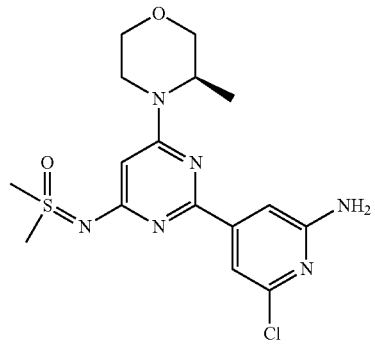

(R)-((2-(2-amino-6-chloropyridin-4-yl)-6-(3-methylmorpholino)pyrimidin-4-yl)imino)dimethyl-λ⁶-sulfanone: To a solution of the product from the previous step (32 mg, 0.021 mmol) in CH₂Cl₂ (215 μL) was added TFA (33 μL, 0.43 mmol) and the resulting mixture was stirred at RT for 2 h. The reaction mixture was concentrated under reduced pressure. The residue was purified by mass-triggered preparative HPLC (Mobile phase: A=0.1% TFA/H₂O, B=0.1% TFA/MeCN; Gradient: B=20-60%; 20 min; Column: XBridge C18, 5 μm, 19 mm×150 mm) to afford the title compound (12.2 mg, 91% yield) as an off-white solid.

¹H NMR (600 MHz, Methanol-d₄) δ 7.15 (d, J=1.0 Hz, 1H), 7.10 (s, 1H), 6.20 (s, 1H), 4.58 (s, 1H), 4.19 (s, 1H), 4.03 (dd, J=11.6, 3.9 Hz, 1H), 3.83 (d, J=11.7 Hz, 1H), 3.73 (dd, J=11.7, 3.2 Hz, 1H), 3.59 (td, J=12.0, 3.1 Hz, 1H), 3.53 (d, J=4.1 Hz, 6H), 3.42 (td, J=13.1, 3.8 Hz, 1H), 1.37 (d, J=6.8 Hz, 3H); MS (ES⁺) C₁₆H₂₁ClN₆O₂S requires: 396/398, found 397/399 [M+H]⁺.

EXAMPLE 14

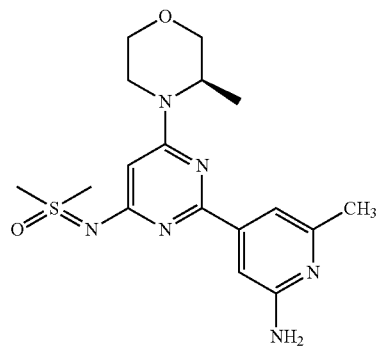

(R)-((2-(2-amino-6-methylpyridin-4-yl)-6-(3-methylmorpholino)pyrimidin-4-yl)imino)dimethyl-λ⁶-sulfanone

Step 1

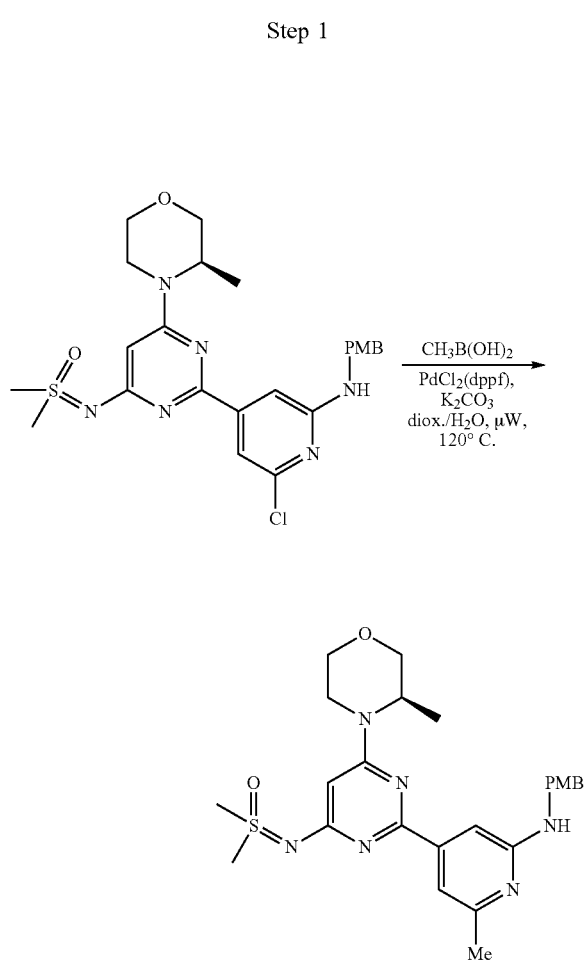

(R)-((2-(2-((4-methoxybenzyl)amino)-6-methylpyridin-4-yl)-6-(3-methylmorpholino)pyrimidin-4-yl)imino)dimethyl-λ⁶-sulfanone: A solution of (R)-((2-(2-chloro-6-((4-methoxybenzyl)amino)pyridin-4-yl)-6-(3-methylmorpholino)pyrimidin-4-yl)imino)dimethyl-λ⁶-sulfanone (synthesized as described for Example 13, step 1) (50 mg, 0.034 mmol), methylboronic acid (2.410 mg, 0.040 mmol) and K₂CO₃ (11.6 mg, 0.084 mmol) in dioxane (153 μL) and water (15 μL) was degassed with N₂ for 30 seconds PdCl₂(dppf)-CH₂Cl2 (1.4 mg, 1.7 μmol) was added and the mixture was degassed with N₂ for an additional 30 seconds. and the resulting mixture was heated at 120° C. for 6 h in a microwave reactor. The reaction mixture was cooled to RT, filtered through CELITE®, washed with CH₂Cl₂ and concentrated under reduced pressure. The residue was purified by mass-triggered preparative HPLC (Mobile phase: A=0.1% TFA/H₂O, B=0.1% TFA/MeCN; Gradient: B=10-40%; 26 min; Column: XBridge C18, 5 μm, 19 mm×150 mm) to afford the title compound (13.5 mg, 56% yield) as a pale yellow solid.

MS (ES⁺) $C_{25}H_{32}N_6O_3S$ requires: 496, found: 497 [M+H]⁺.

Step 2

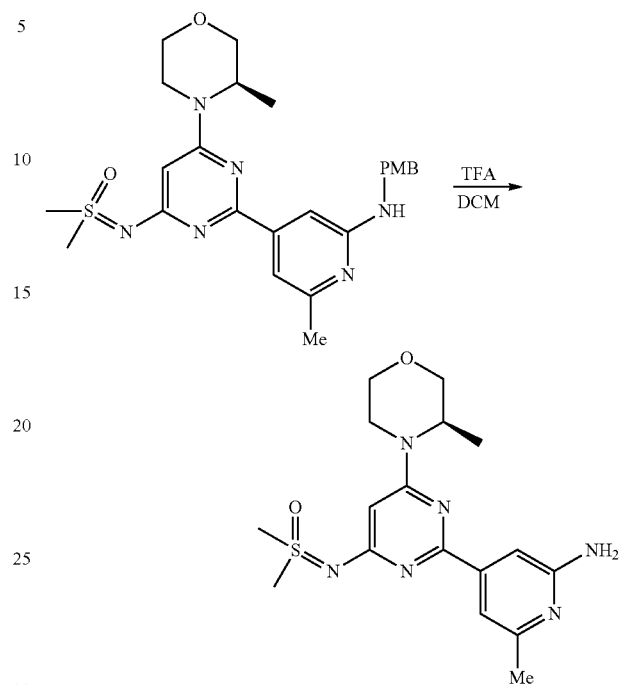

(R)-((2-(2-amino-6-methylpyridin-4-yl)-6-(3-methylmorpholino)pyrimidin-4-yl)imino)dimethyl-λ⁶-sulfanone: To a solution of the product from the previous step (13.5 mg, 0.019 mmol) in CH₂Cl₂ (186 μL) was added TFA (29 μL, 0.37 mmol) and the resulting mixture was stirred at RT for 2 h. The reaction mixture was concentrated under reduced pressure. The residue was purified by mass-triggered preparative HPLC (Mobile phase: A=0.1% TFA/H₂O, B=0.1% TFA/MeCN; Gradient: B=10-40%; 20 min; Column: XBridge C18, 5 μm, 19 mm×150 mm) to afford the title compound (8.6 mg, 76% yield) as an off-white solid.

¹H NMR (600 MHz, Methanol-d4) δ 7.69 (s, 1H), 7.47 (s, 1H), 6.04 (s, 1H), 4.51-4.45 (m, 1H), 4.09 (d, J=12.9 Hz, 1H), 4.00 (dd, J=11.5, 3.9 Hz, 1H), 3.80 (d, J=11.5 Hz, 1H), 3.72 (dd, J=11.6, 3.2 Hz, 1H), 3.57 (td, J=11.9, 3.2 Hz, 1H), 3.49 (s, 6H), 3.32-3.24 (m, overlap MeOH, 1H), 2.55 (s, 3H), 1.29 (d, J=6.8 Hz, 3H); MS (ES⁺) $C_{17}H_{24}N_6O_2S$ requires: 376, found 377 [M+H]⁺.

EXAMPLE 15

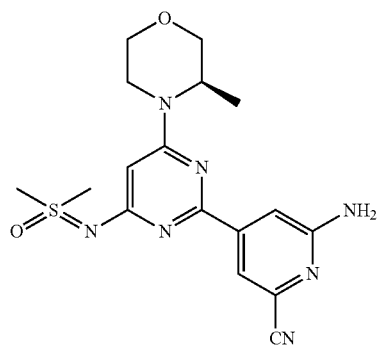 [SMILES: C[C@@H]1COCCN1c1cc(N=S(C)(C)=O)nc(-c2cc(N)nc(C#N)c2)n1]

159

(R)-6-amino-4-(4-((dimethyl(oxo)-λ⁶-sulfaney-
lidene)amino)-6-(3-methylmorpholino)pyrimidin-2-
yl)picolinonitrile

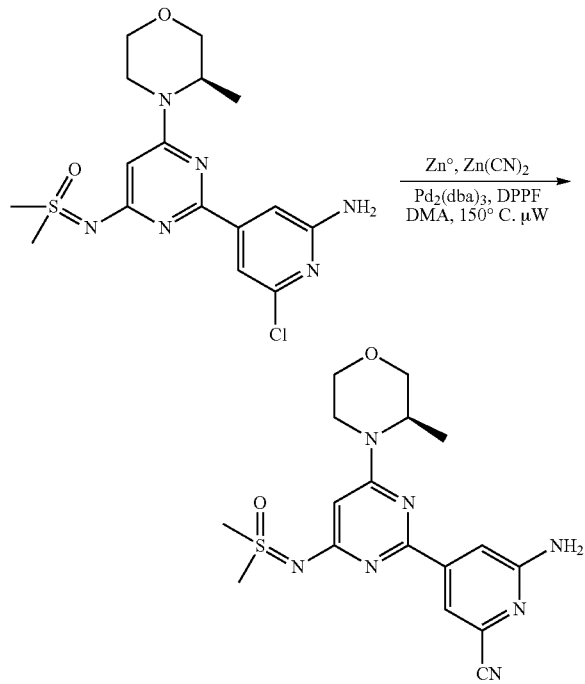

(R)-6-amino-4-(4-((dimethyl(oxo)-λ⁶-sulfaneylidene)
amino)-6-(3-methylmorpholino)pyrimidin-2-yl)picolinonitrile: A microwave vial was charged with Example 13 (95 mg, 0.076 mmol), Pd₂(dba)₃ (7.0 mg, 7.6 μmol), DPPF (2.1 mg, 3.8 μmol), zinc (0.75 mg, 0.011 mmol), dicyanozinc (8.9 mg, 0.076 mmol) and DMA (380 μL). The vial was sealed and the reaction mixture was heated to 150° C. in a microwave reactor for 3 h. The reaction mixture was cooled to RT and directly purified by mass-triggered preparative HPLC (Mobile phase: A=0.1% TFA/H₂O, B=0.1% TFA/MeCN; Gradient: B=10-50%; 26 min; Column: XBridge C18, 5 μm, 19 mm×150 mm) to afford the title compound (23.3 mg, 50% yield) as a pale yellow solid.

¹H NMR (600 MHz, Methanol-d₄) δ 7.58 (s, 1H), 7.44 (s, 1H), 6.19 (s, 1H), 4.58 (s, 1H), 4.28-4.10 (m, 1H), 4.03 (dd, J=11.7, 3.9 Hz, 1H), 3.83 (d, J=11.7 Hz, 1H), 3.73 (dd, J=11.7, 3.2 Hz, 1H), 3.59 (td, J=12.0, 3.1 Hz, 1H), 3.54 (d, J=4.4 Hz, 6H), 3.41 (td, J=13.0, 4.0 Hz, 1H), 1.37 (d, J=6.9 Hz, 3H); MS (ES⁺) C₁₇H₂₁N₇O₂S requires: 387, found: 388 [M+H]⁺.

EXAMPLE 16

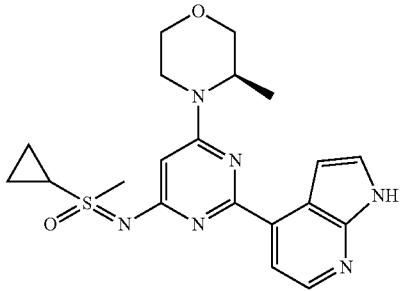 [SMILES: C[C@@H]1COCCN1c1cc(N=S(C)(=O)C2CC2)nc(-c2ccnc3[nH]ccc23)n1]

160

Cyclopropyl(methyl)((6-((R)-3-methylmorpholino)-
2-(1H-pyrrolo[2,3-b]pyridin-4-yl)pyrimidin-4-yl)
imino)-λ⁶-sulfanone Step 1

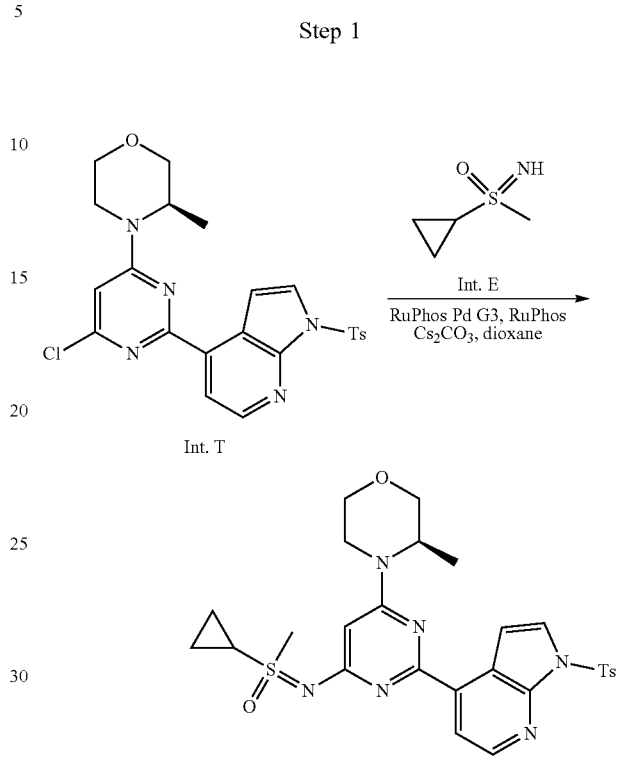

Cyclopropyl(methyl)((6-((R)-3-methylmorpholino)-2-(1-tosyl-1H-pyrrolo[2,3-b]pyridin-4-yl)pyrimidin-4-yl)imino)-λ⁶-sulfanone: A reaction vial was charged with Int. T (300 mg, 0.60 mmol), Int. E (80 mg, 0.67 mmol), Cs₂CO₃ (655 mg, 2.01 mmol), RuPhos Pd G3 (56 mg, 0.067 mmol), RuPhos (31 mg, 0.067 mmol) and dioxane (4 mL). The reaction mixture was purged with N₂, sealed and heated at 80° C. for 3 h. The reaction mixture was cooled to RT, filtered through CELITE® and concentrated under reduced pressure. The residue was purified via silica gel chromatography (0-50% acetone in hexanes) to afford the title compound (130 mg, 37% yield) as a white solid.

MS (ES⁺) C₂₇H₃₀N₆O₄S₂ requires: 566, found: 567 [M+H]⁺.

Step 2

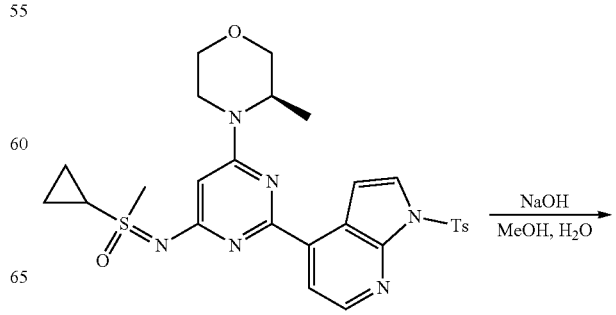

-continued

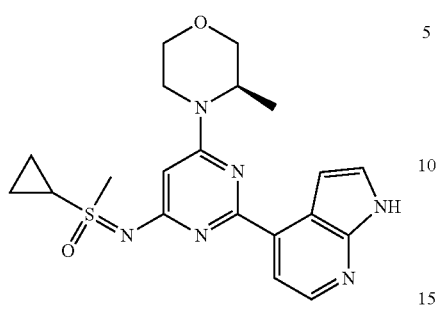

Cyclopropyl(methyl)((6-((R)-3-methylmorpholino)-2-(1H-pyrrolo[2,3-b]pyridin-4-yl)pyrimidin-4-yl)imino)-λ⁶-sulfanone: A reaction vial was charged with the product from the previous step (130 mg, 0.23 mmol), NaOH (184 mg, 4.6 mmol), H₂O (1 mL) and MeOH (2 mL) and the mixture was heated at 70° C. for 2 h. The reaction mixture was cooled to RT and concentrated under reduced pressure. The residue was added MeOH (30 mL) and the resulting mixture was stirred for 5 min., filtered and concentrated under reduced pressure. The residue was purified by reverse phase preparative HPLC (Mobile phase: A=10 mM NH₄HCO₃/H₂O, B=MeCN; Gradient: B=30-60%; 18 min; Column: Welch XB-C18, 10 μm, 150 Å, 21.2 mm×250 mm) to afford the title compound (20 mg, 21% yield) as a white solid.

¹H NMR (500 MHz, DMSO-d₆) δ 11.71 (s, 1H), 8.30 (d, J=5.0 Hz, 1H), 7.90 (dd, J=5.0, 1.8 Hz, 1H), 7.53 (d, J=2.9 Hz, 1H), 7.40 (s, 1H), 5.95 (s, 1H), 4.47 (s, 1H), 4.05 (s, 1H), 3.96 (d, J=8.5 Hz, 1H), 3.75 (d, J=11.2 Hz, 1H), 3.64 (d, J=11.4 Hz, 1H), 3.52 (t, J=13.9 Hz, 4H), 3.16 (s, 1H), 3.00 (s, 1H), 1.18 (dd, J=34.3, 27.3 Hz, 7H); MS (ES⁺) C₂H₂₄N₆O₂S requires: 412, found: 413 [M+H]⁺.

EXAMPLE 17a and 17b

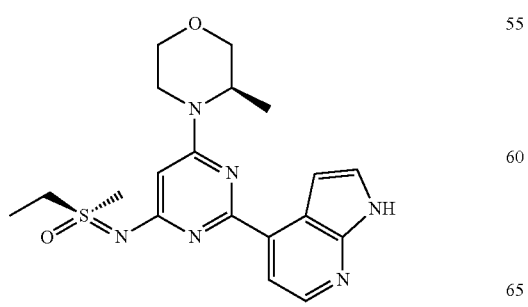

(S)-ethyl(methyl)((6-((R)-3-methylmorpholino)-2-(1H-pyrrolo[2,3-b]pyridin-4-yl)pyrimidin-4-yl)imino)-λ⁶-sulfanone and

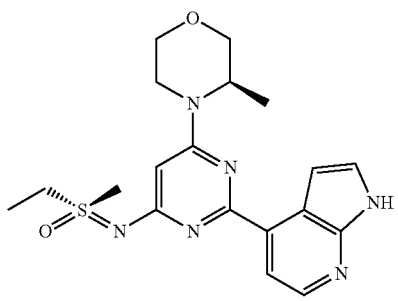 [SMILES: CC[S@@](C)(=O)=Nc1cc(N2CCOC[C@H]2C)nc(-c2ccnc3[nH]ccc23)n1]

(R)-ethyl(methyl)((6-((R)-3-methylmorpholino)-2-(1H-pyrrolo[2,3-b]pyridin-4-yl)pyrimidin-4-yl)imino)-λ⁶-sulfanone Step 1

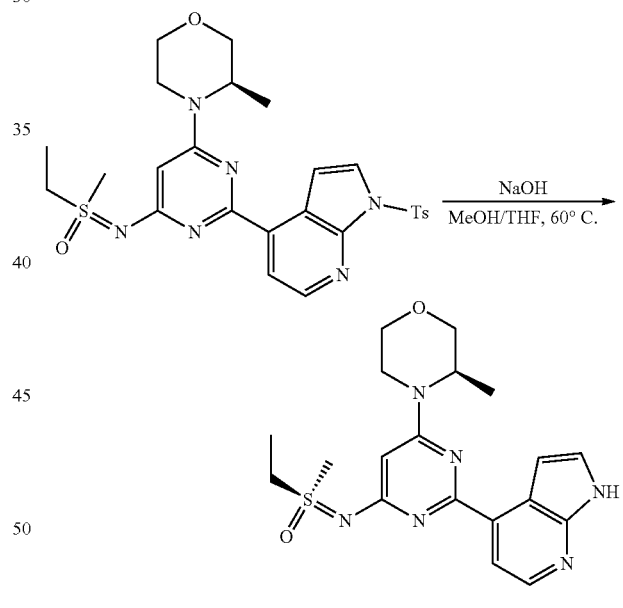

(S)-ethyl(methyl)((6-((R)-3-methylmorpholino)-2-(1H-pyrrolo[2,3-b]pyridin-4-yl)pyrimidin-4-yl)imino)-λ⁶-sulfanone and (R)-ethyl(methyl)((6-((R)-3-methylmorpholino)-2-(1H-pyrrolo[2,3-b]pyridin-4-yl)pyrimidin-4-yl)imino)-λ⁶-sulfanone: To a solution of ethyl(methyl)((6-((R)-3-methylmorpholino)-2-(1-tosyl-1H-pyrrolo[2,3-b]pyridin-4-yl)pyrimidin-4-yl)imino)-λ⁶-sulfanone (synthesis is similar to that described for Example 16) (350 mg, 0.63 mmol) in MeOH (6 mL) and THF (2 mL) was added NaOH (1.5 mL, 4 N aqueous) and the reaction mixture was heated to 60° C. and stirred for 2 h. The reaction mixture was cooled to RT and concentrated under reduced pressure. The residue was purified via silica gel chromatography (0-5% MeOH in CH₂Cl₂) to afford a mixture of the title compounds. The mixture of diastereomers was separated by Chiral SFC (Mobile phase: CO₂/ethanol (1% MeOH Ammonia)=45/55; Flow rate: 80 g/min; 6.5 min; Column temperature: 35° C.; Back pressure: 100 bar; Column: Daicel CHIRALPAK® AD, 10 μm, 20 mm×250 mm) to afford the two diastereomers of unknown absolute stereochemistry at the sulfur atom, title compounds 17a (43 mg, 18% yield, >99% ee) as a white solid and 17b (47 mg, 20% yield, >94% ee) as a white solid.

17a ((R)-ethyl(methyl)-λ⁶-sulfanone or (S)-ethyl(methyl)-λ⁶-sulfanone): ¹H NMR (400 MHz, DMSO-d₆) δ 11.72 (s, 1H), 8.30 (d, J=5.0 Hz, 1H), 7.88 (d, J=5.0 Hz, 1H), 7.63-7.48 (m, 1H), 7.42 (d, J=2.0 Hz, 1H), 5.93 (s, 1H), 4.44 (s, 1H), 4.07 (d, J=12.7 Hz, 1H), 3.96 (dd, J=11.3, 3.2 Hz, 1H), 3.75 (d, J=11.3 Hz, 1H), 3.63 (dd, J=9.1, 5.7 Hz, 2H), 3.61 (d, J=7.5 Hz, 1H), 3.49 (td, J=11.8, 2.8 Hz, 1H), 3.38 (s, 3H), 3.15 (td, J=12.8, 3.6 Hz, 1H), 1.31 (t, J=7.4 Hz, 3H), 1.21 (t, J=7.3 Hz, 3H); MS (ES⁺) C₁₉H₂₄N₆O₂S requires: 400, found: 401 [M+H]⁺; R_t=2.72 min.

17b ((R)-ethyl(methyl)-λ⁶-sulfanone or (S)-ethyl(methyl)-λ⁶-sulfanone): ¹H NMR (400 MHz, DMSO-d₆) δ 11.72 (s, 1H), 8.30 (d, J=5.0 Hz, 1H), 7.88 (d, J=5.0 Hz, 1H), 7.54 (d, J=3.4 Hz, 1H), 7.42 (d, J=3.3 Hz, 1H), 5.93 (s, 1H), 4.47 (s, 1H), 4.05 (d, J=13.2 Hz, 1H), 3.96 (dd, J=11.1, 3.4 Hz, 1H), 3.75 (d, J=11.4 Hz, 1H), 3.70-3.53 (m, 3H), 3.54-3.44 (m, 1H), 3.36 (d, J=13.0 Hz, 3H), 3.15 (td, J=12.7, 3.6 Hz, 1H), 1.32 (q, J=7.7 Hz, 3H), 1.21 (d, J=6.7 Hz, 3H); MS (ES⁺) C₁₉H₂₄N₆O₂S requires: 400, found: 401 [M+H]⁺; R_t=3.28 min.

EXAMPLE 18 (18a and 18b)

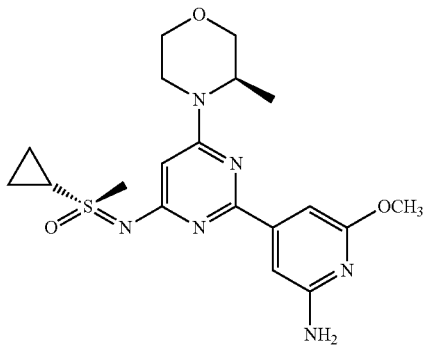 [SMILES: COc1cc(-c2nc(N=[S@](C)(=O)C3CC3)cc(N3CCOC[C@H]3C)n2)cc(N)n1]

(R)-((2-(2-Amino-6-methoxypyridin-4-yl)-6-((R)-3-methylmorpholino)pyrimidin-4-yl)imino)(cyclopropyl)(methyl)-λ⁶-sulfanone and

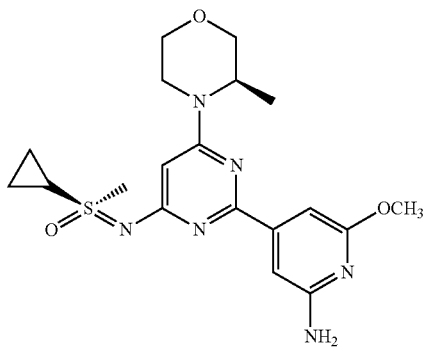 [SMILES: COc1cc(-c2nc(N=[S@@](C)(=O)C3CC3)cc(N3CCOC[C@H]3C)n2)cc(N)n1]

(S)-((2-(2-Amino-6-methoxypyridin-4-yl)-6-((R)-3-methylmorpholino)pyrimidin-4-yl)imino)(cyclopropyl)(methyl)-λ⁶-sulfanone Step 1

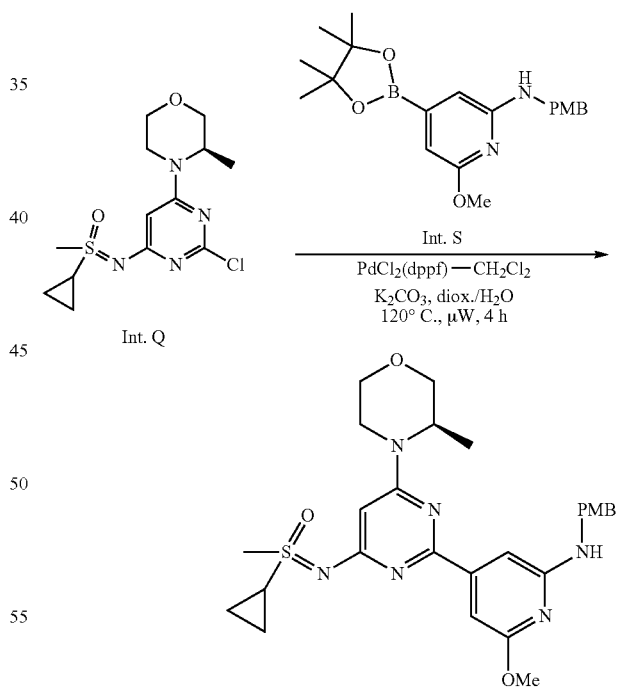

Cyclopropyl((2-(2-methoxy-6-((4-methoxybenzyl)amino)pyridin-4-yl)-6-((R)-3-methylmorpholino)pyrimidin-4-yl)imino)(methyl)-λ⁶-sulfanone: A suspension of Int. Q (590 mg, 1.79 mmol), Int. S (790 mg, 2.14 mmol) and K₂CO₃ (741 mg, 5.37 mmol) in dioxane (15 mL) and water (3 mL) was degassed with N₂ for 1 minute. PdCl₂(dppf)-CH₂Cl₂ (73 mg, 0.090 mmol) was added and the mixture was degassed with N₂ for an additional 1 minute. The reaction mixture was heated to 130° C. in a microwave reactor for 4 h. The mixture was cooled to RT, the layers were separated and the organic layer was concentrated under reduced pressure. The residue was purified via silica gel chromatography (0-2% MeOH in $CH_2Cl_2$) to afford the title compound (910 mg, 95% yield) as a yellow solid.

MS (ES$^+$) $C_{27}H_{34}N_6O_4S$ requires: 538, found: 539 [M+H]$^+$.

Step 2

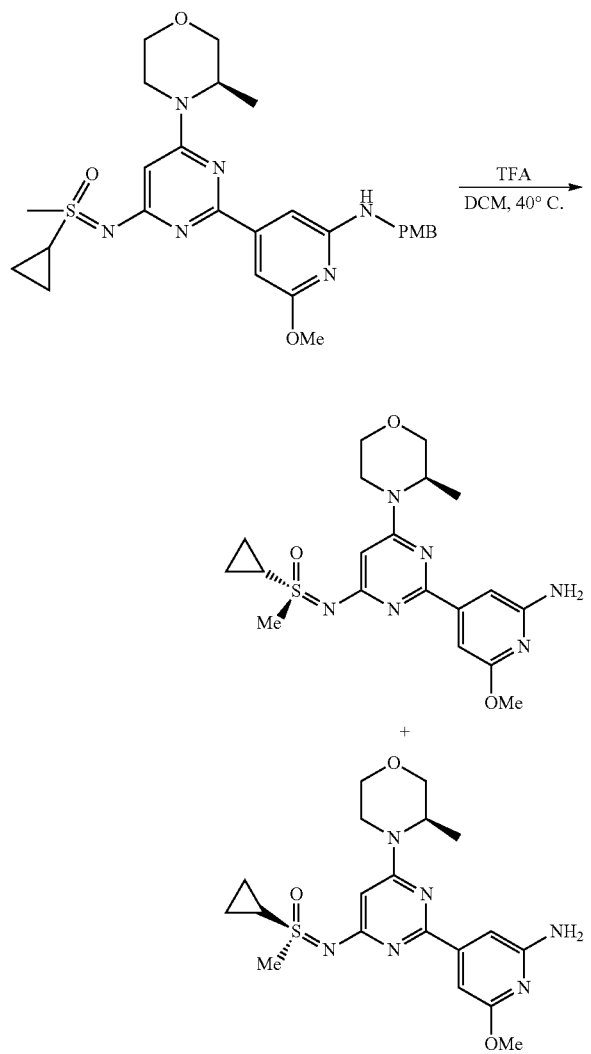

(S)-((2-(2-Amino-6-methoxypyridin-4-yl)-6-((R)-3-methylmorpholino)pyrimidin-4-yl)imino)(cyclopropyl)(methyl)-$\lambda^6$-sulfanone and (R)-((2-(2-Amino-6-methoxypyridin-4-yl)-6-((R)-3-methylmorpholino)pyrimidin-4-yl)imino)(cyclopropyl)(methyl)-$\lambda^6$-sulfanone: To a solution of the product from the previous step (910 mg, 1.69 mmol) in $CH_2Cl_2$ (7 mL) was added TFA (2.5 mL, 34 mmol) and the resulting mixture was stirred at 45° C. for 16 h. The mixture was cooled to RT and neutralized with 6 N NaOH to pH=7, followed by the addition of sat. aq. $NaHCO_3$ (30 mL) and the mixture was stirred vigorously for 5 min. The aqueous layer was extracted with $CH_2Cl_2$ (3×50 mL). The combined organic layers were dried over $Na_2SO_4$, filtered and concentrated under reduced pressure. The residue was purified via silica gel chromatography (0-3% MeOH in $CH_2Cl_2$) to afford a mixture of the title compounds (650 mg, 92% yield). The mixture of diastereomers was separated by Chiral SFC (Mobile phase: $CO_2$/MeOH (0.2% MeOH Ammonia)=45/55; Flow rate: 80 g/min; 7 min; Column temperature: 35° C.; Back pressure: 100 bar; Column: Daicel CHIRALPAK® AD, 10 μm, 20 mm×250 mm) to afford the two diastereomers of unknown absolute stereochemistry at the sulfur atom, compounds 18a (167 mg, 26% yield, 98.6% ee) as a white solid and 18b (230 mg, 35% yield, >99% ee) as a white solid; (R)-cyclopropyl(methyl)-$\lambda^6$-sulfanone and (S)-cyclopropyl(methyl)-$\lambda^6$-sulfanone 18a: $^1$H NMR (400 MHz, DMSO-d$_6$) δ 6.87 (s, 1H), 6.67 (s, 1H), 6.00 (s, 2H), 5.90 (s, 1H), 4.44-4.34 (m, 1H), 4.02 (d, J=13.2 Hz, 1H), 3.92 (dd, J=11.3, 3.2 Hz, 1H), 3.77 (s, 3H), 3.72 (d, J=11.4 Hz, 1H), 3.60 (dd, J=11.3, 3.1 Hz, 1H), 3.55 (s, 3H), 3.45 (td, J=11.6, 2.6 Hz, 1H), 3.09 (td, J=12.7, 3.8 Hz, 1H), 3.06-2.94 (m, 1H), 1.25-1.19 (m, 1H), 1.16 (app. d, overlap, J=6.6 Hz, 3H), 1.14-1.02 (m, 3H); MS (ES$^+$) $C_{19}H_{26}N_6O_3S$ requires: 418, found: 419 [M+H]$^+$; R$_t$=3.03 min.

18b: $^1$H NMR (500 MHz, DMSO-d$_6$) δ 6.88 (d, J=1.2 Hz, 1H), 6.68 (d, J=1.1 Hz, 1H), 5.99 (s, 2H), 5.90 (s, 1H), 4.43-4.34 (m, 1H), 4.03 (d, J=13.3 Hz, 1H), 3.92 (dd, J=11.3, 3.6 Hz, 1H), 3.77 (s, 3H), 3.71 (d, J=11.3 Hz, 1H), 3.60 (dd, J=11.4, 3.1 Hz, 1H), 3.55 (s, 3H), 3.45 (td, J=11.8, 3.1 Hz, 1H), 3.09 (td, J=12.8, 3.8 Hz, 1H), 3.01 (tt, J=7.9, 4.9 Hz, 1H), 1.25-1.19 (m, 1H), 1.16 (app. d, overlap, J=6.7 Hz, 3H), 1.14-1.05 (m, 2H); MS (ES$^+$) $C_{19}H_{26}N_6O_3S$ requires: 418, found: 419 [M+H]$^+$; Rt=3.71 min.

Alternatively, Example 18b can also be prepared from Int. CC, Isomer 1b.

EXAMPLE 19

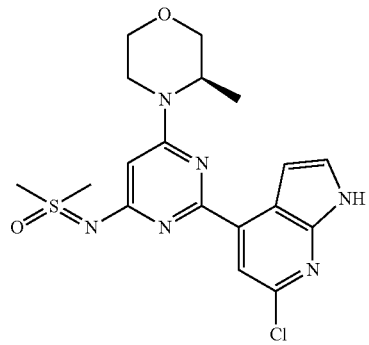

167

(R)-((2-(6-chloro-1H-pyrrolo[2,3-b]pyridin-4-yl)-6-(3-methylmorpholino)pyrimidin-4-yl)imino)dimethyl-λ⁶-sulfanone Step 1

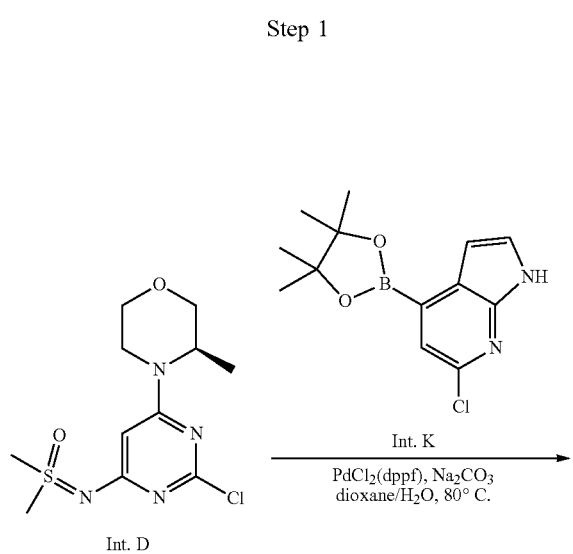

Int. D

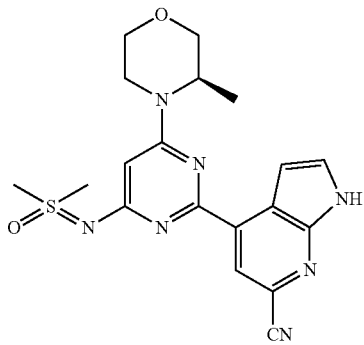 [SMILES: C[C@@H]1COCCN1c1cc(N=S(C)(C)=O)nc(-c2cc(C#N)nc3[nH]ccc23)n1]

Int. K

PdCl₂(dppf), Na₂CO₃
dioxane/H₂O, 80° C.

(R)-((2-(6-chloro-1H-pyrrolo[2,3-b]pyridin-4-yl)-6-(3-methylmorpholino)-pyrimidin-4-yl)imino)dimethyl-λ⁶-sulfanone: A suspension of Int. K (278 mg, 1.00 mmol), Int. D (304 mg, 1.00 mmol), Na₂CO₃ (212 mg, 2.00 mmol) and PdCl₂(dppf) (75 mg, 0.1 mmol) in dioxane (20 mL) and H₂O (4 mL) was degassed with Ar (3×). The reaction mixture was heated to 80° C. and stirred for 16 h under an atmosphere of Ar. The mixture was cooled to RT, filtered through CELITE® and concentrated under reduced pressure. The residue was purified by Prep-TLC (66% EtOAc in petroleum ether) to afford the title compound (130 mg, 31% yield) as a white solid.

¹H NMR (500 MHz, DMSO-d₆) δ 11.98 (s, 1H), 7.86 (s, 1H), 7.59 (s, 1H), 7.45 (s, 1H), 5.95 (s, 1H), 4.42 (s, 1H), 4.01 (dd, J=43.8, 11.0 Hz, 2H), 3.75 (d, J=11.2 Hz, 1H), 3.63 (d, J=9.8 Hz, 1H), 3.46 (d, J=22.0 Hz, 7H), 3.16 (d, J=12.4 Hz, 1H), 1.20 (d, J=6.6 Hz, 3H); MS (ES⁺) C₁₈H₂₁CN₆O₂S requires: 420, found: 421 [M+H]⁺.

168

EXAMPLE 20

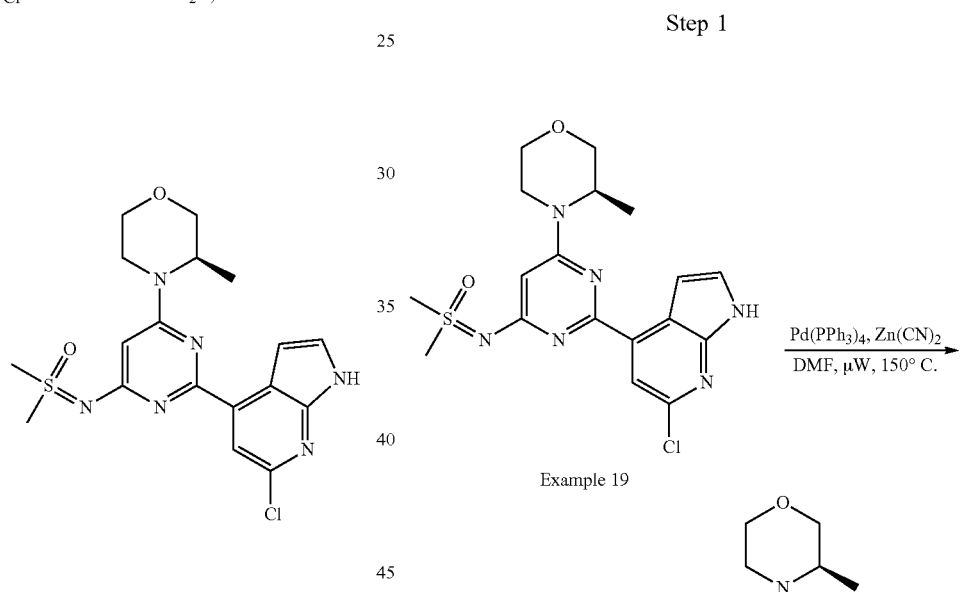

(R)-4-(4-((dimethyl(oxo)-λ⁶-sulfanylidene)amino)-6-(3-methylmorpholino)pyrimidin-2-yl)-1H-pyrrolo[2,3-b]pyridine-6-carbonitrile Step 1

Example 19

Pd(PPh₃)₄, Zn(CN)₂
DMF, μW, 150° C.

(R)-4-(4-((dimethyl(oxo)-λ⁶-sulfanylidene)amino)-6-(3-methylmorpholino)-pyrimidin-2-yl)-1H-pyrrolo[2,3-b]pyridine-6-carbonitrile: A mixture of Example 19 (40 mg, 0.096 mmol), ZnCN₂ (113 mg, 0.96 mmol) and Pd(PPh₃)₄ (110 mg, 0.096 mmol) in DMF (3 mL) was degassed with Ar. The reaction mixture was heated at 150° C. for 2 h in a microwave reactor. The mixture was cooled to RT, filtered through CELITE® and concentrated under reduced pressure. The residue was purified by reverse phase preparative HPLC (Mobile Phase: A=10 mM NH₄HCO₃ in H₂O, B=MeCN; Gradient: B=35-65%; 18 min; 30 mL/min; column: Welch XB-C18 21.2×250 mm, 10 µm) to afford the title compound (13 mg, 33% yield) as a white solid.

$^1$H NMR (500 MHz, DMSO-d$_6$) δ 12.38 (s, 1H), 8.32 (s, 1H), 7.94 (s, 1H), 7.61 (d, J=3.0 Hz, 1H), 5.96 (s, 1H), 4.44 (s, 1H), 4.09 (d, J=12.5 Hz, 1H), 3.97 (d, J=8.5 Hz, 1H), 3.75 (d, J=11.5 Hz, 1H), 3.64 (d, J=8.7 Hz, 1H), 3.53-3.41 (m, 7H), 3.16 (t, J=10.9 Hz, 1H), 1.20 (d, J=6.7 Hz, 3H); MS (ES$^+$) C$_{19}$H$_{21}$N$_7$O$_2$S requires: 411, found: 412 [M+H]$^+$.

EXAMPLE 21

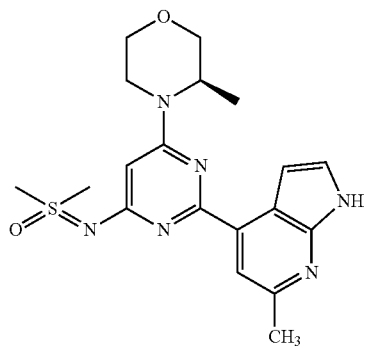 [SMILES: Cc1cc(-c2nc(N=S(C)(C)=O)cc(N3CCOC[C@H]3C)n2)c2cc[nH]c2n1]

(R)-dimethyl((2-(6-methyl-1H-pyrrolo[2,3-b]pyridin-4-yl)-6-(3-methylmorpholino)pyrimidin-4-yl)imino)-λ$^6$-sulfanone Step 1

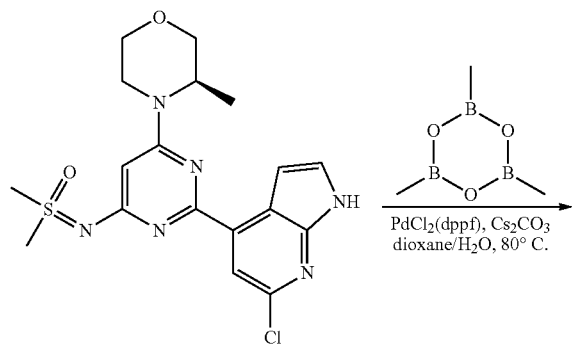

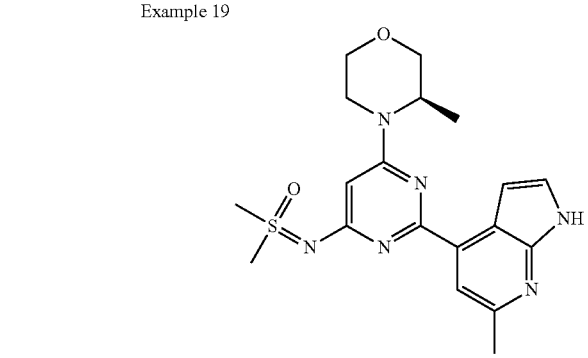

(R)-dimethyl((2-(6-methyl-1H-pyrrolo[2,3-b]pyridin-4-yl)-6-(3-methyl-morpholino)pyrimidin-4-yl)imino)-λ$^6$-sulfanone: A mixture of Example 19 (30 mg, 0.07 mmol), 2,4,6-trimethyl-1,3,5,2,4,6-trioxatriborinane (9 mg, 0.07 mmol), PdCl$_2$(dppf) (5 mg, 0.007 mmol) and Cs$_2$CO$_3$ (70 mg, 0.21 mmol) in dioxane (6 mL) and H$_2$O (1 mL) was degassed with Ar and heated to 80° C. and stirred for 16 h. The reaction mixture was cooled to RT, filtered through CELITE® and concentrated under reduced pressure. The residue was purified by reverse phase preparative HPLC (Mobile Phase: A=10 mM NH$_4$HCO$_3$ in water, B=MeCN; Gradient: B=30-60%; 18 min; 30 mL/min; column: Welch XB-C18 21.2×250 mm, 10 µm) to afford the title compound (4 mg, 14% yield) as a white solid.

$^1$H NMR (500 MHz, DMSO-d$_6$) δ 11.50 (s, 1H), 7.75 (s, 1H), 7.41 (d, J=2.7 Hz, 1H), 7.33 (s, 1H), 5.91 (s, 1H), 4.44 (s, 1H), 4.07 (d, J=13.4 Hz, 1H), 3.96 (d, J=7.7 Hz, 1H), 3.75 (d, J=11.4 Hz, 1H), 3.64 (d, J=8.5 Hz, 1H), 3.50 (d, J=9.0 Hz, 1H), 3.44 (s, 6H), 2.59 (s, 3H), 1.20 (d, J=6.7 Hz, 3H); MS (ES$^+$) C$_{19}$H$_{24}$N$_6$O$_2$S requires: 400, found: 401 [M+H]$^+$.

EXAMPLE 22

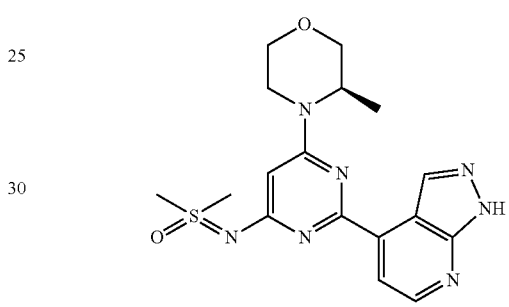

(R)-dimethyl((6-(3-methylmorpholino)-2-(1H-pyrazolo[3,4-b]pyridin-4-yl)pyrimidin-4-yl)imino)-λ$^6$-sulfanone Step 1

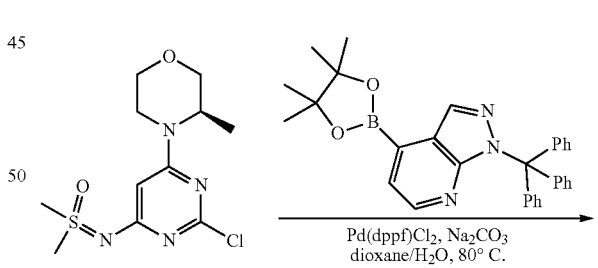

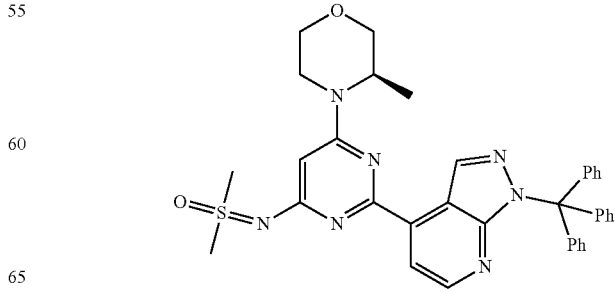

(R)-dimethyl((6-(3-methylmorpholino)-2-(1-trityl-1H-pyrazolo[3,4-b]pyridin-4-yl)pyrimidin-4-yl)imino)-λ⁶-sulfanone: A suspension of 4-(4,4,5,5-tetramethyl-1,3,2-dioxaborolan-2-yl)-1-trityl-1H-pyrazolo[3,4-b]pyridine (60 mg, 0.12 mmol), Int. D (37 mg, 0.12 mmol), Na$_2$CO$_3$ (25 mg, 0.24 mmol) and PdCl$_2$(dppf) (9.0 mg, 0.012 mmol) in dioxane (6 mL) and H$_2$O (1 mL) was degassed with Ar (3×). The reaction mixture was heated to 80° C. and stirred for 16 h under an atmosphere of Ar. The reaction mixture was cooled to RT, filtered through CELITE® and concentrated under reduced pressure. The residue was purified by Prep-TLC (66% EtOAc in petroleum ether) to afford the title compound (45 mg, 60% yield) as a yellow oil.

MS (ES$^+$) C$_{36}$H$_{35}$N$_7$O$_2$S requires: 629, found: 630 [M+H]$^+$.

Step 2

(R)-dimethyl((6-(3-methylmorpholino)-2-(1H-pyrazolo[3,4-b]pyridin-4-yl)-pyrimidin-4-yl)imino)-λ⁶-sulfanone: A solution of the product from the previous step in TFA (1 mL) and CH$_2$Cl$_2$ (4 mL) was stirred at RT for 4 h. The solvent was removed under reduced pressure and the residue was purified by reverse phase preparative HPLC (Mobile Phase: A=10 mM NH$_4$HCO$_3$ in water, B=MeCN; Gradient: B=25-65%; 18 min; 30 mL/min; column: Welch XB-C18 21.2× 250 mm, 10 um) to afford the title compound (14 mg, 52% yield) as a pale yellow solid.

$^1$H NMR (500 MHz, DMSO-d$_6$) δ 13.72 (s, 1H), 8.93 (s, 1H), 8.64 (d, J=4.7 Hz, 1H), 7.99 (d, J=4.8 Hz, 1H), 5.98 (s, 1H), 4.46 (s, 1H), 4.08 (d, J=12.9 Hz, 1H), 3.97 (d, J=8.0 Hz, 1H), 3.76 (d, J=11.4 Hz, 1H), 3.64 (d, J=8.4 Hz, 1H), 3.53-3.43 (m, 7H), 3.22-3.07 (m, 1H), 1.21 (d, J=6.7 Hz, 3H); MS (ES$^+$) C$_{17}$H$_{21}$N$_7$O$_2$S requires: 387, found: 388 [M+H]$^+$.

EXAMPLE 23

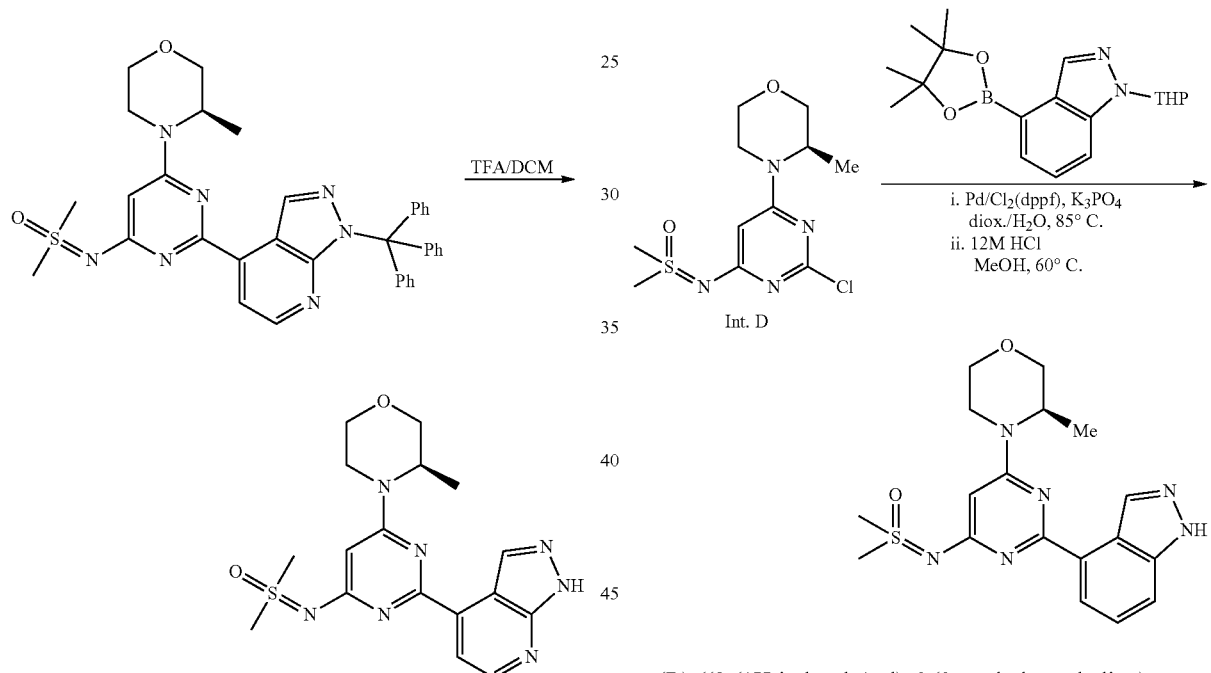

(R)-((2-(1H-indazol-4-yl)-6-(3-methylmorpholino)pyrimidin-4-yl)imino)dimethyl-λ⁶-sulfanone (R)-((2-(1H-indazol-4-yl)-6-(3-methylmorpholino)pyrimidin-4-yl)imino)-dimethyl-λ⁶-sulfanone: A mixture of Int. D (0.21 g, 0.69 mmol), 1-(tetrahydro-2H-pyran-2-yl)-4-(4,4,5,5-tetramethyl-1,3,2-dioxaborolan-2-yl)-1H-indazole (0.27 g, 0.83 mmol), K$_3$PO$_4$ (0.44 g, 2.1 mmol) and PdCl$_2$(dppf)-CH$_2$Cl$_2$ (40 mg, 0.055 mmol) in dioxane (9 mL) and water (2 mL) was degassed with a stream of N$_2$ for ten minutes and then heated to 85° C. for 4 h. The reaction mixture was cooled to RT and concentrated under reduced pressure. The residue was partitioned between EtOAc (30 mL) and H$_2$O (30 mL), the layers were separated, and the aqueous layer was extracted with EtOAc (2×30 mL). The combined organic layers were washed with brine (50 mL), dried over MgSO$_4$, filtered and concentrated under reduced pressure. The residue was dissolved in MeOH (8 mL) and THF (2 mL) at room temperature and to this solution was added concentrated HCl solution (ca. 12 N, 0.1 mL). The reaction mixture was heated to 60° C. for 20 minutes then stirred at RT for 18 h. To the reaction mixture was added sat.

aq. NaHCO$_3$(3 mL) and the mixture was concentrated under reduced pressure. The residue was partitioned between CH$_2$Cl$_2$ (25 mL) and H$_2$O (25 mL), the layers were separated and the aqueous layer was extracted with CH$_2$Cl$_2$ (2×25 mL). The combined organic layers were dried over MgSO$_4$, filtered and concentrated under reduced. The residue was purified via silica gel chromatography (10-30% CH$_3$CN in CH$_2$Cl$_2$) to afford the title compound (0.26 g, quantitative yield) as a yellow solid.

$^1$H NMR (400 MHz, CDCl$_3$) δ ppm 9.08 (d, J=0.75 Hz, 1H), 8.20 (dd, J=7.28, 1.00 Hz, 1H), 7.61 (d, J=8.28 Hz, 1H), 7.46 (dd, J=8.28, 7.28 Hz, 1H), 5.91 (s, 1H), 4.39-4.51 (m, 1H), 3.97-4.19 (m, 2H), 3.74-3.90 (m, 2H), 3.56-3.73 (m, 2H), 3.45 (d, J=1.51 Hz, 6H), 3.26-3.39 (m, 1H), 1.36 (d, J=6.78 Hz, 3H); MS (ES$^+$) C$_{18}$H$_{22}$N$_6$O$_2$S requires: 386, found: 387 [M+H]$^+$.

EXAMPLE 24

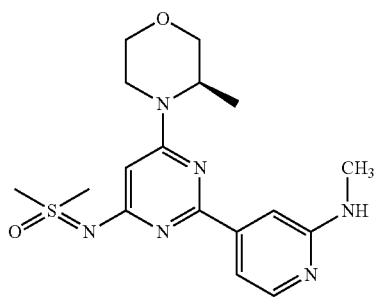

(R)-dimethyl((2-(2-(methylamino)pyridin-4-yl)-6-(3-methylmorpholino)pyrimidin-4-yl)imino)-λ$^6$-sulfanone

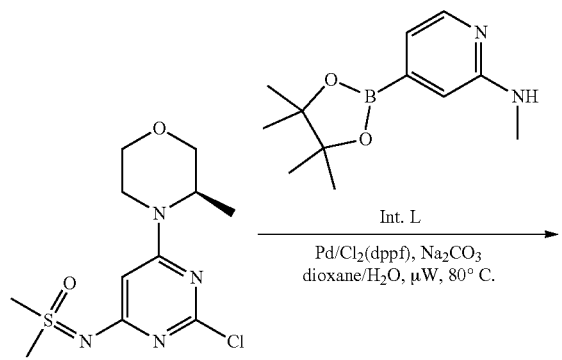

(R)-dimethyl((2-(2-(methylamino)pyridin-4-yl)-6-(3-methylmorpholino)-pyrimidin-4-yl)imino)-λ$^6$-sulfanone: A microwave vial was charged with Int. L (100 mg, 0.42 mmol), Int. D (65 mg, 0.21 mmol), Na$_2$CO$_3$ (133 mg, 1.26 mmol), Pd(dppf)Cl$_2$ (24 mg, 0.03 mmol), dioxane (3 mL) and H$_2$O (1 mL). The vial was purged with N$_2$ and sealed. The reaction mixture was heated at 80° C. for 3 h. The reaction mixture was cooled to RT, filtered through CELITE® and concentrated under reduced pressure. The residue was purified by reverse phase preparative HPLC (Mobile phase: A=10 mM NH$_4$HCO$_3$/H$_2$O, B=MeCN; Gradient: B=25-55%; 18 min; Column: Welch XB-C18, 10 μm, 150 Å, 21.2 mm×250 mm) to afford the title compound (8 mg, 10% yield) as a white solid.

$^1$H NMR (500 MHz, DMSO-d$_6$) δ 8.06 (d, J=5.2 Hz, 1H), 7.29 (s, 1H), 7.24 (d, J=5.3 Hz, 1H), 6.67 (s, 1H), 5.87 (s, 1H), 4.42-4.36 (m, 1H), 4.07-4.01 (m, 1H), 3.92 (d, J=12.1 Hz, 1H), 3.72 (d, J=11.3 Hz, 1H), 3.61 (d, J=8.5 Hz, 1H), 3.45 (d, J=2.5 Hz, 6H), 3.31 (s, 1H), 3.09 (s, 1H), 2.80 (d, J=4.8 Hz, 3H), 1.16 (d, J=6.8 Hz, 3H); MS (ES$^+$) C$_{17}$H$_{24}$N$_6$O$_2$S requires: 376, found: 377 [M+H]$^+$.

EXAMPLE 25

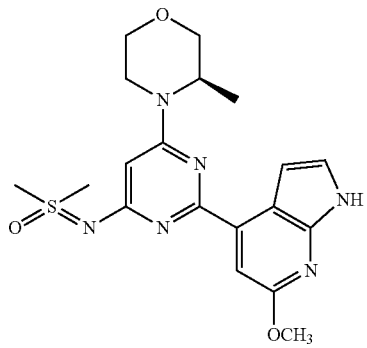

(R)-((2-(6-methoxy-1H-pyrrolo[2,3-b]pyridin-4-yl)-6-(3-methylmorpholino)pyrimidin-4-yl)imino)dimethyl-λ$^6$-sulfanone

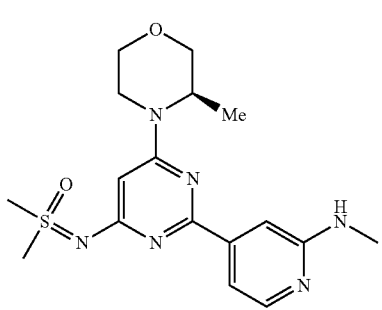

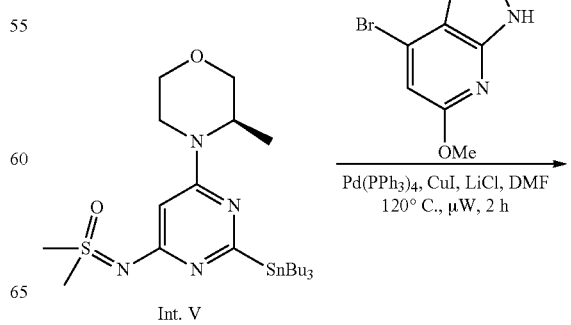

-continued

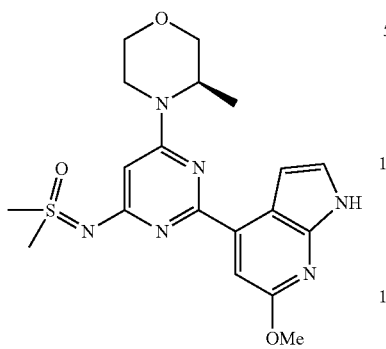

(R)-((2-(6-methoxy-1H-pyrrolo[2,3-b]pyridin-4-yl)-6-(3-methylmorpholino)-pyrimidin-4-yl)imino)dimethyl-$\lambda^6$-sulfanone: A microwave vial was charged with Int. V (34 mg, 0.06 mmol), 4-bromo-6-methoxy-1H-pyrrolo[2,3-b]pyridine (14 mg, 0.06 mmol), CuI (1.2 mg, 0.006 mmol), LiCl (5 mg, 0.12 mmol), Pd(PPh$_3$)$_4$ (7 mg, 0.006 mmol) and DMF (5 mL). The vial was purged with Ar, sealed and heated at 120° C. for 2 h in a microwave reactor. The reaction mixture was cooled to RT, sat. aq. KF (10 mL) was added and the aqueous layer was extracted with EtOAc (3×10 mL). The combined organic layers were dried over Na$_2$SO$_4$, filtered and concentrated under reduced pressure. The residue was purified by reverse phase preparative HPLC (Mobile phase: A=10 mM NH$_4$HCO$_3$/H$_2$O, B=MeCN; Gradient: B=40-70%; 18 min; Column: Welch XB-C18, 10 μm, 21.2×250 mm) to afford the title compound (5 mg, 20% yield) as a white solid.

$^1$H NMR (500 MHz, DMSO-d$_6$) δ 11.55 (s, 1H), 7.35 (s, 1H), 7.26 (d, J=11.3 Hz, 2H), 5.92 (s, 1H), 4.43 (s, 1H), 4.03 (d, J=12.7 Hz, 1H), 3.95 (d, J=7.6 Hz, 1H), 3.91 (s, 3H), 3.75 (d, J=11.2 Hz, 1H), 3.63 (d, J=8.8 Hz, 1H), 3.46 (d, J=21.0 Hz, 7H), 3.14 (t, J=11.0 Hz, 1H), 1.20 (d, J=6.7 Hz, 3H); MS (ES$^+$) C$_{19}$H$_{24}$N$_6$O$_3$S requires: 416, found: 417 [M+H]$^+$.

EXAMPLE 26

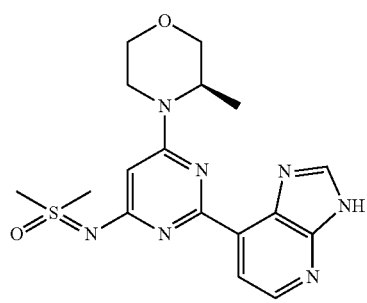 [SMILES: C[C@@H]1COCCN1c1cc(N=S(C)(C)=O)nc(-c2ccnc3[nH]cnc23)n1]

(R)-((2-(3H-imidazo[4,5-b]pyridin-7-yl)-6-(3-methylmorpholino)pyrimidin-4-yl)imino)dimethyl-$\lambda^6$-sulfanone

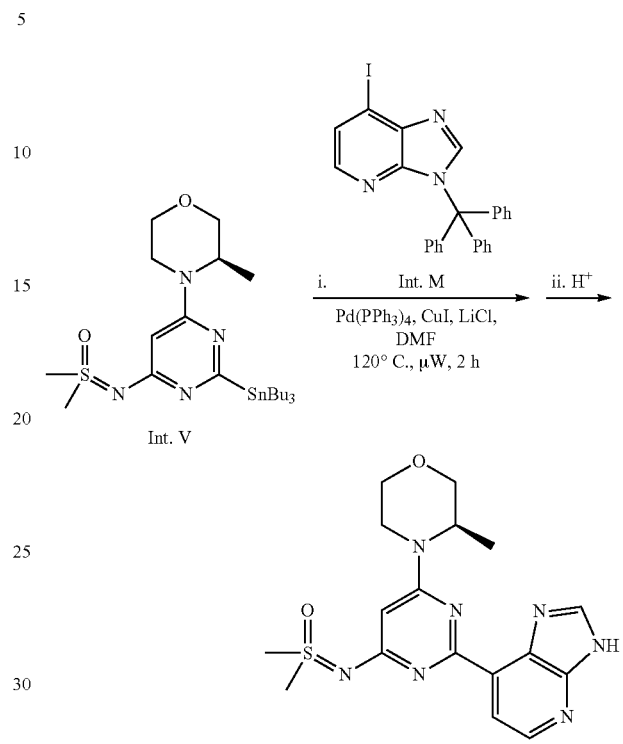

(R)-((2-(3H-imidazo[4,5-b]pyridin-7-yl)-6-(3-methylmorpholino)pyrimidin-4-yl)imino)dimethyl-$\lambda^6$-sulfanone:
A microwave vial was charged with Int. V (150 mg, 0.268 mmol), Int. M (170 mg, 0.35 mmol), LiCl (23 mg, 0.54 mmol), CuI (5 mg, 0.027 mmol), Pd(PPh$_3$)$_4$ (31 mg, 0.027 mmol) and DMF (2 mL). The reaction vial was degassed by bubbling Ar into it the solution, sealed and heated to 120° C. for 90 min. a microwave reactor. The reaction was resubmitted to the microwave cycle until it was judged completed by LCMS with new palladium catalyst added and the reaction vial degassed with Ar prior to each cycle. The reaction mixture was diluted with EtOAc (20 mL), filtered through CELITE®, and concentrated under reduced pressure. The residue was taken up in a 1 N HCl (10 mL) and washed with Et$_2$O (5 mL) and hexanes (5 mL). The aqueous layer was then adjusted to pH >12 with 2 M aq. NaOH and extracted with CH$_2$Cl$_2$ (3×5 mL). The combined organic layers were dried over Na$_2$SO$_4$, filtered and concentrated under reduced pressure. The residue was purified by reverse phase chromatography (Mobile phase: A=0.1% HCO$_2$H/H$_2$O, B=0.1% HCO$_2$H/MeCN; Gradient: B=0-30%; 15 min; Column: Biotage SNAP Ultra C18 30 g, HP-Sphere C18 25 μm). The combined fractions were treated with 0.1 M aq. HCl, concentrated under reduced pressure and lyophilized to afford the titled compound (33.2 mg, 32% yield) as a white solid.

$^1$H NMR (400 MHz, CDCl$_3$) δ ppm 8.71 (d, J=5.27 Hz, 1H) 8.52 (s, 1H) 8.16 (d, J=5.02 Hz, 1H) 5.91 (s, 1H) 4.36-4.52 (m, 1H) 4.13-4.25 (m, 1H) 4.08 (br dd, J=11.54, 3.76 Hz, 1H) 3.82-3.91 (m, 1H) 3.79 (br d, J=2.76 Hz, 1H) 3.64 (br d, J=3.01 Hz, 1H) 3.46-3.52 (m, 1H) 3.43 (s, 6H) 3.29-3.39 (m, 1H) 1.37 (d, J=6.78 Hz, 3H); MS (ES$^+$) C$_{17}$H$_{21}$N$_7$O$_2$S requires: 387, found: 388 [M+H]$^+$.

EXAMPLE 27

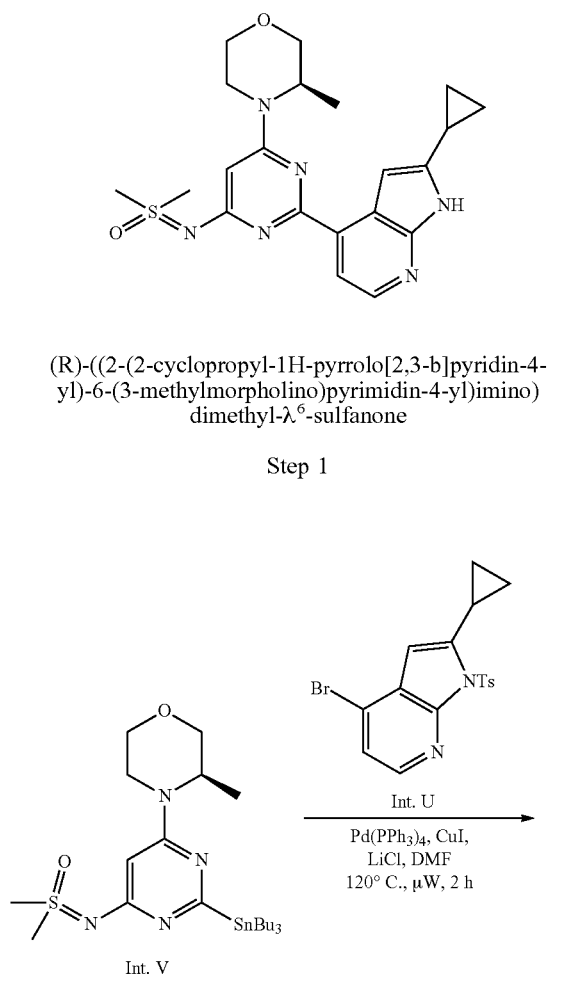

(R)-((2-(2-cyclopropyl-1H-pyrrolo[2,3-b]pyridin-4-yl)-6-(3-methylmorpholino)pyrimidin-4-yl)imino)dimethyl-$\lambda^6$-sulfanone

Step 1

(R)-((2-(2-cyclopropyl-1-tosyl-1H-pyrrolo[2,3-b]pyridin-4-yl)-6-(3-methylmorpholino)pyrimidin-4-yl)imino)dimethyl-$\lambda^6$-sulfanone: A mixture of Int. U (50 mg, 0.13 mmol), Int. V (72 mg, 0.13 mmol), CuI (2 mg, 0.013 mmol), LiCl (3 mg, 0.26 mmol), Pd(PPh$_3$)$_4$ (15 mg, 0.013 mmol) and DMF (5 mL) was degassed with Ar (3×) and then heated at 120° C. for 2 h in a microwave reactor. The mixture was cooled to RT, sat. aq. Na$_2$S$_2$O$_3$ (10 mL) was added, the layers were separated and the aqueous layer was extracted with EtOAc (10 mL×3). The combined organic layers were dried over Na$_2$SO$_4$, filtered and concentrated under reduced pressure. The residue was purified via silica gel chromatography (0-10% EtOAc in hexanes) to afford the title compound (30 mg, 40% yield) as a yellow solid.

MS (ES$^+$) C$_{28}$H$_{32}$N$_6$O$_4$S$_2$ requires: 580, found: 581 [M+H]$^+$.

Step 2

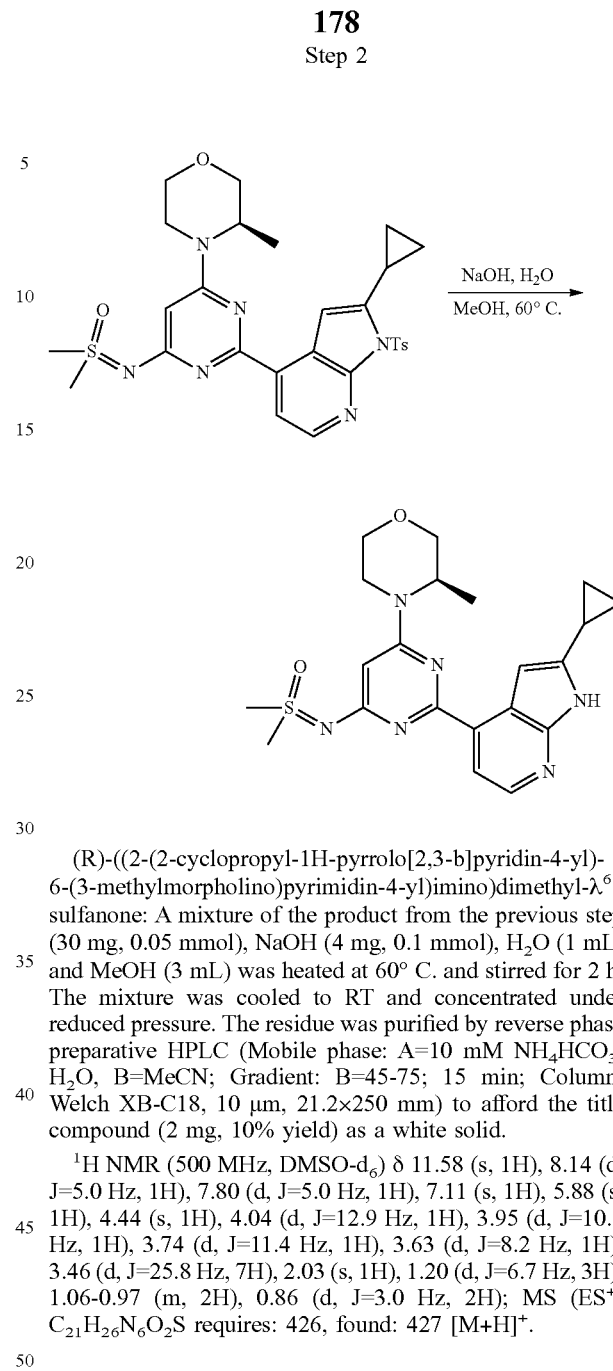

(R)-((2-(2-cyclopropyl-1H-pyrrolo[2,3-b]pyridin-4-yl)-6-(3-methylmorpholino)pyrimidin-4-yl)imino)dimethyl-$\lambda^6$-sulfanone: A mixture of the product from the previous step (30 mg, 0.05 mmol), NaOH (4 mg, 0.1 mmol), H$_2$O (1 mL) and MeOH (3 mL) was heated at 60° C. and stirred for 2 h. The mixture was cooled to RT and concentrated under reduced pressure. The residue was purified by reverse phase preparative HPLC (Mobile phase: A=10 mM NH$_4$HCO$_3$/H$_2$O, B=MeCN; Gradient: B=45-75; 15 min; Column: Welch XB-C18, 10 µm, 21.2×250 mm) to afford the title compound (2 mg, 10% yield) as a white solid.

$^1$H NMR (500 MHz, DMSO-d$_6$) δ 11.58 (s, 1H), 8.14 (d, J=5.0 Hz, 1H), 7.80 (d, J=5.0 Hz, 1H), 7.11 (s, 1H), 5.88 (s, 1H), 4.44 (s, 1H), 4.04 (d, J=12.9 Hz, 1H), 3.95 (d, J=10.9 Hz, 1H), 3.74 (d, J=11.4 Hz, 1H), 3.63 (d, J=8.2 Hz, 1H), 3.46 (d, J=25.8 Hz, 7H), 2.03 (s, 1H), 1.20 (d, J=6.7 Hz, 3H), 1.06-0.97 (m, 2H), 0.86 (d, J=3.0 Hz, 2H); MS (ES$^+$) C$_{21}$H$_{26}$N$_6$O$_2$S requires: 426, found: 427 [M+H]$^+$.

EXAMPLE 28

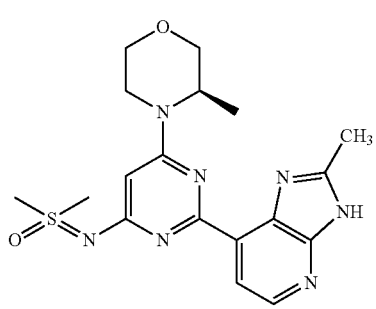 [SMILES: Cc1nc2c(-c3nc(N=S(C)(C)=O)cc(N4CCOC[C@H]4C)n3)ccnc2[nH]1]

(R)-dimethyl((2-(2-methyl-3H-imidazo[4,5-b]pyridin-7-yl)-6-(3-methylmorpholino)pyrimidin-4-yl)imino)-λ⁶-sulfanone Step 1

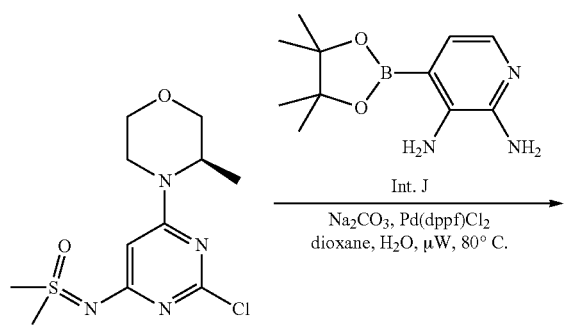

(R)-((2-(2,3-diaminopyridin-4-yl)-6-(3-methylmorpholino)pyrimidin-4-yl)imino)dimethyl-λ⁶-sulfanone: A microwave vial was charged with Int. J (450 mg crude, assumed 1.07 mmol), Int. D (250 mg, 0.82 mmol), Na₂CO₃ (260 mg, 2.46 mmol), Pd(dppf)Cl₂ (48 mg, 0.06 mmol), dioxane (12 mL) and H₂O (4 mL). The vial was purged with N₂ and sealed. The reaction mixture was heated at 80° C. and stirred for 3 h. The reaction mixture was cooled to RT, filtered through CELITE®, and concentrated under reduced pressure. The residue was purified via silica gel chromatography (0-15% MeOH in CH₂Cl₂) to afford the title compound (350 mg, 100% yield) as a brown solid.

MS (ES⁺) C₁₆H₂₃N₇O₂S requires: 377, found: 378 [M+H]⁺.

Step 2

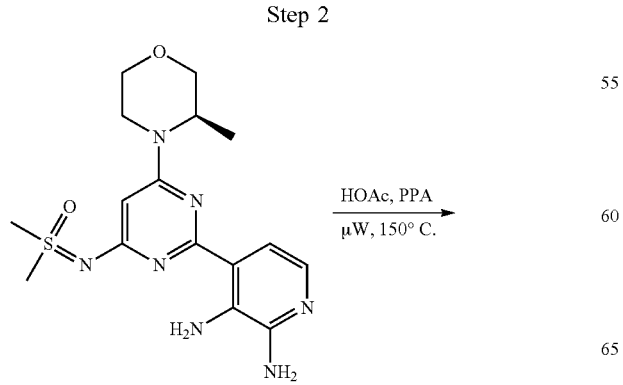

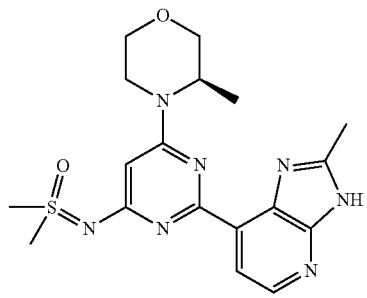

(R)-dimethyl((2-(2-methyl-3H-imidazo[4,5-b]pyridin-7-yl)-6-(3-methyl-morpholino)pyrimidin-4-yl)imino)-λ⁶-sulfanone: A mixture of the product from the previous step (150 mg, 0.4 mmol), HOAc (0.2 mL) and PPA (1 g) were charged in a 20 mL microwave vial and purged with N₂ for 1 min. The vial was sealed and heated at 150° C. for 1.5 h. The reaction mixture was cooled to RT, sat. aq. K₂CO₃ (30 mL) was added and the aqueous layer was extracted with EtOAc (3×50 mL). The combined organic layers were washed with brine (30 mL), dried over Na₂SO₄, filtered and concentrated under reduced pressure. The residue was purified by reverse phase preparative HPLC (Mobile phase: A=10 mM NH₄HCO₃/H₂O, B=MeCN; Gradient: B=25-55%; 18 min; Column: Welch XB-C18, 10 μm, 150 Å, 21.2 mm×250 mm) to afford the title compound (20 mg, 12% yield) as a white solid.

¹H NMR (500 MHz, DMSO-d₆) δ 11.99 (s, 1H), 8.42 (d, J=5.1 Hz, 1H), 7.89 (d, J=5.1 Hz, 1H), 5.97 (s, 1H), 4.47 (s, 1H), 4.14 (s, 1H), 3.95 (d, J=11.1 Hz, 1H), 3.74 (d, J=11.5 Hz, 1H), 3.63 (d, J=8.3 Hz, 1H), 3.47 (s, 7H), 3.19-3.11 (m, 1H), 2.58 (s, 3H), 1.20 (d, J=6.7 Hz, 3H); MS (ES⁺) C₁₈H₂₃N₇O₂S requires: 401, found: 402 [M+H]⁺.

EXAMPLE 29

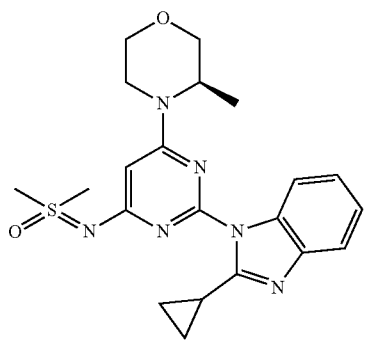 [SMILES: C[C@@H]1COCCN1c1cc(N=S(C)(C)=O)nc(-n2c(C3CC3)nc3ccccc32)n1]

(R)-((2-(2-cyclopropyl-1H-benzo[d]imidazol-1-yl)-6-(3-methylmorpholino)pyrimidin-4-yl)imino)dimethyl-$\lambda^6$-sulfanone

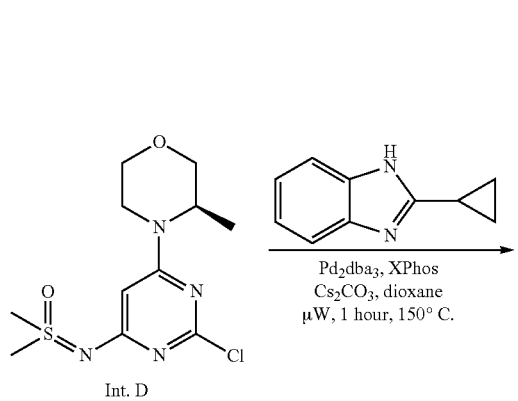

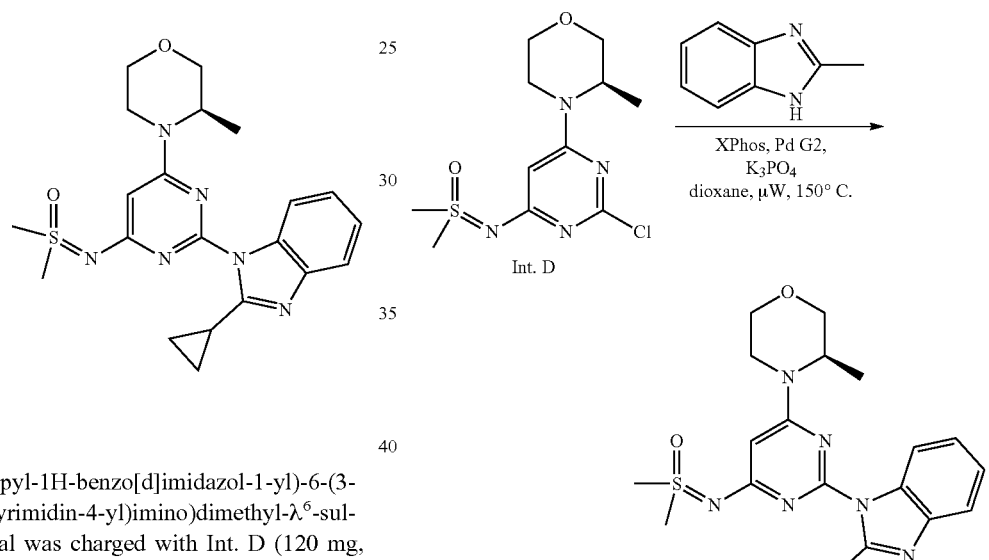

(R)-((2-(2-cyclopropyl-1H-benzo[d]imidazol-1-yl)-6-(3-methylmorpholino)-pyrimidin-4-yl)imino)dimethyl-$\lambda^6$-sulfanone: A reaction vial was charged with Int. D (120 mg, 0.39 mmol), 2-cyclopropyl-1H-benzo[d]imidazole (94 mg, 0.59 mmol), Pd$_2$dba$_3$ (18 mg, 0.02 mmol), XPhos (16 mg, 0.04 mmol), Cs$_2$CO$_3$ (380 mg, 1.17 mmol) and dioxane (6 mL). The vial was purged with N$_2$ for 2 min., sealed and heated to 150° C. for 1 h in a microwave reactor. The reaction mixture was cooled to RT, filtered through CELITE®, and concentrated under reduced pressure. The residue was purified by reverse phase preparative HPLC (Mobile phase: A=10 mM NH$_4$HCO$_3$/H$_2$O, B=MeCN; Gradient: B=40-70%; 15 min; Column: Agela C18, 10 μm, 150 Å, 21.2 mm×250 mm) to afford the title compound (83.0 mg, 50% yield) as a white solid.

$^1$H NMR (500 MHz, DMSO-d$_6$) δ 8.10 (dd, J=6.8, 2.3 Hz, 1H), 7.53 (dd, J=6.5, 2.2 Hz, 1H), 7.24-7.14 (m, 2H), 5.93 (s, 1H), 4.36 (s, 1H), 3.94 (dd, J=16.4, 8.5 Hz, 2H), 3.72 (d, J=11.4 Hz, 1H), 3.61 (dd, J=11.4, 2.9 Hz, 1H), 3.50-3.44 (m, 1H), 3.42 (s, 6H), 3.17 (td, J=13.0, 3.9 Hz, 1H), 3.09-3.01 (m, 1H), 1.21 (d, J=6.7 Hz, 3H), 1.17-1.11 (m, 2H), 1.09-1.02 (m, 2H); MS (ES$^+$) C$_{18}$H$_{22}$N$_6$O$_2$S requires: 426, found: 427 [M+H]$^+$.

EXAMPLE 30

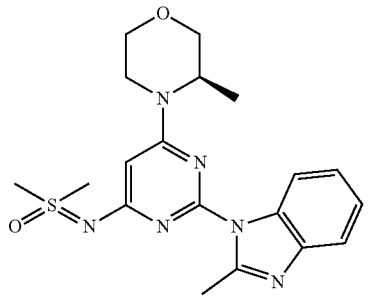 [SMILES: Cc1nc2ccccc2n1-c1nc(N=S(C)(C)=O)cc(N2CCOC[C@H]2C)n1]

(R)-dimethyl((2-(2-methyl-1H-benzo[d]imidazol-1-yl)-6-(3-methylmorpholino)pyrimidin-4-yl)imino)-$\lambda^6$-sulfanone (R)-dimethyl((2-(2-methyl-1H-benzo[d]imidazol-1-yl)-6-(3-methylmorpholino)-pyrimidin-4-yl)imino)-$\lambda^6$-sulfanone: A microwave vial was charged with Int. D (50 mg, 0.165 mmol), 2-methylbenzimidazole (44 mg, 0.329 mmol), XPhos Pd G2 (6.5 mg, 0.008 mmol) and K$_3$PO$_4$ (70 mg, 0.329 mmol). The vial was sealed, purged with Ar, dioxane (2 mL) was added and the solution was degassed by bubbling Ar and the resulting mixture was heated in at 150° C. for 1 h in a microwave reactor. The reaction mixture was cooled to RT, filtered through CELITE®, washed with CH$_2$Cl$_2$ and concentrated under reduced pressure. The residue was purified by flash chromatography (1-5% MeOH in CH$_2$Cl$_2$) to afford the title compound (62 mg, 94% yield) as a white solid.

$^1$H NMR (400 MHz, CDCl$_3$) δ ppm 8.22-8.39 (m, 1H) 7.63-7.89 (m, 1H) 7.30-7.54 (m, 2H) 5.86 (s, 1H) 4.25-4.41 (m, 1H) 4.05 (dd, J=11.54, 3.76 Hz, 1H) 3.90-3.98 (m, 1H) 3.70-3.89 (m, 2H) 3.53-3.68 (m, 1H) 3.26-3.51 (m, 7H) 3.06 (s, 3H) 1.36 (d, J=6.78 HZ, 3H) 1.10-1.32 (M, 1H) 0.91 (S, 1H); MS (ES$^+$) C$_{19}$H$_{24}$N$_6$O$_2$S REQUIRES: 400, FOUND: 401 [M+H]$^+$.

EXAMPLE 31

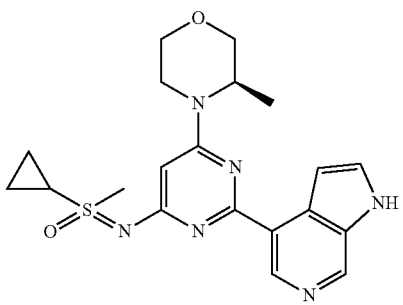 [SMILES: C[C@@H]1COCCN1c1cc(N=S(C)(=O)C2CC2)nc(-c2cncc3[nH]ccc23)n1]

Cyclopropyl(methyl)((6-((R)-3-methylmorpholino)-2-(1H-pyrrolo[2,3-c]pyridin-4-yl)pyrimidin-4-yl)imino)-λ$^6$-sulfanone Synthesis is similar to that described for Example 11, using Int. I.

$^1$H NMR (500 MHz, DMSO-d$_6$) δ 11.72 (s, 1H), 9.02 (d, J=2.3 Hz, 1H), 8.79 (s, 1H), 7.67 (t, J=2.7 Hz, 1H), 7.45 (s, 1H), 5.90 (s, 1H), 4.46 (s, 1H), 4.04 (s, 1H), 3.96 (d, J=7.8 Hz, 1H), 3.75 (d, J=11.4 Hz, 1H), 3.64 (d, J=10.5 Hz, 1H), 3.51 (dd, J=32.0, 6.9 Hz, 4H), 3.14 (s, 1H), 3.01 (d, J=7.6 Hz, 1H), 1.21 (t, J=7.1 Hz, 5H), 1.09 (d, J=7.8 Hz, 2H); MS (ES$^+$) C$_{20}$H$_{24}$N$_6$O$_2$S requires: 412, found: 413 [M+H]$^+$.

EXAMPLE 32

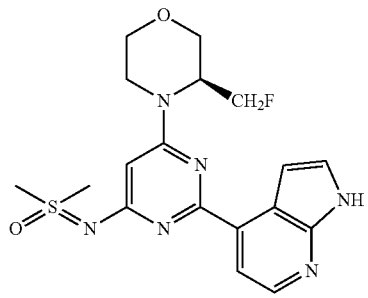

(S)-((6-(3-(fluoromethyl)morpholino)-2-(1H-pyrrolo[2,3-b]pyridin-4-yl)pyrimidin-4-yl)imino)dimethyl-λ$^6$-sulfanone Synthesis is similar to that described for Example 11, using Int. O and 4-(4,4,5,5-tetramethyl-1,3,2-dioxaborolan-2-yl)-1-tosyl-1H-pyrrolo[2,3-b]pyridine.

$^1$H NMR (400 MHz, CDCl$_3$) δ 10.35 (s, 1H), 8.41 (d, J=5.1 Hz, 1H), 8.01 (d, J=5.1 Hz, 1H), 7.61-7.41 (m, 2H), 5.94 (s, 1H), 5.26-5.02 (m, 1H), 4.53 (s, 1H), 4.31-3.96 (m, 3H), 3.83-3.61 (m, 4H), 3.44 (d, J=4.8 Hz, 6H); MS (ES$^+$) C$_{18}$H$_{21}$FN$_6$O$_2$S requires: 404, found: 405 [M+H]$^+$.

EXAMPLE 33

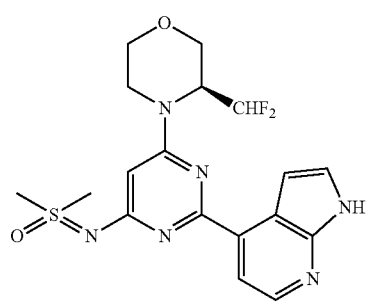 [SMILES: CS(C)(=O)=Nc1cc(N2CCOC[C@H]2C(F)F)nc(-c2ccnc3[nH]ccc23)n1]

(S)-((6-(3-(difluoromethyl)morpholino)-2-(1H-pyrrolo[2,3-b]pyridin-4-yl)pyrimidin-4-yl)imino)dimethyl-λ$^6$-sulfanone Synthesis is similar to that described for Example 11, using Int. W and 4-(4,4,5,5-tetramethyl-1,3,2-dioxaborolan-2-yl)-1-tosyl-1H-pyrrolo[2,3-b]pyridine.

$^1$H NMR (400 MHz, Methanol-d4) δ 8.28 (d, J=5.1 Hz, 1H), 7.99 (d, J=5.2 Hz, 1H), 7.51 (dd, J=21.8, 3.5 Hz, 2H), 6.34 (td, J=56.1, 5.7 Hz, 1H), 6.06 (s, 1H), 4.25 (d, J=12.3 Hz, 1H), 4.06 (dd, J=11.4, 3.6 Hz, 2H), 3.78 (dd, J=12.3, 3.2 Hz, 1H), 3.67 (td, J=11.8, 3.1 Hz, 1H), 3.49 (t, J=7.2 Hz, 7H), 3.43 (dd, J=12.7, 3.8 Hz, 1H), 3.34 (s, 2H), 3.32 (s, 2H); MS (ES$^+$) C$_{18}$H$_{20}$F$_2$N$_6$O$_2$S requires: 422, found: 423 [M+H]$^+$.

EXAMPLE 34

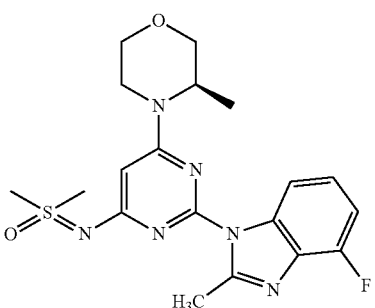

185

(R)-((2-(4-fluoro-2-methyl-1H-benzo[d]imidazol-1-yl)-6-(3-methylmorpholino)pyrimidin-4-yl)imino)dimethyl-λ6-sulfanone Step 1

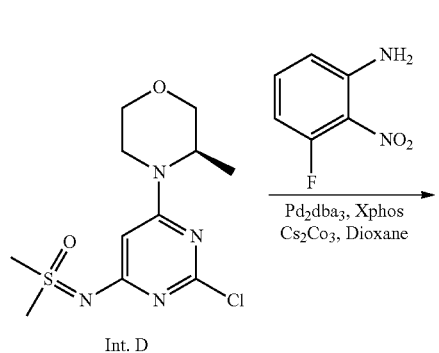

(R)-((2-((3-fluoro-2-nitrophenyl)amino)-6-(3-methylmorpholino)pyrimidin-4-yl)imino)dimethyl-λ6-sulfanone A reaction vial was charged with Int. D (250 mg, 0.82 mmol), 3-fluoro-2-nitroaniline (192 mg, 1.23 mmol), Pd2dba3 (38 mg, 0.041 mmol), XPhos (35 mg, 0.082 mmol), Cs2CO3 (800 mg, 2.47 mmol) and dioxane (10 mL). The vial was purged with N2 for 2 min. and the reaction mixture was heated at 100° C. and stirred for 16 h. The reaction mixture was cooled to RT, filtered through CELITE® and concentrated under reduced pressure. The residue was purified via silica gel chromatography (50-75% EtOAc in hexanes) to afford the title compound (290 mg, 74% yield) as an orange solid.

MS (ES+) $C_{17}H_{21}FN_6O_4S$ requires: 424, found: 425 $[M+H]^+$.

Step 2

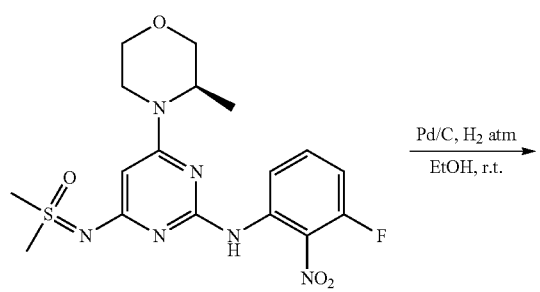

186

-continued

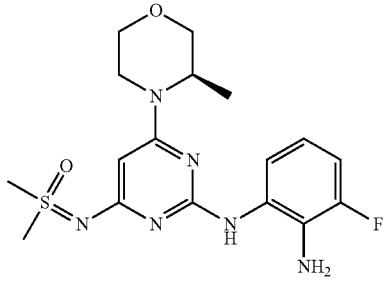

(R)-((2-((2-amino-3-fluorophenyl)amino)-6-(3-methylmorpholino)pyrimidin-4-yl)imino)dimethyl-λ6-sulfanone:
A reaction vessel was charged with the product from the previous step (280 mg, 0.66 mmol), 10% Pd/C (50 mg, 0.047 mmol) and EtOH (40 mL) under an atmosphere of N2. The suspension was degassed with N2 for 1 minute and purged with H2 for 1 minute. The reaction mixture was stirred under an atmosphere of H2 at 1 atm for 2 h. The reaction mixture was purged with N2, filtered through CELITE® and concentrated under reduced pressure to afford the title compound (260 mg, quantitative yield) as a red solid.

MS (ES+) $C_{17}H_{23}FN_6O_2S$ requires: 394, found: 395 $[M+H]^+$.

Step 3

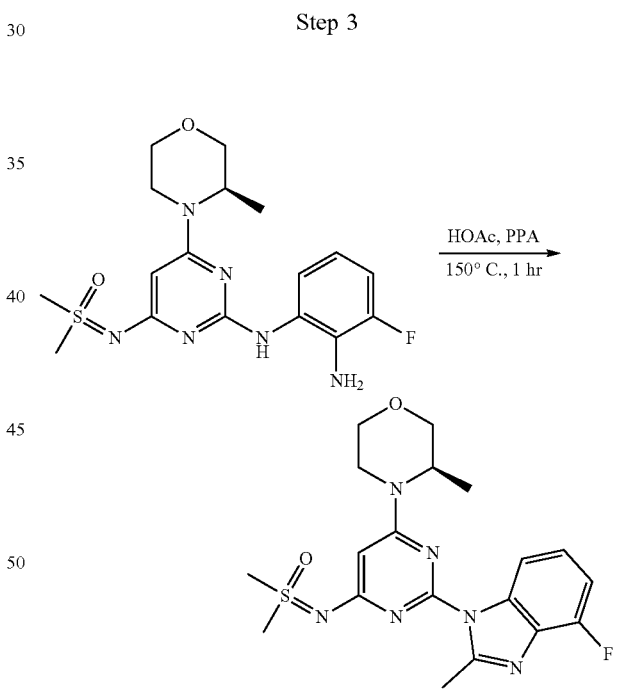

(R)-((2-(4-fluoro-2-methyl-1H-benzo[d]imidazol-1-yl)-6-(3-methylmorpholino)pyrimidin-4-yl)imino)dimethyl-λ6-sulfanone A mixture of the product from the previous step (260 mg, 0.66 mmol) and acetic acid (132 mg, 2.21 mmol) in PPA (5 g) was heated at 150° C. for 3 h. The reaction was cooled to RT, diluted with water (50 mL) and 5 N aq. NaOH was added to adjust to pH=14. The aqueous layer was extracted with EtOAc (3×50 mL) and the combined organic layers were concentrated under reduced pressure. The residue was purified by reverse phase preparative HPLC (Mobile phase: A=10 mM NH4HCO3 in water, B=MeCN; Gradient: B=35-65%; 15 min; Column: Agela C18, 10 μm, 150 Å, 21.2 mm×250 mm) to afford the title compound (146 mg, 53% yield) as a yellow solid.

$^1$H NMR (500 MHz, DMSO-d$_6$) δ 8.10 (d, J=8.2 Hz, 1H), 7.19 (td, J=8.2, 5.1 Hz, 1H), 7.06 (dd, J=10.6, 8.1 Hz, 1H), 5.92 (s, 1H), 4.35 (s, 1H), 4.03-3.85 (m, 2H), 3.72 (d, J=11.4 Hz, 1H), 3.61 (dd, J=11.4, 2.9 Hz, 1H), 3.47 (td, J=11.9, 3.0 Hz, 1H), 3.40 (d, J=2.1 Hz, 6H), 3.17 (td, J=12.9, 3.8 Hz, 1H), 2.85 (s, 3H), 1.21 (d, J=6.7 Hz, 3H); MS (ES$^+$) C$_{19}$H$_{23}$FN$_6$O$_2$S requires: 418, found: 419 [M+H]$^+$.

EXAMPLE 35

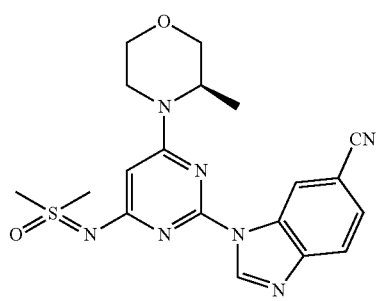 [SMILES: C[C@@H]1COCCN1c1cc(N=S(C)(C)=O)nc(-n2cnc3ccc(C#N)cc32)n1]

(R)-1-(4-((dimethyl(oxo)-λ$^6$-sulfaneylidene)amino)-6-(3-methylmorpholino)pyrimidin-2-yl)-1H-benzo[d]imidazole-6-carbonitrile Step 1

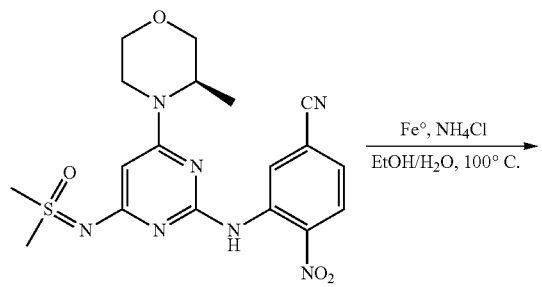

(R)-4-amino-3-((4-((dimethyl(oxo)-λ$^6$-sulfaneylidene)amino)-6-(3-methyl-morpholino)pyrimidin-2-yl)amino)

benzonitrile: To a solution of (R)-3-((4-((dimethyl(oxo)-λ$^6$-sulfaneylidene)amino)-6-(3-methylmorpholino)pyrimidin-2-yl)amino)-4-nitrobenzonitrile (synthesis is similar to that described for Example 34, step 1) (110 mg, 0.255 mmol) in EtOH (1.3 mL) were added ammonium chloride (54.5 mg, 1.02 mmol), water (425 μL), and iron (56.9 mg, 1.02 mmol) and the resulting mixture was stirred at 100° C. for 3 h. The reaction mixture was cooled to RT, filtered through CELITE® and concentrated under reduced pressure. The residue was purified via silica gel chromatography (5-20% MeOH in CH$_2$Cl$_2$) to afford the title compound (83 mg, 81% yield) as a yellow solid.

MS (ES$^+$) C$_{18}$H$_{23}$N$_7$O$_2$S requires: 401, found: 402 [M+H]$^+$.

Step 2

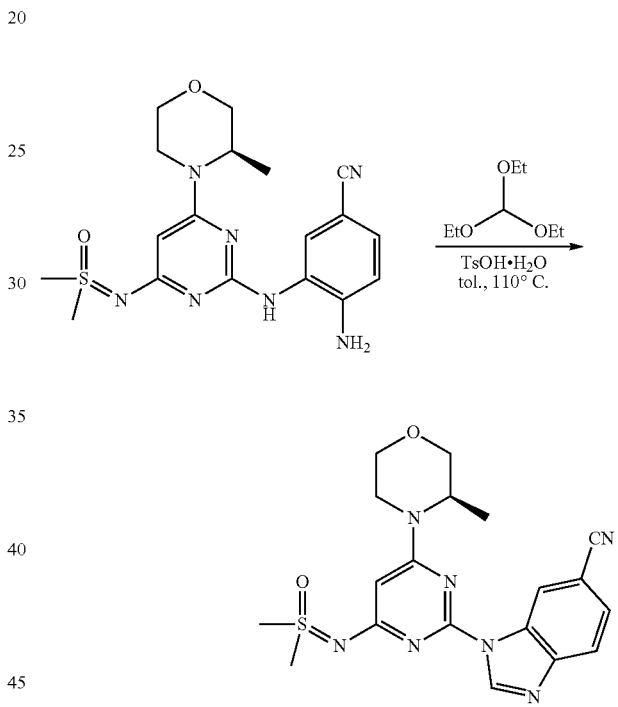

(R)-1-(4-((dimethyl(oxo)-λ$^6$-sulfaneylidene)amino)-6-(3-methylmorpholino)-pyrimidin-2-yl)-1H-benzo[d]imidazole-6-carbonitrile: To a solution of the product from the previous step (30 mg, 0.037 mmol) in toluene (75 μL) were added triethyl orthoformate (12 μL, 0.075 mmol) and Ts-OH hydrate (0.71 mg, 3.7 μmol) and the resulting mixture was heated at 110° C. and stirred for 16 h. The reaction mixture was cooled to RT and concentrated under reduced pressure. The residue was purified by mass-triggered preparative HPLC (Mobile phase: A=0.1% TFA/H$_2$O, B=0.1% TFA/MeCN; Gradient: B=10-40%; 16 min; Column: XBridge C18, 5 μm, 19 mm×150 mm) to afford the title compound (7.9 mg, 33% yield) as a white solid.

$^1$H NMR (600 MHz, Methanol-d4) δ 9.36 (s, 1H), 9.25-9.22 (m, 1H), 7.87 (d, J=8.4 Hz, 1H), 7.69 (dd, J=8.4, 1.6 Hz, 1H), 5.91 (s, 1H), 4.47-4.39 (m, 1H), 4.08-3.98 (m, 2H), 3.82 (d, J=11.5 Hz, 1H), 3.75 (dd, J=11.5, 3.2 Hz, 1H), 3.60 (td, J=12.0, 3.2 Hz, 1H), 3.46 (s, 6H), 3.33-3.27 (m, overlap MeOH, 1H), 1.33 (d, J=6.8 Hz, 3H); MS (ES$^+$) C$_{19}$H$_{21}$N$_7$O$_2$S requires: 411, found: 412 [M+H]$^+$.

EXAMPLE 36

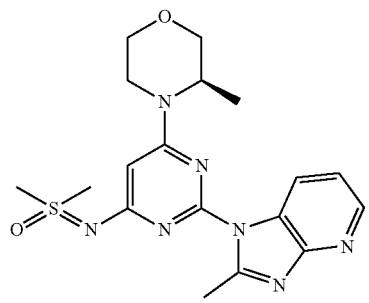 [SMILES: Cc1nc2ncccc2n1-c1nc(N=S(C)(C)=O)cc(N2CCOC[C@H]2C)n1]

(R)-dimethyl((2-(2-methyl-1H-imidazo[4,5-b]pyridin-1-yl)-6-(3-methylmorpholino)pyrimidin-4-yl)imino)-$\lambda^6$-sulfanone

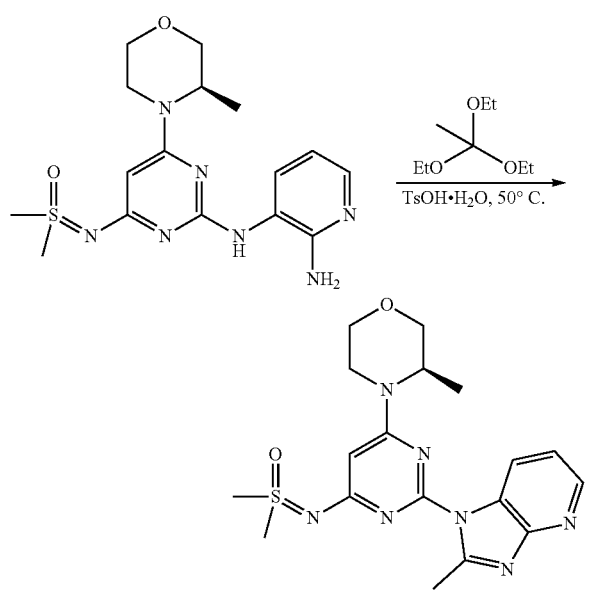

(R)-dimethyl((2-(2-methyl-1H-imidazo[4,5-b]pyridin-1-yl)-6-(3-methylmorpholino)pyrimidin-4-yl)imino)-$\lambda^6$-sulfanone: To a suspension of (R)-((2-((2-aminopyridin-3-yl)amino)-6-(3-methylmorpholino)pyrimidin-4-yl)imino) dimethyl-$\lambda^6$-sulfanone (synthesis is similar to that described for Example 34, step 2) (38 mg, 0.10 mmol) in triethyl orthoacetate (4 mL) was added p-toluenesulfonic acid monohydrate (10 mg, 0.05 mmol) and the resulting mixture was heated to 50° C. for 16 h. The reaction mixture was cooled to RT and directly purified by flash chromatography (0-10% MeOH in CH$_2$Cl$_2$ with 0.5% of aq. NH$_4$OH) to afford the title compound (20 mg, 0.05 mmol) as a solid.

$^1$H NMR (400 MHz, CDCl$_3$) δ ppm 8.63-8.83 (m, 1H) 8.52 (dd, J=4.77, 1.25 Hz, 1H) 7.20-7.34 (m, 2H) 5.82 (s, 1H) 4.17-4.39 (m, 1H) 4.04 (dd, J=11.54, 3.51 Hz, 1H) 3.91 (br d, J=12.30 Hz, 1H) 3.82 (d, J=11.54 Hz, 1H) 3.73 (dd, J=11.54, 3.01 Hz, 1H) 3.59 (td, J=11.86, 3.14 Hz, 1H) 3.27-3.45 (m, 7H) 3.04 (s, 3H) 1.34 (d, J=7.03 Hz, 3H); MS (ES$^+$) C$_{18}$H$_{23}$N$_7$O$_2$S requires: 401, found: 402 [M+H]$^+$.

EXAMPLE 37

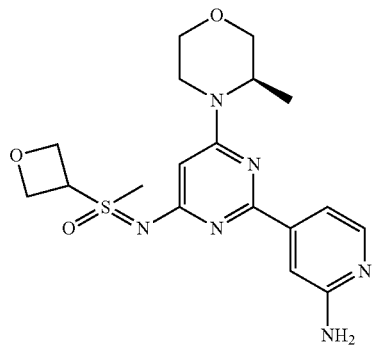 [SMILES: C[C@@H]1COCCN1c1cc(N=S(C)(=O)C2COC2)nc(-c2ccnc(N)c2)n1]

((2-(2-Aminopyridin-4-yl)-6-((R)-3-methylmorpholino)pyrimidin-4-yl)imino)(methyl)(oxetan-3-yl)-$\lambda^6$-sulfanone

Step 1

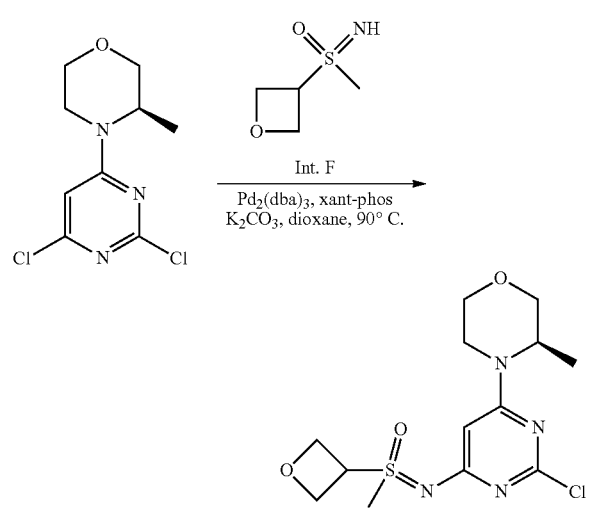

((2-Chloro-6-((R)-3-methylmorpholino)pyrimidin-4-yl)imino)(methyl)(oxetan-3-yl)-$\lambda^6$-sulfanone: To a solution of (R)-4-(2,6-dichloropyrimidin-4-yl)-3-methylmorpholine (synthesized as described, Int. B, step 1) (4.6 g, 18.5 mmol) and Int. F (2.5 g, 18.5 mmol) in dioxane (80 mL) was added Pd$_2$(dba)$_3$ (850 mg, 0.925 mmol), XantPhos (2.14 g, 3.7 mmol) and K$_2$CO$_3$ (6.4 g, 46 mmol) under an atmosphere of N$_2$ and the resulting mixture was heated at 90° C. and stirred for 4 h. The reaction mixture was cooled to RT, filtered through CELITE® and concentrated under reduced pressure. The residue was purified via silica gel chromatography (25-70% EtOAc in hexanes) to afford the title compound (1.8 g, 28% yield) as a white solid.

$^1$H NMR (500 MHz, DMSO-d$_6$) δ 5.86 (s, 1H), 5.07-4.74 (m, 5H), 4.23 (s, 1H), 3.87 (dd, J=11.3, 3.5 Hz, 2H), 3.65 (d, J=11.5 Hz, 1H), 3.53 (dd, J=11.5, 2.9 Hz, 1H), 3.43-3.31 (m, 4H), 3.05 (d, J=3.6 Hz, 1H), 1.12 (d, J=6.7 Hz, 3H); MS (ES$^+$) C$_{13}$H$_{19}$CN$_4$O$_3$S requires: 346, found: 347 [M+H]$^+$.

Step 2

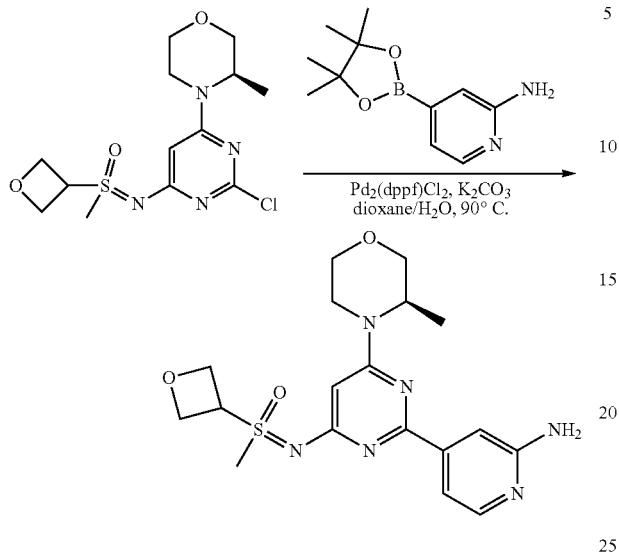

((2-(2-Aminopyridin-4-yl)-6-((R)-3-methylmorpholino)pyrimidin-4-yl)imino)-(methyl)(oxetan-3-yl)-$\lambda^6$-sulfanone:
To a solution of the product from the previous step (120 mg, 0.34 mmol) and 4-(4,4,5,5-tetramethyl-1,3,2-dioxaborolan-2-yl)pyridin-2-amine (61 mg, 0.51 mmol) in dioxane (4 mL) and H$_2$O (1 mL) were added Pd(dppf)Cl$_2$ (25 mg, 0.034 mmol) and K$_2$CO$_3$ (141 mg, 1.02 mmol) under an atmosphere of N$_2$ and the resulting mixture was heated at 90° C. and stirred for 16 h. The reaction mixture was cooled to RT, filtered through CELITE® and concentrated under reduced pressure. The residue was purified by reverse phase preparative HPLC (Mobile phase: A=10 mM NH$_4$HCO$_3$/H$_2$O, B=MeCN; Gradient: B=20-50%; 18 min; Column: Agela C18, 10 μm, 150 Å, 21.2 mm×250 mm) to afford the title compound (42 mg, 31% yield) as a white solid.

$^1$H NMR (500 MHz, DMSO-d$_6$) δ 7.99 (d, J=5.2 Hz, 1H), 7.50-7.03 (m, 2H), 5.97 (d, J=58.0 Hz, 3H), 5.10-4.75 (m, 5H), 4.49-4.26 (m, 1H), 4.15-3.97 (m, 1H), 3.95-3.88 (m, 1H), 3.71 (d, J=11.3 Hz, 1H), 3.60 (dd, J=11.4, 2.8 Hz, 1H), 3.52 (d, J=2.0 Hz, 3H), 3.45 (s, 1H), 3.10 (d, J=3.5 Hz, 1H), 1.16 (d, J=6.7 Hz, 3H); MS (ES$^+$) C$_{18}$H$_{24}$N$_6$O$_3$S requires: 404, found: 405 [M+H]$^+$.

EXAMPLES 38a and 38b

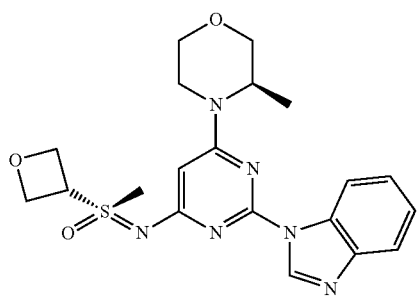 [SMILES: C[C@@H]1COCCN1c1cc(N=[S@](C)(=O)C2COC2)nc(-n2cnc3ccccc32)n1]

(R)-((2-(1H-benzo[d]imidazol-1-yl)-6-((R)-3-methylmorpholino)pyrimidin-4-yl)imino)(methyl)(oxetan-3-yl)-$\lambda^6$-sulfanone and

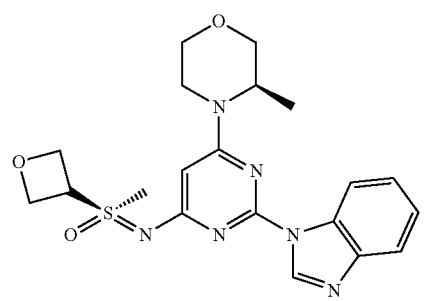 [SMILES: C[C@@H]1COCCN1c1cc(N=[S@@](C)(=O)C2COC2)nc(-n2cnc3ccccc32)n1]

(S)-((2-(1H-benzo[d]imidazol-1-yl)-6-((R)-3-methylmorpholino)pyrimidin-4-yl)imino)(methyl)(oxetan-3-yl)-$\lambda^6$-sulfanone Synthesis is similar to that described for Example 29, using the intermediate from the first step of the Example 37 procedure. The mixture of diastereomers (56 mg, 0.13 mmol) was separated by Chiral SFC (Mobile phase: CO$_2$/MeOH (0.2% MeOH Ammonia)=55/45; Flow rate: 80 g/min; 6.3 min; Column temperature: 35° C.; Back pressure: 100 bar; Column: Daicel CHIRALPAK® OJ, 10 μm, 20 mm×250 mm) to afford the two diastereomers of unknown absolute stereochemistry at the sulfur atom, title compounds 38a (14 mg, 25% yield, >99% ee) as a white solid and 38b (15 mg, 27% yield, >99% ee) as a white solid.

38a ((R)-methyl(oxetan-3-yl)-$\lambda^6$-sulfanone or (S)-methyl(oxetan-3-yl)-$\lambda^6$-sulfanone): $^1$H NMR (500 MHz, DMSO-d$_6$) δ 9.09-8.93 (m, 1H), 8.68-8.50 (m, 1H), 7.81-7.66 (m, 1H), 7.44-7.25 (m, 2H), 5.96-5.86 (m, 1H), 5.06 (dd, J=7.0, 1.1 Hz, 1H), 5.00-4.84 (m, 4H), 4.53-4.36 (m, 1H), 4.12-4.00 (m, 1H), 3.99-3.90 (m, 1H), 3.76-3.70 (m, 1H), 3.68-3.58 (m, 1H), 3.50 (dd, J=19.4, 1.5 Hz, 4H), 3.18 (d, J=3.6 Hz, 1H), 1.24-1.18 (m, 3H); MS (ES$^+$) C$_{20}$H$_{24}$N$_6$O$_3$S requires: 428, found: 429 [M+H]$^+$; R$_t$=0.95 min.

38b ((R)-methyl(oxetan-3-yl)-$\lambda^6$-sulfanone or (S)-methyl(oxetan-3-yl)-$\lambda^6$-sulfanone): $^1$H NMR (500 MHz, DMSO-d$_6$) δ 9.02 (s, 1H), 8.60 (d, J=8.0 Hz, 1H), 7.76 (d, J=7.9 Hz, 1H), 7.49-7.20 (m, 2H), 5.92 (s, 1H), 5.11-5.01 (m, 1H), 4.99-4.85 (m, 4H), 4.47-4.39 (m, 1H), 4.15-4.02 (m, 1H), 3.99-3.91 (m, 1H), 3.72 (s, 1H), 3.66-3.59 (m, 1H), 3.51 (s, 4H), 3.23-3.11 (m, 1H), 1.22 (d, J=6.7 Hz, 3H); MS (ES$^+$) C$_2$H$_{24}$N$_6$O$_3$S requires: 428, found: 429 [M+H]$^+$; R$_t$=1.31 min.

EXAMPLES 39a and 39b

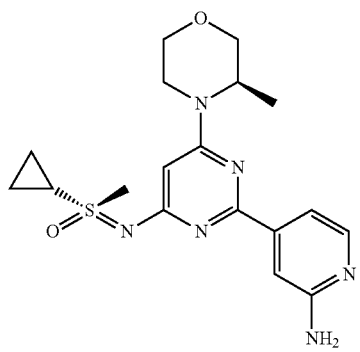 [SMILES: C[C@@H]1COCCN1c1cc(N=[S@](C)(=O)C2CC2)nc(-c2ccnc(N)c2)n1]

(R)-((2-(2-aminopyridin-4-yl)-6-((R)-3-methylmorpholino)pyrimidin-4-yl)imino)(cyclopropyl)(methyl)-$\lambda^6$-sulfanone and

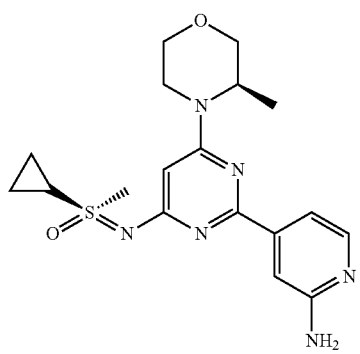 [SMILES: C[C@@H]1COCCN1c1cc(N=[S@@](C)(=O)C2CC2)nc(-c2ccnc(N)c2)n1]

(S)-((2-(2-aminopyridin-4-yl)-6-((R)-3-methylmorpholino)pyrimidin-4-yl)imino)(cyclopropyl)(methyl)-$\lambda^6$-sulfanone Synthesis is similar to that described for Example 24. The mixture of diastereomers (26.8 mg, 0.069 mmol) was separated by Chiral SFC (Mobile phase: n-hexane (0.1% DEA): EtOH (0.1% DEA)=70:30; Flow rate: 80 g/min; 20 min; Column temperature: 35° C.; Back pressure: 100 bar; Column: Gilson-281, AY 20×250 mm, 10 μm) to afford the two diastereomers of unknown absolute stereochemistry at the sulfur atom, title compounds 39a (6.6 mg, 25% yield, >99% ee) as a white solid and 39b (7.1 mg, 27% yield, >99% ee) as a white solid.

39a ((R)-cyclopropyl(methyl)-$\lambda^6$-sulfanone or (S)-cyclopropyl(methyl)-$\lambda^6$-sulfanone): $^1$H NMR (500 MHz, CD$_3$OD) δ 8.03-7.91 (m, 1H), 7.53 (s, 1H), 7.49 (dd, J=5.5, 1.4 Hz, 1H), 5.97 (s, 1H), 4.48 (d, J=4.6 Hz, 1H), 4.11 (d, J=12.0 Hz, 1H), 4.02 (dd, J=11.3, 3.6 Hz, 1H), 3.82 (d, J=11.4 Hz, 1H), 3.75 (dd, J=11.5, 3.0 Hz, 1H), 3.65-3.56 (m, 4H), 3.25 (td, J=12.8, 3.8 Hz, 1H), 3.01 (td, J=7.9, 4.0 Hz, 1H), 1.42 (dd, J=10.2, 5.4 Hz, 1H), 1.31 (dd, J=11.1, 6.2 Hz, 4H), 1.20 (dt, J=11.3, 5.7 Hz, 2H); MS (ES$^+$) C$_{18}$H$_{24}$N$_6$O$_2$S requires: 388, found: 389 [M+H]$^+$; R$_t$=11.35 min.

39b ((R)-cyclopropyl(methyl)-$\lambda^6$-sulfanone or (S)-cyclopropyl(methyl)-$\lambda^6$-sulfanone): $^1$H NMR (500 MHz, CD$_3$OD) δ 7.97 (d, J=5.4 Hz, 1H), 7.53 (s, 1H), 7.49 (dd, J=5.5, 1.3 Hz, 1H), 5.97 (s, 1H), 4.50 (s, 1H), 4.08 (d, J=12.7 Hz, 1H), 4.02 (dd, J=11.4, 3.7 Hz, 1H), 3.82 (d, J=11.3 Hz, 1H), 3.75 (dd, J=11.4, 3.0 Hz, 1H), 3.66-3.55 (m, 4H), 3.25 (td, J=12.9, 3.9 Hz, 1H), 3.05-2.97 (m, 1H), 1.41 (dd, J=10.6, 5.2 Hz, 1H), 1.31 (dd, J=11.8, 5.8 Hz, 4H), 1.20 (dt, J=11.1, 5.6 Hz, 2H); MS (ES$^+$) C$_{18}$H$_{24}$N$_6$O$_2$S requires: 388, found: 389 [M+H]$^+$; R$_t$=15.22 min.

Alternatively, Example 39a can also be prepared from Int. CC, Isomer 1b.

EXAMPLES 40a and 40b

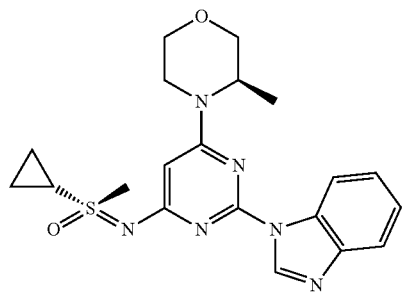 [SMILES: C[C@@H]1COCCN1c1cc(N=[S@](C)(=O)C2CC2)nc(-n2cnc3ccccc32)n1]

(R)-((2-(1H-benzo[d]imidazol-1-yl)-6-((R)-3-methylmorpholino)pyrimidin-4-yl)imino)(cyclopropyl)(methyl)-$\lambda^6$-sulfanone and

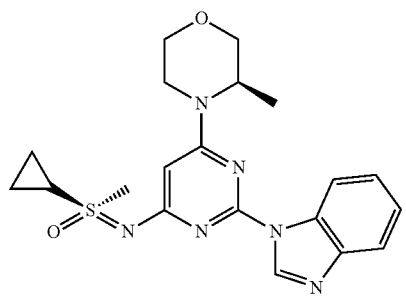 [SMILES: C[C@@H]1COCCN1c1cc(N=[S@@](C)(=O)C2CC2)nc(-n2cnc3ccccc32)n1]

(S)-((2-(1H-benzo[d]imidazol-1-yl)-6-((R)-3-methylmorpholino)pyrimidin-4-yl)imino)(cyclopropyl)(methyl)-$\lambda^6$-sulfanone Synthesis is similar to that described for Example 29. The mixture of diastereomers (31 mg, 0.075 mmol) was separated by Chiral SFC (Mobile phase: CO$_2$/MeOH (0.2% MeOH Ammonia)=50/50; Flow rate: 80 g/min; 10 min; Column temperature: 35° C.; Back pressure: 100 bar; Column: Daicel CHIRALPAK® OD, 10 μm, 20 mm×250 mm) to afford the two diastereomers of unknown absolute stereochemistry at the sulfur atom, title compounds 40a (6.0 mg, 19% yield, >99% ee) as a white solid and 40b (5.0 mg, 16% yield, >98% ee) as a white solid.

40a ((R)-cyclopropyl(methyl)-$\lambda^6$-sulfanone or (S)-cyclopropyl(methyl)-$\lambda^6$-sulfanone): $^1$H NMR (500 MHz, DMSO-d$_6$) δ 9.01 (s, 1H), 8.60 (d, J=7.7 Hz, 1H), 7.74 (d, J=7.4 Hz, 1H), 7.33 (dd, J=13.5, 7.5 Hz, 2H), 5.90 (s, 1H), 4.53-4.29 (m, 1H), 3.95 (d, J=7.7 Hz, 2H), 3.74 (d, J=11.2 Hz, 1H), 3.63 (d, J=11.3 Hz, 1H), 3.50 (d, J=19.7 Hz, 4H), 3.17 (s, 1H), 3.04 (s, 1H), 1.22 (d, J=6.7 Hz, 5H), 1.13 (d, J=19.3 Hz, 2H); MS (ES$^+$) C$_2$H$_{24}$N$_6$O$_2$S requires: 412, found: 413 [M+H]$^+$; R$_f$=3.50 min.

40b ((R)-cyclopropyl(methyl)-λ$^6$-sulfanone or (S)-cyclopropyl(methyl)-λ$^6$-sulfanone): $^1$H NMR (500 MHz, DMSO-d$_6$) δ 9.01 (s, 1H), 8.60 (d, J=7.7 Hz, 1H), 7.74 (d, J=7.6 Hz, 1H), 7.33 (ddd, J=15.1, 13.9, 6.7 Hz, 2H), 5.90 (s, 1H), 4.42 (s, 1H), 4.04 (s, 1H), 3.95 (dd, J=11.3, 3.4 Hz, 1H), 3.74 (d, J=11.4 Hz, 1H), 3.63 (dd, J=11.5, 2.9 Hz, 1H), 3.55-3.45 (m, 4H), 3.22-3.14 (m, 1H), 3.10-3.01 (m, 1H), 1.28-1.18 (m, 5H), 1.17-1.07 (m, 2H); MS (ES$^+$) C$_{20}$H$_{24}$N$_6$O$_2$S requires: 412, found: 413 [M+H]$^+$; Rt=4.44 min.

Alternatively, Example 40b can also be prepared from Int. CC, Isomer 1b.

EXAMPLES 41a and 41b

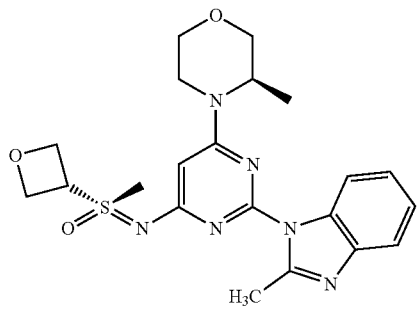 [SMILES: Cc1nc2ccccc2n1-c1nc(N=[S@](C)(=O)C2COC2)cc(N2CCOC[C@H]2C)n1]

(R)-methyl((2-(2-methyl-1H-benzo[d]imidazol-1-yl)-6-((R)-3-methylmorpholino)pyrimidin-4-yl)imino)(oxetan-3-yl)-λ$^6$-sulfanone and

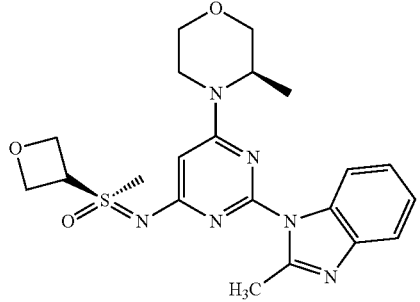 [SMILES: Cc1nc2ccccc2n1-c1nc(N=[S@@](C)(=O)C2COC2)cc(N2CCOC[C@H]2C)n1]

(S)-methyl((2-(2-methyl-1H-benzo[d]imidazol-1-yl)-6-((R)-3-methylmorpholino)pyrimidin-4-yl)imino)(oxetan-3-yl)-λ$^6$-sulfanone Synthesis is similar to that described for Example 29. The mixture of diastereomers (45 mg, 0.1 mmol) was separated by Chiral SFC (Mobile phase: n-Hexane (0.1% DEA): IPA (0.1% DEA)=35:65; Flow rate: 80 g/min; 20 min; Column temperature: 35° C.; Back pressure: 100 bar; Column: Gilson-281, sc 20×250 mm, 10 μm) to afford the two diastereomers of unknown absolute stereochemistry at the sulfur atom, title compounds 41a (7.0 mg, 16% yield, 99% ee) as a white solid and 41b (4.0 mg, 9.0% yield, >93% ee) as a white solid.

41a ((R)-methyl(oxetan-3-yl)-λ$^6$-sulfanone or (S)-methyl(oxetan-3-yl)-λ$^6$-sulfanone): $^1$H NMR (500 MHz, DMSO-d$_6$) δ 8.24 (dd, J=6.1, 3.1 Hz, 1H), 7.58 (dd, J=6.0, 3.0 Hz, 1H), 7.29-7.15 (m, 2H), 6.02-5.86 (m, 1H), 4.89 (dddd, J=17.8, 15.5, 7.8, 6.8 Hz, 5H), 4.40 (s, 1H), 3.92 (d, J=11.3 Hz, 2H), 3.72 (d, J=11.4 Hz, 1H), 3.65-3.55 (m, 1H), 3.44 (dd, J=15.6, 5.9 Hz, 4H), 3.22-3.12 (m, 1H), 2.88-2.77 (m, 3H), 1.29-1.12 (m, 3H); MS (ES$^+$) C$_{21}$H$_{26}$N$_6$O$_3$S requires: 442, found: 443 [M+H]$^+$; R$_f$=13.15 min.

41b ((R)-methyl(oxetan-3-yl)-λ$^6$-sulfanone or (S)-methyl(oxetan-3-yl)-λ$^6$-sulfanone): $^1$H NMR (500 MHz, DMSO-d$_6$) δ 8.30-8.15 (m, 1H), 7.66-7.51 (m, 1H), 7.23 (dd, J=6.0, 3.2 Hz, 2H), 5.95 (s, 1H), 4.84 (s, 5H), 4.41-4.30 (m, 1H), 4.03-3.88 (m, 2H), 3.75-3.67 (m, 1H), 3.64-3.58 (m, 1H), 3.42 (s, 4H), 3.23-3.12 (m, 1H), 2.83 (s, 3H), 1.20 (d, J=6.7 Hz, 3H); MS (ES$^+$) C$_{21}$H$_{26}$N$_6$O$_3$S requires: 442, found: 443[M+H]$^+$; R$_f$=17.06 min.

EXAMPLES 42a and 42b

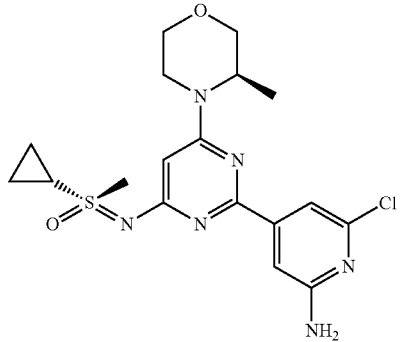 [SMILES: C[C@@H]1COCCN1c1cc(N=[S@](C)(=O)C2CC2)nc(-c2cc(N)nc(Cl)c2)n1]

(R)-((2-(2-amino-6-chloropyridin-4-yl)-6-((R)-3-methylmorpholino)pyrimidin-4-yl)imino)(cyclopropyl)(methyl)-λ$^6$-sulfanone and

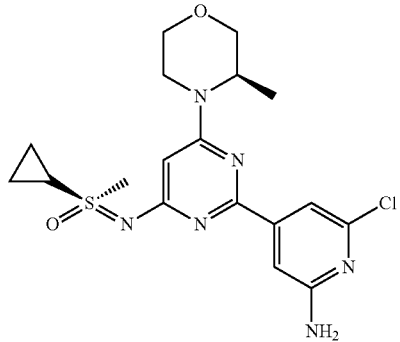 [SMILES: C[C@@H]1COCCN1c1cc(N=[S@@](C)(=O)C2CC2)nc(-c2cc(N)nc(Cl)c2)n1]

(S)-((2-(2-amino-6-chloropyridin-4-yl)-6-((R)-3-methylmorpholino)pyrimidin-4-yl)imino)(cyclopropyl)(methyl)-λ⁶-sulfanone Synthesis is similar to that described for Example 24. The mixture of diastereomers (100 mg, 0.18 mmol) was separated by Chiral SFC (Mobile phase: $CO_2$/ethanol (1% MeOH Ammonia)=40/60; Flow rate: 80 g/min; 12 min; Column temperature: 35° C.; Back pressure: 100 bar; Column: Daicel CHIRALPAK® OJ, 10 μm, 20 mm×250 mm) to afford the two diastereomers of unknown absolute stereochemistry at the sulfur atom, title compounds 42a (13 mg, 20% yield, >99% ee) as a white solid and 42b (20 mg, 31% yield, 96.7% ee) as a yellow solid.

42a ((R)-cyclopropyl(methyl)-λ⁶-sulfanone or (S)-cyclopropyl(methyl)-λ⁶-sulfanone): ¹H NMR (400 MHz, MeOD-d₄) δ 7.41 (s, 2H), 5.97 (s, 1H), 4.45 (s, 1H), 4.05 (dd, J=29.3, 11.7 Hz, 2H), 3.82 (d, J=11.6 Hz, 1H), 3.74 (d, J=8.8 Hz, 1H), 3.63-3.55 (m, 4H), 3.26-3.21 (m, 1H), 3.02-2.95 (m, 1H), 1.41 (s, 1H), 1.31 (dd, J=11.6, 5.8 Hz, 4H), 1.20 (d, J=7.5 Hz, 2H); MS (ES⁺) $C_{18}H_{23}ClN_6O_2S$ requires: 422, found: 423 [M+H]⁺; $R_t$=4.27 min.

42b ((R)-cyclopropyl(methyl)-λ⁶-sulfanone or (S)-cyclopropyl(methyl)-λ⁶-sulfanone): ¹H NMR (400 MHz, MeOD-d₄) δ 7.25 (d, J=1.7 Hz, 2H), 5.88 (s, 1H), 4.36 (d, J=4.8 Hz, 1H), 4.00-3.86 (m, 2H), 3.70 (d, J=11.5 Hz, 1H), 3.62 (dd, J=11.5, 2.8 Hz, 1H), 3.52-3.43 (m, 4H), 3.18-3.10 (m, 1H), 2.92-2.83 (m, 1H), 1.31 (dd, J=11.3, 5.6 Hz, 1H), 1.22-1.17 (m, 4H), 1.09 (dd, J=9.5, 5.3 Hz, 2H); MS (ES⁺) $C_{18}H_{23}ClN_6O_2S$ requires: 422, found: 423 [M+H]⁺; Rt=5.48 min.

Alternatively, Example 42a can also be prepared from Int. CC, Isomer 1b.

EXAMPLES 43a and 43b

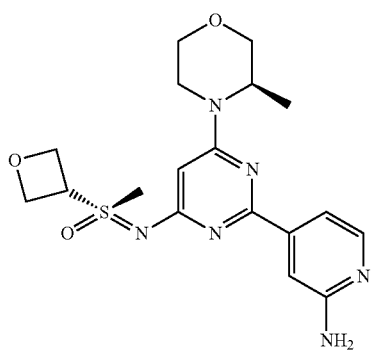 [SMILES: C[C@@H]1COCCN1c1cc(N=[S@](C)(=O)C2COC2)nc(-c2ccnc(N)c2)n1]

(R)-((2-(2-aminopyridin-4-yl)-6-((R)-3-methylmorpholino)pyrimidin-4-yl)imino)(methyl)(oxetan-3-yl)-λ⁶-sulfanone and

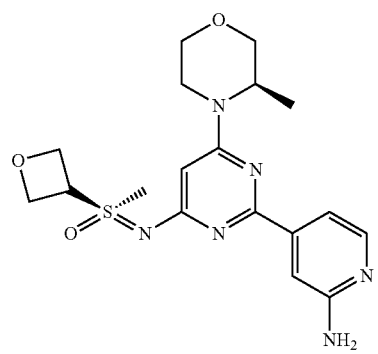 [SMILES: C[C@@H]1COCCN1c1cc(N=[S@@](C)(=O)C2COC2)nc(-c2ccnc(N)c2)n1]

(S)-((2-(2-aminopyridin-4-yl)-6-((R)-3-methylmorpholino)pyrimidin-4-yl)imino)(methyl)(oxetan-3-yl)-λ⁶-sulfanone Synthesis is similar to that described for Example 24. The mixture of diastereomers (36 mg, 0.089 mmol) was separated by Chiral SFC (Mobile phase: n-Hexane (0.1% DEA): EtOH (0.1% DEA)=60:40; Flow rate: 80 g/min; 17 min; Column temperature: 35° C.; Back pressure: 100 bar; Column: Gilson-281, AY 20*250 mm, 10 μm) to afford the two diastereomers of unknown absolute stereochemistry at the sulfur atom, title compounds 43a (9.0 mg, 23% yield, >99% ee) as a white solid and 43b (7.0 mg, 19% yield, >98% ee) as a white solid.

43a ((R)-methyl(oxetan-3-yl)-λ⁶-sulfanone or (S)-methyl(oxetan-3-yl)-λ⁶-sulfanone): ¹H NMR (500 MHz, CD₃OD) δ 7.98 (d, J=5.7 Hz, 1H), 7.59-7.37 (m, 2H), 5.99 (s, 1H), 5.12 (d, J=2.4 Hz, 1H), 5.07-4.96 (m, 4H), 4.52-4.41 (m, 1H), 4.16-4.06 (m, 1H), 4.00 (d, J=3.7 Hz, 1H), 3.82 (d, J=11.4 Hz, 1H), 3.75 (d, J=3.0 Hz, 1H), 3.60 (d, J=2.9 Hz, 1H), 3.52 (s, 3H), 3.25 (d, J=4.1 Hz, 1H), 1.29 (d, J=6.8 Hz, 3H); MS (ES⁺) $C_{18}H_{24}N_6O_3S$ requires: 404, found: 405 [M+H]⁺; $R_t$=9.34 min.

43b ((R)-methyl(oxetan-3-yl)-λ⁶-sulfanone or (S)-methyl(oxetan-3-yl)-λ⁶-sulfanone): ¹H NMR (500 MHz, CD₃OD) δ 7.86 (d, J=5.6 Hz, 1H), 7.44-7.29 (m, 2H), 5.87 (s, 1H), 4.99 (d, J=2.5 Hz, 1H), 4.89 (ddd, J=10.3, 7.5, 4.5 Hz, 4H), 4.40-4.32 (m, 1H), 4.02-3.85 (m, 2H), 3.64 (dt, J=11.4, 7.2 Hz, 2H), 3.47 (d, J=2.9 Hz, 1H), 3.39 (s, 3H), 3.16-3.07 (m, 1H), 1.17 (d, J=6.8 Hz, 3H); MS (ES⁺) $C_{18}H_{24}N_6O_3S$ requires: 404, found: 405 [M+H]⁺; $R_t$=12.75 min.

EXAMPLES 44a and 44b

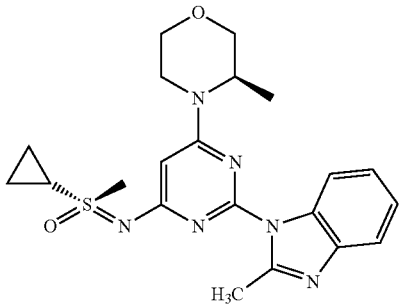 [SMILES: Cc1nc2ccccc2n1-c1nc(N=[S@](C)(=O)C2CC2)cc(N2CCOC[C@H]2C)n1]

(R)-cyclopropyl(methyl)((2-(2-methyl-1H-benzo[d]imidazol-1-yl)-6-((R)-3-methylmorpholino)pyrimidin-4-yl)imino)-$\lambda^6$-sulfanone and

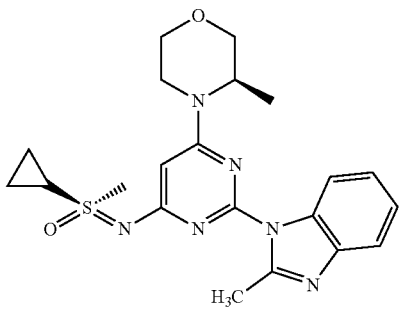 [SMILES: Cc1nc2ccccc2n1-c1nc(N=[S@@](C)(=O)C2CC2)cc(N2CCOC[C@H]2C)n1]

(S)-cyclopropyl(methyl)((2-(2-methyl-1H-benzo[d]imidazol-1-yl)-6-((R)-3-methylmorpholino)pyrimidin-4-yl)imino)-$\lambda^6$-sulfanone Synthesis is similar to that described for Example 30. The mixture of diastereomers (33.8 mg, 0.08 mmol) was separated by Chiral SFC (Mobile phase: n-Hexane (0.1% DEA): EtOH (0.1% DEA)=75:25; Flow rate: 80 g/min; 17 min; Column temperature: 35° C.; Back pressure: 100 bar; Column: Gilson-281, sc 20×250 mm, 10 μm) to afford the two diastereomers of unknown absolute stereochemistry at the sulfur atom, title compounds 44a (5.0 mg, 15% yield, >99% ee) as a white solid and 44b (5.0 mg, 15% yield, >93% ee) as a white solid.

44a ((R)-cyclopropyl(methyl)-$\lambda^6$-sulfanone or (S)-cyclopropyl(methyl)-$\lambda^6$-sulfanone): $^1$H NMR (500 MHz, CD$_3$OD) δ 8.32 (dd, J=6.4, 2.9 Hz, 1H), 7.69-7.54 (m, 1H), 7.38-7.20 (m, 2H), 5.97 (s, 1H), 4.45 (s, 1H), 4.07-3.91 (m, 2H), 3.85-3.72 (m, 2H), 3.67-3.56 (m, 1H), 3.49 (s, 3H), 2.97-2.86 (m, 4H), 1.40 (dd, J=12.6, 10.1 Hz, 1H), 1.35-1.25 (m, 5H), 1.18 (q, J=7.2 Hz, 2H); MS (ES$^+$) C$_{21}$H$_{26}$N$_6$O$_2$S requires: 426, found: 427 [M+H]$^+$; R$_t$=12.98 min.

44b ((R)-cyclopropyl(methyl)-$\lambda^6$-sulfanone or (S)-cyclopropyl(methyl)-$\lambda^6$-sulfanone): $^1$H NMR (400 MHz, CD$_3$OD) δ 8.31 (dd, J=6.5, 2.9 Hz, 1H), 7.67-7.51 (m, 1H), 7.29 (dd, J=6.1, 3.2 Hz, 2H), 5.97 (s, 1H), 4.44-4.34 (m, 1H), 4.02 (d, J=11.4 Hz, 2H), 3.80 (dd, J=22.8, 7.2 Hz, 2H), 3.60 (s, 1H), 3.49 (s, 3H), 2.95-2.87 (m, 4H), 1.43-1.29 (m, 6H), 1.21-1.12 (m, 2H); MS (ES$^+$) C$_{21}$H$_{26}$N$_6$O$_2$S requires: 426, found: 427 [M+H]$^+$; R$_t$=16.31 min.

Alternatively, Example 44b can also be prepared from Int. CC, Isomer 1b.

EXAMPLES 45a and 45b

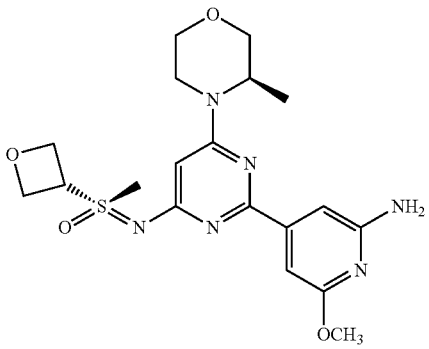 [SMILES: COc1cc(-c2nc(N=[S@](C)(=O)C3COC3)cc(N3CCOC[C@H]3C)n2)cc(N)n1]

(R)-((2-(2-amino-6-methoxypyridin-4-yl)-6-((R)-3-methylmorpholino)pyrimidin-4-yl)imino)(methyl)(oxetan-3-yl)-$\lambda^6$-sulfanone and

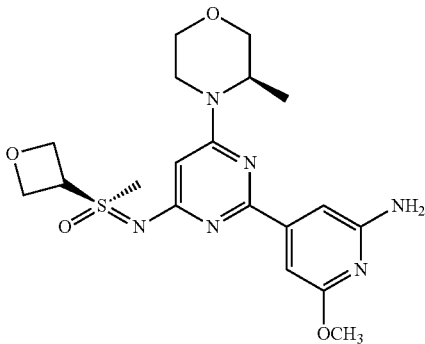 [SMILES: COc1cc(-c2nc(N=[S@@](C)(=O)C3COC3)cc(N3CCOC[C@H]3C)n2)cc(N)n1]

(S)-((2-(2-amino-6-methoxypyridin-4-yl)-6-((R)-3-methylmorpholino)pyrimidin-4-yl)imino)(methyl)(oxetan-3-yl)-$\lambda^6$-sulfanone Synthesis is similar to that described for Example 17. The mixture of diastereomers (300 mg, 0.691 mmol) was separated by Chiral SFC (Mobile phase: CO$_2$, MeOH/CH$_3$CN (1:1) (0.25% i-PrNH$_2$)=65:35; Flow rate: 80 g/min; 5 min; Column temperature: 25° C.; Back pressure: 100 bar; Column: Chiral Technologies Chiralcel OX-H, 21×250 mm) to afford the two diastereomers of unknown absolute stereochemistry at the sulfur atom, title compounds 45a (94 mg, 31% yield, 95% ee) as a tan solid and 45b (125 mg, 42% yield, 96% ee) as a tan solid.

45a ((R)-methyl(oxetan-3-yl)-$\lambda^6$-sulfanone or (S)-methyl(oxetan-3-yl)-$\lambda^6$-sulfanone): $^1$H NMR (600 MHz, DMSO-d$_6$) δ 6.85 (s, 1H), 6.65 (s, 1H), 6.00 (s, 2H), 5.90 (s, 1H), 5.02-4.95 (m, 1H), 4.95 (t, J=6.8 Hz, 1H), 4.90-4.83 (m, 3H), 4.39 (s, 1H), 4.04 (d, J=13.2 Hz, 1H), 3.92 (d, J=11.5 Hz, 1H), 3.77 (s, 3H), 3.71 (d, J=11.3 Hz, 1H), 3.59 (d, J=11.3 Hz, 1H), 3.51 (s, 3H), 3.45 (t, J=12.0 Hz, 1H), 3.09 (t, J=12.9 Hz, 1H), 1.16 (d, J=6.7 Hz, 3H); MS (ES+) $C_{19}H_{26}N_6O_4S$ requires: 434, found: 435 [M+H]+; $R_t$=3.1 min.

45b ((R)-methyl(oxetan-3-yl)-$\lambda^6$-sulfanone or (S)-methyl (oxetan-3-yl)-$\lambda^6$-sulfanone): $^1$H NMR (600 MHz, DMSO-$d_6$) δ 6.85 (s, 1H), 6.65 (s, 1H), 6.01 (s, 2H), 5.90 (s, 1H), 4.97 (dt, J=22.9, 6.7 Hz, 2H), 4.87 (d, J=8.1 Hz, 3H), 4.41 (s, 1H), 4.03 (d, J=13.3 Hz, 1H), 3.92 (d, J=10.9 Hz, 1H), 3.77 (s, 3H), 3.71 (d, J=11.4 Hz, 1H), 3.59 (d, J=11.4 Hz, 1H), 3.50 (s, 3H), 3.44 (t, J=11.9 Hz, 1H), 3.09 (t, J=12.3 Hz, 1H), 1.16 (d, J=6.7 Hz, 3H); MS (ES+) $C_{19}H_{26}N_6O_4S$ requires: 434, found: 435 [M+H]+; $R_t$=3.4 min.

EXAMPLES 46a and 46b

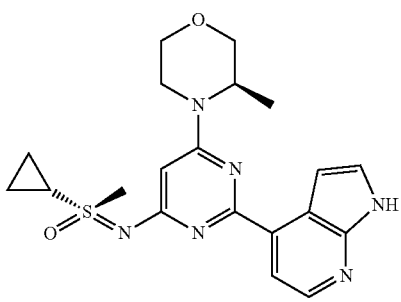 [SMILES: C[C@@H]1COCCN1c1cc(N=[S@](C)(=O)C2CC2)nc(-c2ccnc3[nH]ccc23)n1]

(R)-cyclopropyl(methyl)((6-((R)-3-methylmorpholino)-2-(1H-pyrrolo[2,3-b]pyridin-4-yl)pyrimidin-4-yl)imino)-$\lambda^6$-sulfanone and

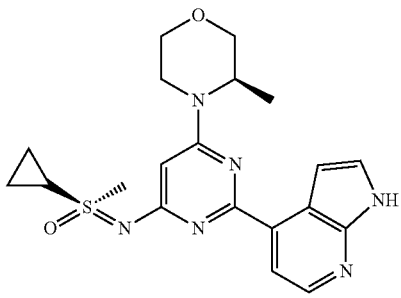 [SMILES: C[C@@H]1COCCN1c1cc(N=[S@@](C)(=O)C2CC2)nc(-c2ccnc3[nH]ccc23)n1]

(S)-cyclopropyl(methyl)((6-((R)-3-methylmorpholino)-2-(1H-pyrrolo[2,3-b]pyridin-4-yl)pyrimidin-4-yl)imino)-$\lambda^6$-sulfanone 46a ((R)-cyclopropyl(methyl)-$\lambda^6$-sulfanone or (S)-cyclopropyl(methyl)-$\lambda^6$-sulfanone); synthesized from Int. CC, Isomer 1a similar to that as described for Example 10: (20 mg, 32% yield, >99% ee) as a white solid. $^1$H NMR (400 MHz, DMSO-d6) δ 11.73 (s, 1H), 8.30 (d, J=5.0 Hz, 1H), 7.90 (d, J=5.0 Hz, 1H), 7.60-7.51 (m, 1H), 7.41 (s, 1H), 5.95 (s, 1H), 4.47 (s, 1H), 4.01 (dd, J=36.7, 10.5 Hz, 2H), 3.75 (d, J=11.1 Hz, 1H), 3.64 (d, J=8.7 Hz, 1H), 3.57-3.44 (m, 4H), 3.15 (t, J=12.7 Hz, 1H), 3.00 (s, 1H), 1.21 (d, J=6.7 Hz, 5H), 1.14-1.01 (m, 2H); MS (ES+) $C_{20}H_{24}N_6O_2S$ requires: 412, found: 413 [M+H]+; Rt=3.20 min.

46b ((R)-cyclopropyl(methyl)-$\lambda^6$-sulfanone or (S)-cyclopropyl(methyl)-$\lambda^6$-sulfanone); synthesized from Int. CC, Isomer 1b similar to that as described for Example 10: $^1$H NMR (400 MHz, DMSO-$d_6$) δ 11.73 (s, 1H), 8.30 (d, J=5.0 Hz, 1H), 7.90 (d, J=5.0 Hz, 1H), 7.59-7.48 (m, 1H), 7.44-7.28 (m, 1H), 5.95 (s, 1H), 4.45 (s, 1H), 4.01 (dd, J=36.7, 10.5 Hz, 2H), 3.75 (d, J=11.5 Hz, 1H), 3.64 (d, J=9.4 Hz, 1H), 3.55 (s, 3H), 3.48 (d, J=11.8 Hz, 1H), 3.16 (s, 1H), 3.02 (s, 1H), 1.20 (d, J=6.7 Hz, 5H), 1.10 (s, 2H); MS (ES+) $C_2H_{24}N_6O_2S$ requires: 412, found: 413 [M+H]+; $R_t$=2.09 min.

EXAMPLE 47

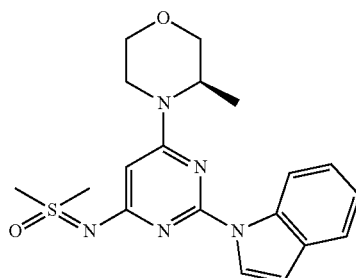

(R)-((2-(1H-indol-1-yl)-6-(3-methylmorpholino)pyrimidin-4-yl)imino)dimethyl-$\lambda^6$-sulfanone

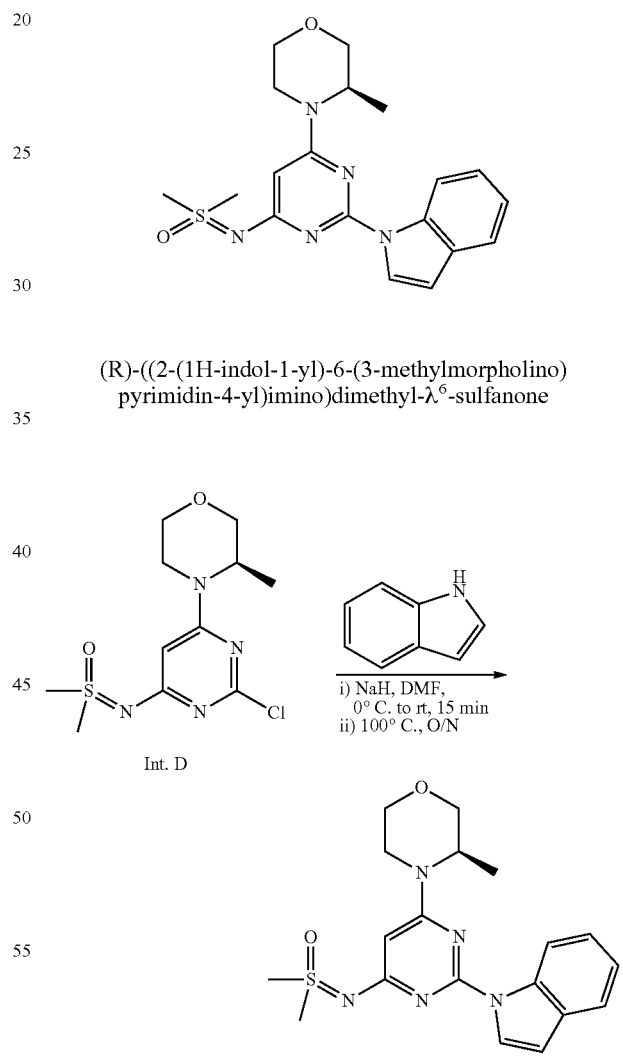

(R)-((2-(1H-indol-1-yl)-6-(3-methylmorpholino)pyrimidin-4-yl)imino)dimethyl-$\lambda^6$-sulfanone: To a solution of indole (43 mg, 0.360 mmol) in DMF (0.75 mL) 0° C. was added NaH (60% wt., 16 mg, 0.394 mmol) and the resulting solution was allowed to slowly warm up to RT and stirred over 15 min. The reaction mixture was added a solution of Int. D (100 mg, 0.328 mmol) in a DMF (0.75 mL) and the reaction mixture was heated to 100° C. and stirred for 16 h. The reaction mixture was cooled to RT, partitioned between water (15 mL) and EtOAc (5 mL), the layers were separated and the aqueous layer was extracted with EtOAc (3×5 mL). The combined organic layers were washed with brine, dried over $Na_2SO_4$, filtered and concentrated under reduced pressure. The residue was purified by flash chromatography (5-100% EtOAc in hexanes) to afford the title compound (42 mg, 33% yield) as a white solid.

$^1$H NMR (400 MHz, $CDCl_3$) δ ppm 8.77 (d, J=8.28 Hz, 1H) 8.20 (d, J=3.76 Hz, 1H) 7.62 (d, J=8.03 Hz, 1H) 7.30-7.46 (m, 1H) 7.12-7.27 (m, 1H) 6.64 (d, J=3.51 Hz, 1H) 5.75 (s, 1H) 4.38 (br d, J=8.28 Hz, 1H) 3.95-4.13 (m, 2H) 3.83 (s, 1H) 3.80 (br d, J=3.01 Hz, 1H) 3.59-3.69 (m, 1H) 3.50 (d, J=7.03 Hz, 1H) 3.44 (s, 4H) 3.34 (s, 1H) 1.36 (d, J=7.03 Hz, 3H) 1.23 (t, J=7.03 Hz, 1H) 0.91 (s, 1H); MS ($ES^+$) $C_{19}H_{23}N_5O_2S$ requires: 385, found: 386 $[M+H]^+$.

EXAMPLE 48

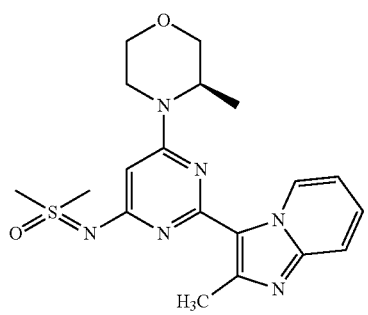 [SMILES: Cc1nc2ccccn2c1-c1nc(N=S(C)(C)=O)cc(N2CCOC[C@H]2C)n1]

(R)-dimethyl((2-(2-methylimidazo[1,2-a]pyridin-3-yl)-6-(3-methylmorpholino)pyrimidin-4-yl)imino)-$λ^6$-sulfanone

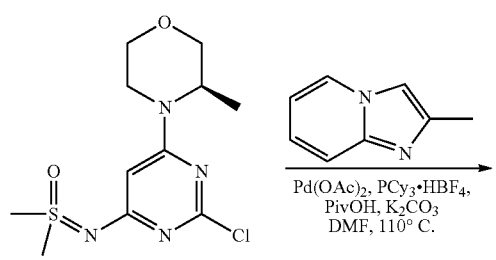

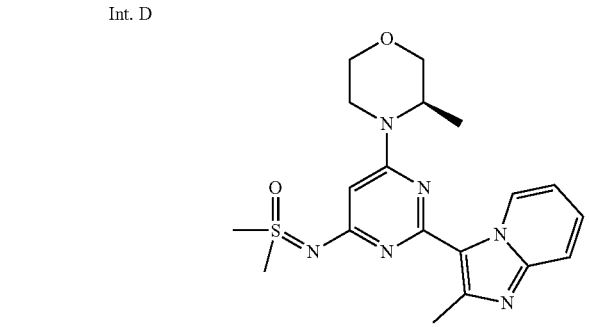

(R)-dimethyl((2-(2-methylimidazo[1,2-a]pyridin-3-yl)-6-(3-methylmorpholino)-pyrimidin-4-yl)imino)-$λ^6$-sulfanone hydrochloride: A reaction vial was charged with Int. D (50 mg, 0.0165 mmol), 2-methylimidazo[1,2-a]pyridine (33 mg, 0.25 mmol), $Pd(OAc)_2$ (1.8 mg, 0.008 mmol), tricyclohexylphosphonium tetrafluoroborate (6.3 mg, 0.017 mmol), pivalic acid (5.0 mg, 0.05 mmol) and $K_2CO_3$ (46 mg, 0.33 mmol). The vial was sealed, purged with Ar, DMF (1 mL) was added and the resulting mixture was heated to 110° C. for 1 h. The reaction mixture was cooled to RT, filtered through CELITE®, washed with $CH_2Cl_2$ and concentrated under reduced pressure. The residue was purified by flash chromatography (0-10% MeOH in $CH_2Cl_2$) followed by reverse phase chromatography (Mobile phase: A=0.1% $HCO_2H/H_2O$, B=0.1% $HCO_2H/MeCN$; Gradient: B=5-50%; 15 min; Column: Biotage SNAP Ultra C18 30 g, HP-Sphere C18 25 μm). The combined fractions were treated with 0.1 M aq. HCl, concentrated under reduced pressure and lyophilized to afford the title compound (26 mg, 36% yield) as a white solid.

$^1$H NMR (400 MHz, DMSO-$d_6$) δ ppm 10.23 (dt, J=7.03, 1.00 Hz, 1H) 8.01 (d, J=1.00 Hz, 2H) 7.48-7.56 (m, 1H) 5.96 (s, 1H) 4.33-4.47 (m, 2H) 3.91-3.99 (m, 3H) 3.70-3.81 (m, 2H) 3.60-3.69 (m, 1H) 3.45-3.54 (m, 1H) 3.43 (s, 6H) 3.15 (br d, J=3.76 Hz, 1H) 2.90 (s, 3H) 1.13-1.30 (m, 4H); MS ($ES^+$) $C_{19}H_{24}N_6O_2S$ requires: 400, found: 401 $[M+H]^+$.

EXAMPLE 49

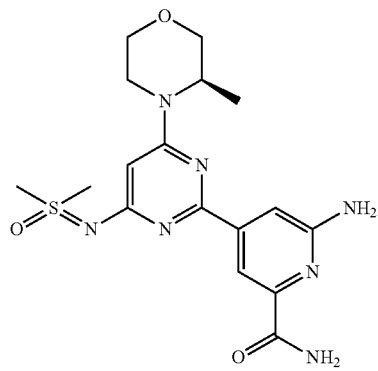 [SMILES: C[C@@H]1COCCN1c1cc(N=S(C)(C)=O)nc(-c2cc(N)nc(C(N)=O)c2)n1]

(R)-6-amino-4-(4-((dimethyl(oxo)-$λ^6$-sulfaneylidene)amino)-6-(3-methylmorpholino)pyrimidin-2-yl)picolinamide Step 1

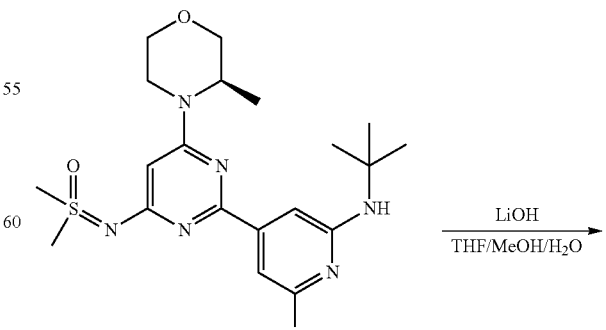

Int. BB

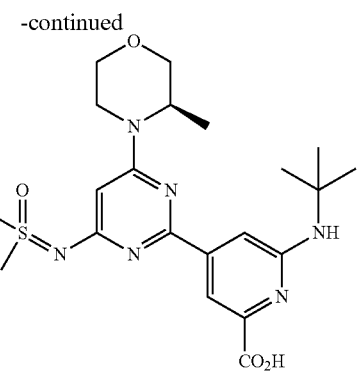

(R)-6-(tert-butylamino)-4-(4-((dimethyl(oxo)-λ⁶-sulfaneylidene)amino)-6-(3-methylmorpholino)pyrimidin-2-yl)picolinic acid: To a solution of Int. BB (30 mg, 0.063 mmol) in THF (225 μL), MeOH (45.0 μL) and water (45.0 μL) was added LiOH (1.5 mg, 0.063 mmol) and the resulting mixture was stirred at RT for 12 h. The mixture was filtered and concentrated under reduced pressure. The residue was purified by mass-triggered preparative HPLC (Mobile phase: A=0.1% TFA/H₂O, B=0.1% TFA/MeCN; Gradient: B=20-50%; 20 min; Column: XBridge C18, 5 μm, 19 mm×150 mm) to afford the title compound (15 mg, 0.026 mmol, 41.3% yield) as a pale yellow solid.

MS (ES⁺) $C_{21}H_{30}N_6O_4S$ requires: 462, found: 463 [M+H]⁺.

Step 2

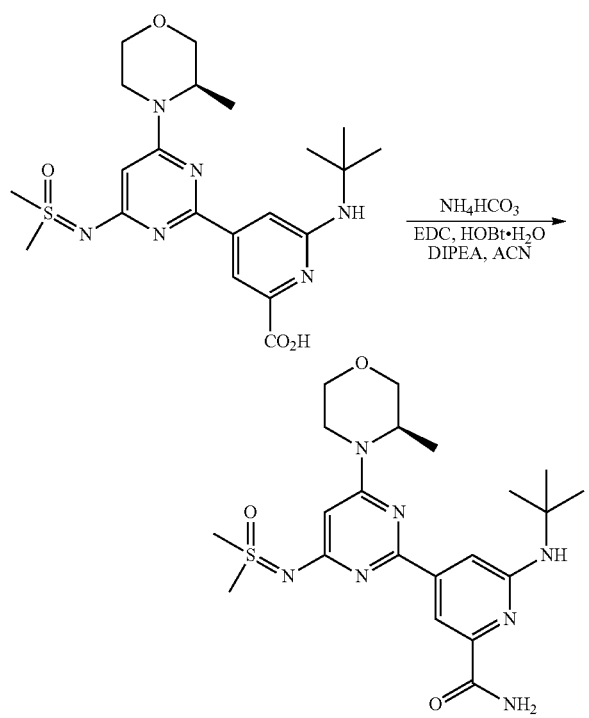

(R)-6-(tert-butylamino)-4-(4-((dimethyl(oxo)-λ⁶-sulfaneylidene)amino)-6-(3-methylmorpholino)pyrimidin-2-yl)picolinamide: To a solution of the product form the previous step (15 mg, 0.026 mmol) in acetonitrile (130 μL) were added ammonium bicarbonate (8.2 mg, 0.10 mmol), EDC (9.97 mg, 0.052 mmol), HOBt hydrate (8.0 mg, 0.052 mmol) and DIPEA (14 μL, 0.078 mmol) and the resulting mixture was stirred at RT for 2 h. The mixture was filtered through a Whatman™ syringe filter (13 mm, 0.45 μm) and directly purified by mass-triggered preparative HPLC (Mobile phase: A=0.1% TFA/H₂O, B=0.1% TFA/MeCN; Gradient: B=20-50%; 16 min; Column: XBridge C18, 5 μm, 19 mm×150 mm) to afford the title compound (12 mg, 80% yield) as a pale yellow solid.

MS (ES⁺) $C_{21}H_{31}N_7O_3S$ requires: 461, found: 462 [M+H]⁺.

Step 3

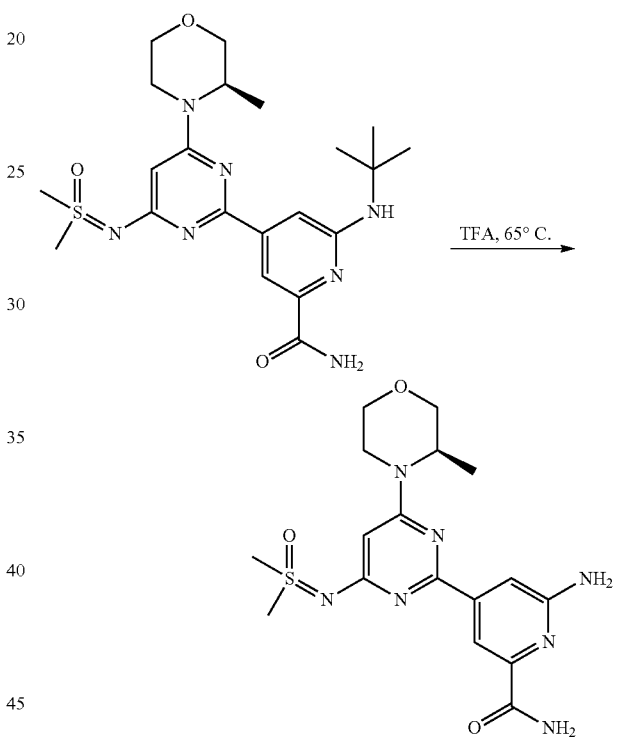

(R)-6-amino-4-(4-((dimethyl(oxo)-λ⁶-sulfaneylidene)amino)-6-(3-methyl-morpholino)pyrimidin-2-yl)picolinamide: A solution of the product from the previous step (6.6 mg, 0.011 mmol) in TFA (57 μL) was stirred at 65° C. for 24 h. The mixture was cooled to RT, diluted with CH₂Cl₂ (2 mL) and concentrated under reduced pressure. The residue was purified by mass-triggered preparative HPLC (Mobile phase: A=0.1% TFA/H₂O, B=0.1% TFA/MeCN; Gradient: B=10-40%; 20 min; Column: Column: XBridge C18, 5 μm, 19 mm×150 mm) to afford the title compound (4 mg, 55% yield) as a white solid.

¹H NMR (600 MHz, Methanol-d₄) δ 8.10 (s, 1H), 7.81 (s, 1H), 6.11 (s, 1H), 4.54 (s, 1H), 4.19 (s, 1H), 4.02 (dd, J=11.4, 3.7 Hz, 1H), 3.82 (d, J=11.6 Hz, 1H), 3.73 (dd, J=11.7, 3.1 Hz, 1H), 3.59 (td, J=12.0, 2.8 Hz, 1H), 3.51 (s, 6H), 3.38-3.27 (m, overlap MeOH, 1H), 1.33 (d, J=6.9 Hz, 3H); MS (ES⁺) $C_{17}H_{23}N_7O_3S$ requires: 405, found: 406 [M+H]⁺.

EXAMPLE 50

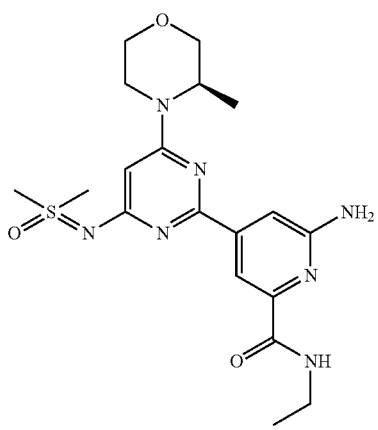 [SMILES: CCNC(=O)c1cc(-c2nc(N=S(C)(C)=O)cc(N3CCOC[C@H]3C)n2)cc(N)n1]

(R)-6-amino-4-(4-((dimethyl(oxo)-λ⁶-sulfaneylidene)amino)-6-(3-methylmorpholino)pyrimidin-2-yl)-N-ethylpicolinamide Step 1

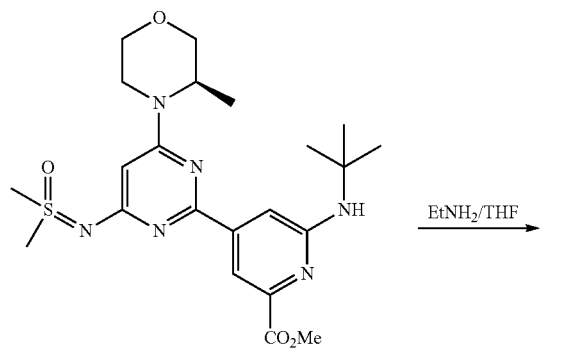

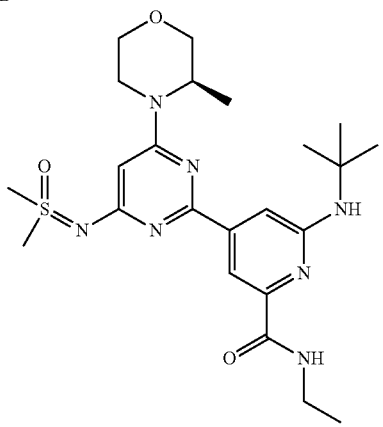

(R)-6-(tert-butylamino)-4-(4-((dimethyl(oxo)-λ⁶-sulfaneylidene)amino)-6-(3-methylmorpholino)pyrimidin-2-yl)-N-ethylpicolinamide: A mixture of Int. BB (30 mg, 0.063 mmol) and ethanamine (2.0 M in THF, 629 μL, 1.26 mmol) was stirred at 65° C. for 16 h. Another aliquot of ethanamine (2.0 M THF, 629 μL, 1.259 mmol) was added and the mixture was heated at 65° C. for an additional 24 h. The mixture was cooled to RT and concentrated under reduced pressure. The residue was purified by mass-triggered preparative HPLC (Mobile phase: A=0.1% TFA/H₂O, B=0.1% TFA/MeCN; Gradient: B=30-70%; 20 min; Column: XBridge C18, 5 μm, 19 mm×150 mm) to afford the title compound (15 mg, 49% yield) as a pale yellow solid.

MS (ES⁺) $C_{23}H_{35}N_7O_3S$ requires: 489, found: 490 [M+H]⁺.

Step 2

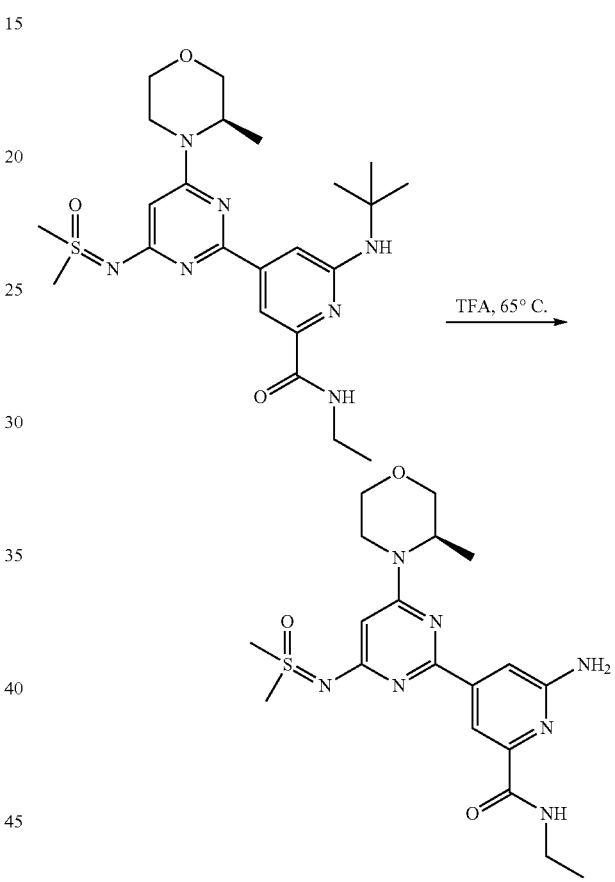

(R)-6-amino-4-(4-((dimethyl(oxo)-λ⁶-sulfaneylidene)amino)-6-(3-methyl-morpholino)pyrimidin-2-yl)-N-ethylpicolinamide: A solution of the product from the previous step (10 mg, 0.020 mmol) in TFA (102 μL) was stirred at 65° C. for 24 h. The mixture was cooled to RT, diluted with CH₂Cl₂ (2 mL) and concentrated under reduced pressure. The residue was purified by mass-triggered preparative HPLC (Mobile phase: A=0.1% TFA/H₂O, B=0.1% TFA/MeCN; Gradient: B=10-40%; 20 min; Column: XBridge C18, 5 μm, 19 mm×150 mm) to afford the title compound (6 mg, 44% yield) as a white solid.

¹H NMR (600 MHz, Methanol-d₄) δ 8.02 (s, 1H), 7.71 (s, 1H), 6.13 (s, 1H), 4.56 (s, 1H), 4.21 (s, 1H), 4.03 (dd, J=11.7, 3.8 Hz, 1H), 3.83 (d, J=11.6 Hz, 1H), 3.73 (dd, J=11.6, 3.2 Hz, 1H), 3.59 (td, J=12.0, 2.4 Hz, 2H), 3.51 (s, 6H), 3.46 (q, J=7.3 Hz, 2H), 3.39-3.32 (m, overlap MeOH, 1H), 1.34 (d, J=6.8 Hz, 3H), 1.25 (t, J=7.2 Hz, 3H); MS (ES⁺) $C_{19}H_{27}N_7O_3S$ requires: 433, found: 434 [M+H]⁺.

EXAMPLE 51

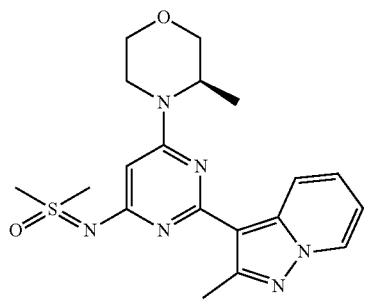 [SMILES: Cc1nn2ccccc2c1-c1nc(N=S(C)(C)=O)cc(N2CCOC[C@H]2C)n1]

(R)-dimethyl((6-(3-methylmorpholino)-2-(2-methylpyrazolo[1,5-a]pyridin-3-yl)pyrimidin-4-yl)imino)-λ⁶-sulfanone

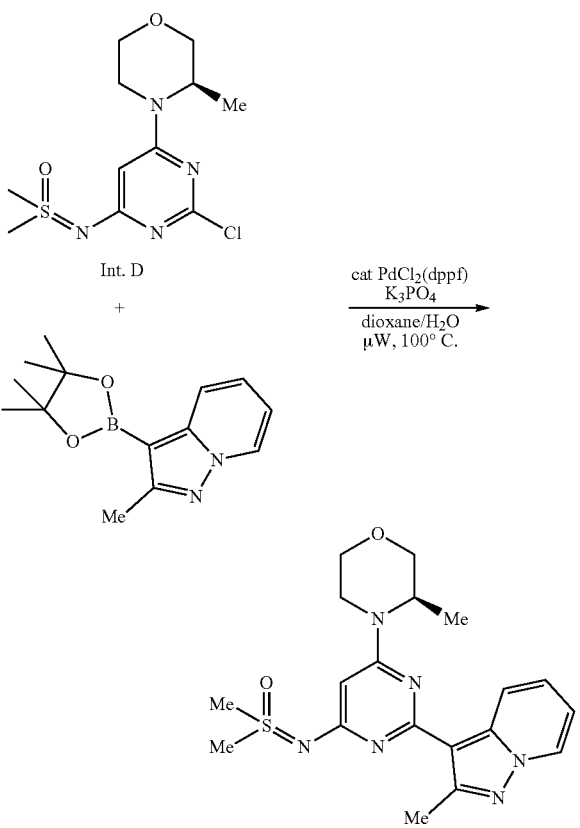

(R)-dimethyl((6-(3-methylmorpholino)-2-(2-methylpyrazolo[1,5-a]pyridin-3-yl)pyrimidin-4-yl)imino)-λ⁶-sulfanone: A microwave reaction vial was charged with Int. D (0.10 g, 0.33 mmol), 2-methyl-3-(4,4,5,5-tetramethyl-1,3,2-dioxaborolan-2-yl)pyrazolo[1,5-a]pyridine (0.10 g, 0.38 mmol), PdCl₂(dppf)-CH₂Cl₂ (0.030 g, 0.040 mmol) and K₃PO₄ (0.22 g, 1.04 mmol) in dioxane (3 mL) and water (0.8 mL) and the mixture was degassed with a stream of N₂ for five minutes. The vial was sealed and heated at 100° C. for 40 minutes in a microwave reactor. The reaction mixture was cooled to RT, partitioned between EtOAc (20 mL) and brine (20 mL), the layers were separated and the aqueous layer was extracted EtOAc (2×20 mL). The combined organic layers were dried over MgSO⁴, filtered and concentrated under reduced pressure. The residue was purified via silica gel chromatography (1-8% MeOH in CH₂Cl₂) to afford the title compound (78 mg, 59% yield) as a white solid.

$^1$H NMR (400 MHz, CDCl₃) δ ppm 8.71 (d, J=8.78 Hz, 1H), 8.41 (d, J=6.78 Hz, 1H), 7.19-7.35 (m, 1H), 6.79 (td, J=6.84, 1.38 Hz, 1H), 5.75 (s, 1H), 4.32-4.50 (m, 1H), 3.91-4.14 (m, 2H), 3.74-3.90 (m, 2H), 3.57-3.70 (m, 1H), 3.40 (d, J=7.78 Hz, 6H), 3.29 (td, J=12.74, 3.89 Hz, 1H), 2.87 (s, 3H), 1.33 (d, J=6.78 Hz, 3H); MS (ES⁺) C₁₉H₂₄N₆O₂S requires: 400, found: 401 [M+H]⁺.

EXAMPLE 52

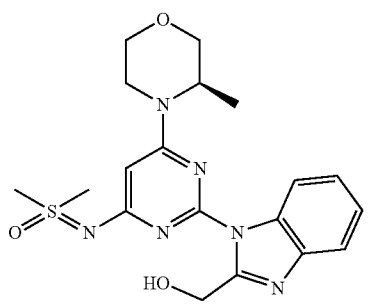 [SMILES: C[C@@H]1COCCN1c1cc(N=S(C)(C)=O)nc(-n2c(CO)nc3ccccc32)n1]

(R)-((2-(2-(hydroxymethyl)-1H-benzo[d]imidazol-1-yl)-6-(3-methylmorpholino)pyrimidin-4-yl)imino)dimethyl-λ⁶-sulfanone

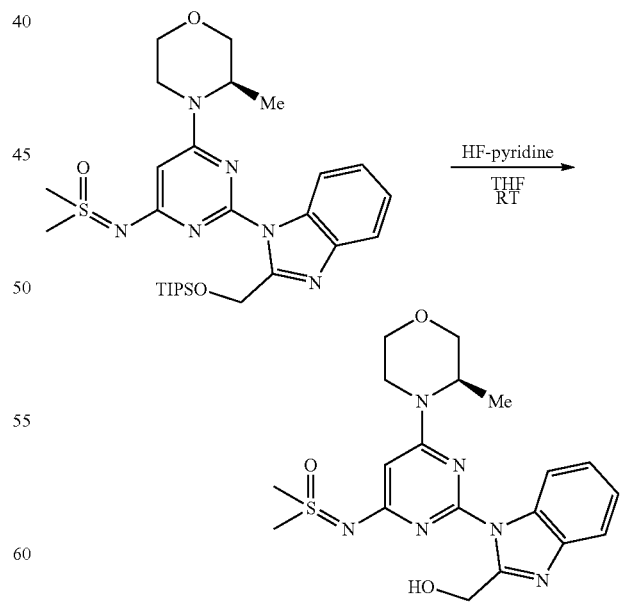

(R)-((2-(2-(hydroxymethyl)-1H-benzo[d]imidazol-1-yl)-6-(3-methylmorpholino)pyrimidin-4-yl)imino)dimethyl-λ⁶-sulfanone: To a solution of (R)-dimethyl((6-(3-methylmorpholino)-2-(2-(((triisopropylsilyl)oxy)methyl)-1H-benzo[d]

imidazol-1-yl)pyrimidin-4-yl)imino)-λ⁶-sulfanone (synthesis is similar to that described for Example 30, derived from Intermed. FF) (0.081 g, 0.14 mmol) in THF (5 mL) was added HF pyridine, 30% (HF ca. 70%, 1.3 mL) and the resulting mixture was stirred at RT for 1 h. The reaction mixture was poured into sat. aq. NaHCO$_3$(50 mL) and stirred vigorously for 15 min. The layers were separated and the aqueous layer was extracted with CH$_2$Cl$_2$ (2×50 mL). The combined organic layers were dried over MgSO$_4$, filtered and concentrated under reduced pressure. The residue was purified via reverse phase C18 chromatography (10-100% MeCN in 0.1% TFA/H$_2$O). The combined fractions were made alkaline by the addition of sat. aq. NaHCO$_3$and the aqueous layer was extracted with CH$_2$Cl$_2$ (2×50 mL). The combined organic layers were dried over MgSO$_4$, filtered and concentrated under reduced pressure to afford the title compound (0.052 g, 88% yield) as a white solid.

$^1$H NMR (400 MHz, CDCl$_3$) δ ppm 8.32-8.50 (m, 1H), 7.63-7.80 (m, 1H), 7.20-7.36 (m, 2H), 5.74 (s, 1H), 5.14 (s, 2H), 4.12-4.27 (m, 1H), 3.96 (br dd, J=11.42, 3.64 Hz, 1H), 3.81 (br d, J=13.05 Hz, 1H), 3.61-3.77 (m, 2H), 3.51 (td, J=11.92, 3.01 Hz, 1H), 3.19-3.36 (m, 8H), 1.27 (d, J=6.78 Hz, 3H); MS (ES$^+$) C$_{19}$H$_{24}$N$_6$O$_3$S requires: 416, found: 417 [M+H]$^+$.

EXAMPLE 53

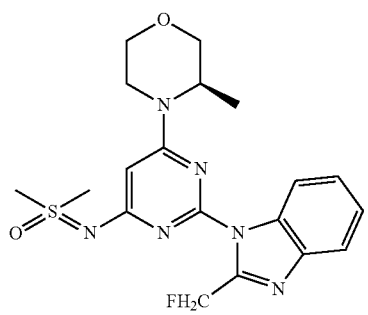

(R)-((2-(2-(fluoromethyl)-1H-benzo[d]imidazol-1-yl)-6-(3-methylmorpholino)pyrimidin-4-yl)imino)dimethyl-λ⁶-sulfanone

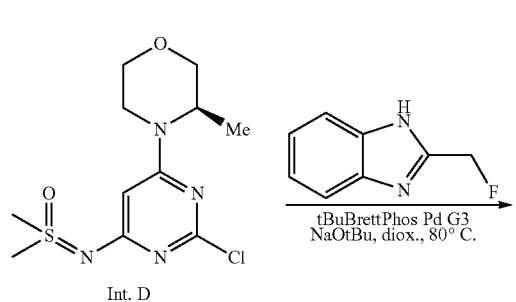

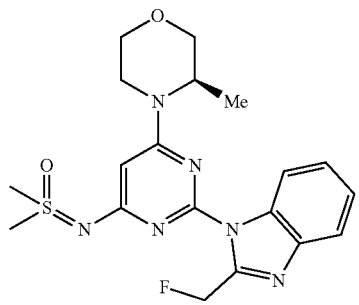

(R)-((2-(2-(fluoromethyl)-1H-benzo[d]imidazol-1-yl)-6-(3-methylmorpholino)-pyrimidin-4-yl)imino)dimethyl-λ⁶-sulfanone: A mixture of Int. D (0.152 g, 0.499 mmol), 2-(fluoromethyl)-1H-benzo[d]imidazole (0.090 g, 0.60 mmol), sodium tert-butoxide (0.086 g, 0.90 mmol) and t-BuBrettPhos Palladacycle G3 (0.021 g, 0.025 mmol) in dioxane (5 mL) was degassed with a stream of N$_2$ for five minutes and the resulting mixture was heated to 80° C. for 18 h. The reaction mixture was cooled to RT, filtered through CELITE® and concentrated under reduced pressure. The residue was purified via silica gel chromatography (10% CH$_3$CN in CH$_2$Cl$_2$) to afford the title compound (102 mg, 49% yield) as a white solid.

$^1$H NMR (400 MHz, CDCl$_3$) δ ppm 8.40 (d, J=8.03 Hz, 1H), 7.77 (br d, J=7.53 Hz, 1H), 7.23-7.46 (m, 2H), 5.85-6.16 (m, 2H), 5.74 (s, 1H), 4.22 (br d, J=4.52 Hz, 1H), 3.80-4.02 (m, 2H), 3.60-3.79 (m, 2H), 3.52 (td, J=11.92, 3.01 Hz, 1H), 3.14-3.39 (m, 7H), 1.27 (d, J=6.78 Hz, 3H); MS (ES$^+$) C$_{19}$H$_{23}$FN$_6$O$_2$S requires: 418, found: 419 [M+H]$^+$.

EXAMPLE 54

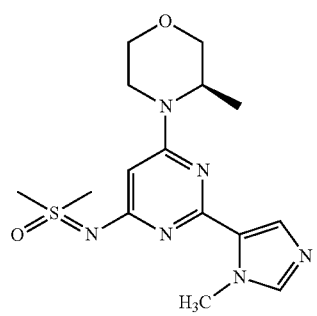 [SMILES: C[C@@H]1COCCN1c1cc(N=S(C)(C)=O)nc(-c2cncn2C)n1]

(R)-dimethyl((2-(1-methyl-1H-imidazol-5-yl)-6-(3-methylmorpholino)pyrimidin-4-yl)imino)-λ⁶-sulfanone

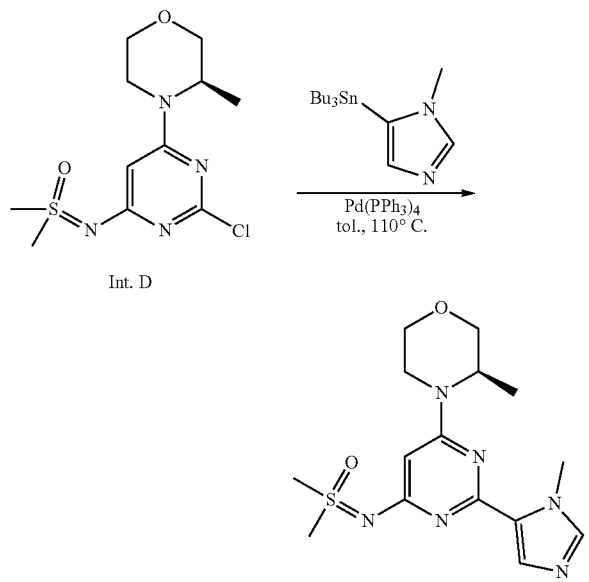

Int. D (R)-dimethyl((2-(1-methyl-1H-imidazol-5-yl)-6-(3-methylmorpholino)pyrimidin-4-yl)imino)-λ⁶-sulfanone: A solution of Int. D (50 mg, 0.164 mmol), 1-methyl-5-(tributylstannyl)-1H-imidazole (77 mg, 0.20 mmol) in toluene (820 μL) was degassed with $N_2$ for 1 minute. Pd(Ph₃P)₄ (19 mg, 0.016 mmol) was added and the mixture was degassed with $N_2$ for an additional 30 seconds, and the reaction mixture was heated at 110° C. for 16 h. The reaction mixture was cooled to RT, filtered through CELITE®, washed with $CH_2Cl_2$ and concentrated under reduced pressure. The residue was purified by mass-triggered preparative HPLC (Mobile phase: A=0.1% TFA/H₂O, B=0.1% TFA/MeCN; Gradient: B=0-30%; 20 min; Column: XBridge C18, 5 μm, 19 mm×150 mm) to afford the title compound (5.4 mg, 6% yield) as a white solid.

¹H NMR (600 MHz, Methanol-d₄) δ 8.88 (s, 1H), 8.12 (s, 1H), 5.97 (s, 1H), 4.42-4.36 (m, 1H), 4.28 (s, 3H), 4.03-3.94 (m, 2H), 3.80 (d, J=11.5 Hz, 1H), 3.71 (dd, J 11.6, 3.2 Hz, 1H), 3.57 (td, J=11.9, 3.1 Hz, 1H), 3.44 (s, 6H), 3.32-3.23 (n, overlap MeOH, 1H), 1.29 (d, J=6.8 Hz, 3H); MS (ES⁺) $C_{15}H_{22}N_6O_2S$ requires: 350, found: 351 [M+H]⁺.

The compounds reported in Table 2 were synthesized using the method described for the previously disclosed Examples. The appropriate sulfoximines were prepared as described for Intermediates C.

TABLE 2

Example compounds 55-125.

| Ex | Structure | IUPAC Name | MWt | [M + H] | Ex. Method |
|---|---|---|---|---|---|
| 55 | 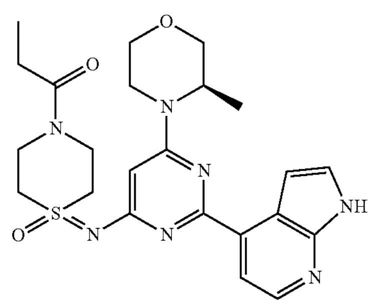 [SMILES: CCC(=O)N1CCS(=O)(=Nc2cc(N3CCOC[C@H]3C)nc(-c3ccnc4[nH]ccc34)n2)CC1] | (R)-1-(1-((6-(3-methylmorpholino)-2-(1H-pyrrolo[2,3-b]-pyridin-4-yl)pyrimidin-4-yl)imino)-1-oxido-1λ⁶-thiomorpholino)propan-1-one | 483 | 484 | 12 |
| 56 | 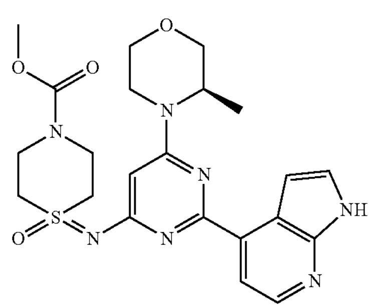 [SMILES: COC(=O)N1CCS(=O)(=Nc2cc(N3CCOC[C@H]3C)nc(-c3ccnc4[nH]ccc34)n2)CC1] | Methyl (R)-1-((6-(3-methylmorpholino)-2-(1H-pyrrolo[2,3-b]-pyridin-4-yl)pyrimidin-4-yl)imino)-1λ⁶-thiomorpholine-4-carboxylate 1-oxide | 485 | 486 | 12 |

TABLE 2-continued

Example compounds 55-125.

| Ex | Structure | IUPAC Name | MWt | [M + H] | Ex. Method |
|---|---|---|---|---|---|
| 57 | 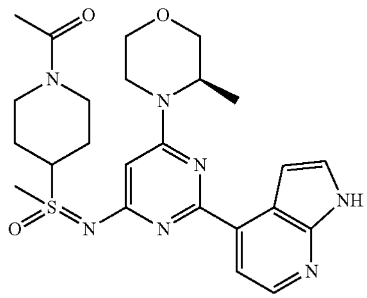 [SMILES: CC(=O)N1CCC(S(C)(=O)=Nc2cc(N3CCOC[C@H]3C)nc(-c3ccnc4[nH]ccc34)n2)CC1] | (1-Acetylpiperidin-4-yl)-(methyl)((6-((R)-3-methylmorpholino)-2-(1H-pyrrolo[2,3-b]-pyridin-4-yl)pyrimidin-4-yl)imino)-$\lambda^6$-sulfanone | 497 | 498 | 12 |
| 58 | 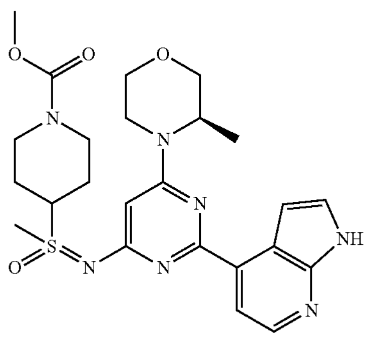 [SMILES: CCC(=O)N1CCC(S(C)(=O)=Nc2cc(N3CCOC[C@H]3C)nc(-c3ccnc4[nH]ccc34)n2)CC1] | Methyl 4-(S-methyl-N-(6-((R)-3-methyl-morpholino)-2-(1H-pyrrolo[2,3-b]pyridin-4-yl)pyrimidin-4-yl)-sulfonimidoyl)piperidine-1-carboxylate | 513 | 514 | 12 |
| 59 | 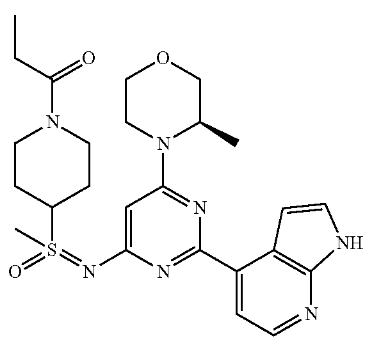 | Methyl((6-((R)-3-methylmorpholino)-2-(1H-pyrrolo[2,3-b]-pyridin-4-yl)pyrimidin-4-yl)imino)(1-propionyl-piperidin-4-yl)-$\lambda^6$-sulfanone | 511 | 512 | 12 |
| 60 | 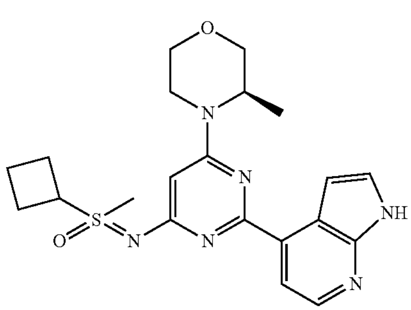 [SMILES: C[C@@H]1COCCN1c1cc(N=S(C)(=O)C2CCC2)nc(-c2ccnc3[nH]ccc23)n1] | Methyl((6-((R)-3-methylmorpholino)-2-(1H-pyrrolo[2,3-b]-pyridin-4-yl)pyrimidin-4-yl)imino)(oxetan-3-yl)-$\lambda^6$-sulfanone | 428 | 429 | 12 |

TABLE 2-continued

Example compounds 55-125.

| Ex | Structure | IUPAC Name | MWt | [M + H] | Ex. Method |
|---|---|---|---|---|---|
| 61 | 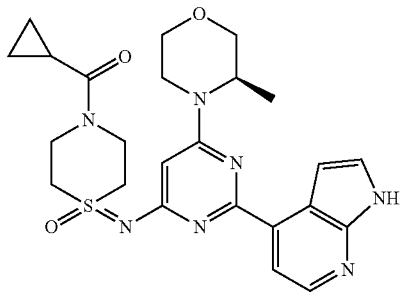 [SMILES: C[C@@H]1COCCN1c1cc(N=S2(=O)CCN(C(=O)C3CC3)CC2)nc(-c2ccnc3[nH]ccc23)n1] | (R)-cyclopropyl(1-((6-(3-methylmorpholino)-2-(1H-pyrrolo[2,3-b]-pyridin-4-yl)pyrimidin-4-yl)imino)-1-oxido-1$\lambda^6$-thiomorpholino)-methanone | 495 | 496 | 12 |
| 62 | 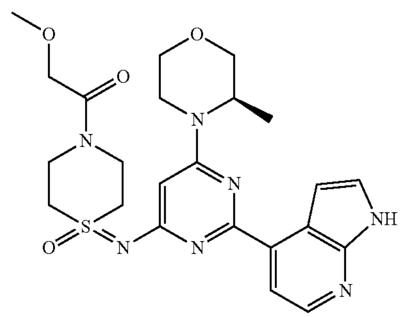 [SMILES: COCC(=O)N1CCS(=O)(=Nc2cc(N3CCOC[C@H]3C)nc(-c3ccnc4[nH]ccc34)n2)CC1] | (R)-2-methoxy-1-(1-((6-(3-methylmorpholino)-2-(1H-pyrrolo[2,3-b]-pyridin-4-yl)pyrimidin-4-yl)imino)-1-oxido-1$\lambda^6$-thiomorpholino)ethan-1-one | 499 | 500 | 12 |
| 63 | 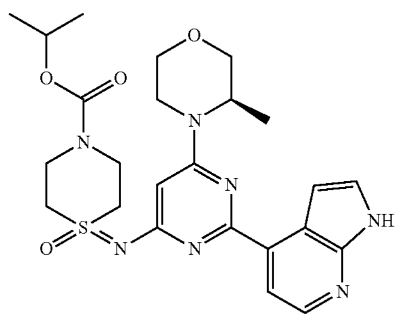 [SMILES: CC(C)OC(=O)N1CCS(=O)(=Nc2cc(N3CCOC[C@H]3C)nc(-c3ccnc4[nH]ccc34)n2)CC1] | Isopropyl (R)-1-((6-(3-methylmorpholino)-2-(1H-pyrrolo[2,3-b]-pyridin-4-yl)pyrimidin-4-yl)imino)-1$\lambda^6$-thiomorpholine-4-carboxylate 1-oxide | 513 | 514 | 12 |
| 64 | 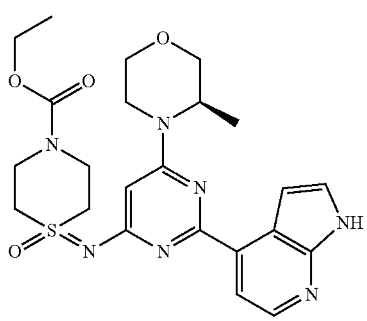 [SMILES: CCOC(=O)N1CCS(=O)(=Nc2cc(N3CCOC[C@H]3C)nc(-c3ccnc4[nH]ccc34)n2)CC1] | Ethyl (R)-1-((6-(3-methylmorpholino)-2-(1H-pyrrolo[2,3-b]-pyridin-4-yl)pyrimidin-4-yl)imino)-1$\lambda^6$-thiomorpholine-4-carboxylate 1-oxide | 499 | 500 | 12 |
| 65 | 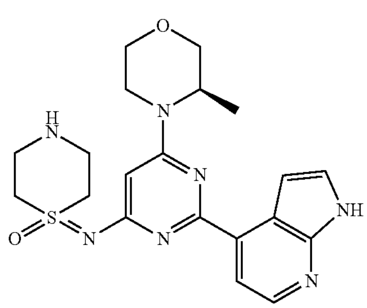 [SMILES: C[C@@H]1COCCN1c1cc(N=S2(=O)CCNCC2)nc(-c2ccnc3[nH]ccc23)n1] | (R)-1-((6-(3-methyl-morpholino)-2-(1H-pyrrolo[2,3-b]pyridin-4-yl)pyrimidin-4-yl)imino)-1$\lambda^6$-thiomorpholine 1-oxide | 427 | 428 | 12 |

TABLE 2-continued

Example compounds 55-125.

| Ex | Structure | IUPAC Name | MWt | [M + H] | Ex. Method |
|---|---|---|---|---|---|
| 66 | 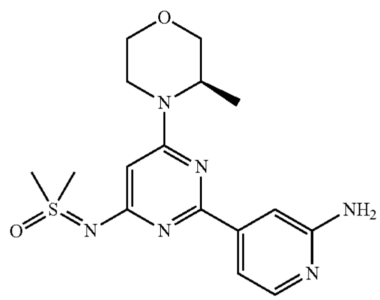 [SMILES: C[C@@H]1COCCN1c1cc(N=S(C)(C)=O)nc(-c2ccnc(N)c2)n1] | (R)-((2-(2-aminopyridin-4-yl)-6-(3-methyl-morpholino)pyrimidin-4-yl)imino)dimethyl-λ⁶-sulfanone | 362 | 363 | 24 |
| 67 | 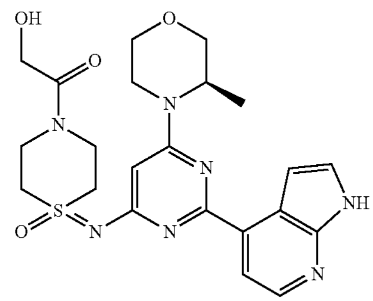 [SMILES: C[C@@H]1COCCN1c1cc(N=S2(=O)CCN(C(=O)CO)CC2)nc(-c2ccnc3[nH]ccc23)n1] | (R)-2-hydroxy-1-(1-((6-(3-methylmorpholino)-2-(1H-pyrrolo[2,3-b]-pyridin-4-yl)pyrimidin-4-yl)imino)-1-oxido-1λ⁶-thiomorpholino)ethan-1-one | 485 | 486 | 12 |
| 68 | 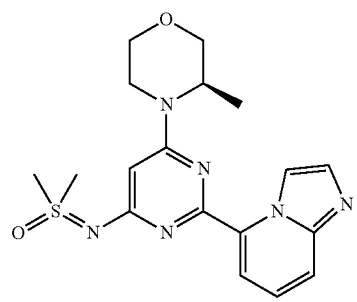 [SMILES: C[C@@H]1COCCN1c1cc(N=S(C)(C)=O)nc(-c2cccc3nccn23)n1] | (R)-((2-(imidazo[1,2-a]-pyridin-5-yl)-6-(3-methylmorpholino)-pyrimidin-4-yl)-imino)dimethyl-λ⁶-sulfanone | 386 | 387 | 25 |
| 69 | 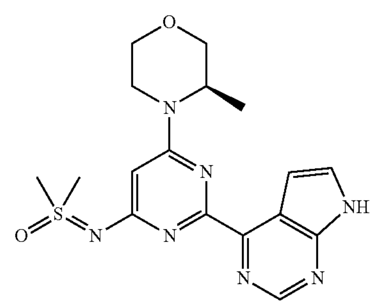 [SMILES: C[C@@H]1COCCN1c1cc(N=S(C)(C)=O)nc(-c2ncnc3[nH]ccc23)n1] | (R)-dimethyl((6-(3-methylmorpholino)-2-(7H-pyrrolo[2,3-d]-pyrimidin-4-yl)-pyrimidin-4-yl)imino)-λ⁶-sulfanone | 387 | 388 | 11 |
| 70 | 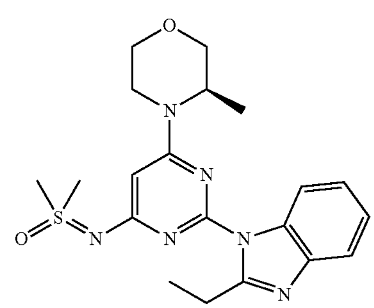 [SMILES: CCc1nc2ccccc2n1-c1nc(N=S(C)(C)=O)cc(N2CCOC[C@H]2C)n1] | (R)-((2-(2-ethyl-1H-benzo[d]imidazol-1-yl)-6-(3-methyl-morpholino)pyrimidin-4-yl)imino)dimethyl-λ⁶-sulfanone | 414 | 415 | 30 |

TABLE 2-continued

Example compounds 55-125.

| Ex | Structure | IUPAC Name | MWt | [M + H] | Ex. Method |
|---|---|---|---|---|---|
| 71 | 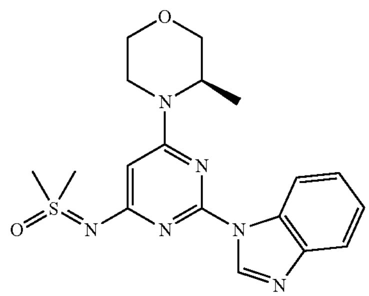 [SMILES: C[C@@H]1COCCN1c1cc(N=S(C)(C)=O)nc(-n2cnc3ccccc32)n1] | (R)-((2-(1H-benzo[d]imidazol-1-yl)-6-(3-methylmorpholino)-pyrimidin-4-yl)imino)-dimethyl-$\lambda^6$-sulfanone | 386 | 387 | 30 |
| 72 | 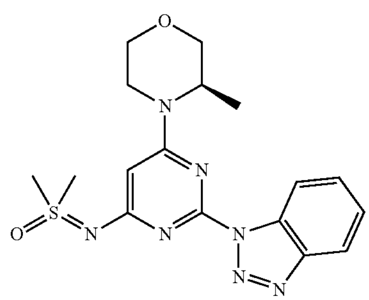 [SMILES: C[C@@H]1COCCN1c1cc(N=S(C)(C)=O)nc(-n2nnc3ccccc32)n1] | (R)-((2-(1H-benzo[d]-[1,2,3]triazol-1-yl)-6-(3-methylmorpholino)-pyrimidin-4-yl)imino)-dimethyl-$\lambda^6$-sulfanone | 387 | 388 | 30 |
| 73 | 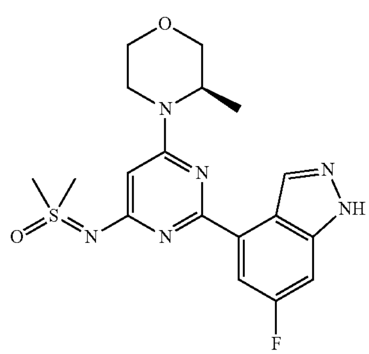 [SMILES: C[C@@H]1COCCN1c1cc(N=S(C)(C)=O)nc(-c2cc(F)cc3[nH]ncc23)n1] | (R)-((2-(6-fluoro-1H-indazol-4-yl)-6-(3-methylmorpholino)-pyrimidin-4-yl)imino)-dimethyl-$\lambda^6$-sulfanone | 404 | 405 | 25 |
| 74 | 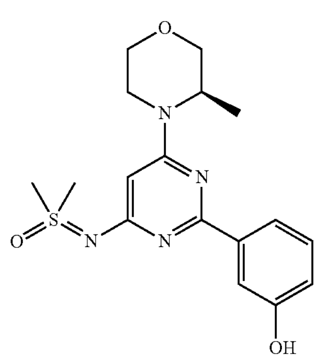 [SMILES: C[C@@H]1COCCN1c1cc(N=S(C)(C)=O)nc(-c2cccc(O)c2)n1] | (R)-((2-(3-hydroxy-phenyl)-6-(3-methyl-morpholino)pyrimidin-4-yl)imino)dimethyl-$\lambda^6$-sulfanone | 362 | 363 | 24 |

TABLE 2-continued

Example compounds 55-125.

| Ex | Structure | IUPAC Name | MWt | [M + H] | Ex. Method |
|---|---|---|---|---|---|
| 75 | 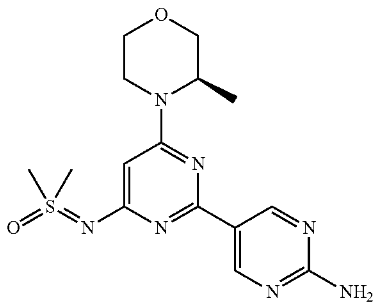 | (R)-((2'-amino-6-(3-methylmorpholino)-[2,5'-bipyrimidin]-4-yl)imino)-dimethyl-λ⁶-sulfanone | 363 | 364 | 24 |
| 76 | 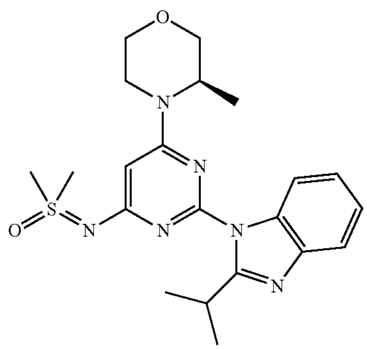 [SMILES: CC(C)c1nc2ccccc2n1-c1nc(N=S(C)(C)=O)cc(N2CCOC[C@H]2C)n1] | (R)-((2-(2-isopropyl-1H-benzo[d]imidazol-1-yl)-6-(3-methylmorpholino)-pyrimidin-4-yl)imino)-dimethyl-λ⁶-sulfanone | 428 | 429 | 30 |
| 77 | 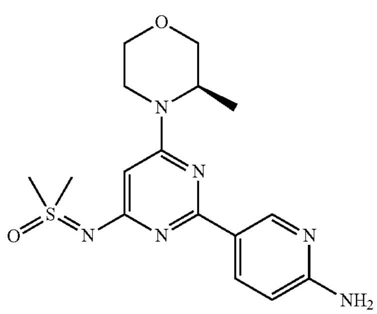 [SMILES: C[C@@H]1COCCN1c1cc(N=S(C)(C)=O)nc(-c2ccc(N)nc2)n1] | (R)-((2-(6-aminopyridin-3-yl)-6-(3-methyl-morpholino)pyrimidin-4-yl)imino)dimethyl-λ⁶-sulfanone | 362 | 363 | 24 |
| 78 | 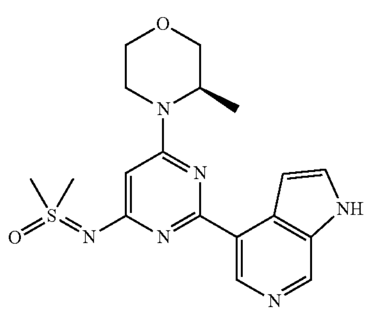 [SMILES: C[C@@H]1COCCN1c1cc(N=S(C)(C)=O)nc(-c2cncc3[nH]ccc23)n1] | (R)-dimethyl((6-(3-methylmorpholino)-2-(1H-pyrrolo[2,3-c]-pyridin-4-yl)pyrimidin-4-yl)imino)-λ⁶-sulfanone | 386 | 387 | 25 |

TABLE 2-continued

Example compounds 55-125.

| Ex | Structure | IUPAC Name | MWt | [M + H] | Ex. Method |
|---|---|---|---|---|---|
| 79 | 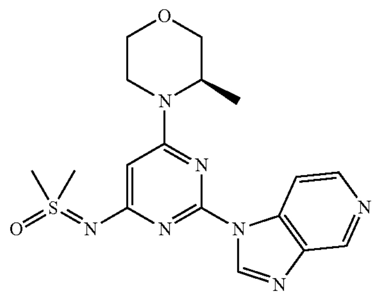 [SMILES: C[C@@H]1COCCN1c1cc(N=S(C)(C)=O)nc(-n2cnc3cnccc32)n1] | (R)-((2-(1H-imidazo[4,5-c]pyridin-1-yl)-6-(3-methylmorpholino)-pyrimidin-4-yl)imino)-dimethyl-$\lambda^6$-sulfanone | 387 | 388 | 36 |
| 80 | 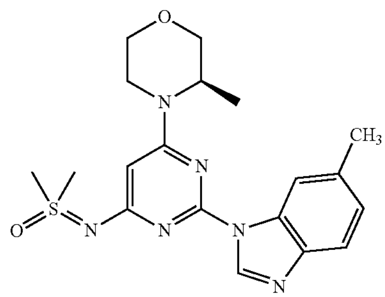 [SMILES: Cc1ccc2ncn(-c3nc(N=S(C)(C)=O)cc(N4CCOC[C@H]4C)n3)c2c1] | (R)-dimethyl((2-(6-methyl-1H-benzo[d]-imidazol-1-yl)-6-(3-methylmorpholino)-pyrimidin-4-yl)imino)-$\lambda^6$-sulfanone | 400 | 401 | 34 |
| 81 | 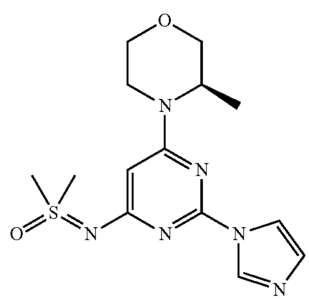 [SMILES: C[C@@H]1COCCN1c1cc(N=S(C)(C)=O)nc(-n2ccnc2)n1] | (R)-((2-(1H-imidazol-1-yl)-6-(3-methyl-morpholino)pyrimidin-4-yl)imino)dimethyl-$\lambda^6$-sulfanone | 336 | 337 | 30 |
| 82 | 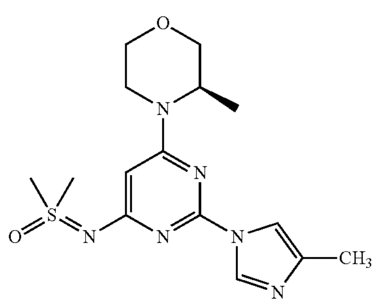 [SMILES: Cc1cn(-c2nc(N=S(C)(C)=O)cc(N3CCOC[C@H]3C)n2)cn1] | (R)-dimethyl((2-(4-methyl-1H-imidazol-1-yl)-6-(3-methyl-morpholino)pyrimidin-4-yl)imino)-$\lambda^6$-sulfanone | 350 | 351 | 30 |
| 83 | 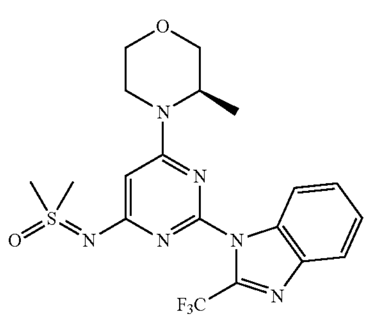 [SMILES: C[C@@H]1COCCN1c1cc(N=S(C)(C)=O)nc(-n2c(C(F)(F)F)nc3ccccc32)n1] | (R)-dimethyl((6-(3-methylmorpholino)-2-(2-(trifluoromethyl)-1H-benzo[d]imidazol-1-yl)-pyrimidin-4-yl)imino)-$\lambda^6$-sulfanone | 454 | 455 | 34 |

TABLE 2-continued

Example compounds 55-125.

| Ex | Structure | IUPAC Name | MWt | [M + H] | Ex. Method |
|---|---|---|---|---|---|
| 84 | 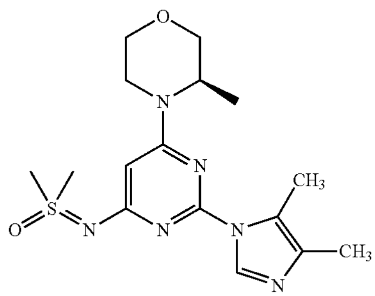 [SMILES: Cc1ncn(-c2nc(N=S(C)(C)=O)cc(N3CCOC[C@H]3C)n2)c1C] | (R)-((2-(4,5-dimethyl-1H-imidazol-1-yl)-6-(3-methylmorpholino)-pyrimidin-4-yl)-imino)dimethyl-$\lambda^6$-sulfanone | 364 | 365 | 30 |
| 85 | 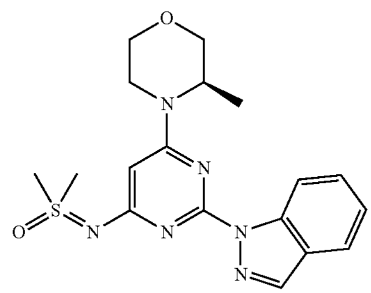 [SMILES: C[C@@H]1COCCN1c1cc(N=S(C)(C)=O)nc(-n2ncc3ccccc32)n1] | (R)-((2-(1H-indazol-1-yl)-6-(3-methyl-morpholino)pyrimidin-4-yl)imino)dimethyl-$\lambda^6$-sulfanone | 386 | 387 | 30 |
| 86 | 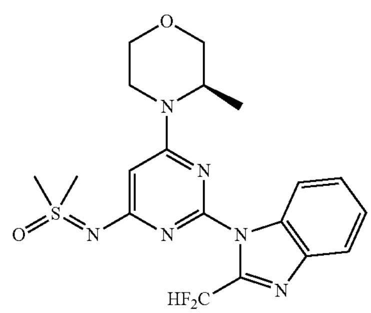 | (R)-((2-(2-(difluoro-methyl)-1H-benzo[d]-imidazol-1-yl)-6-(3-methylmorpholino)-pyrimidin-4-yl)imino)-dimethyl-$\lambda^6$-sulfanone | 436 | 437 | 34 |
| 87 | 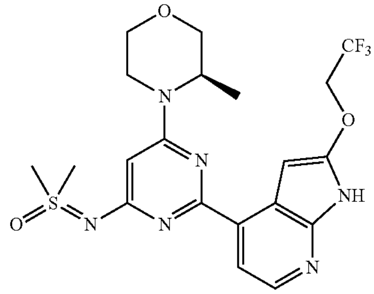 [SMILES: C[C@@H]1COCCN1c1cc(N=S(C)(C)=O)nc(-c2ccnc3[nH]c(OCC(F)(F)F)cc23)n1] | (R)-dimethyl((6-(3-methylmorpholino)-2-(2-(2,2,2-trifluoroethoxy)-1H-pyrrolo[2,3-b]pyridin-4-yl)pyrimidin-4-yl)imino)-$\lambda^6$-sulfanone | 484 | 485 | 25 |
| 88 | 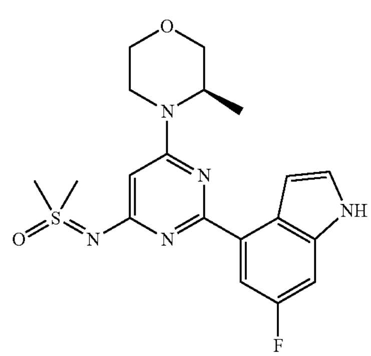 [SMILES: C[C@@H]1COCCN1c1cc(N=S(C)(C)=O)nc(-c2cc(F)cc3[nH]ccc23)n1] | (R)-((2-(6-fluoro-1H-indol-4-yl)-6-(3-methylmorpholino)-pyrimidin-4-yl)imino)-dimethyl-$\lambda^6$-sulfanone | 403 | 404 | 11 |

TABLE 2-continued

Example compounds 55-125.

| Ex | Structure | IUPAC Name | MWt | [M + H] | Ex. Method |
|---|---|---|---|---|---|
| 89 | 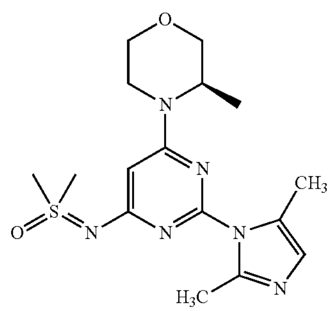 [SMILES: Cc1cnc(C)n1-c1nc(N=S(C)(C)=O)cc(N2CCOC[C@H]2C)n1] | (R)-((2-(2,5-dimethyl-1H-imidazol-1-yl)-6-(3-methylmorpholino)-pyrimidin-4-yl)imino)-dimethyl-$\lambda^6$-sulfanone | 364 | 365 | 30 |
| 90 | 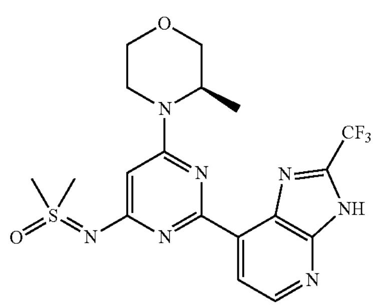 [SMILES: C[C@@H]1COCCN1c1cc(N=S(C)(C)=O)nc(-c2ccnc3[nH]c(C(F)(F)F)nc23)n1] | (R)-dimethyl((6-(3-methylmorpholino)-2-(2-(trifluoromethyl)-3H-imidazo[4,5-b]pyridin-7-yl)pyrimidin-4-yl)imino)-$\lambda^6$-sulfanone | 455 | 456 | 34 |
| 91 | 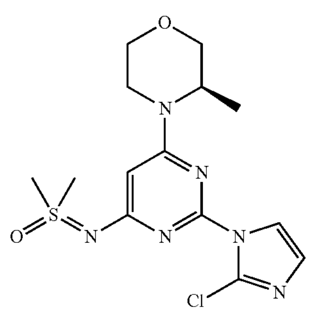 [SMILES: C[C@@H]1COCCN1c1cc(N=S(C)(C)=O)nc(-n2ccnc2Cl)n1] | (R)-((2-(2-chloro-1H-imidazol-1-yl)-6-(3-methylmorpholino)-pyrimidin-4-yl)imino)-dimethyl-$\lambda^6$-sulfanone | 370 | 371 | 30 |
| 92 | 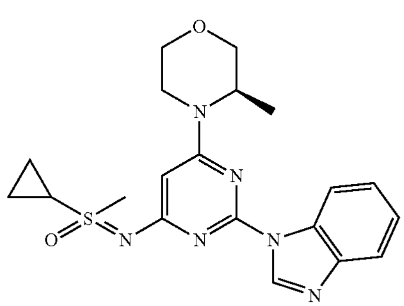 [SMILES: C[C@@H]1COCCN1c1cc(N=S(C)(=O)C2CC2)nc(-n2cnc3ccccc32)n1] | ((2-(1H-benzo[d]-imidazol-1-yl)-6-((R)-3-methylmorpholino)-pyrimidin-4-yl)imino)-(cyclopropyl)(methyl)-$\lambda^6$-sulfanone | 412 | 413 | 29 |
| 93 | 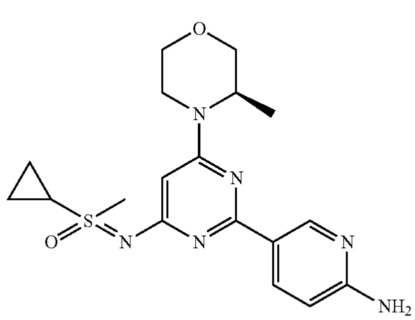 [SMILES: C[C@@H]1COCCN1c1cc(N=S(C)(=O)C2CC2)nc(-c2ccc(N)nc2)n1] | ((2-(6-aminopyridin-3-yl)-6-((R)-3-methyl-morpholino)pyrimidin-4-yl)imino)(cyclopropyl)-(methyl)-$\lambda^6$-sulfanone | 388 | 389 | 24 |

TABLE 2-continued

Example compounds 55-125.

| Ex | Structure | IUPAC Name | MWt | [M + H] | Ex. Method |
|---|---|---|---|---|---|
| 94 | 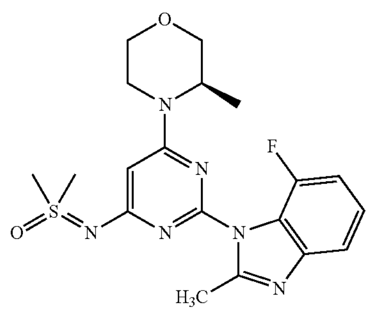 [SMILES: Cc1nc2cccc(F)c2n1-c1nc(N=S(C)(C)=O)cc(N2CCOC[C@H]2C)n1] | (R)-((2-(7-fluoro-2-methyl-1H-benzo[d]-imidazol-1-yl)-6-(3-methylmorpholino)-pyrimidin-4-yl)imino)-dimethyl-$\lambda^6$-sulfanone | 418 | 419 | 34 |
| 95 | 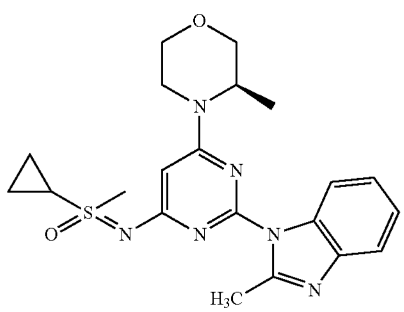 [SMILES: Cc1nc2ccccc2n1-c1nc(N=S(C)(=O)C2CC2)cc(N2CCOC[C@H]2C)n1] | Cyclopropyl(methyl)((2-(2-methyl-1H-benzo[d]-imidazol-1-yl)-6-((R)-3-methylmorpholino)-pyrimidin-4-yl)imino)-$\lambda^6$-sulfanone | 426 | 427 | 29 |
| 96 | 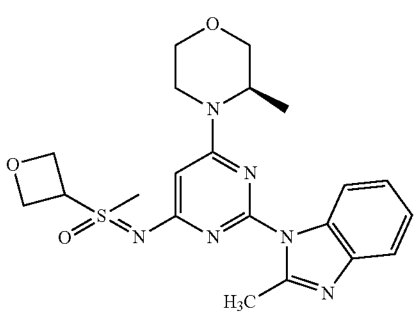 [SMILES: Cc1nc2ccccc2n1-c1nc(N=S(C)(=O)C2COC2)cc(N2CCOC[C@H]2C)n1] | Methyl((2-(2-methyl-1H-benzo[d]imidazol-1-yl)-6-((R)-3-methyl-morpholino)pyrimidin-4-yl)imino)(oxetan-3-yl)-$\lambda^6$-sulfanone | 442 | 443 | 29 |
| 97 | 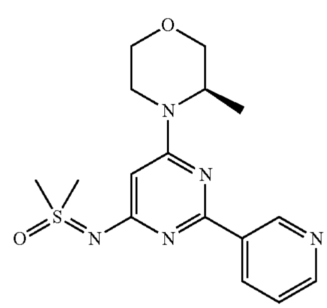 [SMILES: C[C@@H]1COCCN1c1cc(N=S(C)(C)=O)nc(-c2cccnc2)n1] | (R)-dimethyl((6-(3-methylmorpholino)-2-(pyridin-3-yl)pyrimidin-4-yl)imino)-$\lambda^6$-sulfanone | 347 | 348 | 10 |
| 98 | 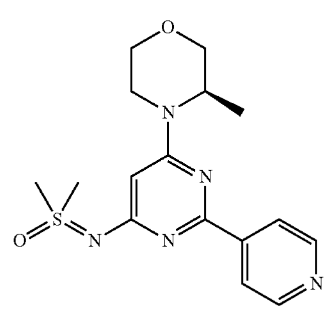 [SMILES: C[C@@H]1COCCN1c1cc(N=S(C)(C)=O)nc(-c2ccncc2)n1] | (R)-dimethyl((6-(3-methylmorpholino)-2-(pyridin-4-yl)pyrimidin-4-yl)imino)-$\lambda^6$-sulfanone | 347 | 348 | 10 |

TABLE 2-continued

Example compounds 55-125.

| Ex | Structure | IUPAC Name | MWt | [M + H] | Ex. Method |
|----|-----------|------------|-----|---------|------------|
| 99 | 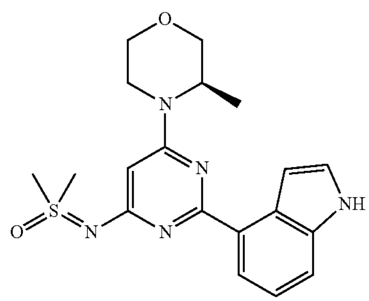 [SMILES: C[C@@H]1COCCN1c1cc(N=S(C)(C)=O)nc(-c2cccc3[nH]ccc23)n1] | (R)-((2-(1H-indol-4-yl)-6-(3-methylmorpholino)-pyrimidin-4-yl)imino)-dimethyl-$\lambda^6$-sulfanone | 385 | 386 | 11 |
| 100 | 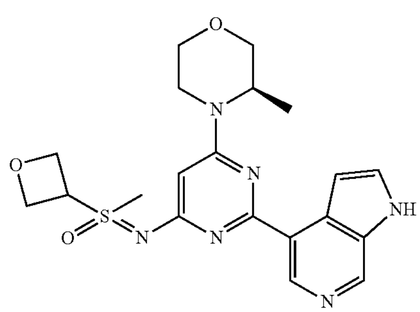 [SMILES: C[C@@H]1COCCN1c1cc(N=S(C)(=O)C2COC2)nc(-c2cncc3[nH]ccc23)n1] | Methyl((6-((R)-3-methylmorpholino)-2-(1H-pyrrolo[2,3-c]-pyridin-4-yl)pyrimidin-4-yl)imino)(oxetan-3-yl)-$\lambda^6$-sulfanone | 428 | 429 | 11 |
| 101 | 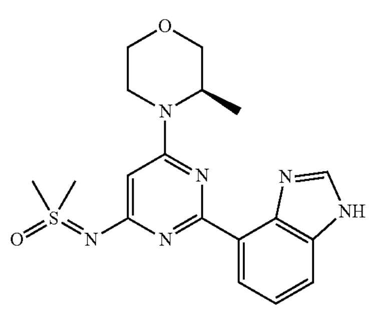 | (R)-((2-(1H-benzo[d]-imidazol-4-yl)-6-(3-methylmorpholino)-pyrimidin-4-yl)imino)-dimethyl-$\lambda^6$-sulfanone | 386 | 387 | 10 |
| 102 | 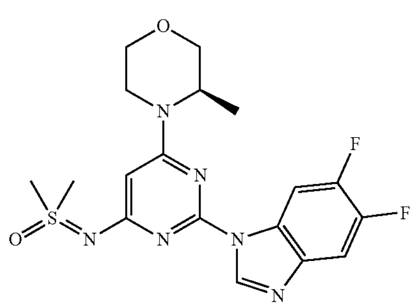 [SMILES: C[C@@H]1COCCN1c1cc(N=S(C)(C)=O)nc(-n2cnc3cc(F)c(F)cc32)n1] | (R)-((2-(5,6-difluoro-1H-benzo[d]imidazol-1-yl)-6-(3-methylmorpholino)-pyrimidin-4-yl)imino)-dimethyl-$\lambda^6$-sulfanone | 422 | 423 | 29 |

TABLE 2-continued

Example compounds 55-125.

| Ex | Structure | IUPAC Name | MWt | [M + H] | Ex. Method |
|---|---|---|---|---|---|
| 103 | 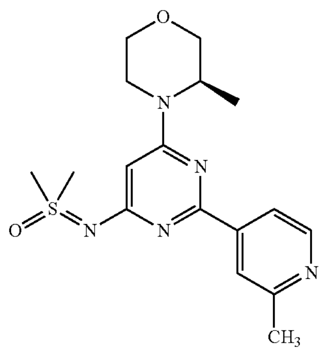 | (R)-dimethyl((6-(3-methylmorpholino)-2-(2-methylpyridin-4-yl)-pyrimidin-4-yl)imino)-$\lambda^6$-sulfanone | 361 | 362 | 10 |
| 104 | 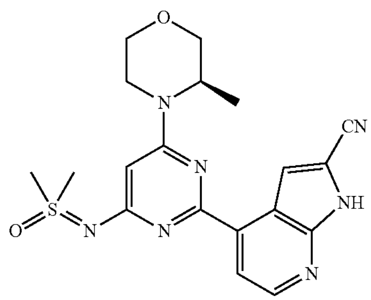 [SMILES: C[C@@H]1COCCN1c1cc(N=S(C)(C)=O)nc(-c2ccnc3[nH]c(C#N)cc23)n1] | (R)-4-(4-((dimethyl(oxo)-16-sulfaneylidene)-amino)-6-(3-methyl-morpholino)pyrimidin-2-yl)-1H-pyrrolo[2,3-b]-pyridine-2-carbonitrile | 411 | 412 | 11 |
| 105 | 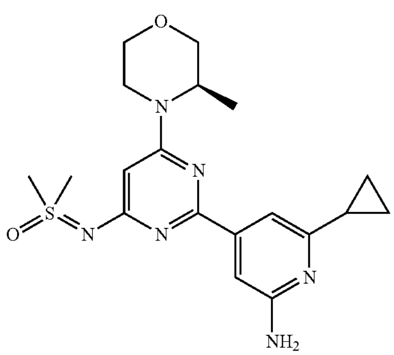 [SMILES: C[C@@H]1COCCN1c1cc(N=S(C)(C)=O)nc(-c2cc(N)nc(C3CC3)c2)n1] | (R)-((2-(2-amino-6-cyclopropylpyridin-4-yl)-6-(3-methylmorpholino)-pyrimidin-4-yl)imino)-dimethyl-$\lambda^6$-sulfanone | 402 | 403 | 14 |
| 106 | 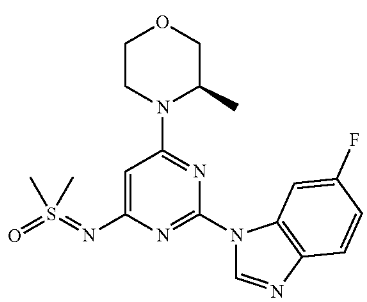 [SMILES: C[C@@H]1COCCN1c1cc(N=S(C)(C)=O)nc(-n2cnc3ccc(F)cc32)n1] | (R)-((2-(6-fluoro-1H-benzo[d]imidazol-1-yl)-6-(3-methylmorpholino)-pyrimidin-4-yl)imino)-dimethyl-$\lambda^6$-sulfanone | 404 | 405 | 35 |

TABLE 2-continued

Example compounds 55-125.

| Ex | Structure | IUPAC Name | MWt | [M + H] | Ex. Method |
|---|---|---|---|---|---|
| 107 | 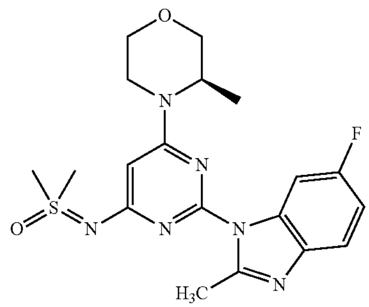 | (R)-((2-(6-fluoro-2-methyl-1H-benzo[d]-imidazol-1-yl)-6-(3-methylmorpholino)-pyrimidin-4-yl)imino)-dimethyl-λ⁶-sulfanone | 418 | 419 | 35 |
| 108 | 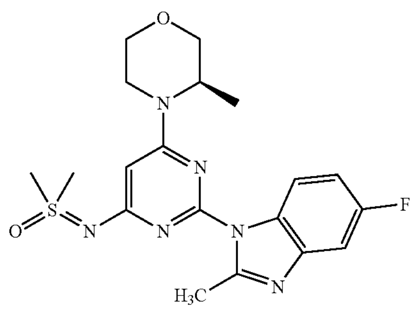 [SMILES: Cc1nc2cc(F)ccc2n1-c1nc(N=S(C)(C)=O)cc(N2CCOC[C@H]2C)n1] | (R)-((2-(5-fluoro-2-methyl-1H-benzo[d]-imidazol-1-yl)-6-(3-methylmorpholino)-pyrimidin-4-yl)imino)-dimethyl-λ⁶-sulfanone | 418 | 419 | 35 |
| 109 | 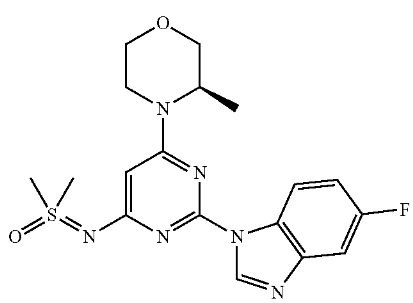 [SMILES: C[C@@H]1COCCN1c1cc(N=S(C)(C)=O)nc(-n2cnc3cc(F)ccc32)n1] | (R)-((2-(5-fluoro-1H-benzo[d]imidazol-1-yl)-6-(3-methylmorpholino)-pyrimidin-4-yl)imino)-dimethyl-λ⁶-sulfanone | 404 | 405 | 35 |
| 110 | 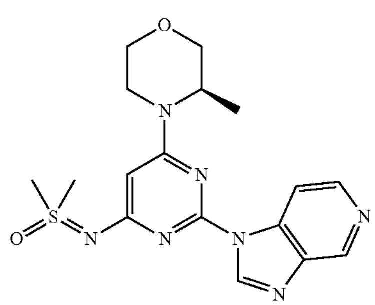 [SMILES: C[C@@H]1COCCN1c1cc(N=S(C)(C)=O)nc(-n2cnc3cnccc32)n1] | (R)-((2-(1H-imidazo[4,5-c]pyridin-1-yl)-6-(3-methylmorpholino)-pyrimidin-4-yl)imino)-dimethyl-λ⁶-sulfanone | 387 | 388 | 35 |

TABLE 2-continued

Example compounds 55-125.

| Ex | Structure | IUPAC Name | MWt | [M + H] | Ex. Method |
|---|---|---|---|---|---|
| 111 | 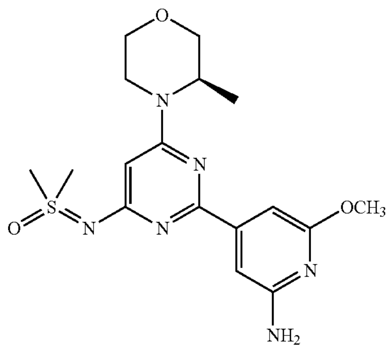 [SMILES: COc1cc(-c2nc(N=S(C)(C)=O)cc(N3CCOC[C@H]3C)n2)cc(N)n1] | (R)-((2-(2-amino-6-methoxypyridin-4-yl)-6-(3-methylmorpholino)-pyrimidin-4-yl)imino)-dimethyl-$\lambda^6$-sulfanone | 392 | 393 | 17 |
| 112 | 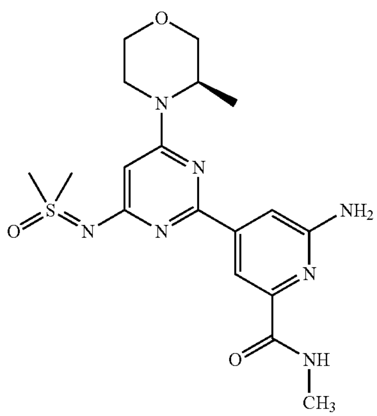 [SMILES: CNC(=O)c1cc(-c2nc(N=S(C)(C)=O)cc(N3CCOC[C@H]3C)n2)cc(N)n1] | (R)-6-amino-4-(4-((dimethyl(oxo)-$\lambda^6$-sulfaneylidene)amino)-6-(3-methylmorpholino)-pyrimidin-2-yl)-N-methylpicolinamide | 419 | 420 | 50 |
| 113 | 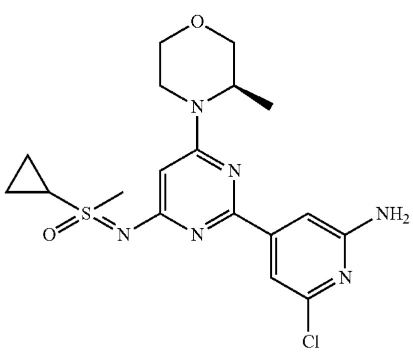 [SMILES: C[C@@H]1COCCN1c1cc(N=S(C)(=O)C2CC2)nc(-c2cc(N)nc(Cl)c2)n1] | ((2-(2-amino-6-chloropyridin-4-yl)-6-((R)-3-methyl-morpholino)pyrimidin-4-yl)imino)(cyclopropyl)-(methyl)-$\lambda^6$-sulfanone | 422 | 423 | 13 |
| 114 | 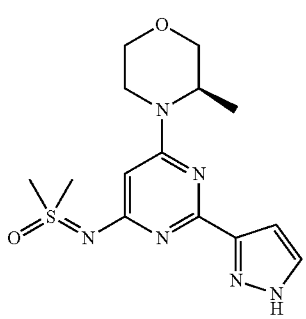 [SMILES: C[C@@H]1COCCN1c1cc(N=S(C)(C)=O)nc(-c2cc[nH]n2)n1] | (R)-dimethyl((6-(3-methylmorpholino)-2-(1H-pyrazol-3-yl)-pyrimidin-4-yl)imino)-$\lambda^6$-sulfanone | 336 | 337 | 10 |

TABLE 2-continued

Example compounds 55-125.

| Ex | Structure | IUPAC Name | MWt | [M + H] | Ex. Method |
|---|---|---|---|---|---|
| 115 | 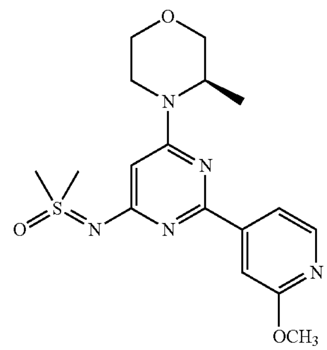 [SMILES: COc1cc(-c2nc(N=S(C)(C)=O)cc(N3CCOC[C@H]3C)n2)ccn1] | (R)-((2-(2-methoxy-pyridin-4-yl)-6-(3-methylmorpholino)-pyrimidin-4-yl)imino)-dimethyl-$\lambda^6$-sulfanone | 377 | 378 | 10 |
| 116 | 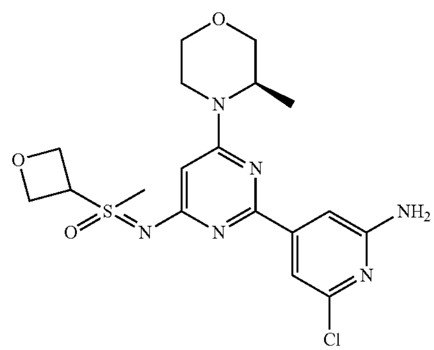 [SMILES: C[C@@H]1COCCN1c1cc(N=S(C)(=O)C2COC2)nc(-c2cc(N)nc(Cl)c2)n1] | ((2-(2-Amino-6-chloropyridin-4-yl)-6-((R)-3-methyl-morpholino)pyrimidin-4-yl)imino)(methyl)-(oxetan-3-yl)-$\lambda^6$-sulfanone | 438 | 439 | 13 |
| 117 | 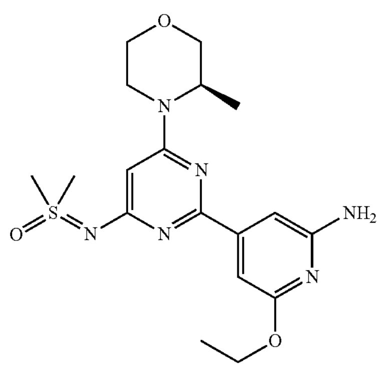 [SMILES: CCOc1cc(-c2nc(N=S(C)(C)=O)cc(N3CCOC[C@H]3C)n2)cc(N)n1] | (R)-((2-(2-amino-6-ethoxypyridin-4-yl)-6-(3-methylmorpholino)-pyrimidin-4-yl)imino)-dimethyl-$\lambda^6$-sulfanone | 406 | 407 | 17 |
| 118 | 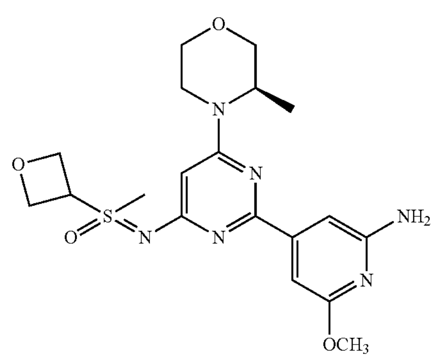 [SMILES: COc1cc(-c2nc(N=S(C)(=O)C3COC3)cc(N3CCOC[C@H]3C)n2)cc(N)n1] | ((2-(2-Amino-6-methoxypyridin-4-yl)-6-((R)-3-methyl-morpholino)pyrimidin-4-yl)imino)(methyl)-(oxetan-3-yl)-$\lambda^6$-sulfanone | 434 | 435 | 17 |

TABLE 2-continued

Example compounds 55-125.

| Ex | Structure | IUPAC Name | MWt | [M + H] | Ex. Method |
|---|---|---|---|---|---|
| 119 | 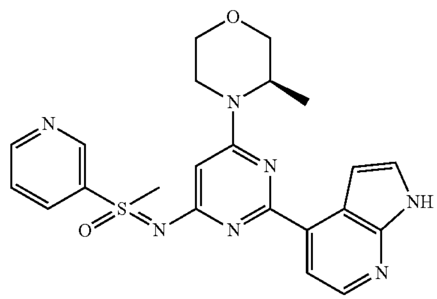 [SMILES: C[C@@H]1COCCN1c1cc(N=S(C)(=O)c2cccnc2)nc(-c2ccnc3[nH]ccc23)n1] | Methyl((6-((R)-3-methylmorpholino)-2-(1H-pyrrolo[2,3-b]-pyridin-4-yl)pyrimidin-4-yl)imino)(pyridin-3-yl)-$\lambda^6$-sulfanone | 449 | 450 | 16 |
| 120 | 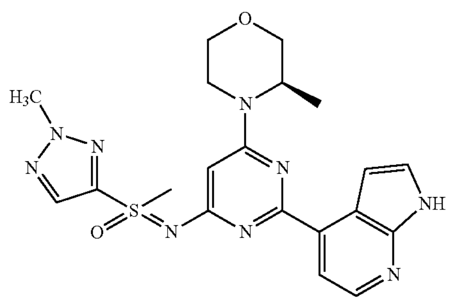 [SMILES: C[C@@H]1COCCN1c1cc(N=S(C)(=O)c2cnn(C)n2)nc(-c2ccnc3[nH]ccc23)n1] | Methyl(1-methyl-1H-pyrazol-4-yl)((6-((R)-3-methylmorpholino)-2-(1H-pyrrolo[2,3-b]-pyridin-4-yl)pyrimidin-4-yl)imino)-$\lambda^6$-sulfanone | 452 | 453 | 16 |
| 121 | 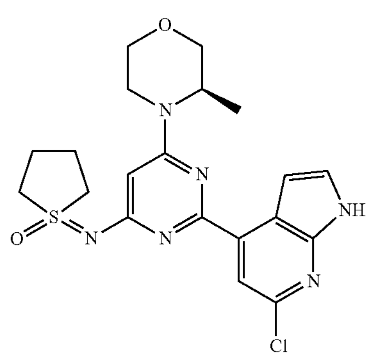 [SMILES: C[C@@H]1COCCN1c1cc(N=S2(=O)CCCC2)nc(-c2cc(Cl)nc3[nH]ccc23)n1] | (R)-1-((2-(6-chloro-1H-pyrrolo[2,3-b]pyridin-4-yl)-6-(3-methyl-morpholino)pyrimidin-4-yl)imino)tetrahydro-1H-1$\lambda^6$-thiophene 1-oxide | 446 | 447 | 19 |
| 122 | 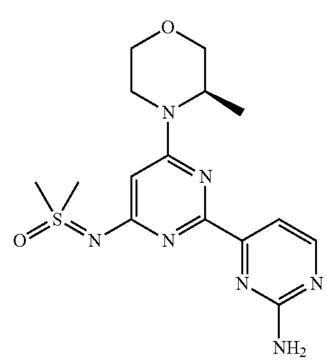 [SMILES: C[C@@H]1COCCN1c1cc(N=S(C)(C)=O)nc(-c2ccnc(N)n2)n1] | (R)-((2'-amino-6-(3-methylmorpholino)-[2,4'-bipyrimidin]-4-yl)imino)dimethyl-$\lambda^6$-sulfanone | 363 | 364 | 25 |

TABLE 2-continued

Example compounds 55-125.

| Ex | Structure | IUPAC Name | MWt | [M + H] | Ex. Method |
|---|---|---|---|---|---|
| 123 | 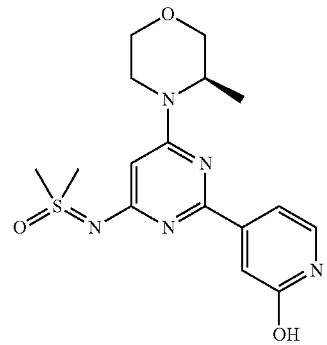 [SMILES: C[C@@H]1COCCN1c1cc(N=S(C)(C)=O)nc(-c2ccnc(O)c2)n1] | (R)-((2-(2-hydroxypyridin-4-yl)-6-(3-methylmorpholino)-pyrimidin-4-yl)imino)-dimethyl-$\lambda^6$-sulfanone | 363 | 364 | 10 |
| 124 | 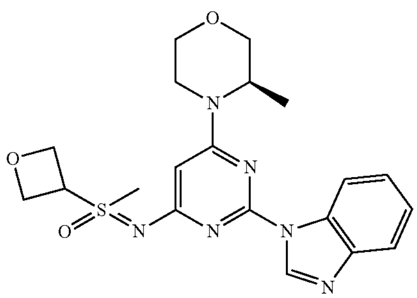 [SMILES: C[C@@H]1COCCN1c1cc(N=S(C)(=O)C2COC2)nc(-n2cnc3ccccc32)n1] | ((2-(1H-benzo[d]-imidazol-1-yl)-6-((R)-3-methylmorpholino)-pyrimidin-4-yl)imino)-(methyl)(oxetan-3-yl)-$\lambda^6$-sulfanone | 428 | 429 | 29 |
| 125 | 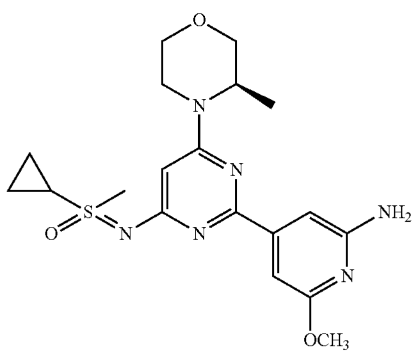 [SMILES: COc1cc(-c2nc(N=S(C)(=O)C3CC3)cc(N3CCOC[C@H]3C)n2)cc(N)n1] | ((2-(2-Amino-6-methoxypyridin-4-yl)-6-((R)-3-methyl-morpholino)pyrimidin-4-yl)imino)(cyclopropyl)-(methyl)-$\lambda^6$-sulfanone | 418 | 419 | 18 |

The activity of the compounds in Examples 1-125 as ATR inhibitors is illustrated in the following assay. The other compounds listed below, which have not yet been made and/or tested, are predicted to have activity in this assay as well.

| Structure | IUPAC Name |
|---|---|
| 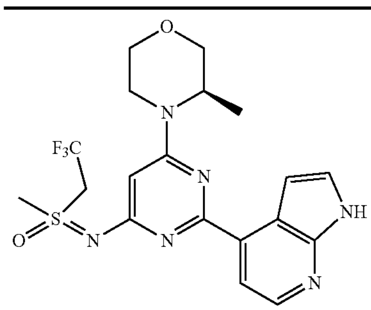 | methyl 2,2,2-trifluoroethyl ({6-[(3R)-3-methylmorpholin-4-yl]-2-{1H-pyrrolo[2,3-b]pyridin-4-yl}pyrimidin-4-yl}imino)-$\lambda^6$-sulfanone |

ATR/ATRIP Enzymatic Assay

Human full-length FLAG-TEV-ATR and His$_6$-ATRIP were co-expressed in HEK293 cells. The cell pellet (20 g) was harvested and lysed in 100 mL of lysis buffer (20 mM Tris-HCl pH 7.5 at room temperature, 137 mM NaCl, 10% glycerol, 1 mM DTT, 1% (v/v) Tween-20, 0.1% (v/v) NP-40, complete protease inhibitor cocktail tablets, phosphatase inhibitor cocktail tablets, 2 mM MgCl$_2$, 0.2 mM EDTA, and 1 mM ATP). After sonication and centrifugation, the supernatant was incubated at 4° C. for 3 hours with 1 mL of anti-FLAG resin (Sigma catalog #A2220) that had been pre-equilibrated in buffer A (20 mM Tris-HCl pH 7.5 at room temperature, 137 mM NaCl, 10% glycerol, 1 mM DTT, 2 mM MgCl$_2$, and 0.2 mM EDTA). The sample was loaded into a column, and then washed with buffer A three times. Protein was subsequently eluted with 2 ml of buffer B (buffer A+200 g/ml 3×FLAG peptide).

The ability of new chemical matter to inhibit the ATR catalytic activity in this ATR/ATRIP complex was assessed using a Caliper-based assay. A 2× enzyme solution (i.e., 4 nM enzyme) was prepared using 1× Kinase Reaction Buffer (25 mM HEPES pH 8, 0.0055% Brij-35, 10 mM MnCl$_2$, and 1 mM DTT). A 2× peptide solution was then prepared consisting of 10 uM FAM-labeled RAD17 peptide (GL Biochem, catalog #524315) in 1× Kinase Reaction Buffer supplemented with 2 µM ATP. 10 µL of the 2× enzyme solution was transferred to an assay plate containing 60 nL of test compound (from a 3× serial dilution) in 100% DMSO. Following a 30 minute incubation at 28° C., 10 µL of the 2× peptide solution was then transferred to the same assay plate. The reaction was allowed to incubate at 28° C. for 6 hours. After adding 30 µL of stop buffer (100 mM HEPES pH 7.5, 0.015% Brij-35, 0.2% Coating-3 Reagent (PerkinElmer, catalog #PN760050), and 50 mM EDTA), data were collected on a Caliper instrument. Conversion values were converted to inhibition values via the following equation: % inhibition=(max−conversion)/(max−min)*100, whereby "max" corresponds to the DMSO control and "min" corresponds to the low control. IC$_{50}$ values were calculated using the following equation in XLFit: Y=Bottom+(Top−Bottom)/1+(IC$_{50}$/X)^HillSlope).

pCHK1 Cellular Assay

Inhibitors of ATR kinase are effective at inhibiting the ATR-driven phosphorylation of the downstream target Chk1 kinase at Serine 345, following the addition of 4-nitroquinoline N-oxide, a chemical used to induce DNA damage. Cellular IC$_{50}$ for the inhibitors of ATR described herein were measured in HT-29 colorectal adenocarcinoma cells. HT-29 cells were routinely maintained in McCoy's 5A media (ATCC Catalog #30-2007) supplemented with 10% fetal bovine serum (Sigma Catalog #F2442) and 1× Penicillin-Streptomycin (Gibco Catalog #15140-122) using a humidified incubator (37° C., 5% CO$_2$, and ambient 02). In preparation for the CHK1 (p-Ser345) ALPHASCREEN® SUREFIRE® assay, cells were harvested and resuspended in McCoy's 5A media supplemented with 10% fetal bovine serum and 1× Penicillin-Streptomycin. Cells were seeded onto a 384-well black CELLSTAR® Tissue Culture Plate (VWR Catalog #89085-314) at a density of 13,000 cells/well in a volume of 40 µL. The microplate was incubated overnight (approximately 20 hours) at 37° C. with 5% CO$_2$ and ambient 02. Stock solutions of the test compounds were prepared in 100% DMSO (Sigma, Catalog #D2650) and serially diluted 1:3 using 100% DMSO. Compounds were additionally diluted 1:33 in culture medium, and 10 L/well were transferred to the tissue culture plate. Following the compound addition the microplate was incubated at 37° C. for 90 minutes. 10 µL of 4-nitroquinoline N-oxide (Sigma Aldrich Catalog #N8141-1G) diluted in media (final concentration 12 uM) were added to the tissue culture plate followed by a 120 minute incubation at 37° C. The cells were then washed with PBS and lysed using 10 µL/well SUREFIRE® Kit lysis buffer diluted to 1× in water (PerkinElmer Catalog #TGRCHK1S50K), with mixing on an orbital shaker at 500 rpm for 20 min at RT. Lysates were frozen at −20° C. overnight.

4 µL/well of lysate was then transferred from the tissue culture plate to a 384-well, white, low volume, PROXIPLATE™ (PerkinElmer Catalog #600828). 5 µL/well of the acceptor bead solution, prepared by diluting SUREFIRE® Kit activation buffer (PerkinElmer Catalog #TGRCHK1S50K) and ALPHASCREEN® Protein A acceptor beads (PerkinElmer Catalog #6760617R) in SUREFIRE® Kit reaction buffer (PerkinElmer Catalog #TGRCHK1S50K), were added to the lysates under subdued light and incubated at room temperature for 120 min. 2 uL/well of the donor bead solution, prepared by diluting ALPHASCREEN® Streptavidin donor beads (PerkinElmer Catalog #6760617R) in SUREFIRE® Kit dilution buffer (PerkinElmer Catalog #TGRCHK1S50K), were added under subdued light and incubated at room temperature for an addition 120 minutes. The pCHK1 ALPHASCREEN® signal was measured using an ENVISION® plate reader (PerkinElmer). IC$_{50}$ values were calculated using a four-parameter logistic curve fit using Genedata Screener software. Percent of control for each compound concentration was calculated by the following formula: 100*(Compound−Min)/(Max−Mn) where "Max" is the high control, DMSO, and "Min" is the low control, 5 uM ATR inhibitor.

TABLE 3

ATR/ATRIP Enzyme IC$_{50}$ values

| Ex | ATR-ATRIP IC$_{50}$, nM | pCHK1 IC$_{50}$ (nM) |
|---|---|---|
| 1 | 1 | 46 |
| 2 | 5 | 64 |
| 3 | 2 | 44 |
| 4 | 8 | 86 |
| 5 | 3 | 48 |
| 6 | N.A. | 212 |
| 7 | 4 | 77 |
| 8 | N.A. | 167 |
| 9 | N.A. | 136 |
| 10 | 26 | 909 |
| 11 | 7 | 17 |
| 12 | 4 | 56 |
| 13 | 104 | 73 |
| 14 | 122 | 463 |
| 15 | 182 | 335 |
| 16 | 3 | 20 |
| 17a | 4 | 38 |
| 17b | 7 | 61 |
| 18a | 258 | 408 |
| 18b | 71 | 49 |
| 19 | 8 | 131 |
| 20 | 67 | 798 |
| 21 | 21 | 311 |
| 22 | 77 | 669 |
| 23 | 31 | 1718 |
| 24 | 36 | 1986 |
| 25 | 22 | 39 |
| 26 | 81 | 131 |
| 27 | 405 | 1855 |
| 28 | 246 | 575 |
| 29 | 10 | 92 |
| 30 | 3 | 47 |
| 31 | 1.6 | 14 |
| 32 | 259 | 10000 |
| 33 | 47 | 1617 |
| 34 | 3 | 895 |
| 35 | 195 | 1177 |
| 36 | 50 | 4668 |
| 37 | 306 | 87 |
| 38a | 0.7 | 56 |
| 38b | 1.4 | 563 |
| 39a | 48 | 26 |
| 39b | 525 | 1356 |
| 40a | 0.8 | 402 |
| 40b | 0.3 | 30 |
| 41a | 15 | 945 |
| 41b | 0.8 | 28 |
| 42a | 31 | 25 |
| 42b | 284 | 940 |
| 43a | 153 | 44 |
| 43b | 387 | 399 |
| 44a | 6 | 902 |
| 44b | 0.4 | 18 |
| 45a | 110 | 65 |
| 45b | 419 | 431 |
| 46a | 8 | 179 |
| 46b | 1 | 8 |
| 47 | 3 | 1372 |
| 48 | 34 | 263 |

TABLE 3-continued

ATR/ATRIP Enzyme $IC_{50}$ values

| Ex | ATR-ATRIP $IC_{50}$, nM | pCHK1 $IC_{50}$ (nM) |
|---|---|---|
| 49 | 159 | 7586 |
| 50 | 486 | 8232 |
| 51 | 55 | 439 |
| 52 | 0.9 | 44 |
| 53 | 0.5 | 14 |
| 54 | 978 | 3033 |
| 55 | 4 | 61 |
| 56 | 2 | 27 |
| 57 | 15 | 202 |
| 58 | 15 | 175 |
| 59 | 21 | 183 |
| 60 | 4 | 41 |
| 61 | 3 | 77 |
| 62 | 5 | 89 |
| 63 | 4 | 169 |
| 64 | 2 | 68 |
| 65 | 20 | 372 |
| 66 | 207 | 198 |
| 67 | 3 | 168 |
| 68 | 244 | 1448 |
| 69 | 59 | 676 |
| 70 | 3 | 48 |
| 71 | 2 | 138 |
| 72 | 23 | 4414 |
| 73 | 27 | 2317 |
| 74 | 73 | 6099 |
| 75 | 63 | 1668 |
| 76 | 17 | 408 |
| 77 | 135 | 3385 |
| 78 | 5 | 22 |
| 79 | 233 | 6070 |
| 80 | 6 | 720 |
| 81 | 353 | 219 |
| 82 | 134 | 670 |
| 83 | 45 | 1569 |
| 84 | 158 | 1828 |
| 85 | 20 | 7684 |
| 86 | 0.4 | 28 |
| 87 | 316 | 164 |
| 88 | 2 | 58 |
| 89 | 435 | 653 |
| 90 | 1072 | 133 |
| 91 | 334 | 228 |
| 92 | 4 | 46 |
| 93 | 115 | 48 |
| 94 | 326 | 10000 |
| 95 | 0.9 | 20 |
| 96 | 3 | 57 |
| 97 | 208 | 776 |
| 98 | 117 | 252 |
| 99 | 3 | 99 |
| 100 | 3 | 26 |
| 101 | 17 | 158 |
| 102 | 10 | 904 |
| 103 | 218 | 1217 |
| 104 | 88 | 244 |
| 105 | 14 | 757 |
| 106 | 3 | 351 |
| 107 | 7 | 339 |
| 108 | 2 | 110 |
| 109 | 2 | 341 |
| 110 | 143 | 4326 |
| 111 | 123 | 273 |
| 112 | 205 | 4888 |
| 113 | 72 | 51 |
| 114 | 480 | 1113 |
| 115 | 307 | 3623 |
| 116 | 105 | 58 |
| 117 | 277 | 564 |
| 118 | 158 | 136 |
| 119 | 17 | 175 |
| 120 | 26 | 250 |

TABLE 3-continued

ATR/ATRIP Enzyme $IC_{50}$ values

| Ex | ATR-ATRIP $IC_{50}$, nM | pCHK1 $IC_{50}$ (nM) |
|---|---|---|
| 121 | 24 | 133 |
| 122 | 594 | 6478 |
| 123 | 821 | >10000 |

N.A. = not available

Anti-Tumor Effects in Mouse Xenografts

The effect of compounds 1, 39a, 30, and 18b on tumor growth was assessed in a LoVo (human colorectal) mouse xenograft model. Female CD1 nude mice were injected subcutaneously in the right flank with a suspension of LoVo cells (1 million cells/100 ul PBS+100 ul Matrigel; cells purchased from ATCC and cultured following ATCC's guideline). After implantation, tumor volume (TV) was measured weekly and mice bearing tumors with volumes between 200-250 mm$^3$ were randomized into treatment groups of 5 to 10 mice each. Mice were dosed by oral gavage, once daily for 21 days with either vehicle or 1, 39a, 30, and 18b at the doses reported in Table 4. The doses were scaled to the body weights (BW) of individual animals at a dosing volume of 10 mL/Kg. Throughout the duration of study tumor growth was assessed by caliper measurement and treatment response was determined by percent tumor growth inhibition (% TGI; calculated as TGI %=100−([TV$_{end-treat}$−TV$_{start-treat}$]/[TV$_{end-cntrl}$−TV$_{tart-cntrl}$]; where TV$_{end-treat}$, TV$_{start-treat}$, TV$_{end-cntrl}$ and TV$_{tart-cntrl}$ are the median tumor volumes for the compound treated and control groups respectively at the end and at the start of the study. Mouse body weight was measured bi-weekly, and reported as percentage of mean BW change from Day 1. Significant tumor growth inhibition was observed for all the compounds, as shown in Table 4, with no body weight loss.

TABLE 4

Anti-tumor effect in LoVo xenograft model in CD1 nude mice

| Ex. | Dose (mg/Kg) | Tumor Growth Inhibition % (TGI %; day 21) | Body Weight Change % (BW %; day 21) |
|---|---|---|---|
| 1 | 100 | 96* | +9.8 |
| 39a | 25 | 59* | +0.9 |
| 30 | 10 | 73* | +7.3 |
| 18b | 10 | 81* | +0.4 |

\* = p < 0.05 \*\*, two-tailed test;

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this disclosure, and without departing from the spirit and scope thereof, can make various changes and modifications of the disclosure to adapt it to various usages and conditions.

What is claimed is:

1. A method for preparing a compound of Formula 203

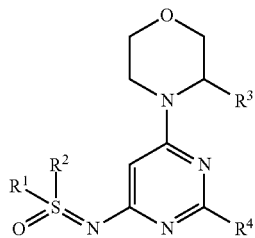

(203)

wherein

R$^1$ and R$^2$ are independently chosen from C$_{1-4}$alkyl, C$_{1-4}$haloalkyl, C$_{3-6}$cycloalkyl, C$_{3-6}$heterocycloalkyl, C$_{5-10}$aryl, and 5-10 membered heteroaryl, any of which is optionally substituted with one or more R$^5$ groups, or R$^1$ and R$^2$, together with the sulfur to which they are both attached, form a 4, 5, 6, or 7-membered heterocycloalkyl ring which is optionally substituted with one or more R$^5$ groups;

R$^3$ is chosen from hydrogen, C$_{1-6}$alkyl, and C$_{1-6}$haloalkyl;

R$^4$ is chosen from C$_{5-10}$aryl or 5-10 membered heteroaryl, either of which is optionally substituted with one or more R$^6$ groups;

each R$^5$ is independently chosen from NR$^8$R$^9$, halogen, cyano, hydroxy, oxo, alkyl, haloalkyl, C$_{3-6}$cycloalkyl, 3-6 membered heterocycloalkyl, hydroxyalkyl, OR$^8$, NR$^7$C(O)R$^8$, NR$^7$C(O)OR$^8$, NR$^7$C(O)NR$^8$R$^9$, C(O)R$^8$, C(O)OR$^8$, and C(O)NR$^8$R$^9$;

each R$^6$ is independently chosen from NR$^{11}$R$^{12}$, halogen, cyano, hydroxy, oxo, alkyl, haloalkyl, C$_{3-6}$cycloalkyl, 3-6 membered heterocycloalkyl, hydroxyalkyl, OR$^{11}$, NR$^{10}$C(O)R$^{11}$, NR$^{10}$C(O)OR$^{11}$, NR$^{10}$C(O)NR$^{11}$R$^{12}$, C(O)R$^{11}$, C(O)OR$^{11}$, and C(O)NR$^{11}$R$^{12}$;

each R$^7$, R$^8$ and R$^9$ is independently chosen from hydrogen, C$_{1-4}$alkyl, C$_{3-6}$cycloalkyl, and 3-6 membered heterocycloalkyl, any of which is optionally substituted with halo, hydroxy, C$_{1-3}$alkyl, C$_{1-3}$haloalkyl and C$_{1-3}$alkoxy; or any two of R$^7$, R$^8$ and R$^9$, together with the atom to which they are both attached can form a 3-7 membered cycloalkyl or heterocycloalkyl ring; and each R$^{10}$, R$^{11}$ and R$^{12}$ is independently chosen from hydrogen, C$_{1-4}$alkyl, C$_{3-6}$cycloalkyl, 3-6 membered heterocycloalkyl, any of which is optionally substituted with one or more groups chosen from halo, hydroxy and alkoxy; or any two of R$^{10}$, R$^{11}$ and R$^{12}$, together with the atom to which they are both attached, can form a 3-7 membered cycloalkyl or heterocycloalkyl ring, said method comprising reacting a compound of formula 202

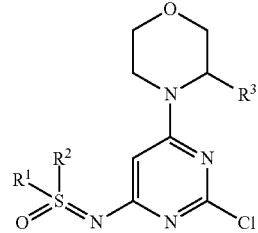

(202)

with a compound of formula

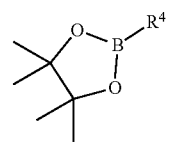

to yield a compound of formula 203.

2. The method of claim 1, wherein said reacting occurs in the presence of PdCl$_2$(dppf).

3. The method of claim 2, wherein said reacting occurs in the presence of dioxane.

4. The method of claim 1, wherein the compound of formula 203 comprises a mixture of diastereomers.

5. The method of claim 4, further comprising separating the mixture of diastereomers.

6. The method of claim 1, wherein R$^3$ is chosen from methyl, fluoromethyl, difluoromethyl, and trifluoromethyl.

7. The method of claim 1, wherein R$^4$ is 5-10 membered heteroaryl and is optionally substituted with one or more R$^6$ groups.

8. The method of claim 7, wherein R$^4$ is chosen from 1H-pyrazol-1-yl, 1H-pyrazol-3-yl, 1H-pyrazol-4-yl, 1H-imidazol-1-yl, 1H-imidazol-2-yl, 1H-imidazol-4-yl, pyridin-3-yl, pyridin-4-yl, pyrimidin-4-yl, 1H-indol-1-yl, 1H-indol-4-yl,1H-indazol-1-yl,1H-indazol-4-yl, 1H-benzo[d]imidazol-1-yl, 1H-benzo[d]imidazol-4-yl,1H-pyrrolo[2,3-b]pyridin-4-yl, 1H-pyrrolo[2,3-c]pyridin-4-yl, pyrazolo[1,5-a]pyridin-3-yl, imidazo[1,2-a]pyridin-3-yl, imidazo[1,2-a]pyridin-5-yl, 1H-imidazo[4,5-c]pyridin-1-yl, 7H-pyrrolo[2,3-d]pyrimidin-4-yl,1H-pyrazolo[3,4-b]pyridin-4-yl, 3H-imidazo[4,5-b]pyridin-7-yl, and 1H-benzo[d][1,2,3]triazol-1-yl, any of which is optionally substituted with one or two R$^6$ groups.

9. The method of claim 7, wherein R$^4$ is pyridine and is optionally substituted with one or more R$^6$ groups.

10. The method of claim 1, wherein:

each R$^6$ is independently chosen from NR$^{11}$R$^{12}$, halogen, cyano, hydroxy, oxo, OR$^{11}$, NR$^{10}$C(O)R$^{11}$, NR$^{10}$C(O)OR$^{11}$, NR$^{10}$C(O)NR$^{11}$R$^{12}$, C(O)R$^{11}$, C(O)OR$^{11}$, and C(O)NR$^{11}$R$^{12}$;

each R⁵ is independently chosen from C(O)R⁸, C(O)OR⁸, and C(O)NR⁸R⁹;

R¹ and R² are independently chosen from $C_{1-4}$alkyl, $C_{3-6}$cycloalkyl, and 3-6 membered heterocycloalkyl; and R⁴ is chosen from pyrrolo[2,3-b]pyridin-4-yl, 1H-pyrrolo[2,3-b]pyridin-4-yl, pyrrolo[2,3-c]pyridin-4-yl, benzo[d]imidazol-1-yl, any of which is optionally substituted with one or two R⁶ groups.

11. The method of claim 10, wherein each R⁶ is independently selected from NR¹¹R¹², halogen, cyano, hydroxy, and oxo.

12. The method of claim 11, wherein R¹ and R² are independently chosen from methyl, cyclopropyl, and oxetan-3-yl.

13. A product of the method of claim 1.

14. A method for preparing a compound of Formula 205

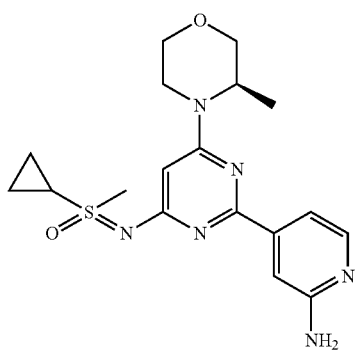

(205)

said method comprising reacting a compound of formula 204

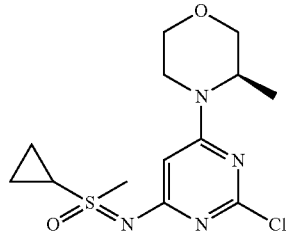

(204)

with a compound of formula

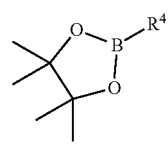

wherein R⁴ is 2-(methylamino)pyridin-4-yl, to yield a compound of formula 205.

15. The method of claim 14, wherein said reacting occurs in the presence of $PdCl_2(dppf)$.

16. The method of claim 15, wherein said reacting occurs in the presence of $Na_2CO_3$.

17. The method of claim 15, wherein said reacting occurs in the presence of dioxane.

18. The method of claim 15, wherein said reacting occurs in the presence of water.

19. The method of claim 15, further comprising separating the mixture of diastereomers.

20. The method of claim 19, wherein the step of separating the mixture of diastereomers is accomplished with chiral supercritical fluid chromatography (SFC).

21. A product of the method of claim 14.

* * * * *